(12) United States Patent
Liu et al.

(10) Patent No.: US 10,167,299 B2
(45) Date of Patent: Jan. 1, 2019

(54) 1-(3-AMINOPROPYL) SUBSTITUTED CYCLIC AMINE COMPOUNDS, PREPARATION METHOD THEREFOR, AND PHARMACEUTICAL COMPOSITIONS AND USES THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Beili Wu, Shanghai (CN); Yongtang Zheng, Shanghai (CN); Xin Xie, Shanghai (CN); Hualiang Jiang, Shanghai (CN); Panfeng Peng, Shanghai (CN); Ronghua Luo, Shanghai (CN); Jing Li, Shanghai (CN); Jian Li, Shanghai (CN); Ya Zhu, Shanghai (CN); Ying Chen, Shanghai (CN); Haonan Zhang, Shanghai (CN); Liumeng Yang, Shanghai (CN); Yu Zhou, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/109,101

(22) PCT Filed: Dec. 29, 2014

(86) PCT No.: PCT/CN2014/095421
§ 371 (c)(1),
(2) Date: Jun. 29, 2016

(87) PCT Pub. No.: WO2015/101265
PCT Pub. Date: Jul. 9, 2015

(65) Prior Publication Data
US 2017/0044187 A1 Feb. 16, 2017

(30) Foreign Application Priority Data
Dec. 30, 2013 (CN) .......................... 2013 1 0746752

(51) Int. Cl.
| C07D 519/00 | (2006.01) |
| C07D 409/14 | (2006.01) |
| C07D 451/04 | (2006.01) |
| C07D 401/14 | (2006.01) |
| A61K 45/06 | (2006.01) |
| A61K 31/46 | (2006.01) |
| A61K 31/4545 | (2006.01) |
| A61K 31/454 | (2006.01) |

(52) U.S. Cl.
CPC .......... *C07D 519/00* (2013.01); *A61K 31/454* (2013.01); *A61K 31/4545* (2013.01); *A61K 31/46* (2013.01); *A61K 45/06* (2013.01); *C07D 401/14* (2013.01); *C07D 409/14* (2013.01); *C07D 451/04* (2013.01)

(58) Field of Classification Search
CPC .... C07D 519/00; C07D 409/14; C07D 45/04; C07D 401/141; C07D 451/04; C07D 401/14; A61K 45/06; A61K 31/46; A61K 31/4545; A61K 31/454
See application file for complete search history.

(56) References Cited

U.S. PATENT DOCUMENTS 6,511,994 B2   1/2003   Kim et al.

FOREIGN PATENT DOCUMENTS

| WO | 2005/007656 A1 | 1/2005 |
| WO | 2006/136917 A1 | 12/2006 |
| WO | 2012/177660 A2 | 12/2012 |

OTHER PUBLICATIONS

Baba, M., "A small-molecule, nonpeptide CCR5 antagonist with highly potent and selective anti-HIV-1 activity." Proceedings of the National Academy of Sciences 96.10 (1999): 5698-5703.*
International Search Report (English translation) corresponding to PCT/CN2014/095421 dated Apr. 1, 2015 (2 pages).
Extended European Search Report corresponding to EP 14877091.0 (PCT/CN2014/095421) dated May 9, 2017; 8 pages.

(Continued)

*Primary Examiner* — John M Mauro
(74) *Attorney, Agent, or Firm* — Mintz, Levin, Cohn, Ferris, Glovsky and Popeo, P.C.

(57) ABSTRACT

Provided are 1-(3-aminopropyl) substituted cyclic amine compounds as represented by frmula (I), pharmaceutically acceptable salts, enantiomers, diastereoisomers, racemates and mixtures thereof, and a method of synthesizing said 1-(3-aminopropyl) substituted cyclic amine compounds by using aromatic heterocyclic formaldehyde as raw material. Said compounds can be used as CCR 5 antagonist for the treatment of HIV infection.

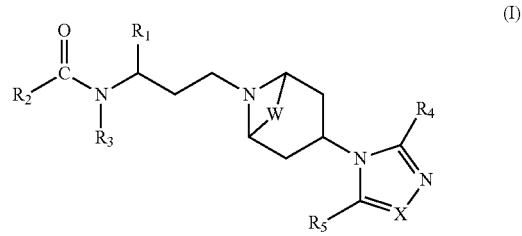

41 Claims, No Drawings

(56) References Cited

OTHER PUBLICATIONS

Barber, Christopher G. et al., "1-Amido-1-phyl-3-piperidinylbutanes—CCR5 antagonists for the treatment of HIV: Part 2," *Bioorganic & Medicinal Chemistry Letters* (available online Jan 10, 2009); 19:1499-1503.

* cited by examiner

1-(3-AMINOPROPYL) SUBSTITUTED CYCLIC AMINE COMPOUNDS, PREPARATION METHOD THEREFOR, AND PHARMACEUTICAL COMPOSITIONS AND USES THEREOF

TECHNICAL FIELD

The present invention relates to the field of pharmaceutical chemistry and pharmacotherapeutics, particularly to 1-(3-aminopropyl) substituted cyclic amine compounds, preparation method thereof, pharmaceutical compositions containing such compounds and uses thereof.

BACKGROUND ART

AIDS, Acquired Immune Deficiency Syndrome, is such a Syndrome that humans are infected with human immunodeficiency virus, HIV, followed by immunodeficiency and a series of opportunistic infections and tumors are triggered, severe case of which can lead to death. According to the World Health Organization (WHO), there were 34 million HIV carriers and AIDS patients in the world in 2011, 2.7 million persons were newly infected and 1.8 million patients died. Chinese Center for Disease Control and Prevention estimated that there were 780000 HIV carriers and AIDS patients in China by the end of 2011, 48000 persons were newly infected and 28000 patients died. At present, China is facing high peak of AIDS morbidity and mortality.

At present, medicaments for treating AIDS in clinic are divided into following classes: reverse transcriptase inhibitors, including nucleoside reverse transcriptase inhibitors and non-nucleoside reverse transcriptase inhibitors; protease inhibitors; integrase inhibitors and entry inhibitors. Entry inhibitors can be divided into CCR5 antagonists, CXCR4 antagonists, adhesion inhibitors and fusion inhibitors according to different targets during the entry of HIV into host cells. So far the main therapy for the treatment of AIDS is highly active antiretroviral therapy (HAART) which advocates combination of several drugs acting on different stages of HIV replication to achieve effective anti-HIV effect. In the past decade, highly active antiretroviral therapy has largely reduced the mortality rate of HIV-infected patients. However, the dosage regimen of HAART is complex and drugs combination can cause long-term severe side effects. Therefore, the development of anti-HIV drugs having new action mechanisms has very important significance.

Chemokines are a class of cytokines guiding directed migration of lymphocytes and have an important role in inflammation, tissue repair, immune surveillance, extravasation of white blood cells, tumorigenesis and embryonic development. Chemokines are proteins belonging to a small molecule cytokine family which currently have about 45 members. Their common features are that they have small molecular weight (about 8-10 kDa) and they contain four position-conserved cysteine (Cys) residues to ensure tertiary structure. According to whether other amino acid is contained between two Cys close to N-terminal, the family is divided into four categories: CC, CXC, CX3C and C chemokine. Wherein, CC chemokine and CXC chemokine are the most important two categories.

The functions of chemokine are mediated by chemokine receptor in vivo. Currently, chemokine receptor is named according to the characteristics of chemokine bound specifically (for example, if its ligand belonged to a CC chemokine subfamily, then it is named CCR). Chemokine receptors belong to the seven transmembrane G-protein coupled receptors (GPCR), are selectively expressed on the surface of target cells, wherein N-terminal thereof is outside the cell and C terminal is in the cell, and they contain seven very conservative transmembrane region consisting of α-helix. So far 19 chemokine receptors have been found. They are CCR1-11, CXCR1-6, XCR1, and CX3CR1. Modulators of chemokine receptor can be used in a variety of diseases, such as inflammatory or allergic diseases and the like.

Studies have shown that CD4 molecule on Th cell is essential for HIV invasion, but only CD4 is not enough to mediate fusion of HIV with cell. Further researches have found that chemokine receptors involve in the HIV invasion process and are known as HIV coreceptors. Coreceptors can be divided into two categories. One is coreceptor CCR5 distributed on the surface of macrophages and involved in entrance of macrophage tropism (M-tropism) HIV into host cells. The other is coreceptor CCR4 distributed on the surface of T cell and involved in entrance of T cell tropism (T-tropism) HIV into host cells. In the initial stages of infection, almost all HIV-1 subtypes use CCR5 as a coreceptor. Therefore, CCR5 plays a very important role in the HIV infection.

It has been found in experiments in vitro that chemokine RANTES, MIP-1α and MIP-1β that can bind to CCR5 can inhibit HIV infection by inhibiting the M-tropism HIV from entering into cells. In the experiment, benign results were obtained bu knockouting gene expressing CCR5 in mice. However, some studies indicate that the immune function of mouse can be changed in some models. In 1996, it was reported that there are natural CCR5 gene-deficient homozygous individuals and such individuals can well protect themselves from HIV infection without any other health problems. Subsequently, it was found that compared with no CCR5 allele-deficient HIV-infected patients, heterozygous individuals with only one CCR5 allele can obviously delay the progression of AIDS. Therefore, CCR5 can be used as a good anti-HIV target.

Macromolecular CCR5 antagonist can bind specifically to the specific extracellular portion of CCR5 to produce inhibiting effects without major toxic effects, but it is unstable, easy to be digested and degraded, expensive, and can not be orally administrated nd even cause the body to produce antibody-induced immune response. Therefore, companies and research institutions have conducted a great deal of effective research on non-peptide small molecule CCR5 antagonist and developed a number of highly active small molecule CCR5 antagonists such as TAK-220, TBR652, Vicriviroc and Maraviroc (trade name Selzentry) approved for marketing by FDA in 2007.

In summary, there is an urgent need to develop compounds as CCR5 antagonist having potential drug use in the art.

SUMMARY OF THE INVENTION

The object of the present invention is to provide 1-(3-aminopropyl) substituted cyclic amine compounds having CCR5 antagonist activity as represented by formula (I), pharmaceutically acceptable salts, enantiomers, diastereoisomers, racemates or mixtures thereof, and a method for synthesizing said 1-(3-aminopropyl) substituted cyclic amine compounds by using aromatic heterocyclic formaldehyde as raw material.

A further object of the present invention is to provide a pharmaceutical composition comprising the above compounds.

A further object of the present invention is to provide a use of above compound in the preparation of medicaments for the treatment of HIV infection.

In one aspect of the present invention, a 1-(3-aminopropyl) substituted cyclic amine compound of formula (I), a pharmaceutically acceptable salt, enantiomer, diastereoisomer, racemate or a mixture thereof is provided:

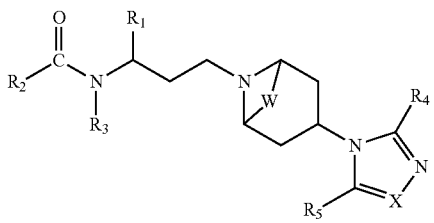

I

Wherein,

W is absent or —CH$_2$CH$_2$—; X is N or CR$_6$;

R$_1$ is selected from a 5 to 7-membered heteroaryl unsubstituted or substituted with 1-3 substituents, wherein said heteroaryl contains 1 to 3 heteroatoms selected from oxygen, sulfur or nitrogen and each of said substituents is independently selected from a halogen, a C1-C4 straight or branched alkyl, a C1-C4 straight or branched haloalkyl, a C1-C4 straight or branched alkyloxy, a C1-C4 straight or branched haloalkoxy, —NR$_{10}$R$_{11}$, —C(=O)R$_{12}$, a C1-C4 straight or branched alkanoyloxy, a cyano, a nitro and a hydroxy, or two adjacent substituents together with the attached carbon atom form a 5-7 membered ring;

each of R$_{10}$ and R$_{11}$ is independently selected from a group consisting of H, a C1-C4 straight or branched alkyl and —C(=O)R$_{13}$;

R$_{12}$ is selected from a group consisting of a C1-C4 straight or branched alkyl, a C1-C4 straight or branched alkyloxy, a hydroxyl, an amino (NH$_2$) and a C1-C4 straight or branched alkylamino;

R$_{13}$ is selected from a group consisting of H and a C1-C4 straight or branched alkyl;

R$_2$ is selected from the following groups unsubstituted or substituted with 1-3 substituents: a C1-C6 straight or branched alkyl, a C3-C7 cycloalkyl, a 4 to 7-membered heterocyclic group, a C6-C12 aryl or a 5-7 membered heteroaryl; wherein, said substituent is selected from a group consisting of a halogen, a hydroxy, a C1-C4 straight or branched alkyl, a C1-C4 straight or branched haloalkyl, a C1-C4 straight or branched alkyloxy, a C1-C4 straight or branched alkyl carbonyl, a C1-C4 straight or branched haloalkoxy, a C1-C4 straight or branched alkylsulfonyl, a C1-C4 straight or branched alkylsulfonylcarbamoyl, a tetrazolyl, a cyano, a nitro, an amino, a carboxy, a phenyl and a phenoxy;

each of R$_3$, R$_4$ and R$_5$ is independently selected from a group consisting of a hydrogen, a C1-C6 straight or branched alkyl and a C3-C7 cycloalkyl;

R$_6$ is selected from a group consisting of H and a C1-C6 straight or branched alkyl; alternatively, R$_5$ and R$_6$ may bind together with

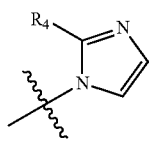

to form

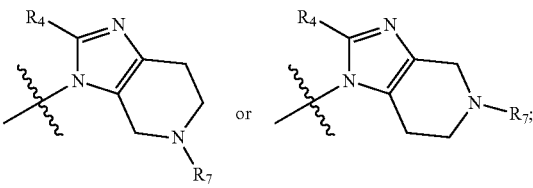

R$_7$ is selected from a group consisting of H, C(=O)R$_8$, C(=O)OR$_8$, C(=O)NR$_8$R$_9$, SO$_2$R$_8$ and the following groups substituted by 1-3 substituents: a C1-C6 straight or branched alkyl, a C3-C7 cycloalkyl, a 4 to 7-membered heterocyclic group, a benzyl, a C6-C12 aryl and a 5 to 7-membered heteroaryl; wherein said substituent is selected from a halogen, a hydroxy, a C1-C4 straight or branched alkyloxy, a C1-C4 straight or branched alkyl, a C1-C4 straight or branched haloalkyl, a C1-C4 straight or branched haloalkoxy, a cyano, a nitro, an amino and a carboxyl;

each of R$_8$ and R$_9$ is independently selected from a group consisting of a hydrogen and the following groups unsubstituted or substituted with 1-3 substituents: a C1-C6 straight or branched alkyl, a C3-C7 cycloalkyl, a 4 to 7-membered heterocyclic group, a benzyl, a C6-C12 aryl and a 5-7 membered heteroaryl; wherein said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, a nitro, an amino, and a carboxyl.

In another preferred embodiment, 1-(3-aminopropyl) substituted cyclic amine compound of formula (I) is S configuration or R configuration, preferably, S configuration.

Preferably, R$_1$ is selected from the following groups unsubstituted or substituted with 1-3 substituents:

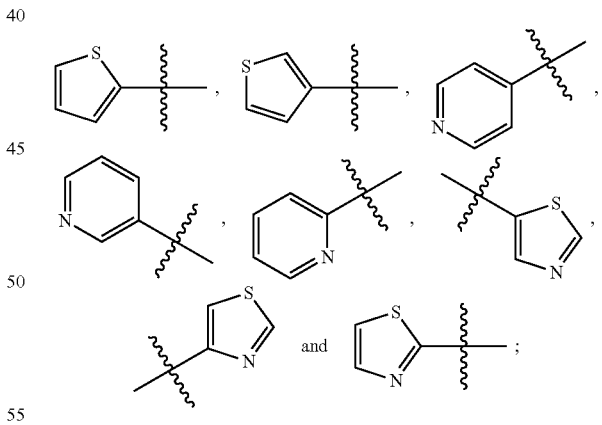

said substituent is selected from a group consisting of a halogen, a C1-C4 straight or branched alkyl, a C1-C4 straight or branched haloalkyl, a C1-C4 straight or branched alkoxy, —NR$_{10}$R$_{11}$, —C(=O)R$_{12}$, a C1-C4 straight or branched alkylcarbonyloxy, a C1-C4 straight or branched haloalkoxy, a cyano, a nitro and a hydroxyl, or two adjacent substituents together with the attached carbon atom form a 5-7 membered ring; preferably, the substituent is selected from a group consisting of a halogen, a C1-C2 alkyl, a C1-C2 haloalkyl, a C1-C2 alkoxy, NR$_{10}$R$_{11}$, —C(=O)R$_{12}$, a C1-C2 alkylcarbonyloxy, a C1-C2 haloalkoxy, a cyano, a nitro and a hydroxyl or two adjacent substituents together with the attached carbon atom form a 5-7 membered carbocycle, a 5-7 membered heteroaryl ring or a 5-7 membered heterocycle; and most preferably, the substituent is selected from a group consisting of a halogen, a methyl, a methoxy, an ethyl, an amino, a hydroxyl, a cyano, a nitro, an acetyl, a formamido, an acetamido, a carbamoyl, N-methylcarbamoyl, N,N-dimethylcarbamoyl, a formyloxy, an acetoxy, a methoxycarbonyl, a trifluoromethyl and a trifluoromethoxy, or two adjacent substituents together with the attached carbon atom form a benzene ring, a cyclopentene ring or dioxole ring.

Preferably, each of $R_{10}$ and $R_{11}$ is independently selected from a group consisting of H, a C1-C2 alkyl and —C(=O)$R_{13}$.

Preferably, $R_{12}$ is selected from a group consisting of a C1-C2 alkyl, a C1-C2 alkoxy, a hydroxy, an amino ($NH_2$) and a C1-C2 alkylamino.

Preferably, $R_{13}$ is selected from a group consisting of H and a C1-C2 straight or branched alkyl.

Preferably, $R_2$ is selected from the following groups unsubstituted or substituted with 1-3 substituents: a C1-C4 straight or branched alkyl, a C3-C7 cycloalkyl, a 4-7 membered heterocyclic group and a phenyl, wherein, said substituent is selected from a group consisting of a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, a cyano, a nitro, an amino, a carboxyl, a phenyl, a halophenyl, a phenoxy and a halophenoxy; more preferably, $R_2$ is selected from a C1-C4 straight or branched alkyl, a cyclopropyl, a cyclobutyl, a cyclopentyl, a cyclohexyl, a tetrahydropyran-4-yl, a 1-methylpiperidin-4-yl, 1-acetylpiperidin-4-yl, 1-methylsulfonylpiperidin-4-yl,

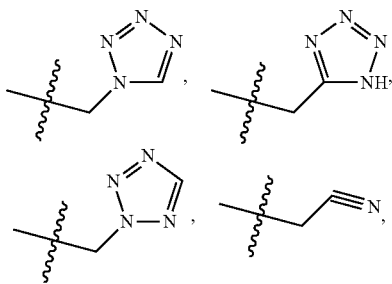

4-fluorobenzyl, a phenyl, a difluorocyclohexyl (preferably, 4,4-difluorocyclohexyl) (similarly hereinafter), ethylcyclohexyl and phenoxymethyl.

Preferably, each of $R_3$, $R_4$ and $R_5$ is independently selected from a group consisting of H, a C1-C4 straight or branched alkyl and a C3-C7 cycloalkyl; more preferably, each of $R_3$, $R_4$ and $R_5$ is independently selected from a group consisting of H, a methyl, an ethyl, an n-propyl, an isopropyl, an n-butyl, a sec-butyl, a tertiary butyl, a cyclopropyl, a cyclobutyl, a cyclopentyl and a cyclohexyl; most preferably, each of $R_3$, $R_4$ and $R_5$ is independently selected from a group consisting of H, a methyl, an ethyl, an n-propyl, an isopropyl, an n-butyl, a sec-butyl, a tert-butyl and a cyclopropyl.

Preferably, $R_6$ is selected from a group consisting of H and a C1-C4 straight or branched alkyl, more preferably, $R_6$ is selected from a group consisting of H, a methyl and an ethyl.

Alternatively, $R_5$ and $R_6$ can bind together with

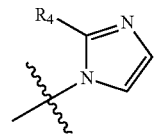

to form

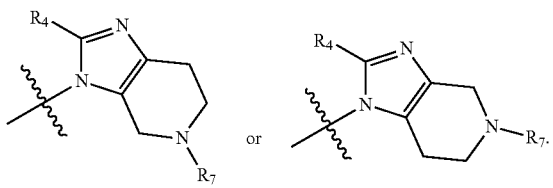

Preferably, $R_7$ is selected from a group consisting of H, C(=O)$R_8$, C(=O)O$R_8$, C(=O)N$R_8R_9$, SO$_2R_8$ and the following groups substituted with 1-3 substituents: a C1-C4 straight or branched alkyl, a C3-C7 cycloalkyl, a 4-7 membered heterocyclic group, a benzyl and a phenyl, wherein, said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, a nitro, an amino and a carboxyl; more preferably, $R_7$ is selected from a group consisting of H, C(=O)$R_8$ and SO$_2R_8$;

each of $R_8$ and $R_9$ is independently selected from a group consisting of H and the following groups unsubstituted or substituted with 1-3 substituents: a C1-C4 straight or branched alkyl, a C1-C4 straight or branched haloalkyl, a C3-C7 cycloalkyl, a 4-7 membered heterocyclic group, a benzyl, a phenyl and a 5-7 membered heteroaryl, wherein said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, a nitro, an amino and a carboxyl, preferably said substituent is selected from a group consisting of a halogen, a hydroxy, a methoxy, an ethoxy, a methyl, an ethyl, a trifluoromethyl, a trifluoromethoxy, a cyano, a nitro, an amino and a carboxyl; preferably, each of $R_8$ and $R_9$ is independently selected from a group consisting of H, a C1-C4 straight or branched alkyl, a C1-C4 straight or branched haloalkyl, a C3-C7 cycloalkyl, a benzyl and a phenyl; more preferably, each of $R_8$ and $R_9$ is independently selected from a group consisting of a methyl, an ethyl, an n-propyl, a cyclopropyl, an isopropyl, an n-butyl, a sec-butyl and a tert-butyl.

In a preferable embodiment, a 1-(3-aminopropyl) substituted cyclic amine compound of formula (II), pharmaceutically acceptable salt, enantiomer, diastereoisomer, racemate or mixture thereof is provided:

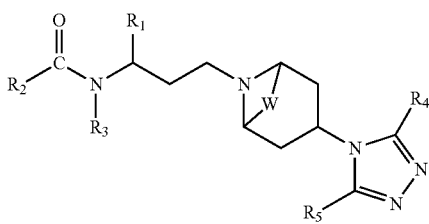

wherein the definitions of $R_1$, $R_2$, $R_3$, $R_4$, $R_5$ and W are described as those in formula (I).

In formula II, preferably. $R_1$ is selected from the following groups unsubstituted or substituted with 1-3 substituents:

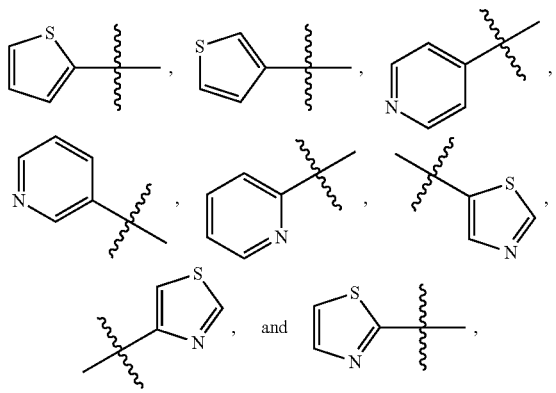

said substituent is selected from a group consisting of a halogen, a C1-C4 straight or branched alkyl, a C1-C4 straight or branched haloalkyl, a C1-C4 straight or branched alkoxy, a C1-C4 straight or branched alkylcarbonyloxy, a C1-C4 straight or branched haloalkoxy, $NR_{10}R_{11}$, —C(=O)$R_{12}$, a cyano, a nitro and a hydroxyl, or two adjacent substituents together with the attached carbon atom form a 5-7 membered ring; preferably, said substituent is selected from a group consisting of a halogen, a C1-C2 alkyl, a C1-C2 haloalkyl, a C1-C2 alkylcarbonyloxy, a C1-C2 alkoxy, a C1-C2 haloalkoxy, $NR_{10}R_{11}$, —C(=O)$R_{12}$, a cyano, a nitro and a hydroxyl, or two adjacent substituents together with the attached carbon atom form a 5-7 membered carbocycle, 5-7 membered heteroaryl ring or 5-7 membered heterocycle; most preferably, said substituent is selected from a group consisting of a halogen, a methyl, a trifluoromethyl, a trifluoromethoxy, a methoxy, an ethyl, an amino, a cyano, a nitro, an acetyl, a formamido, an acetamido, a carbamoyl, N-methylcarbamoyl, N,N-dimethylcarbamoyl, an acetoxy, a formyloxy and a methoxycarbonyl, or two adjacent substituents together with the attached carbon atom form a benzene ring, a cyclopentene ring or dioxole ring;

each of $R_{10}$ and $R_{11}$ is independently selected from a group consisting of H, a C1-C4 straight or branched alkyl and —C(=O)$R_{13}$; preferably, each of $R_{10}$ and $R_{11}$ is independently selected from a group consisting of H, a C1-C2 alkyl and —C(=O)$R_{13}$;

$R_{12}$ is selected from a group consisting of a C1-C4 straight or branched alkyl, a C1-C4 straight or branched alkoxy, a hydroxy, an amino ($NH_2$) and a C1-C4 straight or branched alkylamino; preferably, $R_{12}$ is selected from a group consisting of a C1-C2 alkyl, a C1-C2 alkoxy, a hydroxy, an amino ($NH_2$) and a C1-C2 alkylamino;

$R_{13}$ is selected from a group consisting of H and a C1-C4 straight or branched alkyl; preferably, $R_{13}$ is selected from a group consisting of H and a C1-C2 straight or branched alkyl;

$R_2$ is selected from the following groups unsubstituted or substituted with 1-3 substituents: a phenyl, a C1-C4 straight or branched alkyl and a C3-C7 cycloalkyl, wherein said substituent is selected from a group consisting of a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, an amino, a phenyl, a halophenyl, a phenoxy and a halophenoxy; more preferably, $R_2$ is selected from a group consisting of a methyl, an ethyl, a cyclopropyl, a cyclobutyl, a cyclopentyl, a cyclohexyl, tetrahydropyran-4-yl, 1-methylpiperidin-4-yl, 1-acetylpiperidin-4-yl, 1-methylsulfonylpiperidin-4-yl,

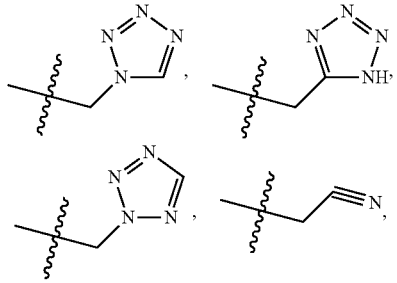

4-fluorobenzyl, a phenyl, an ethylcyclohexyl and a difluorocyclohexyl;

each of $R_3$, $R_4$ and $R_5$ is independently selected from a group consisting of H and a C1-C4 straight or branched alkyl; more preferably, each of $R_3$, $R_4$ and $R_5$ is independently selected from a group consisting of H, a methyl, an ethyl, an n-propyl, an isopropyl, an n-butyl, a sec-butyl and a tert-butyl; most preferably, each of $R_3$, $R_4$ and $R_5$ is independently selected from a group consisting of H, a methyl, an ethyl, an n-propyl, and an isopropyl.

In another preferable embodiment, a 1-(3-aminopropyl) substituted cyclic amine compound of formula (III), pharmaceutically acceptable salt, enantiomer, diastereoisomer, racemate or mixture thereof is provided:

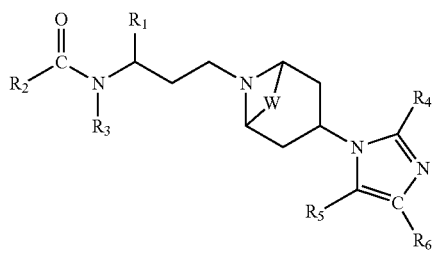

wherein the definitions of $R_1$, $R_2$, $R_3$, $R_4$, $R_5$, $R_6$ and W are described as those in formula I.

In formula III, preferably, $R_1$ is selected from the following groups unsubstituted or substituted with 1-3 substituents:

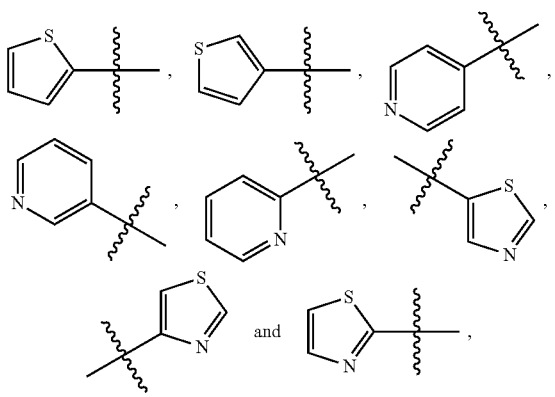

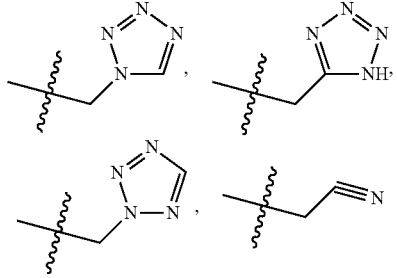

said substituent is selected from a group consisting of a halogen, a C1-C4 straight or branched alkyl, a C1-C4 straight or branched haloalkyl, a C1-C4 straight or branched alkylcarbonyloxy, a C1-C4 straight or branched alkoxy, a C1-C4 straight or branched haloalkoxy, $NR_{10}R_{11}$, —C(=O)$R_{12}$, a cyano, a nitro and a hydroxyl, or two adjacent substituents together with the attached carbon atom form a 5-7 membered ring; preferably, said substituent is selected from a group consisting of a halogen, a C1-C2 alkyl, a C1-C2 haloalkyl, a C1-C2 alkoxy, a C1-C2 alkylcarbonyloxy, a C1-C2 haloalkoxy, $NR_{10}R_{11}$, —C(=O)$R_{12}$, a cyano, a nitro and a hydroxyl, or two adjacent substituents together with the attached carbon atom form a 5-7 membered carbocycle, 5-7 membered heteroaryl ring or 5-7 membered heterocycle; most preferably, said substituent is selected from a group consisting of a halogen, a methyl, a trifluoromethyl, a trifluoromethoxy, a methoxy, an ethyl, an amino, a cyano, a nitro, an acetyl, a formamido, an acetamido, a carbamoyl, N-methylcarbamoyl, N,N-dimethylcarbamoyl, a formyloxy, an acetoxy and a methoxycarbonyl, or two adjacent substituents together with the attached carbon atom form a benzene ring, a cyclopentene ring or dioxole ring;

each of $R_{10}$ and $R_{11}$ is independently selected from a group consisting of H, a C1-C4 straight or branched alkyl and —C(=O)$R_{13}$; preferably, each of $R_{10}$ and $R_{11}$ is independently selected from a group consisting of H, a C1-C2 alkyl and —C(=O)$R_{13}$;

$R_{12}$ is selected from a group consisting of a C1-C4 straight or branched alkyl, a C1-C4 straight or branched alkoxy, a hydroxy, an amino ($NH_2$) and a C1-C4 straight or branched alkylamino; preferably, $R_{12}$ is selected from a group consisting of a C1-C2 alkyl, a C1-C2 alkoxy, a hydroxy, an amino ($NH_2$) and a C1-C2 alkylamino;

$R_{13}$ is selected from a group consisting of H and a C1-C4 straight or branched alkyl; preferably, $R_{13}$ is selected from a group consisting of H and a C1-C2 straight or branched alkyl; $R_2$ is selected from the following groups unsubstituted or substituted with 1-3 substituents: a C1-C4 straight or branched alkyl and a C3-C7 cycloalkyl, wherein said substituent is selected from a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, a cyano and an amino; more preferably, $R_2$ is selected from a group consisting of a methyl, an ethyl, a cyclopropyl, a cyclobutyl, a cyclopentyl, a cyclohexyl, a tetrahydropyran-4-yl, 1-methylpiperidin-4-yl, 1-acetylpiperidin-4-yl, 1-methylsulfonylpiperidin-4-yl,

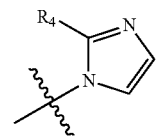

and a difluorocyclohexyl;

each of $R_3$ and $R_4$ is independently selected from a group consisting of H and a C1-C4 straight or branched alkyl; more preferably, each of $R_3$ and $R_4$ is independently selected from a group consisting of H, a methyl, an ethyl, an n-propyl, an isopropyl, an n-butyl, a sec-butyl and a tert-butyl; most preferably, each of $R_3$ and $R_4$ is independently selected from a group consisting of H, a methyl and an ethyl;

$R_5$ and $R_6$ can bind together with to form

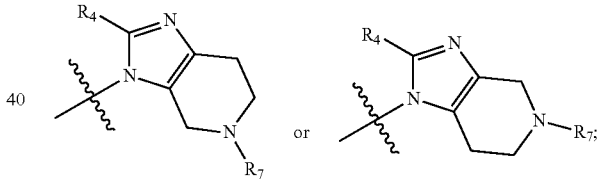

$R_7$ is selected from a group consisting of H, C(=O)$R_8$, C(=O)O$R_8$, C(=O)N$R_8R_9$ and SO$_2R_8$; more preferably, $R_7$ is selected from a group consisting of H, C(=O)$R_8$ and SO$_2R_8$;

each of $R_8$ and $R_9$ is independently selected from a group consisting of H and the following groups unsubstituted or substituted with 1-3 substituents: a C1-C4 straight or branched alkyl, a C1-C4 straight or branched haloalkyl, a C3-C7 cycloalkyl and a benzyl, wherein said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy and an amino; preferably said substituent is selected from a group consisting of a halogen, a hydroxy, a methoxy, an ethoxy, a methyl, an ethyl, a trifluoromethyl, a trifluoromethoxy and an amino; preferably, each of $R_8$ and $R_9$ is independently selected from a group consisting of H, a C1-C4 straight or branched alkyl, a C1-C4 straight or branched haloalkyl and a C3-C7 cycloalkyl; more preferably, each of $R_8$ and $R_9$ is independently selected from a group consisting of a methyl, an ethyl, an n-propyl, a cyclopropyl, an isopropyl, an n-butyl, a sec-butyl and a tert-butyl.

In another preferable embodiment, each of $R_1$, $R_2$, $R_3$, $R_4$, $R_5$, $R_6$, $R_7$, $R_8$, $R_9$, $R_{10}$, $R_{11}$, $R_{12}$, $R_{13}$, W and X in the compound of formula I of the present invention independently and preferably is the corresponding group in compounds 1-172 prepared in examples.

The definitions in the present invention are listed as follows: halogen includes F, Cl, Br and I; C3-C7 cycloalkyl refers to a cycloalkyl containing 3-7 carbon atoms on the ring, and includes (but not limited to) cyclopropyl, cyclobutyl, cyclopentyl, cyclohexyl and cycloheptyl; C6-C12 aryl refers to a aromatic ring group containing 6-12 carbon atoms on the ring without heteroatom, and includes (but not limited to) phenyl and naphthyl; 4-7 membered heterocyclic group refers to a nonaromatic cyclic group containing 4-7 atoms and at least one heteroatom which is selected from O, N or S on the ring, and includes (but not limited to) azetidinyl, tetrahydrofuranyl, piperazinyl, morpholinyl and piperidinyl; 5-7 membered heteroaryl refers to to an aromatic cyclic group containing 5-7 atoms and at least one heteroatom which is selected from O, N or S on the ring, and includes (but not limited to) thienyl, thiazolyl, pyridyl, furyl, pyrrolyl, pyrazolyl, imidazolyl, oxazolyl, pyrimidinyl and triazinyl. 5-7 membered ring refers to a ring containing 5-7 atoms on the ring with or without a heteroatom which is selected from O, N or S, and includes 5-7 membered carbocycle (saturated or unsaturated ring containing only carbon atoms), 5-7 membered heteroaryl ring (aromatic ring containing 5-7 atoms and at least one heteroatom which is selected from O, N or S on the ring), and 5-7 membered heterocycle (nonaromatic ring containing 5-7 atoms and at least one heteroatom which is selected from O, N or S on the ring), and includes (but not limited to) benzene ring, cyclopentene ring, cyclohexene ring, cycloheptene ring, dioxole ring and the like.

As used herein, the terms "aryl", "phenyl", "phenoxy", "heteroaryl", "heteroaromatic ring" and "heterocycle" include substituted or unsubstituted forms, wherein the substituted form may include, for example, 1 to 5 identical or different non-hydrogen substituents, and the representative substituent includes (but not limited to) C1-C4 alkyl, C3-C4 cycloalkyl, halogen (fluorine, chlorine, bromine or iodine), C1-C4 haloalkyl, or combinations thereof.

As used herein, the term "C1-C4 straight or branched alkylamino" includes mono- or di-substituted amino, and for di-substituted amino, alkyl substituents can be identical or different. Representative example includes (but not limited to) —NH(CH$_3$), —N(CH$_3$)$_2$, —N(CH$_3$)(C$_2$H$_5$)

In particular, 1-(3-aminopropyl) substituted cyclic amine compounds according to the present invention are preferably selected from any one of Compound 1-Compound 172 prepared in the Examples or pharmaceutically acceptable salts thereof.

In another aspect of the present invention, a method for preparing the 1-(3-aminopropyl) substituted cyclic amine compound of formula I is provided. The compound is prepared by using substituted pyridylaldehyde or substituted thiophene carboxaldehyde as raw material through step-wise Mannich reaction, removal of sulfinyl, BOC protection, ester reduction, oxidation, reductive amination, deprotection and condensation reaction. The method is carried out through the following process, wherein $R_1$, $R_2$, $R_4$, $R_5$, $R_6$, X and W are defined as described above.

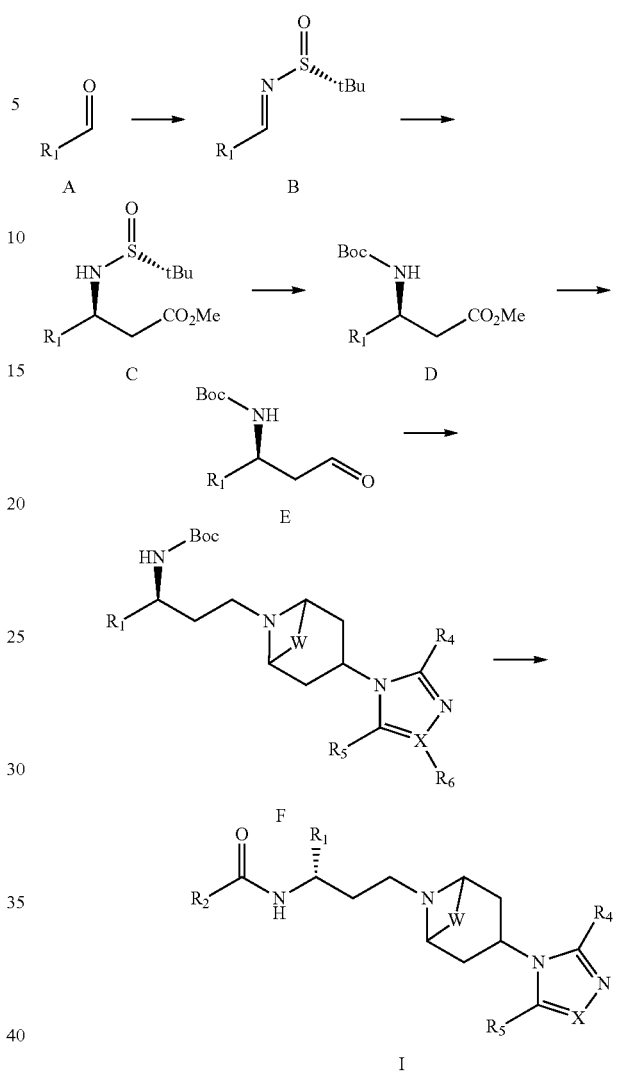

1) Sulfinylimine Compound B is obtained from Compound A through imidization.

As an example, compound A is dissolved in tetrahydrofuran, substituted tetrahydrofuran, methylene chloride or diethyl ether and stirred at room temperature, to which was sequentially added (R)-tert-butyl sulfinamide and tetraethyl titanate. After reacting for 3-6 hours under nitrogen protection, water is added and the filtrate is obtained through filtration. Sulfinylimine compound B is obtained by organic solvent extraction and column chromatography separation.

2) Compound C is obtained from Sulfinylimine compound B through Mannich reaction.

As an example, N,N-diisopropylethylamine or triethylamine is dissolved in tetrahydrofuran, substituted tetrahydrofuran, methylene chloride or diethyl ether at −20-0° C., n-butyl lithium solution in hexane is added dropwise slowly under nitrogen. After reacting for 30 to 120 minutes, the mixture is cooled to −78° C. and methyl acetate is added. After reacting for 30 to 120 minutes, a solution of chlorotitanium triisopropoxide is added. After reacting for 30 to 60 minutes, compound B is added. After reacting for 3-6 hours, the reaction is quenched with saturated ammonium chloride solution. The filtrate is obtained through filtration. Compound C is obtained by organic solvent extraction and column chromatography separation.

3) Compound D is obtained from Compound C through removal of sulfinyl and BOC protection.

As an example, compound C is dissolved in methanol or ethanol, and an acid solution is added and stirred for 2-5 hours at room temperature. Upon concentration, the mixture is dissolved in dichloromethane or ethyl acetate, a base and di-tert-butyl dicarbonate are added and stirred for 2-5 hours at room temperature. The system is concentrated, extracted with an organic solvent and separated by column chromatography to give compound D.

4) Compound E is obtained from Compound D through ester reduction and oxidation.

As one example, compound is dissolved in tetrahydrofuran, substituted tetrahydrofuran or diethyl ether at 0-20° C., and a solution of lithium aluminum hydride is slowly added dropwise and stirred for 2-4 hours at room temperature. The reaction is quenched with water, washed with a basic solution and filtered. The organic phase is washed with saturated brine, dried and concentrated. The concentrate is dissolved in dichloromethane, and Dess-Martin periodinane (DMP) is added and stirred for 0.5-6 hours. A saturated solution of sodium bicarbonate is added, and compound E is obtained by the organic solvent extraction and column chromatographic separation.

5) Compound F is obtained from Compound E and compound

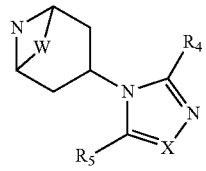

through reductive amination reaction.

As an example, compound E is dissolved in tetrahydrofuran, dichloromethane or 1,2-dichloroethane, and

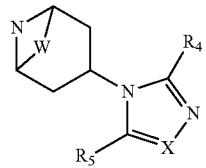

and triacetoxy sodium borohydride are added and stirred for 8-16 hours at room temperature. Water is added, and the mixture is extracted with an organic solvent and separated by column chromatography to give compound F.

6) Compound F is subjected to deprotection and condensation reaction with

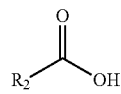

to give compound I.

As an example, compound F is dissolved in methanol or ethanol, and acid solution is added and stirred for 2-5 hours at room temperature. The reaction mixture is concentrated and dissolved in N,N-dimethylformamide A base,

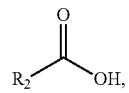

condensing agent such as benzotriazole-1-yloxy-tris(dimethylamino) phosphonium hexafluorophosphate (BOP) or 1-ethyl-(3-dimethylaminopropyl) carbodiimide hydrochloride salt (EDCI) etc. are added successively and stirred at room temperature for 8-16 hours. Water is added, and the mixture is extracted with an organic solvent and separated by column chromatography to give compound I.

In above method, the acid used in each step may be an organic or inorganic acid, the organic acid may be acetic acid, trifluoroacetic acid, formic acid, and the inorganic acid may be hydrogen chloride, sulfuric acid or phosphoric acid; the base may be inorganic or organic bases, the inorganic base is selected from a group consisting of sodium carbonate, potassium carbonate, cesium carbonate, sodium bicarbonate, potassium phosphate, monopotassium phosphate, sodium hydroxide, lithium hydroxide and potassium hydroxide, and the organic base is selected from a group consisting of triethylamine, pyridine, diazabicyclo (DBU) and N,N-diisopropylethylamine (of DIPEA); the organic solvent may be selected from a group consisting of tetrahydrofuran (THF), acetonitrile, acetone, 1,4-dioxane, alcohols, diethyl ether, N,N-dimethylformamide, ethylene glycol dimethyl ether, N,N-dimethylformamide (DMF) and dimethylsulfoxide (DMSO); and the condensing agent used in step 6) may be 1-ethyl-(3-dimethylaminopropyl)carbodiimide hydrochloride (EDCI), benzotriazole-1-yl oxy-tris(dimethylamino)phosphonium hexafluorophosphate (BOP), 2-(7-azabenzotriazole)-N,N,N',N'-tetramethyluronium hexafluorophosphate (HATU) or N,N'-dicyclohexyl carbodiimide (DCC) and the like.

In another aspect of the invention, a pharmaceutical composition is provided comprising the 1-(3-aminopropyl) substituted cyclic amine compounds according to the present invention, a pharmaceutically acceptable salt, enantiomer, diastereoisomer, racemate or mixture thereof and optionally a pharmaceutically acceptable carrier. The pharmaceutical composition may be used in therapy in vivo and has biocompatibility. The pharmaceutical composition may be prepared into various forms depending on different route of administration. The pharmaceutical composition of the present invention may be used as CCR5 antagonist for treating HIV infection.

The pharmaceutical composition of the present invention may be provided in various forms, such as tablet, capsule, powder, syrup, solution, suspension, aerosol etc., and may be present in a suitable solid or liquid carrier or diluent and suitable disinfectant container for injection or infusion. The pharmaceutical composition may also comprise odor, flavor, etc., and a desirable ratio is that the compound of formula I as active ingredient accounts for 65% or more based on the total weight, and the rest accounts for 0.5-40%, preferably 1-20%, or preferably is 1 to 10% of a pharmaceutically acceptable carrier, diluent or solution or a salt solution.

The compound according to the present invention as described above may be clinically used to mammals including humans and animals by mouth, nose, skin, lung, or gastrointestinal tract, etc., and more preferably by mouth. Daily dose is preferably 0.01-200 mg/kg body weight, administered at once, or 0.01-100 mg/kg body weight in divided doses. No matter what administration method, optimal dose for an individual should be determined based on the specific treatment. Under normal conditions, a small dose is given at the beginning and the dose is gradually increased until the most suitable dose is found.

In another aspect of the invention, a use of 1-(3-aminopropyl) substituted cyclic amine compound according to the present invention, a pharmaceutically acceptable salt, enantiomer, diastereoisomer, racemate or mixture thereof in the preparation of CCR5 antagonist is provided.

In a further aspect of the present invention, a use of 1-(3-aminopropyl) substituted cyclic amine compound according to the present invention, a pharmaceutically acceptable salt, enantiomer, diastereoisomer, racemate or mixture thereof in the preparation of a medicament for treating CCR5-mediated disease is provided.

In a further aspect of the present invention, a use of 1-(3-aminopropyl) substituted cyclic amine compound according to the present invention, a pharmaceutically acceptable salt, enantiomer, diastereoisomer, racemate or mixture thereof in the preparation of a medicament for treating HIV infection is provided.

In a further aspect of the present invention, a method for treating the disease mediated by CCR5 is provided, which comprises administering 1-(3-aminopropyl) substituted cyclic amine compound of the present invention, a pharmaceutically acceptable salt, enantiomer, diastereoisomer, racemate or mixture thereof or a pharmaceutical composition containing one of 1-(3-aminopropyl) substituted cyclic amine compound according to the present invention, a pharmaceutically acceptable salt, enantiomer, diastereoisomer, racemate or mixture thereof to a patient in need thereof. In an embodiment, the disease mediated by CCR5 is HIV infection.

DETAILED DESCRIPTION

The present invention will be further illustrated by the following examples. These examples are intended to illustrate the present invention, but not limit the invention in any way. Unless otherwise stated, all parameters as well as the rest of the description in examples are based on weight.

For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer.

Analysis data of the samples were measured by the following instruments. NMR was measured by GEMINI-300, Bruker AMX-400 and INVOA-600 nuclear magnetic resonance, wherein, TMS (tetramethylsilane) was used as an internal standard, the chemical shift unit was ppm, and coupling constant unit was Hz. Mass spectra was measured by Finnigan MAT-711, MAT-95 and LCQ-DECA mass spectrometer and IonSpec4.7 Tesla mass spectrometer.

Column chromatography was carried out on 200-300 mesh silica gel (Qingdao Marine Chemical Plant). TLC silica gel plate was HSGF-254 thin layer chromatography prefabricated panel produced by Yantai Chemical Plant. The boiling range of petroleum ether was 60-90° C. UV light was used and iodine cylinder was used for development. Unless otherwise indicated, the conventional reagents and pharmaceuticals used in the following examples were purchased from Sinopharm. The reagents and solvents used in the experiments are processed according to specific conditions.

EXAMPLE 1

Synthesis of Compound 1

4,4-difluoro-N-[3-[4-(3-isopropyl-5-methyl-4H-1,2,4-triazol-4-yl)-piperidin-1-yl]-1-(thiophen-2-yl)propyl]cyclohexane-1-carboxamide

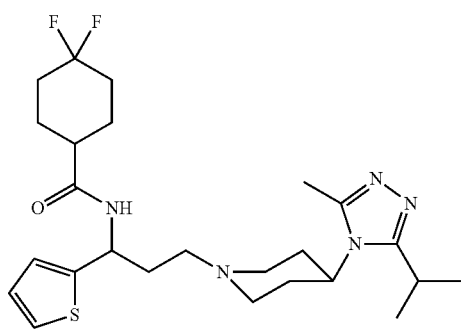 [SMILES: Cc1nnc(C(C)C)n1C1CCN(CCC(NC(=O)C2CCC(F)(F)CC2)c2cccs2)CC1]

Synthesis Route

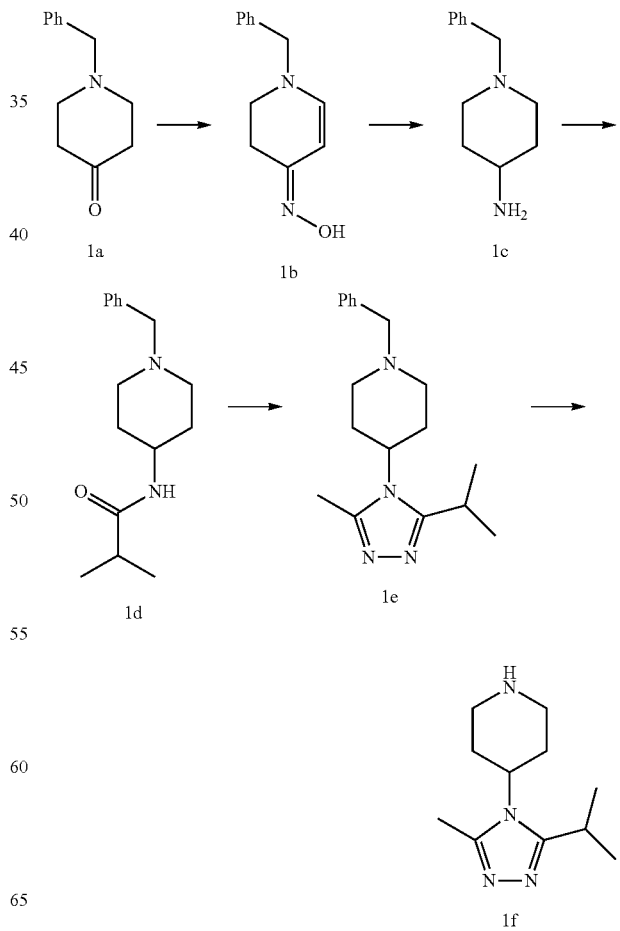

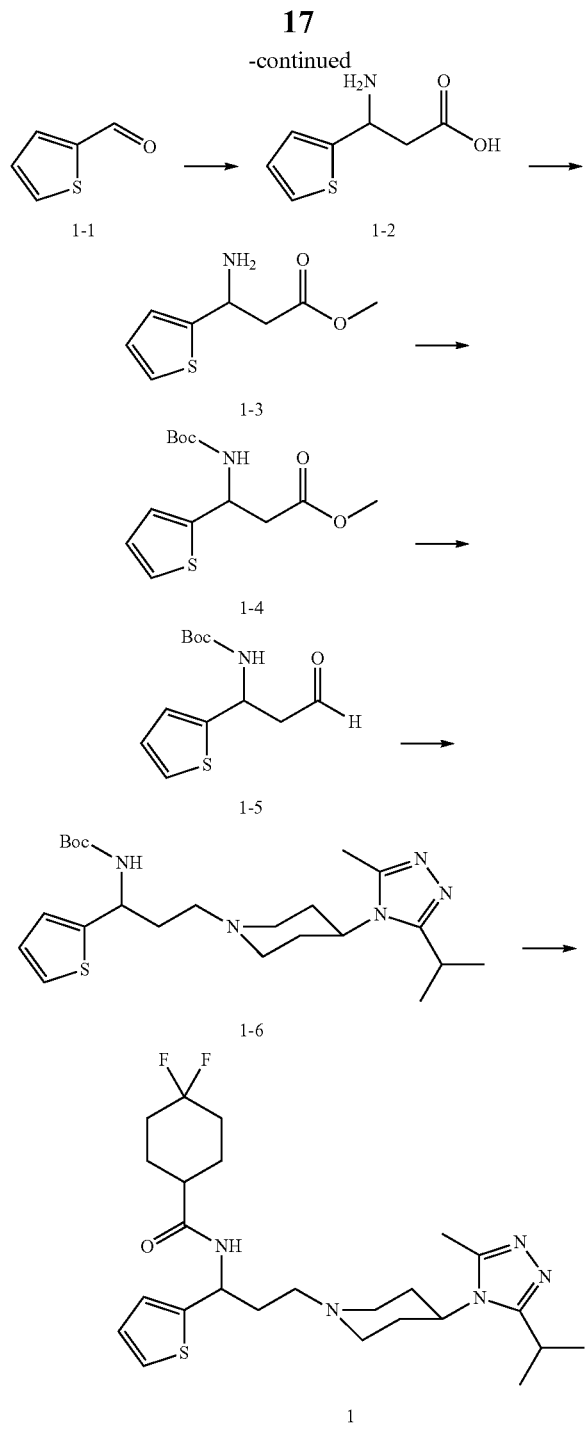

Synthesis of Compound 1b compound 1a (1.89 g, 10 mmol) was dissolved in 50 mL of absolute ethanol, and potassium carbonate (2.76 g, 20 mmol) and hydroxylamine hydrochloride (1.04 g, 15 mmol) were added successively and stirred at room temperature for 6 hours. After the mixture was concentrated, water was added. Then the mixture was extracted with ethyl acetate, washed with saturated brine, dried over anhydrous sodium sulfate and concentrated to give white solids 1b (2.04 g, yield 100%), MS: 205.0 [M+H]+.

Synthesis of Compound 1c

Compound 1b (2.04 g, 10 mmmol) was dissolved in 50 mL of anhydrous n-amyl alcohol and stirred at reflux, to which was added sodium (2.76 g, 120 mmol) in batches. The reaction was maintained for 2.5 hours. Then the reaction mixture was cooled, adjusted with 1M hydrochloric acid to PH 12 and extracted with water. The combined aqueous phase was adjusted with 1M sodium hydroxide to PH 8. Then the mixture was extracted by ethyl acetate, washed with saturated brine, dried over anhydrous sodium sulfate and concentrated to give colourless liquid 1c (1.71 g, yield 90%), MS: 191.0 [M+H]+.

Synthesis of Compound 1d

Compound 1c (1.90 g, 10 mmmol) was dissolved in 30 mL of dichloromethane, and sodium carbonate (1.59 g, 15 mmol) was added and stirred at room temperature. Isobutyryl chloride (1.6 g, 15 mmol) was slowly added dropwise and the reaction was maintained for 2 hours. Then the reaction mixture was extracted by dichloromethane, washed with saturated brine, dried over anhydrous sodium sulfate and concentrated to give white solids 1d (2.60 g, yield 100%), MS: 191.0 [M+H]+.

Synthesis of Compound 1e

Compound 1d (1.30 g, 5 mmmol) was dissolved in 20 mL of dichloromethane and phosphorous pentachloride (1.248 g, 5 mmmol) was slowly added under ice-bath and stirred for 2 hours at room temperature. Then 5 mL of t-amyl alcohol and acetic hydrazide (0.74 g, 10 mmol) were added and stirred for 16 hours at room temperature. The mixture was concentrated and redissolved in 10 mL toluene and 10 mL dioxane. Then 32 mg p-toluenesulfonic acid was added. The reaction was refluxed for 5 hour and water was added. The mixture was adjusted to pH 8, extracted with dichloromethane, washed with saturated brine, dried over anhydrous sodium sulfate and separated by column chromatography to give white solids 1e (0.99 g, yield 67%), MS: 299.01 [M+H]+.

Synthesis of Compound 1f

Compound 1e (0.507 g, 1.7 mmol) was dissolved in 10 mL methanol and 20% palladium hydroxide (0.14 g, 0.7 mmol) and ammonium formate (0.535 g, 8.5 mmol) were added. The reaction mixture was stirred at reflux for 2.5 hours and then filtered. The reaction solution was concentrated and separated by column chromatography to give white solids if (0.336 g, yield 95%), MS: 209.0 [M+H]+.

Synthesis of Compound 1-2

Compound 1-1 (2.00 g, 17.83 mmol) was dissolved in 5.5 mL of ethanol, to which was successively added ammonium acetate (2.74 g, 35.58 mmol) and malonic acid (1.85 g, 17.78 mmol). The reaction was kept with stirring and refluxed for 7 hours. White turbidity appeared in the clear reaction solution. Then the reaction mixture was filtered and washed with hot ethanol (3×10 mL) to give white solids 1-2 (2.20 g, yield 72%), MS: 172.0 [M+H]+.

Synthesis of Compound 1-3

At room temperature, thionyl chloride (4.0 mL) was slowly added dropwise to a solution of 1-1 (8.55 g, 50.0 mmol) in anhydrous methanol (30.0 mL) with stirring, and the reaction was stirred at reflux for 16 hours. Analysis showed that the reaction was completed. Then the reaction mixture was concentrated and saturated potassium carbonate was added to the residue to adjust PH to 8. Then the mixture was extracted with ethyl acetate, washed with saturated brine, dried over anhydrous sodium sulfate and concentrated to give white solids 1-3 (8.78 g, yield 95%), MS: 185.9 [M+H]+.

Synthesis of Compound 1-4

Compound 1-3 (6.72 g, 36.4 mmol) was dissolved in 50 mL methanol, triethylamine (7.6 mL, 54.6 mmol) and di-tert-butyl dicarbonate (11.9 g, 54.6 mmol) were added successively and stirred at room temperature for 3 hours. The system was concentrated, extracted with ethyl acetate, washed with saturated sodium bicarbonate solution and brine, dried over anhydrous sodium sulfate, and concentrated to give a colorless oily product 1-4 (10.16 g, yield 98%), MS: 286.1 [M+H]+.

Synthesis of Compound 1-5

Under ice-bath, compound 1-4 (285 mg, 1 mmol) was dissolved in 5 mL of anhydrous tetrahydrofuran, and 1.0 M solution of lithium aluminum hydride (1.1 mL, 1.1 mmol) was slowly added dropwise. The mixture was warmed to room temperature and stirred for 2 hours. The reaction was quenched with water, and the mixture was washed with 15% sodium hydroxide aqueous solution and filtered. Then the organic phase was washed with brine, dried over anhydrous sodium sulfate, and concentrated to give a colorless oily liquid. The colorless oily liquid was dissolved in dichloromethane (5 mL), and Dess-Martin periodinane (466.4 mg, 1.1 mmol) was added and stirred for 2 hours. Then saturated sodium bicarbonate solution was added, and the mixture was extracted with dichloromethane, successively washed with saturated sodium bicarbonate solution and saturated brine, dried over anhydrous sodium sulfate, concentrated and separated by column chromatography to give colorless oily liquid 1-5 (156 mg, yield 61%), MS: 256.1 [M+H]+.

Synthesis of Compound 1-6

Compound 1-5 (512 mg, 2 mmol) was dissolved in 5 mL of dichloromethane, and compound if (468 mg, 2 mmol) and triacetoxy sodium borohydride (466 mg, 2.2 mmol) were successively added and stirred for 12 hours at room temperature. Water was added, and then the mixture was extracted by dichloromethane, washed with saturated brine, dried over anhydrous sodium sulfate, concentrated, and separated by column chromatography to give a pale yellow oily liquid 1-6 (664 mg, yield 70%), MS: 474.3 [M+H]+.

Synthesis of Compound 1

Compound 1-6 (47.4 mg, 0.1 mmol) was dissolved in 1 mL of methanol, and 1 mL solution of HCl in dioxane (4M) was added and stirred for 2 hours at room temperature. The reaction mixture was concentrated, dissolved in 1 mL N,N-dimethylformamide, followed by adding triethylamine (28 μL, 0.2 mmol), 4,4-difluoro-cyclohexanecarboxylic acid (18 mg, 0.11 mmol), benzotriazole-1-yloxy-tris(dimethylamino) phosphonium hexafluorophosphate salt (BOP) (46.4 mg, 0.11 mmol) and stirred for 12 hours at room temperature. Water was added, then the mixture was extracted with ethyl acetate, washed with saturated brine, dried over anhydrous sodium sulfate, concentrated and separated by column chromatography to give white solids 1 (25.6 mg, yield 52%), MS: 494.31 [M+H]+. $^1$H-NMR (400 Hz, CDCl$_3$): δ7.28 (t, 1H), 7.11 (d, 1H), 6.97 (d, 1H), 5.17 (m,1H), 3.90 (m, 1H), 3.00 (m, 1H), 2.50 (s, 3H), 2.43 (m,2H), 2.26-1.99 (m,10H), 1.99-1.61 (m, 9H), 1.34 (d, 6H).

EXAMPLE 2

Synthesis of Compound 2

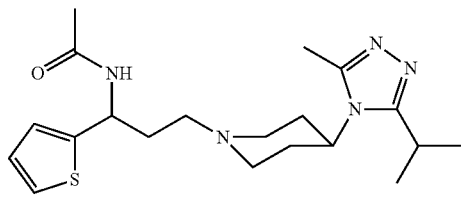 [SMILES: CC(=O)NC(CCN1CCC(n2c(C)nnc2C(C)C)CC1)c1cccs1]

N-[3-[4-(3-isopropyl-5-methyl-4H-1,2,4-triazol-4-yl)-piperidin-1-yl]-1-(thiophen-2-yl)propyl]acetamide According to the synthesis method of Example 1, acetic acid was used to replace 4,4-difluoro-cyclohexanecarboxylic acid in Example 1 to obtain compound 2. MS: 390.2 [M+H]+. $^1$H-NMR (400 Hz, CDCl$_3$): δ7.26 (t, 1H), 7.15 (d, 1H), 6.99 (d, 1H), 5.21 (m,1H), 3.95 (m, 1H), 3.10 (m, 1H), 2.51 (s, 3H), 2.43 (m,2H), 2.20-1.69 (m,14H), 1.35 (d, 6H).

EXAMPLE 3

Synthesis of Compound 3

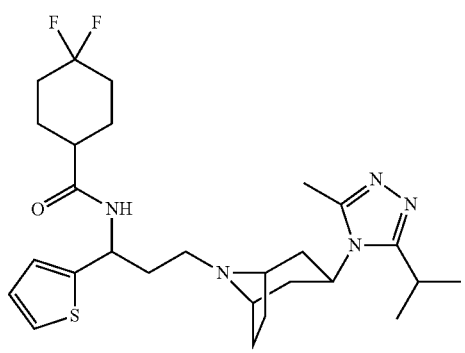

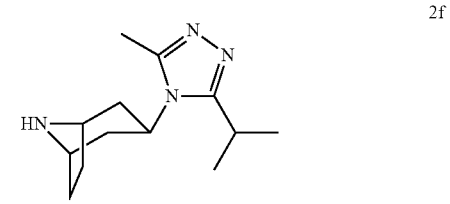

2f

21

4,4-difluoro-N-[3-[exo-3-(3-isopropyl-5-methyl-4H-1,2,4-triazol-4-yl)-8-azabicyclo[3.2.1]octane-8-yl]-1-(thiophen-2-yl)propyl]cyclohexane-1-carboxamide Synthesis of Compound 2f According to the synthesis method of compound 1f in Example 1, N-benzyltropinone was used to replace 1a in Example 1 to obtain compound 2f.

Synthesis of Compound 3

According to the synthesis method of Example 1, compound 2f was used to replace 1f in Example 1 to obtain compound 3, MS: 520.3 [M+H]+. $^1$H-NMR (400 Hz, CDCl$_3$): δ7.27 (t, 1H), 7.14 (d, 1H), 6.95 (d, 1H), 5.14 (m,1H), 3.91 (m, 1H), 3.03 (m, 1H), 2.52 (s, 3H), 2.40 (m,2H), 2.27-1.93 (m,12H), 1.93-1.62 (m, 9H), 1.32 (d, 6H).

EXAMPLE 4

Synthesis of Compound 4

N-[3-[exo-3-(3-isopropyl-5-methyl-4H-1,2,4-triazol-4-yl)-8-azabicyclo[3.2.1]octane-8-yl]-1-(thiophen-2-yl)propyl]acetamide

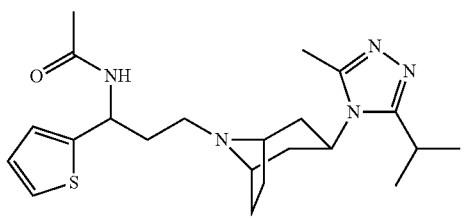 [SMILES: CC(=O)NC(CCN1C2CCC1CC(n1c(C)nnc1C(C)C)C2)c1cccs1]

According to the synthesis method of Example 1. Acetic acid was used to replace 4,4-difluoro-cyclohexanecarboxylic acid in Example 1 and compound 2f was used to replace 1f in Example 1 to obtain compound 4, MS: 416.2 [M+H]+. $^1$H-NMR (400 Hz, CDCl$_3$): δ7.23 (t, 1H), 7.15 (d, 1H), 6.99 (d, 1H), 5.21 (m,1H), 3.95 (m, 1H), 3.03 (m, 1H), 2.54 (s, 3H), 2.40 (m,2H), 2.25-1.67 (m, 14H), 1.32 (d, 6H).

EXAMPLE 5

Synthesis of Compound 5

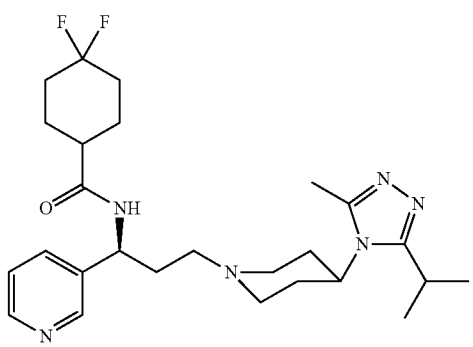 [SMILES: Cc1nnc(C(C)C)n1C1CCN(CC[C@H](NC(=O)C2CCC(F)(F)CC2)c2cccnc2)CC1]

22

4,4-difluoro-N-[(1S)-3-[4-(3-isopropyl-5-methyl-4H-1,2,4-triazol-4-yl)-piperidin-1-yl]-1-(pyridin-3-yl)propyl]cyclohexane-1-carboxamide Synthesis Route

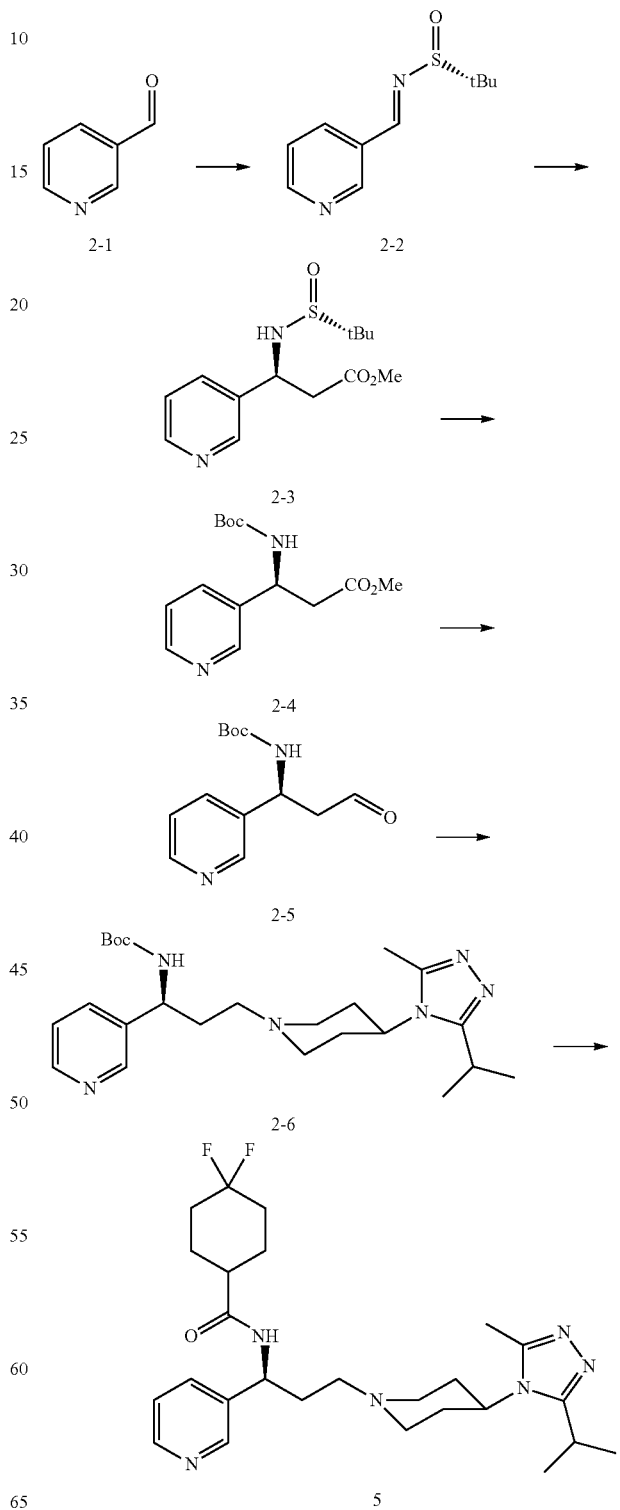

Synthesis of Compound 2-2

Compound 2-1 (1.07 g, 10 mmol) was dissolved in tetrahydrofuran (20 mL) and stirred at room temperature, to which was sequentially added (R)-tert-butyl sulfinamide (1.33 g, 11 mmol) and tetraethyl titanate (4.56 g, 20 mmol). Under nitrogen, the reaction was carried out for 3 hours. Then water was added, the mixture was filtered and the filtrate was extracted with ethyl acetate, washed with saturated brine, dried over anhydrous sodium sulfate, concentrated and separated by column chromatography to give a colorless liquid 2-2 (1.94 g, yield 92%), MS: 211.2 [M+H]+.

Synthesis of Compound 2-3

At 0° C., N,N-diisopropylamine (1.13 mL, 8 mmol) was dissolved in 10 mL of tetrahydrofuran and 2.4 M n-butyl lithium solution (3.3 mL, 8 mmol) was slowly added dropwise under nitrogen. After reacting for 30 minutes, the mixture was cooled to −78° C. Methyl acetate (0.58 g, 8 mmol) was added and reacted for 45 minutes. 2M solution of titanium triisopropoxide chloride (8 mL, 16 mmol) was added and reacted for 30 minutes. Then compound 2-2 (0.84 g, 4 mmol) was added and reacted for 3 hours. The reaction was quenched with saturated ammonium chloride solution, the mixture was filtered. The filtrate was extracted with ethyl acetate, washed with saturated brine, dried over anhydrous sodium sulfate, and concentrated and separated by column chromatography to give colourless liquid 2-3 (0.87 g, yield 74%), MS: 286.2 [M+H]+.

Synthesis of Compound 2-4

Compound 2-3 (2.85 g, 10 mmol) was dissolved in 20 mL of methanol, and 10 mL of 4 M HCl in dioxane was added and stirred for 2 hours at room temperature. The reaction mixture was concentrated, and then triethylamine (2.8 mL, 20 mmol) and di-tert-butyl dicarbonate (3.26 g, 15 mmol) were successively added and stirred at room temperature for 3 hours. The system was concentrated, extracted with ethyl acetate, washed with saturated sodium bicarbonate solution and saturated brine, dried over anhydrous sodium sulfate, concentrated and separated by column chromatography to give the product 2-4 (2.43 g, yield 87%) as a colorless oil, MS: 281.1 [M+H]+.

Synthesis of Compound 2-5

Under ice-bath, compound 2-4 (280 mg, 1 mmol) was dissolved in 5 mL of dry tetrahydrofuran, 1.0 M solution of lithium aluminum hydride (1.1 mL, 1.1 mmol) was slowly added dropwise and then the mixture was warmed to room temperature and stirred for 2 hours. The reaction was quenched with water, washed with 15% aqueous solution of sodium hydroxide and filtered. The organic phase was washed with saturated brine, dried over anhydrous sodium sulfate and concentrated to give a colorless oily liquid. The colorless oily liquid was dissolved in dichloromethane (5 mL), and then Dess-Martin periodinane (466.4 mg, 1.1 mmol) was added and stirred for 2 hours. Then saturated sodium bicarbonate solution was added, and the mixture was extracted with dichloromethane, successively washed with saturated sodium bicarbonate solution and saturated brine, dried over anhydrous sodium sulfate, concentrated and separated by column chromatography to give a colorless oily liquid 2-5 (158 mg, yield 63%), MS: 251.1 [M+H]+.

Synthesis of Compound 2-6

Compound 2-5 (502 mg, 2 mmol) was dissolved in 5 mL of dichloromethane, and compound if (468 mg, 2 mmol) and sodium triacetoxyborohydride (466 mg, 2.2 mmol) were successively added and stirred for 12 hours at room temperature. Water was added, and then the mixture was extracted with dichloromethane, washed with saturated brine, dried over anhydrous sodium sulfate, concentrated and separated by column chromatography to give a pale yellow oily liquid 2-6 (686 mg, yield 71%), MS: 469.31 [M+H]+.

Synthesis of Compound 5

Compound 2-6 (46.8 mg, 0.1 mmol) was dissolved in 1 mL of methanol, and then 1 mL of 4 M HCl in dioxane was added and stirred for 2 hours at room temperature. The mixture was concentrated and then dissolved in 1 mL N,N-dimethylformamide, followed by successively adding triethylamine (28 μL, 0.2 mmol), 4,4-difluoro-cyclohexanecarboxylic acid (18 mg, 0.11 mmol), benzotriazol-1-yloxy-tris (dimethylamino) phosphonium hexafluorophosphate salt (BOP) (46.4 mg, 0.11 mmol). The mixture was stirred for 12 hours at room temperature, and then water was added. The mixture was extracted with ethyl acetate, washed with saturated brine, dried over anhydrous sodium sulfate, concentrated and separated by column chromatography (DCM:CH$_3$OH=8:1) to give white solids 5 (27.7 mg, yield 57%), MS: 89.31 [M+H]+. $^1$H-NMR (400 Hz, CDCl$_3$): δ8.58 (s, 1H), 8.38 (d, 1H), 7.81 (d, 1H), 7.37 (t, 1H), 5.17 (m, 1H), 3.90 (m, 1H), 3.00 (m, 1H), 2.50 (s, 3H), 2.43 (m,2H), 2.26-1.99 (m,10H), 1.99-1.61 (m, 9H), 1.34 (d, 6H).

EXAMPLE 6

Synthesis of Compound 6

4,4-difluoro-N-[(1S)-3-[exo-3-(3-isopropyl-5-methyl-4H-1,2,4-triazol-4-yl)-8-azabicyclo[3.2.1]octane-8-yl]-1-(pyridin-3-yl)propyl]cyclohexane-1-carboxamide

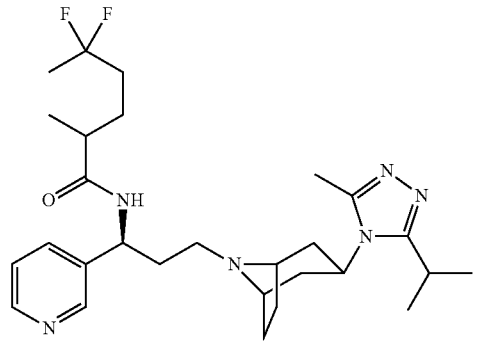 [SMILES: Cc1nnc(C(C)C)n1C1CC2CCC(C1)N2CC[C@H](NC(=O)C(C)CCC(C)(F)F)c1cccnc1]

According to the synthesis method of Example 5, compound 2f was used to replace if in Example 5 to obtain compound 6, MS: 514.9 [M+H]+. $^1$H-NMR (400 Hz, CDCl$_3$): δ8.57 (s, 1H), 8.39 (d, 1H), 7.80 (d, 1H), 7.37 (t, 1H), 5.17 (m,1H), 3.90 (m, 1H), 3.00 (m, 1H), 2.50 (s, 3H), 2.43 (m,2H), 2.27-1.96 (m,12H), 1.96-1.60 (m, 9H), 1.34 (d, 6H).

EXAMPLE 7

Synthesis of Compound 7

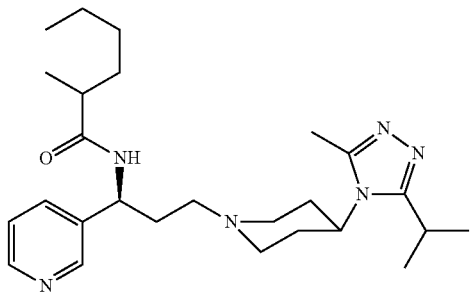 [SMILES: CCCCC(C)C(=O)N[C@@H](CCN1CCC(n2c(C)nnc2C(C)C)CC1)c1cccnc1]

N-[(1S)-3-[4-(3-isopropyl-5-methyl-4H-1,2,4-tri-azol-4-yl)-piperidin-1-yl]-1-(pyridin-3-yl)propyl]cyclohexane-1-carboxamide According to the synthesis method of Example 5, cyclohexanecarboxylic acid was used to replace 4,4-difluoro-cyclohexanecarboxylic acid in Example 5 to obtain compound 7, MS: 453.0 [M+H]+. $^1$H-NMR (400 Hz, CDCl$_3$): δ8.59 (s, 1H), 8.37 (d, 1H), 7.80 (d, 1H), 7.35 (t, 1H), 5.17 (m,1H), 3.90 (m, 1H), 3.00 (m, 1H), 2.50 (s, 3H), 2.43 (m,2H), 2.26-1.99 (m,11H), 1.99-1.61 (m, 10H), 1.34 (d, 6H).

EXAMPLE 8

Synthesis of Compound 8

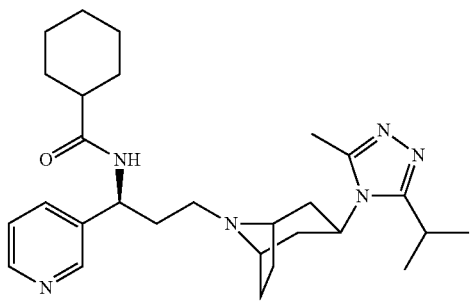 [SMILES: Cc1nnc(C(C)C)n1C1CC2CCC(C1)N2CC[C@H](NC(=O)C1CCCCC1)c1cccnc1]

N-[(1S)-3-[exo-3-(3-isopropyl-5-methyl-4H-1,2,4-triazol-4-yl)-8-azabicyclo[3.2.1]octane-8-yl]-1-(pyridin-3-yl)propyl]cyclohexane-1-carboxamide According to the synthesis method of Example 5, Compound 2f was used to replace if in Example 5 and cyclohexanecarboxylic acid was used to replace 4,4-difluoro-cyclohexanecarboxylic acid in example 5 to obtain compound 8, MS:

479.0 [M+H]+. $^1$H-NMR (400 Hz, CDCl$_3$): δ8.59 (s, 1H), 8.48 (d, 1H), 7.86 (d, 1H), 7.38 (t, 1H), 5.17 (m,1H), 3.90 (m, 1H), 3.00 (m, 1H), 2.50 (s, 3H), 2.43 (m,2H), 2.27-1.96 (m,12H), 1.96-1.60 (m, 11H), 1.34 (d, 6H).

EXAMPLE 9

Synthesis of Compound 9

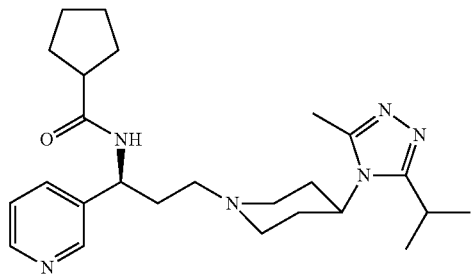 [SMILES: Cc1nnc(C(C)C)n1C1CCN(CC[C@H](NC(=O)C2CCCC2)c2cccnc2)CC1]

N-[(1S)-3-[4-(3-isopropyl-5-methyl-4H-1,2,4-tri-azol-4-yl)-piperidin-1-yl]-1-(pyridin-3-yl)propyl]cyclopentane-1-carboxamide According to the synthesis method of Example 5, cyclopentanecarboxylic acid was used to replace 4,4-difluoro-cyclohexanecarboxylic acid in Example 5 to obtain compound 9, MS: 439.0 [M+H]+. $^1$H-NMR (400 Hz, CDCl$_3$): δ8.59 (s, 1H), 8.37 (d, 1H), 7.80 (d, 1H), 7.35 (t, 1H), 5.18 (m,1H), 3.91 (m, 1H), 3.02 (m, 1H), 2.53 (s, 3H), 2.40 (m,2H), 2.25-1.97 (m,10H), 1.97-1.60 (m, 9H), 1.33 (d, 6H).

EXAMPLE 10

Synthesis of Compound 10

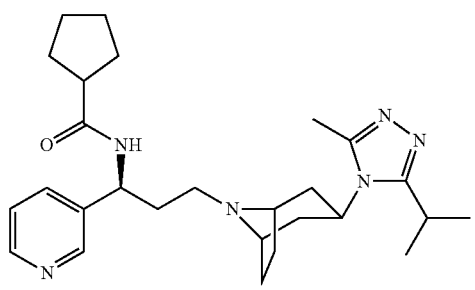 [SMILES: Cc1nnc(C(C)C)n1C1CC2CCC(C1)N2CC[C@H](NC(=O)C1CCCC1)c1cccnc1]

N-[(1S)-3-[exo-3-(3-isopropyl-5-methyl-4H-1,2,4-triazol-4-yl)-8-azabicyclo[3.2.1]octane-8-yl]-1-(pyridin-3-yl)propyl]cyclopentane-1-carboxamide According to the synthesis method of Example 5, Compound 2f was used to replace if in Example 5 and cyclopentanecarboxylic acid was used to replace 4,4-difluoro-cyclohexanecarboxylic acid in Example 5 to obtain compound 10, MS: 464.9 [M+H]+. $^1$H-NMR (400 Hz, CDCl$_3$): δ8.59 (s, 1H), 8.48 (d, 1H), 7.86 (d, 1H), 7.38 (t, 1H), 5.16 (m,1H), 3.93 (m, 1H), 3.07 (m, 1H), 2.45 (s, 3H), 2.42 (m,2H), 2.27-1.96 (m,12H), 1.96-1.61 (m, 9H), 1.35 (d, 6H).

EXAMPLE 11

Synthesis of Compound 11

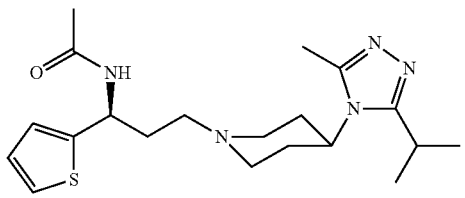

N-[(1S)-3-[4-(3-isopropyl-5-methyl-4H-1,2,4-triazol-4-yl)-piperidin-1-yl]-1-(thiophen-2-yl)propyl] acetamide According to the synthesis method of Example 5, Compound 1-1 was used to replace compound 2-1 in Example 5 and acetic acid was used to replace 4,4-difluoro-cyclohexanecarboxylic acid in Example 5 to obtain compound 11, MS: 390.2 [M+H]+. $^1$H-NMR (400 Hz, CDCl$_3$): δ7.26 (t, 1H), 7.15 (d, 1H), 6.99 (d, 1H), 5.21 (m,1H), 3.95 (m, 1H), 3.10 (m, 1H), 2.51 (s, 3H), 2.43 (m,2H), 2.20-1.69 (m,14H), 1.35 (d, 6H).

EXAMPLE 12

Synthesis of Compound 12

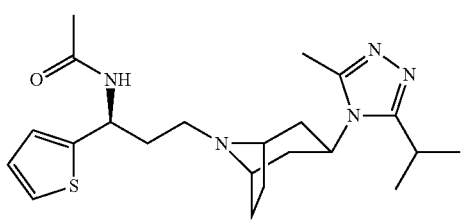 [SMILES: CC(=O)N[C@@H](CCN1C2CCC1CC(n1c(C)nnc1C(C)C)C2)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]acetamide According to the synthesis method of Example 5, Compound 1-1 was used to replace compound 2-1 in Example 5, compound 2f was used to replace if in Example 5 and acetic acid was used to replace 4,4-difluoro-cyclohexanecarboxylic acid in Example 5 to obtain compound 12, MS: 416.2 [M+H]+. $^1$H-NMR (400 Hz, CDCl$_3$): δ7.23 (t, 1H), 7.15 (d, 1H), 6.99 (d, 1H), 5.21 (m,1H), 3.95 (m, 1H), 3.03 (m, 1H), 2.54 (s, 3H), 2.40 (m,2H), 2.25-1.67 (m,14H), 1.32 (d, 6H).

EXAMPLE 13

Synthesis of Compound 13

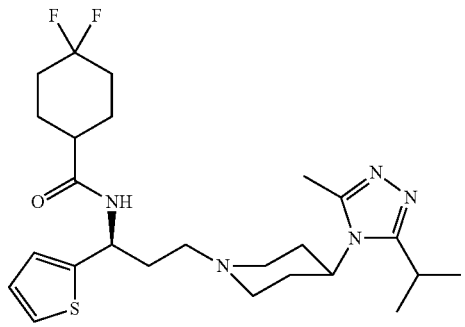 [SMILES: Cc1nnc(C(C)C)n1C1CCN(CC[C@H](NC(=O)C2CCC(F)(F)CC2)c2cccs2)CC1]

4,4-difluoro-N-[(1S)-3-[4-(3-isopropyl-5-methyl-4H-1,2,4-triazol-4-yl)-piperidin-1-yl]-1-(thiophen-2-yl)propyl]cyclohexane-1-carboxamide According to the synthesis method of Example 5, compound 1-1 was used to replace compound 2-1 in Example 5 to obtain compound 13, MS: 493.9 [M+H]+. $^1$H-NMR (400 Hz, CDCl$_3$): δ7.27 (t, 1H), 7.13 (d, 1H), 6.95 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 14

Synthesis of Compound 14

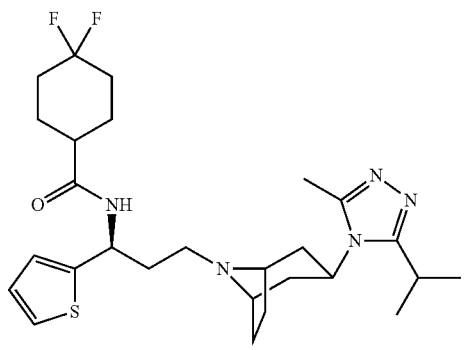 [SMILES: Cc1nnc(C(C)C)n1C1CC2CCC(C1)N2CC[C@H](NC(=O)C1CCC(F)(F)CC1)c1cccs1]

4,4-difluoro-N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]cyclohexane-1-carboxamide According to the synthesis method of Example 5, Compound 1-1 was used to replace compound 2-1 in Example 5 and compound 2f was used to replace if in Example 5 to obtain compound 14, MS: 520.0 [M+H]+. $^1$H-NMR (400 Hz, CDCl$_3$): δ7.27 (t, 1H), 7.14 (d, 1H), 6.95 (d, 1H), 5.14 (m,1H), 3.91 (m, 1H), 3.03 (m, 1H), 2.52 (s, 3H), 2.40 (m,2H), 2.27-1.93 (m,12H), 1.93-1.62 (m, 9H), 1.32 (d, 6H).

EXAMPLE 15

Synthesis of Compound 15

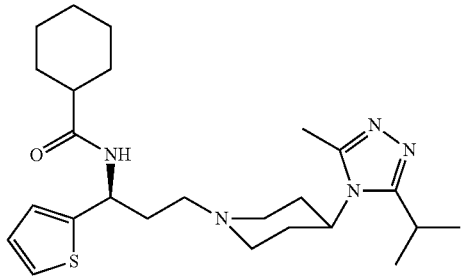 [SMILES: Cc1nnc(C(C)C)n1C1CCN(CC[C@H](NC(=O)C2CCCCC2)c2cccs2)CC1]

N-[(1S)-3-[4-(3-isopropyl-5-methyl-4H-1,2,4-triazol-4-yl)-piperidin-1-yl]-1-(thiophen-2-yl)propyl]cyclohexane-1-carboxamide According to the synthesis method of Example 5, Compound 1-1 was used to replace compound 2-1 in Example 5, and cyclohexanecarboxylic acid was used to replace 4,4-difluoro-cyclohexane carboxylic acid in Example 5 to obtain compound 15, MS: 457.91 [M+H]+. $^1$H-NMR (400 Hz, CDCl$_3$): δ7.28 (t, 1H), 7.13 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,12H), 1.93-1.61 (m, 9H), 1.36 (d, 6H).

EXAMPLE 16

Synthesis of Compound 16

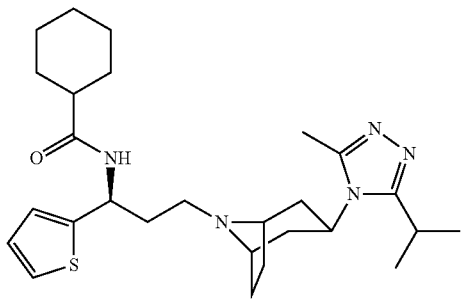 [SMILES: Cc1nnc(C(C)C)n1C1CC2CCC(C1)N2CC[C@H](NC(=O)C1CCCCC1)c1cccs1]

N-[(1S)-3-[exo-3-(3-isopropyl-5-methyl-4H-1,2,4-triazol-4-yl)-8-azabicyclo[3.2.1]octane-8-yl]-1-[(thiophen-2-yl)propyl]cyclohexane-1-carboxamide According to the synthesis method of Example 5, Compound 1-1 was used to replace compound 2-1 in Example 5, compound 2f was used to replace if in Example 5 and cyclohexanecarboxylic acid was used to replace 4,4-difluoro-cyclohexanecarboxylic acid in Example 5 to obtain compound 16, MS: 483.9 [M+H]+. $^1$H-NMR (400 Hz, CDCl$_3$): δ7.28 (t, 1H), 7.13 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 17

Synthesis of Compound 17

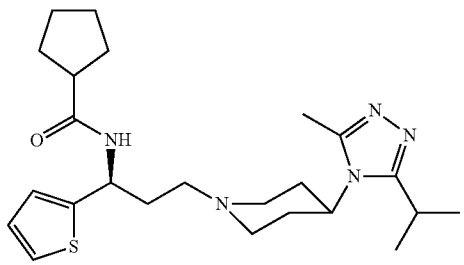 [SMILES: Cc1nnc(C(C)C)n1C1CCN(CC[C@H](NC(=O)C2CCCC2)c2cccs2)CC1]

N-[(1S)-3-[4-(3-isopropyl-5-methyl-4H-1,2,4-triazol-4-yl)-piperidin-1-yl]-1-(thiophen-2-yl)propyl]cyclopentane-1-carboxamide According to the synthesis method of Example 5, Compound 1-1 was used to replace compound 2-1 in Example 5, and cyclopentanecarboxylic acid was used to replace 4,4-difluoro-cyclohexane carboxylic acid in Example 5 to obtain compound 17, MS: 443.9 [M+H]+. $^1$H-NMR (400 Hz, CDCl$_3$): δ7.27 (t, 1H), 7.13 (d, 1H), 6.95 (d, 1H), 5.19 (m,1H), 3.91 (m, 1H), 3.01 (m, 1H), 2.54 (s, 3H), 2.43 (m,2H), 2.29-1.95 (m,10H), 1.95-1.61 (m, 9H), 1.33 (d, 6H).

EXAMPLE 18

Synthesis of Compound 18

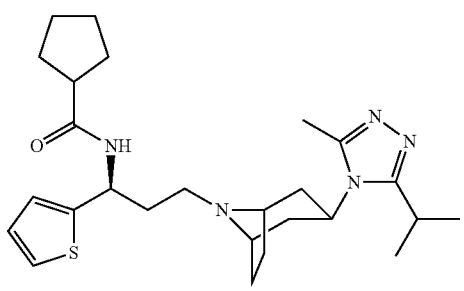 [SMILES: Cc1nnc(C(C)C)n1C1CC2CCC(C1)N2CC[C@H](NC(=O)C1CCCC1)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]cyclopentane-1-carboxamide According to the synthesis method of Example 5. Compound 1-1 was used to replace compound 2-1 in example 5, compound 2f was used to replace if in Example 5 and cyclopentanecarboxylic acid was used to replace 4,4-difluoro-cyclohexanecarboxylic acid in Example 5 to obtain compound 18, MS: 469.9 [M+H]+. $^1$H-NMR (400 Hz, CDCl$_3$): δ7.25 (t, 1H), 7.13 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 19

Synthesis of Compound 19

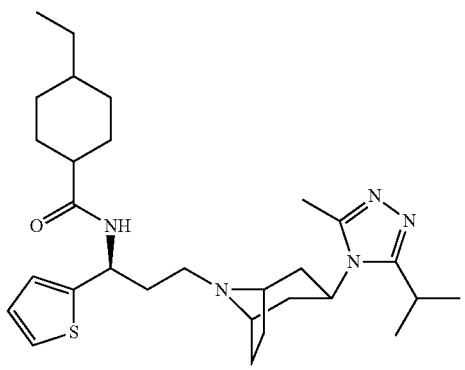 [SMILES: CCC1CCC(C(=O)N[C@@H](CCN2C3CCC2CC(n2c(C)nnc2C(C)C)C3)c2cccs2)CC1]

4-ethyl-N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]cyclopentane-1-carboxamide According to the synthesis method of Example 5, Compound 1-1 was used to replace compound 2-1 in Example 5, compound 2f was used to replace if in Example 5 and 4-methylcyclohexane carboxylic acid was used to replace 4,4-difluoro-cyclohexanecarboxylic acid in Example 5 to obtain compound 19, MS: 511.9 [M+H]+. $^1$H-NMR (400 Hz, CDCl$_3$): δ7.25 (t, 1H), 7.15 (d, 1H), 6.97 (d, 1H), 5.19 (m,1H), 3.91 (m, 1H), 3.02 (m, 1H), 2.54 (s, 3H), 2.43 (m,2H), 2.29-1.93 (m,15H), 1.93-1.61 (m, 12H), 1.33 (d, 6H).

EXAMPLE 20

Synthesis of Compound 20

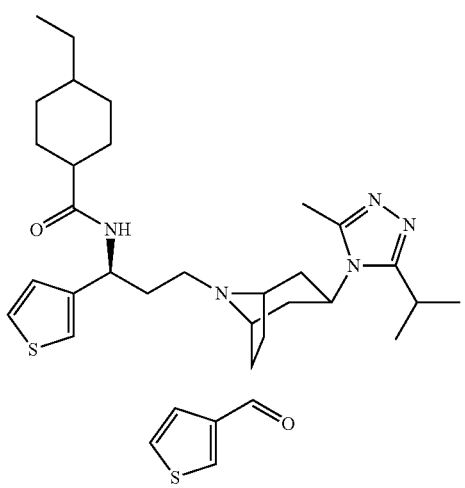

4-ethyl-N-[(1S)-3-[exo-3-(3-isopropyl-5-methyl-4H-1,2,4-triazol-4-yl)-8-azabicyclo[3.2.1]octane-8-yl]-1-(thiophen-3-yl)propyl]cyclopentane-1-carboxamide According to the synthesis method of Example 5, Compound 3-1 was used to replace compound 2-1 in Example 5, compound 2f was used to replace if in Example 5 and 4-methylcyclohexane carboxylic acid was used to replace 4,4-difluoro-cyclohexanecarboxylic acid in Example 5 to obtain compound 20, MS: 511.9 [M+H]+. $^1$H-NMR (400 Hz, CDCl$_3$): δ7.25 (t, 1H), 7.15 (s, 1H), 6.97 (d, 1H), 5.19 (m,1H), 3.91 (m, 1H), 3.02 (m, 1H), 2.54 (s, 3H), 2.43 (m,2H), 2.29-1.93 (m,15H), 1.93-1.61 (m, 12H), 1.33 (d, 6H).

EXAMPLE 21

Synthesis of Compound 21

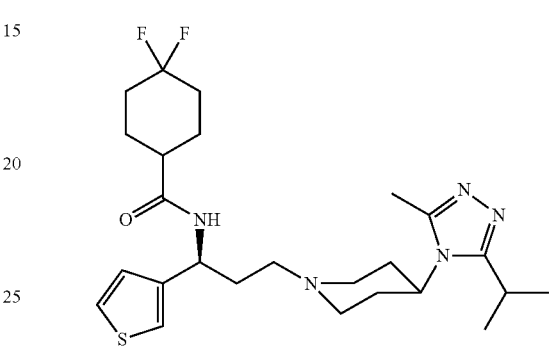

4,4-difluoro-N-[(1S)-3-[4-(3-isopropyl-5-methyl-4H-1,2,4-triazol-4-yl)-piperidin-1-yl]-1-(thiophen-3-yl)propyl]cyclohexane-1-carboxamide According to the synthesis method of Example 5, Compound 3-1 was used to replace compound 2-1 in Example 5 to obtain compound 21, MS: 493.9 [M+H]+. $^1$H-NMR (400 Hz, CDCl$_3$): δ7.26 (t, 1H), 7.15 (s, 1H), 6.97 (d, 1H), 5.17 (m,1H), 3.94 (m, 1H), 3.05 (m, 1H), 2.53 (s, 3H), 2.43 (m,2H), 2.25-1.95 (m,10H), 1.95-1.61 (m, 9H), 1.34 (d, 6H).

EXAMPLE 22

Synthesis of Compound 22

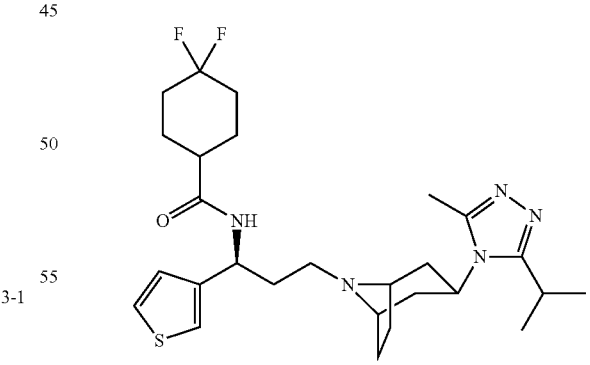

4,4-difluoro-N-[(1S)-3-[exo-3-(3-isopropyl-5-methyl-4H-1,2,4-triazol-4-yl)-8-azabicyclo[3.2.1]octane-8-yl]-1-(thiophen-3-yl)propyl]cyclohexane-1-carboxamide According to the synthesis method of Example 5, Compound 3-1 was used to replace compound 2-1 in Example 5, and compound 2f was used to replace if in Example 5 to obtain compound 22, MS: 520.0 [M+H]+. ¹H-NMR (400 Hz, CDCl₃): δ7.26 (d, 1H), 7.14 (s, 1H), 6.95 (d, 1H), 5.14 (m,1H), 3.91 (m, 1H), 3.03 (m, 1H), 2.52 (s, 3H), 2.40 (m,2H), 2.28-1.93 (m,12H), 1.93-1.65 (m, 9H), 1.35 (d, 6H).

EXAMPLE 23

Synthesis of Compound 23

N-[(1S)-3-[4-(3-isopropyl-5-methyl-4H-1,2,4-triazol-4-yl)-piperidin-1-yl]-1-(thiophen-3-yl)propyl]cyclohexane-1-carboxamide

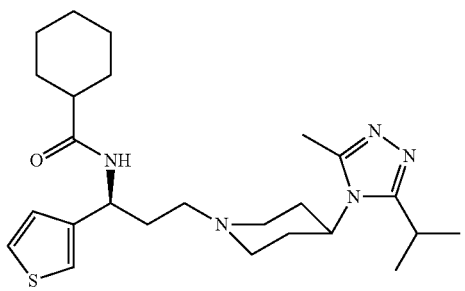 [SMILES: Cc1nnc(C(C)C)n1C1CCN(CC[C@H](NC(=O)C2CCCCC2)c2ccsc2)CC1]

According to the synthesis method of Example 5, Compound 3-1 was used to replace compound 2-1 in Example 5, and cyclohexanecarboxylic acid was used to replace 4,4-difluoro-cyclohexane carboxylic acid in Example 5 to obtain compound 23, MS: 457.9 [M+H]+. ¹H-NMR (400 Hz, CDCl₃): δ7.27 (d, 1H), 7.13 (s, 1H), 6.94 (d, 1H), 5.19 (m,1H), 3.91 (m, 1H), 3.05 (m, 1H), 2.54 (s, 3H), 2.43 (m,2H), 2.25-1.93 (m, 12H), 1.93-1.61 (m, 9H), 1.35 (d, 6H).

EXAMPLE 24

Synthesis of Compound 24

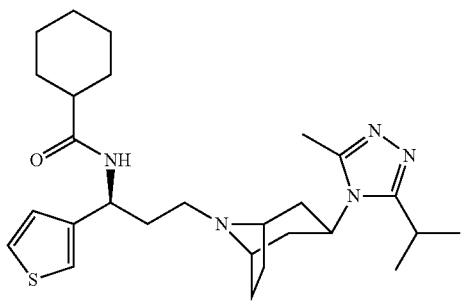 [SMILES: Cc1nnc(C(C)C)n1C1CC2CCC(C1)N2CC[C@H](NC(=O)C1CCCCC1)c1ccsc1]

N-[(1S)-3-[exo-3-(3-isopropyl-5-methyl-4H-1,2,4-triazol-4-yl)-8-azabicyclo[3.2.1]octane-8-yl]-[4(thiophen-3-yl)propyl]cyclohexane-1-carboxamide According to the synthesis method of Example 5, Compound 3-1 was used to replace compound 2-1 in Example 5, compound 2f was used to replace if in Example 5 and cyclohexanecarboxylic acid was used to replace 4,4-difluoro-cyclohexanecarboxylic acid in Example 5 to obtain compound 24, MS: 483.9 [M+H]+. ¹H-NMR (400 Hz, CDCl₃): δ7.23 (d, 1H), 7.12 (s, 1H), 6.94 (d, 1H), 5.19 (m,1H), 3.91 (m, 1H), 3.02 (m, 1H), 2.54 (s, 3H), 2.43 (m,2H), 2.27-1.93 (m,13H), 1.93-1.61 (m, 10H), 1.34 (d, 6H).

EXAMPLE 25

Synthesis of Compound 25

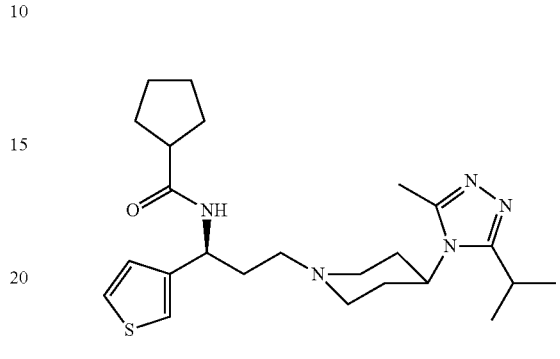

N-[(1S)-3-[4-(3-isopropyl-5-methyl-4H-1,2,4-triazol-4-yl)-piperidin-1-yl]-1-(thiophen-3-yl)propyl]cyclopentane-1-carboxamide According to the synthesis method of Example 5, Compound 3-1 was used to replace compound 2-1 in Example 5, and cyclopentanecarboxylic acid was used to replace 4,4-difluoro-cyclohexane carboxylic acid in Example 5 to obtain compound 25, MS: 443.9 [M+H]+. ¹H-NMR (400 Hz, CDCl₃): δ7.27 (d, 1H), 7.13 (s, 1H), 6.95 (d, 1H), 5.19 (m,1H), 3.91 (m, 1H), 3.03 (m, 1H), 2.54 (s, 3H), 2.43 (m,2H), 2.271.95 (m,10H), 1.95-1.61 (m, 9H), 1.33 (d, 6H).

EXAMPLE 26

Synthesis of Compound 26

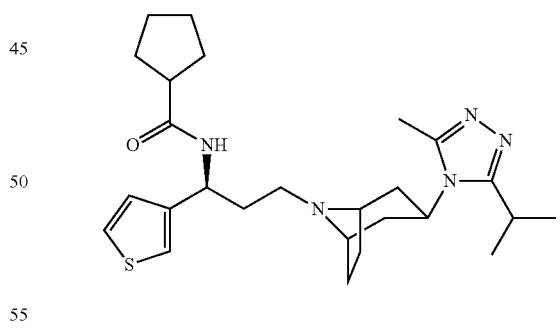

N-[(1S)-3-[exo-3(3-isopropyl-5-methyl-4H-1,2,4-triazol-4-yl)-8-azabicyclo[3.2.1]octane-8-yl]-1-(thiophen-3-yl)propyl]cyclopentane-1-carboxamide According to the synthesis method of Example 5, Compound 3-1 was used to replace compound 2-1 in Example 5, compound 2f was used to replace if in Example 5 and cyclopentanecarboxylic acid was used to replace 4,4-fluoro-cyclohexanecarboxylic acid in Example 5 to obtain compound 26, MS: 469.9 [M+H]+. ¹H-NMR (400 Hz, CDCl₃): δ7.25 (d, 1H), 7.13 (s, 1H), 6.97 (d, 1H), 5.19

(m,1H), 3.91 (m, 1H), 3.02 (m, 1H), 2.54 (s, 3H), 2.43 (m,2H), 2.25-1.93 (m,11H), 1.93-1.61 (m, 10H), 1.35 (d, 6H).

EXAMPLE 27

Synthesis of Compound 27

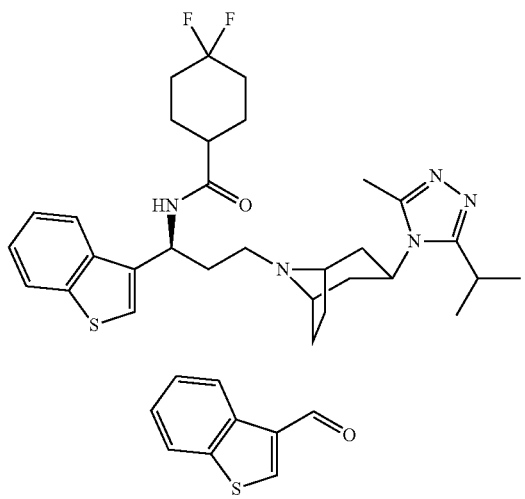

4,4-difluoro-N-[(1S)-3-[exo-3-(3-isopropyl-5-methyl-4H-1,2,4-triazol-4-yl)-8-azabicyclo[3.2.1]octane-8-yl]-1-(benzothiophen-3-yl)propyl]cyclohexane-1-carboxamide According to the synthesis method of Example 5, Compound 4-1 was used to replace compound 2-1 in Example 5, and compound 2f was used to replace if in Example 5 to obtain compound 27, MS: 570.3 [M+H]+. ¹H-NMR (400 Hz, CDCl₃): δ7.36 (d, 1H), δ7.26 (d, 2H), 7.14 (s, 1H), 6.95 (d, 1H), 5.14 (m,1H), 3.91 (m, 1H), 3.03 (m, 1H), 2.52 (s, 3H), 2.40 (m,2H), 2.28-1.93 (m,12H), 1.93-1.65 (m, 9H), 1.35 (d, 6H).

EXAMPLE 28

Synthesis of Compound 28

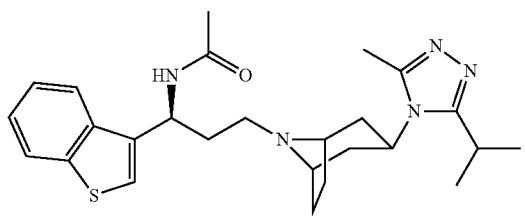 [SMILES: CC(=O)N[C@@H](CCN1C2CCC1CC(n1c(C)nnc1C(C)C)C2)c1csc2ccccc12]

N-[(1S)-3-[exo-3-(3-isopropyl-5-methyl-4H-1,2,4-triazol-4-yl)-8-azabicyclo[3.2.1]octane-8-yl]-1-(benzothiophen-3-yl)propyl]acetamide According to the synthesis method of Example 5, Compound 5-1 was used to replace compound 2-1 in Example 5, compound 2f was used to replace if in Example 5 and acetic acid was used to replace 4,4-difluoro-cyclohexanecarboxylic acid in Example 5 to obtain compound 28, MS: 520.3 [M+H]+. ¹H-NMR (400 Hz, CDCl₃): δ7.35 (d, 1H), δ7.23 (t, 2H), 7.15 (d, 1H), 6.99 (d, 1H), 5.21 (m,1H), 3.95 (m, 1H), 3.03 (m, 1H), 2.54 (s, 3H), 2.40 (m,2H), 2.25-1.67 (m,14H), 1.32 (d, 6H).

EXAMPLE 29

Synthesis of Compound 29

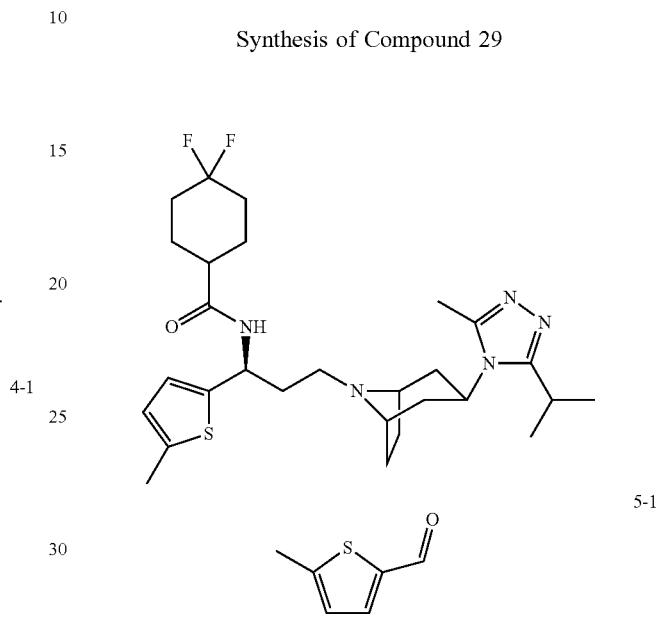

4,4-difluoro-N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]cyclohexane-1-carboxamide According to the synthesis method of Example 5, Compound 5-1 was used to replace compound 2-1 in Example 5, and compound 2f was used to replace if in Example 5 to obtain compound 29, MS: 534.2 [M+H]+δ7.27 (d, 1H), 7.20 (d, 1H), 5.14 (m,1H), 3.91 (m, 1H), 3.03 (m, 1H), 2.52 (s, 3H), 2.40 (m,5H), 2.27-1.93 (m,12H), 1.93-1.62 (m, 9H), 1.32 (d, 6H).

EXAMPLE 30

Synthesis of Compound 30

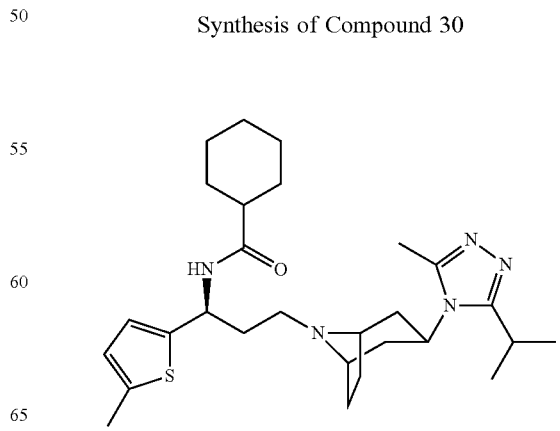

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]cyclohexane-1-carboxamide According to the synthesis method of Example 5, Compound 5-1 was used to replace compound 2-1 in Example 5, compound 2f was used to replace if in Example 5 and cyclohexanecarboxylic acid was used to replace 4,4-difluoro-cyclohexanecarboxylic acid in Example 5 to obtain compound 30, MS: 498.2 [M+H]+. ¹H-NMR (400 Hz, CDCl₃): δ7.28 (d, 1H), 7.21 (d, 1H), 5.19 (m,1H), 3.91 (m, 1H), 3.02 (m, 1H), 2.54 (s, 3H), 2.43 (m,5H), 2.26-1.93 (m,13H), 1.93-1.61 (m, 10H), 1.36 (d, 6H).

EXAMPLE 31

Synthesis of Compound 31

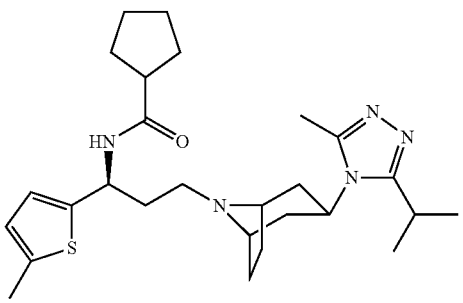 [SMILES: Cc1ccc([C@H](CCN2C3CCC2CC(n2c(C)nnc2C(C)C)C3)NC(=O)C2CCCC2)s1]

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]cyclopentane-1-carboxamide According to the synthesis method of Example 5, Compound 5-1 was used to replace compound 2-1 in Example 5, compound 2f was used to replace if in Example 5 and cyclopentanecarboxylic acid was used to replace 4,4-difluoro-cyclohexanecarboxylic acid in Example 5 to obtain compound 31, MS: 484.2 [M+H]+. ¹H-NMR (400 Hz, CDCl₃): δ7.25 (d, 1H), 7.17 (d, 1H), 5.19 (m,1H), 3.91 (m, 1H), 3.02 (m, 1H), 2.54 (s, 3H), 2.43 (m,5H), 2.27-1.93 (m,11H), 1.93-1.61 (m, 10H), 1.35 (d, 6H).

EXAMPLE 32

Synthesis of Compound 32

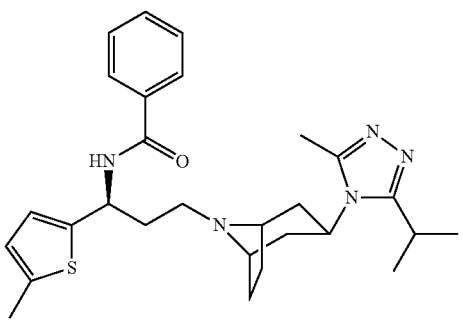 [SMILES: Cc1ccc([C@H](CCN2C3CCC2CC(n2c(C)nnc2C(C)C)C3)NC(=O)c2ccccc2)s1]

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]benzamide According to the synthesis method of Example 5, Compound 5-1 was used to replace compound 2-1 in Example 5, compound 2f was used to replace if in Example 5 and benzoic acid was used to replace 4,4-difluoro-cyclohexanecarboxylic acid in Example 5 to obtain compound 32, MS: 492.2 [M+H]+. ¹H-NMR (400 Hz, CDCl₃): δ7.70 (d, 2H), 7.45 (d, 3H), 7.23 (t, 1H), 7.15 (d, 1H), 5.21 (m,1H), 3.95 (m, 1H), 3.03 (m, 1H), 2.54 (s, 3H), 2.40 (m,5H), 2.25-1.67 (m,11H), 1.32 (d, 6H).

EXAMPLE 33

Synthesis of Compound 33

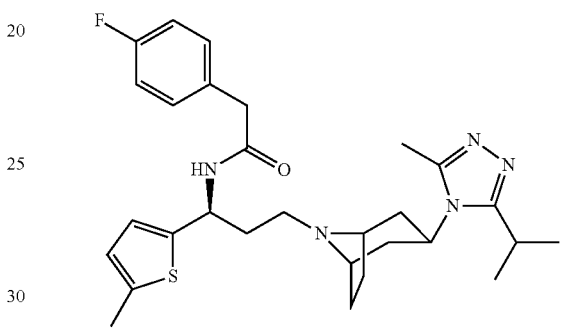

4-fluoro-N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]phenylacetamide According to the synthesis method of Example 5, Compound 5-1 was used to replace compound 2-1 in Example 5, compound 2f was used to replace if in Example 5 and p-fluorophenylacetic acid was used to replace 4,4-difluoro-cyclohexanecarboxylic acid in Example 5 to obtain compound 33, MS: 524.2 [M+H]+. ¹H-NMR (400 Hz, CDCl₃): δ7.50 (d, 2H), 7.35 (d, 2H), 7.23 (t, 1H), 7.15 (d, 1H), 5.21 (m,1H), 3.95 (m, 1H), 3.37 (s, 2H), 3.03 (m, 1H), 2.54 (s, 3H), 2.40 (m,5H), 2.25-1.67 (m,11H), 1.32 (d, 6H).

EXAMPLE 34

Synthesis of Compound 34

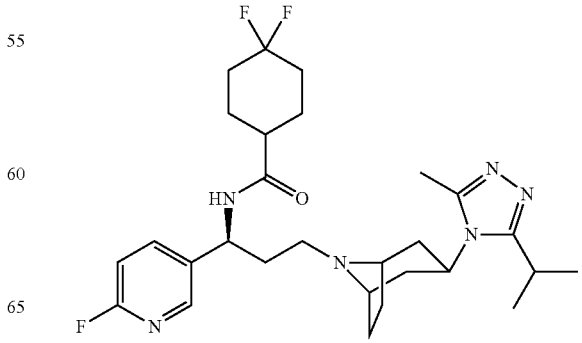

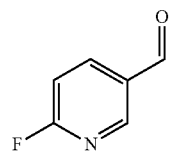

6-1

4,4-difluoro-N-[(1S)-3-[exo-3-(3-isopropyl-5-methyl-4H-1,2,4-triazol-4-yl)-8-azabicyclo[3.2.1]octane-8-yl]-1-(6-fluoropyridin-2-yl)propyl]cyclohexane-1-carboxamide According to the synthesis method of Example 5, Compound 6-1 was used to replace compound 2-1 in Example 5, and compound 2f was used to replace if in Example 5 to obtain compound 34, MS: 533.2 [M+H]+. $^1$H-NMR (400 Hz, CDCl$_3$): δ8.19 (d, 1H), 7.80 (d, 1H), 7.37 (t, 1H), 5.17 (m,1H), 3.90 (m, 1H), 3.00 (m, 1H), 2.50 (s, 3H), 2.43 (m,2H), 2.27-1.96 (m,12H), 1.96-1.60 (m, 9H), 1.34 (d, 6H).

EXAMPLE 35

Synthesis of Compound 35

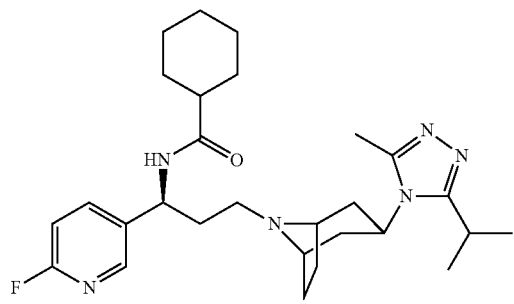 [SMILES: Cc1nnc(C(C)C)n1C1CC2CCC(C1)N2CC[C@H](NC(=O)C1CCCCC1)c1ccc(F)nc1]

N-[(1S)-3-[exo-3-(3-isopropyl-5-methyl-4H-1,2,4-triazol-4-yl)-8-azabicyclo[3.2.1]octane-8-yl]-1-(6-fluoropyridin-2-yl)propyl]cyclohexane-1-carboxamide According to the synthesis method of Example 5, Compound 6-1 was used to replace compound 2-1 in Example 5, compound 2f was used to replace if in Example 5 and cyclohexanecarboxylic acid was used to replace 4,4-difluoro-cyclohexanecarboxylic acid in Example 5 to obtain compound 35, MS: 497.2 [M+H]+. $^1$H-NMR (400 Hz, CDCl$_3$): δ8.08 (d, 1H), 7.66 (d, 1H), 7.31 (t, 1H), 5.17 (m,1H), 3.90 (m, 1H), 3.00 (m, 1H), 2.50 (s, 3H), 2.43 (m,2H), 2.27-1.96 (m,12H), 1.96-1.60 (m, 11H), 1.34 (d, 6H).

EXAMPLE 36

Synthesis of Compound 36

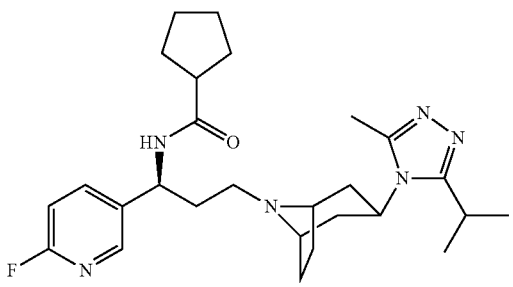 [SMILES: Cc1nnc(C(C)C)n1C1CC2CCC(C1)N2CC[C@H](NC(=O)C1CCCC1)c1ccc(F)nc1]

N-[(1S)-3-[exo-3-(3-isopropyl-5-methyl-4H-1,2,4-triazol-4-yl)-8-azabicyclo[3.2.1]octane-8-yl]-1-(6-fluoropyridin-2-yl)propyl]cyclopentane-1-carboxamide According to the synthesis method of Example 5, Compound 6-1 was used to replace compound 2-1 in Example 5, compound 2f was used to replace if in Example 5 and cyclopentanecarboxylic acid was used to replace 4,4-difluoro-cyclohexanecarboxylic acid in Example 5 to obtain compound 36, MS: 483.2 [M+H]+. $^1$H-NMR (400 Hz, CDCl$_3$): δ8.29 (s, 1H), 7.86 (d, 1H), 7.48 (t, 1H), 5.16 (m,1H), 3.93 (m, 1H), 3.07 (m, 1H), 2.45 (s, 3H), 2.42 (m,2H), 2.27-1.96 (m,12H), 1.96-1.61 (m, 9H), 1.35 (d, 6H).

EXAMPLE 37

Synthesis of Compound 37

4,4-difluoro-N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]cyclohexane-1-carboxamide

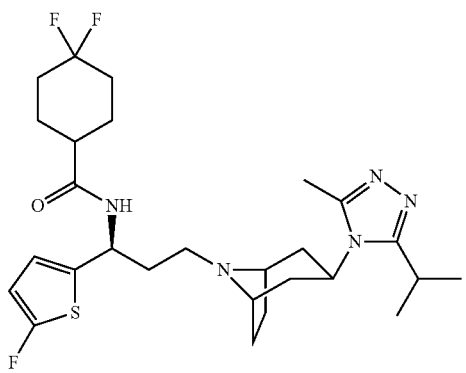

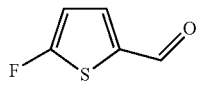

7-1

According to the synthesis method of Example 5, Compound 7-1 was used to replace compound 2-1 in Example 5, and compound 2f was used to replace if in Example 5 to obtain compound 37, MS: 538.2 [M+H]+. ¹H-NMR (400 Hz, CDCl₃): δ7.07 (d, 1H), 6.95 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 38

Synthesis of Compound 38

N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]cyclohexane-1-carboxamide

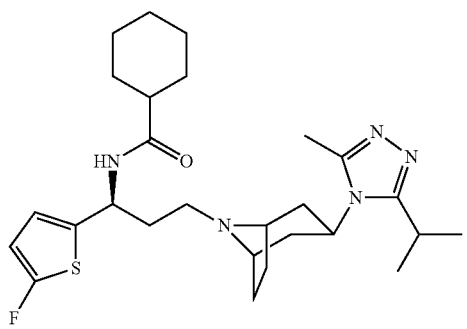 [SMILES: Cc1nnc(C(C)C)n1C1CC2CCC(C1)N2CC[C@H](NC(=O)C1CCCCC1)c1ccc(F)s1]

According to the synthesis method of Example 5, Compound 7-1 was used to replace compound 2-1 in Example 5, compound 2f was used to replace if in Example 5 and cyclohexanecarboxylic acid was used to replace 4,4-difluoro-cyclohexanecarboxylic acid in Example 5 to obtain compound 38, MS: 502.2 [M+H]+. ¹H-NMR (400 Hz, CDCl₃): δ7.13 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 39

Synthesis of Compound 39

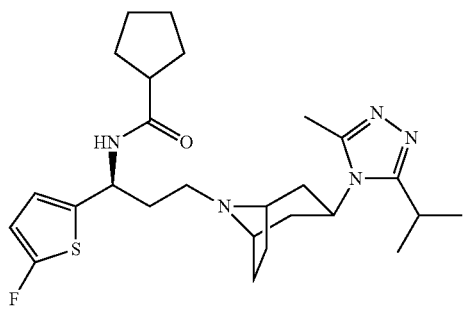 [SMILES: Cc1nnc(C(C)C)n1C1CC2CCC(C1)N2CC[C@H](NC(=O)C1CCCC1)c1ccc(F)s1]

N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]cyclopentane-1-carboxamide According to the synthesis method of Example 5, Compound 7-1 was used to replace compound 2-1 in Example 5, compound 2f was used to replace if in Example 5 and cyclopentanecarboxylic acid was used to replace 4,4-difluoro-cyclohexanecarboxylic acid in Example 5 to obtain compound 39, MS: 488.2 [M+H]+. ¹H-NMR (400 Hz, CDCl₃): δ7.10 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 40

Synthesis of Compound 40

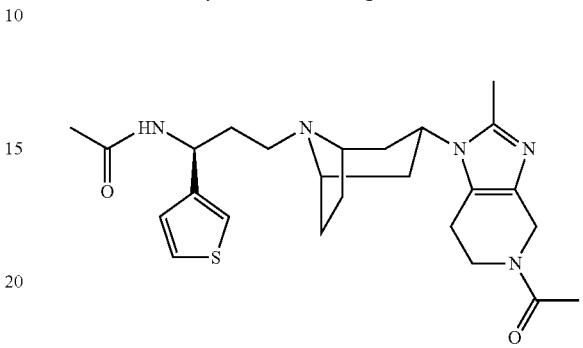

N-{(1S)-1-(thiophen-3-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide Synthesis Route

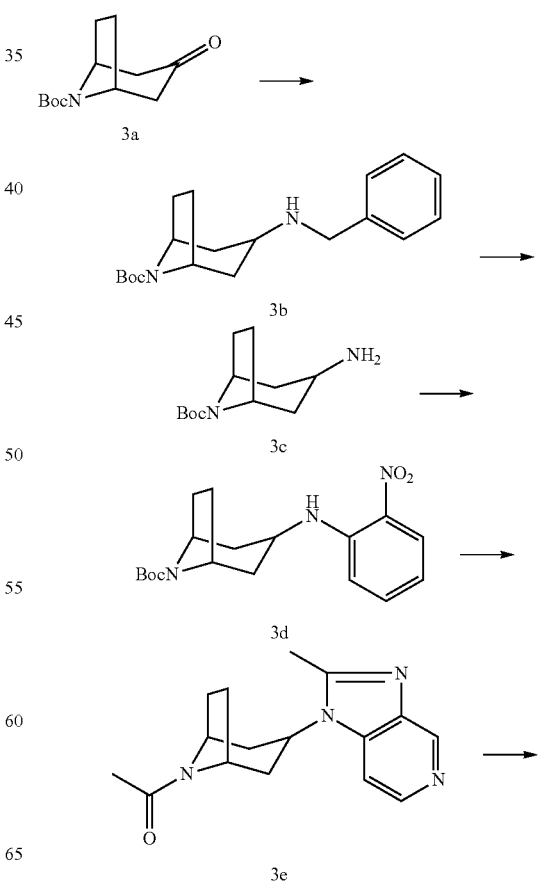

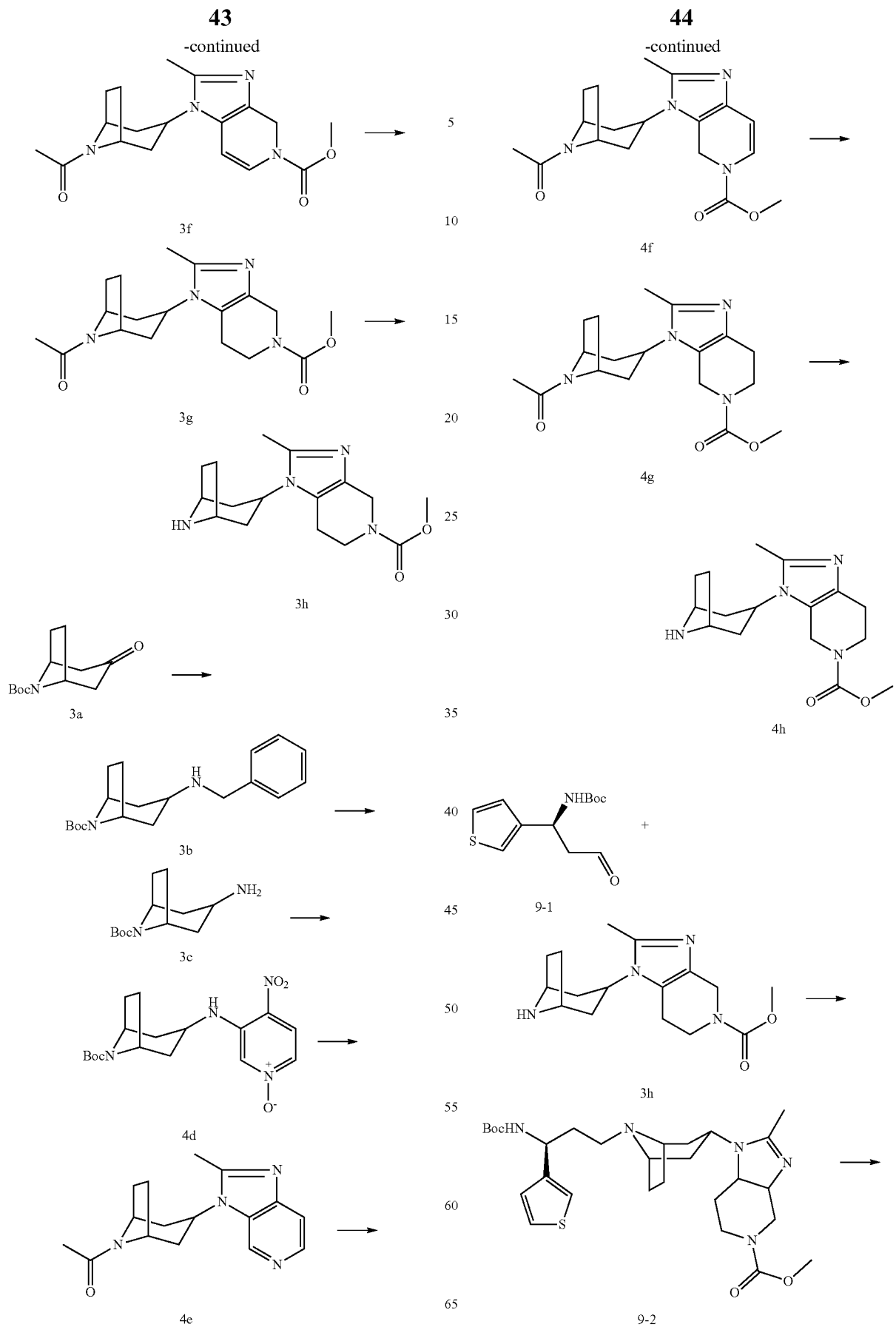

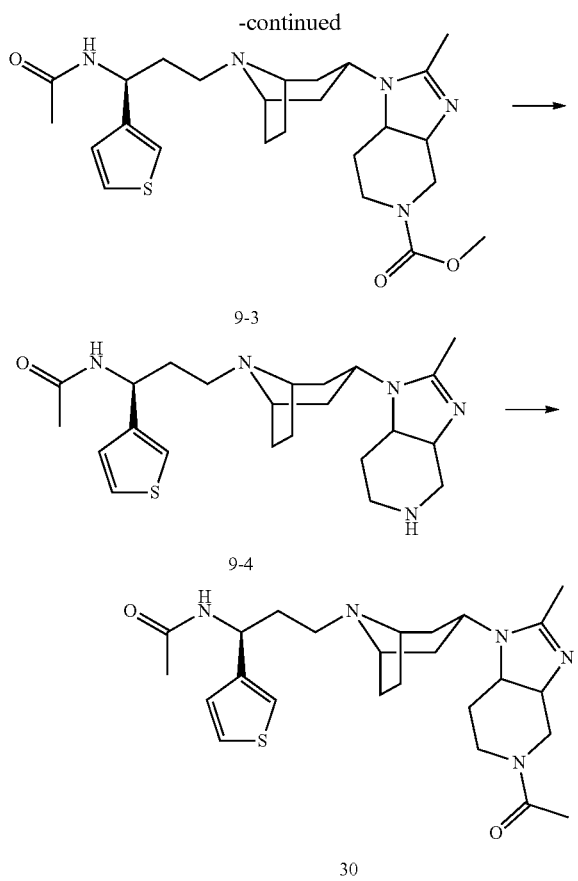

9-3

9-4

30

Synthesis of Compound 3b

Compound 3a (10.0 g, 44.4 mmol), benzylamine (4.85 ml, 49.7 mmol) and sodium triacetyl borohydride (14.11 g, 66.6 mmol) were dissolved in a mixed solvent of acetic acid and dichloromethane (1:9 v/v, 290 ml) and stirred for 16 hours at room temperature. After the solvent was removed by rotary evaporation, the residue was dissolved in ethyl acetate, washed with saturated sodium carbonate solution, dried over anhydrous magnesium sulfate, evaporated to dryness in vacuo and separated by column chromatography to give compound 3b (7.0 g, 50%), MS: 317.2 [M+H]+.

Synthesis of Compound 3c

Compound 3b (7.0 g, 22.2 mmol), ammonium formate (7.0 g, 111 mmol), and 20% palladium hydroxide/carbon (0.7 g of) was dispersed in ethanol (200 ml) and reacted for 2 hours at 50° C. After cooled, the reaction solution was filtered by suction. Then the filtrate was subjected to rotary evaporation and column chromatography separation to give compound 3c (4.7 g, 94%).

Synthesis of Compound 3d

Compound 3c (3.0 g, 13.2 mmol), 4-ethoxy-3-nitropyridine (2.7 g, 13.2 mmol) and DIPEA (1.89 g, 14.6 mmol) were dissolved in N-methylpyrrolidinone (5 ml). The reaction mixture was heated to 120° C. for 18 hours. The reaction solution was cooled, extracted with ethyl acetate, washed with water, dried over magnesium sulfate, and concentrated. Then ether was added to precipitate solids, and compound 3d (1.5 g, 33%) was obtained by suction filtration. MS: 347.2 [M+H]+.

Synthesis of Compound 3e

Compound 3d (4.4 g, 12.6 mmol) and iron powder (2.11 g, 37.8 mmol) were dissolved in acetic acid (50 ml) and heated to 60° C. for 2 hours. Then acetic anhydride (8 ml) was added and heated to 140° C. for 18 hours. After cooled, the reaction solution was filtered by suction. Then the filtrate was subjected to rotary evaporation and the residue was dispersed in dichloromethane (200 ml) and water (200 ml). The solution was adjusted with 2N sodium hydroxide to pH 9 and then filtered by suction. Then the filtrate was extracted with dichloromethane, dried over magnesium sulfate and evaporated to dryness in vacuo to give compound 3e (3.27 g, 91%). MS: 285.1 [M+H]+.

Synthesis of Compound 3f

Compound 3e (10 g, 35.2 mmol) was dissolved in ethanol (95 ml) and water (5 ml), and under nitrogen methyl chloroformate (3.3 ml, 42.2 mmol) was slowly added dropwise at −70° C. The mixture was stirred for 45 minutes and then sodium borohydride (4.0 g, 105.7 mmol) was added in batches. The mixture was slowly warmed to room temperature and crushed ice was added and stirred for another 10 minutes. Ethanol was removed by rotary evaporation and the residue was added to 2M aqueous hydrochloric acid (100 ml) and washed with ethyl acetate. The aqueous layer was adjusted with solid potassium hydroxide to pH 9, extracted with dichloromethane, dried over magnesium sulfate and separated by column chromatography to give compound 3f (9 g, 74%), MS: 345.1 [M+H]+.

Synthesis of Compound 3g

Compound 3f (6.75 g, 19.6 mmol) was dissolved in ethanol (60 ml) and 10% Pd/C (500 mg) was added. The hydrogenation reaction was carried out at 50° C. for 5 h. The reaction mixture was filtered by suction, and the filtrate was evaporated to dryness in vacuo and then separated by column chromatography to give compound 3g (6.2 g, 91%), MS: 346.2 [M+H]+.

Synthesis of Compound 3h

Compound 3g (10.58 g, 30 mmol) was dissolved in 2M sulfuric acid, and heated to 100° C. for 18 hours. The solid potassium hydroxide was added to adjust pH to 11-12. The mixture was extracted with dichloromethane and separated by column chromatography to give compound 3h (7.4 g, 80%), MS: 304.1 [M+H]+.

Synthesis of Compound 4h

According to the synthesis method of compound 3h, 3-fluoro-4-nitropyridine N-oxide was used to replace 4-ethoxy-3-nitropyridine in the synthesis of compound 3h in Example 30.

Synthesis of Compound 9-2

According to the synthesis method of compound 2-6, Compound 3-1 was used to replace compound 2-1 in Example 5, and compound 3h was used to replace if in Example 5 to obtain compound 9-2, MS: 545.3 [M+H]+.

Synthesis of Compound 9-3

Compound 9-2 (109 mg, 0.2 mmol) was dissolved in 1 mL of methanol and 1 mL 4M solution of HCl in dioxane was added and stirred for 2 hours at room temperature. The mixture was concentrated and dissolved in 1 mL N,N-dimethylformamide, followed by adding triethylamine (30.3 mg, 0.3 mmol), acetic acid (49 mg, 0.3 mmol), benzotriazol-1-yloxy-tris(dimethylamino) phosphonium hexafluorophosphate (BOP) (126.5 mg, 0.3 mmol), and stirred for 12 hours at room temperature. Water was added, and then the mixture was extracted with ethyl acetate, washed with saturated brine, dried over anhydrous sodium sulfate, concentrated and separated by column chromatography to give white solids 9-3 (56.7 mg, yield 58%), MS: 487.2 [M+H]+.

Synthesis of Compound 9-4

Compound 9-3 (85 mg, 0.17 mmol) was dissolved in isopropanol (2 ml) and 2M sodium hydroxide solution (3 ml). The reaction mixture was heated at reflux for 48 hours, extracted with ethyl acetate, and separated by column chromatography to give compound 9-4 (55 mg, 73%), MS: 429.1 [M+H]+.

Synthesis of Compound 40

Compound 9-4 (55 mg, 0.13 mmol) was dissolved in 4 ml of tetrahydrofuran and triethylamine (17 mg, 0.17 mmol) was added. Then acetyl chloride (18 mg, 0.17 mmol) was added dropwise and stirred for 2 hours at room temperature. The mixture was extracted with ethyl acetate and separated by column chromatography to give compound 40 (50 mg, 91%), MS: 500.3 [M+H]+. $^1$H-NMR (400 Hz, CDCl$_3$): δ7.25 (m,1H), 7.04 (m, 1H), 6.97 (m,1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,6H), 1.69-1.53 (m, 4H).

EXAMPLE 41

Synthesis of Compound 41

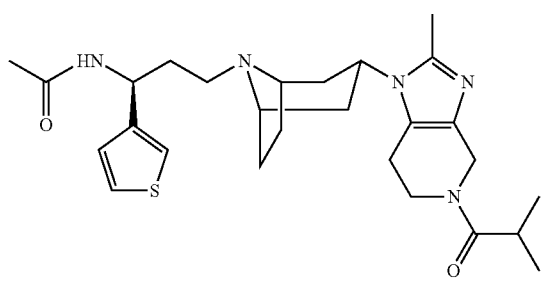 [SMILES: CC(=O)N[C@@H](CCN1C2CCC1CC(n1c(C)nc3c1CCN(C(=O)C(C)C)C3)C2)c1ccsc1]

N-{(1S)-1-(thiophen-3-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, isobutyryl chloride was used to replace acetyl chloride in Example 40 to obtain compound 41, MS: 498.3 [M+H]+. $^1$H-NMR (400 Hz, CDCl$_3$): δ7.14 (m, 1H), 7.07 (m, 1H), 6.97 (m,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,6H), 1.69-1.53 (m,4H), 1.13-1.06 (m,6H).

EXAMPLE 42

Synthesis of Compound 42

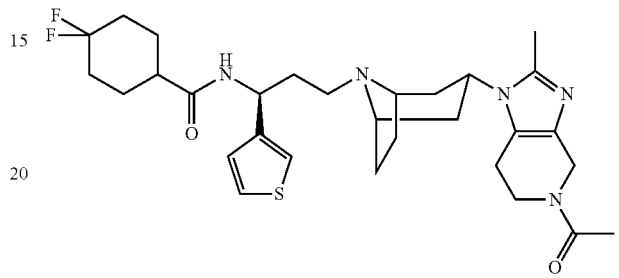

4,4-difluoro-N-{(1S)-1-(thiophen-3-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}cyclohexane-1-carboxamide According to the synthesis method of compound 40, 4,4-difluoro-cyclohexane carboxylic acid was used to replace acetic acid in Example 40 to obtain compound 42, MS: 574.3 [M+H]+. $^1$H-NMR (400 Hz, CDCl$_3$): δ7.14 (m, 1H), 7.07 (m, 1H), 6.97 (m,1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,9H), 1.69-1.53 (m,9H).

EXAMPLE 43

Synthesis of Compound 43

4,4-difluoro-N-{(1S)-1-(thiophen-3-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}cyclohexane-1-carboxamide

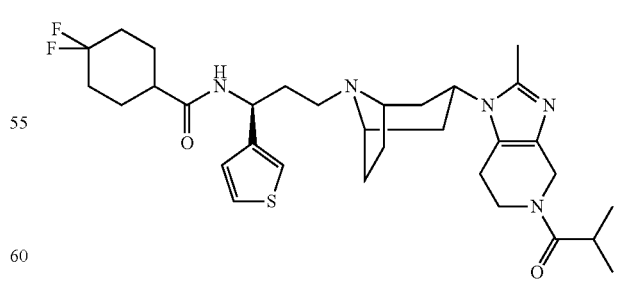

According to the synthesis method of compound 40, isobutyryl chloride was used to replace acetyl chloride in Example 40 and 4,4-difluoro-cyclohexanecarboxylic acid was used to replace acetic acid in Example 40 to obtain compound 43, MS: 602.3 [M+H]+. $^1$H-NMR (400 Hz, CDCl₃): δ7.14 (m, 1H), 7.03 (m, 1H), 6.97 (m,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,8H), 1.69-1.53 (m, 10H), 1.13-1.06 (m,6H).

EXAMPLE 44

Synthesis of Compound 44

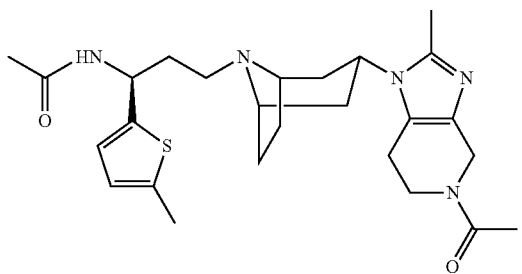 [SMILES: CC(=O)N[C@@H](CCN1C2CCC1CC(n1c(C)nc3c1CCN(C(C)=O)C3)C2)c1ccc(C)s1]

N-{(1S)-1-(5-methylthiophen-2-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 5-1 was used to replace 3-1 in Example 40 to obtain compound 44, MS: 470.3 [M+H]+. ¹H-NMR (400 Hz, CDCl₃): δ7.10 (d,1H), 7.04 (d, 1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,5H), 2.36-1.84 (m,6H), 1.59-1.30 (m, 4H).

EXAMPLE 45

Synthesis of Compound 45

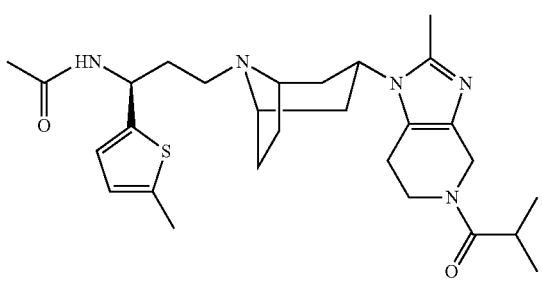 [SMILES: CC(=O)N[C@@H](CCN1C2CCC1CC(n1c(C)nc3c1CCN(C(=O)C(C)C)C3)C2)c1ccc(C)s1]

N-{(1S)-1-(5-methylthiophen-2-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, isobutyryl chloride was used to replace acetyl chloride in Example 40 and compound 5-1 was used to replace 3-1 in Example 40 to obtain compound 45, MS: 498.3 [M+H]+. ¹H-NMR (400 Hz, CDCl₃): δ7.14 (d, 1H), 7.07 (d, 1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,5H), 2.36-1.84 (m,6H), 1.69-1.53 (m,4H), 1.13-1.06 (m,6H).

EXAMPLE 46

Synthesis of Compound 46

N-{(1S)-1-(5-methylthiophen-2-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}cyclohexane-1-carboxamide

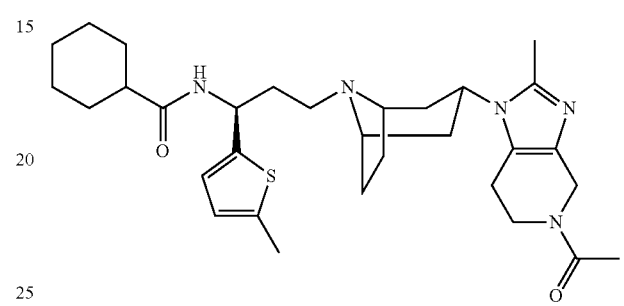

According to the synthesis method of compound 40, Cyclohexanecarboxylic acid was used to replace acetic acid in Example 40 and compound 5-1 was used to replace 3-1 in Example 40 to obtain compound 46, MS: 538.3 [M+H]+. ¹H-NMR (400 Hz, CDCl₃): δ7.14 (d, 1H), 7.03 (d, 1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,5H), 2.36-1.84 (m,9H), 1.69-1.53 (m, 11H), 1.13-1.06 (m,6H).

EXAMPLE 47

Synthesis of Compound 47

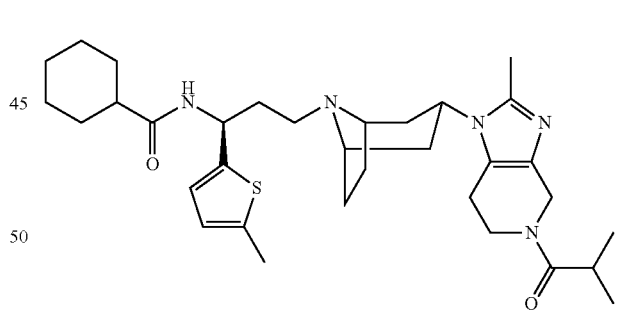

N-{(1S)-1-(5-methylthiophen-2-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}cyclohexane-1-carboxamide According to the synthesis method of compound 40, isobutyryl chloride was used to replace acetyl chloride in Example 40, compound 5-1 was used to replace 3-1 in Example 40 and cyclohexanecarboxylic acid was used to replace acetic acid in Example 40 to obtain compound 47, MS: 566.3 [M+H]+. ¹H-NMR (400 Hz, CDCl₃): δ7.14 (d, 1H), 7.03 (d, 1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,8H), 1.69-1.53 (m, 12H), 1.13-1.06 (m,6H).

EXAMPLE 48

Synthesis of Compound 48

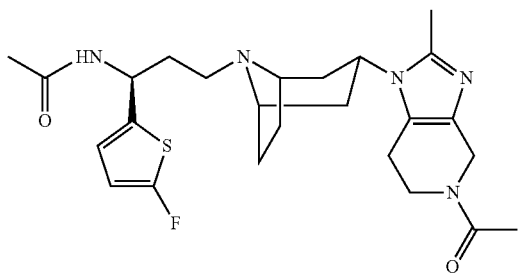 [SMILES: CC(=O)N[C@@H](CCN1C2CCC1CC(n1c(C)nc3c1CCN(C(C)=O)C3)C2)c1ccc(F)s1]

N-{(1S)-1-(5-fluorothiophen-2-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 7-1 was used to replace 3-1 in Example 40 to obtain compound 48, MS: 488.3 [M+H]+. $^1$H-NMR (400 Hz, CDCl$_3$): δ7.10 (d,1H), 6.97 (d,1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,6H), 1.59-1.30 (m, 4H).

EXAMPLE 49

Synthesis of Compound 49

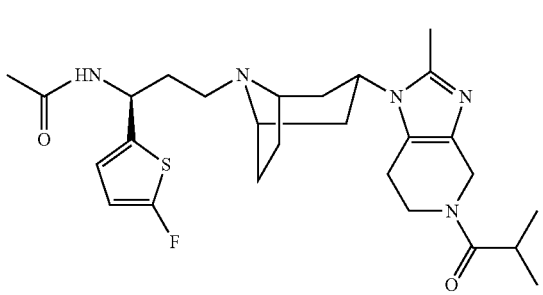 [SMILES: CC(=O)N[C@@H](CCN1C2CCC1CC(n1c(C)nc3c1CCN(C(=O)C(C)C)C3)C2)c1ccc(F)s1]

N-{(1S)-1-(5-fluorothiophen-2-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, isobutyryl chloride was used to replace acetyl chloride in Example 40, and compound 7-1 was used to replace 3-1 in Example 40 to obtain compound 49, MS: 516.3 [M+H]+. $^1$H-NMR (400 Hz, CDCl$_3$): δ7.07 (d, 1H), 6.97 (d,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,6H), 1.69-1.53 (m, 4H), 1.13-1.06 (m,6H).

EXAMPLE 50

Synthesis of Compound 50

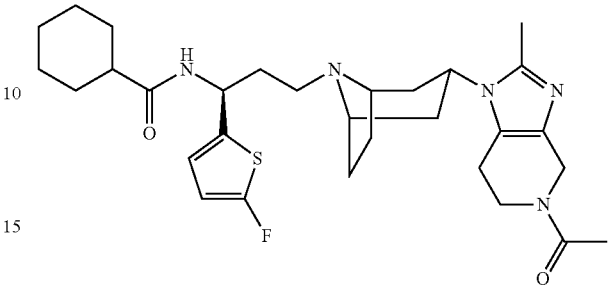

N-{(1S)-1-(5-fluorothiophen-2-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}cyclohexane-1-carboxamide According to the synthesis method of compound 40, Cyclohexanecarboxylic acid was used to replace acetic acid in Example 40, and compound 7-1 was used to replace 3-1 in Example 30 to obtain compound 50, MS: 556.3 [M+H]+. $^1$H-NMR (400 Hz, CDCl$_3$): δ7.03 (m, 1H), 6.97 (m,1H), 5.17 (m, 1H), 4.65 (m,1H), 4.43 (m,2H), 4.19 (m,2H), 3.63 (m,2H), 3.27 (m,1H), 2.83-2.69 (m,2H), 2.51-2.39 (m,2H), 2.36-1.84 (m,9H), 1.69-1.53 (m, 11H), 1.13-1.06 (m,6H).

EXAMPLE 51

Synthesis of Compound 51

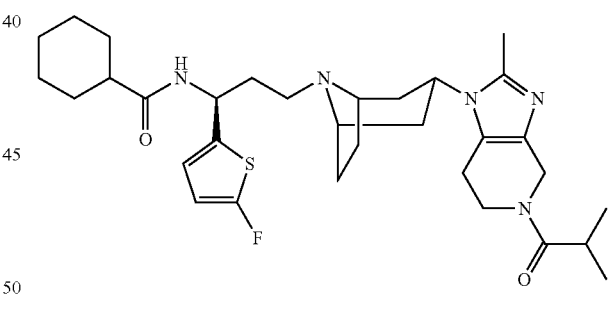

N-{(1S)-1-(5-fluorothiophen-2-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}cyclohexane-1-carboxamide According to the synthesis method of compound 40, Cyclohexanecarboxylic acid was used to replace acetic acid in Example 40, compound 7-1 was used to replace 1-1 in Example 30 and isobutyryl chloride was used to replace acetyl chloride in Example 40 to obtain compound 51, MS: 584.3 [M+H]+. $^1$H-NMR (400 Hz, CDCl$_3$): δ7.05 (m, 1H), 6.97 (m,1H), 5.17 (m, 1H), 4.65 (m,1H), 4.43 (m,2H), 4.09 (m,2H), 3.43 (m,2H), 3.07 (m,1H), 2.85-2.69 (m,2H), 2.51-2.39 (m,2H), 2.36-1.84 (m,8H), 1.69-1.53 (m, 12H), 1.13-1.06 (m,6H).

EXAMPLE 52

Synthesis of Compound 52

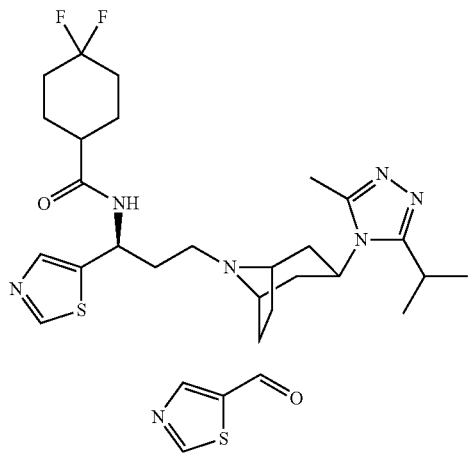

4,4-difluoro-N-[(1S)-3-[exo-3-(3-isopropyl-5-methyl-4H-1,2,4-triazol-4-yl)-8-azabicyclo[3.2.1]octane-8-yl]-1-(thiazol-5-yl)propyl]cyclohexane-1-carboxamide According to the synthesis method of Example 5, Compound 8-1 was used to replace compound 2-1 in Example 5 and compound 2f was used to replace compound 1f in Example 5 to obtain compound 52, MS: 520.9 [M+H]+. $^1$H-NMR (400 Hz, CDCl$_3$): δ8.27 (s, 1H), 7.14 (s, 1H), 5.14 (m,1H), 3.91 (m, 1H), 3.03 (m, 1H), 2.52 (s, 3H), 2.40 (m,2H), 2.27-1.93 (m,12H), 1.93-1.62 (m, 9H), 1.32 (d, 6H).

EXAMPLE 53

Synthesis of Compound 53

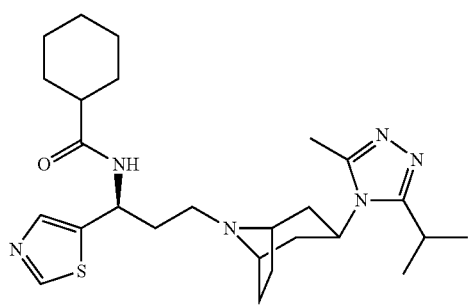 [SMILES: Cc1nnc(C(C)C)n1C1CC2CCC(C1)N2CC[C@H](NC(=O)C1CCCCC1)c1cncs1]

N-[(1S)-3-[exo-3-(3-isopropyl-5-methyl-4H-1,2,4-triazol-4-yl)-8-azabicyclo[3.2.1]octane-8-yl]-1-(thiazol-5-yl)propyl]cyclohexane-1-carboxamide According to the synthesis method of Example 5, Compound 8-1 was used to replace compound 2-1 in example 5, compound 2f was used to replace compound 1f in example 5 and cyclohexane carboxylic acid was used to replace 4,4-difluoro-cyclohexanecarboxylic acid in example 5 to obtain compound 53, MS: 484.9 [M+H]+. $^1$H-NMR (400 Hz, CDCl$_3$): δ8.28 (s, 1H), 7.23 (s, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 54

Synthesis of Compound 54

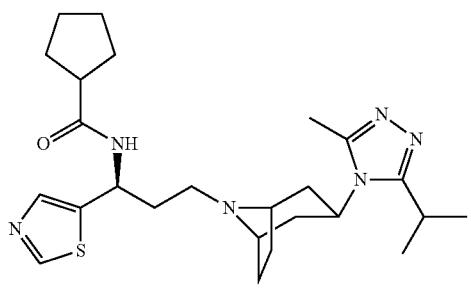 [SMILES: Cc1nnc(C(C)C)n1C1CC2CCC(C1)N2CC[C@H](NC(=O)C1CCCC1)c1cncs1]

N-[(1S)-3-[exo-3-(3-isopropyl-5-methyl-4H-1,2,4-triazol-4-yl)-8-azabicyclo[3.2.1]octane-8-yl]-1-(thiazol-5-yl)propyl]cyclopentane-1-carboxamide According to the synthesis method of Example 5, Compound 8-1 was used to replace compound 2-1 in Example 5, compound 2f was used to replace compound 1f in Example 5 and cyclopentane carboxylic acid was used to replace 4,4-difluoro-cyclohexanecarboxylic acid in Example 5 to obtain compound 54, MS: 470.9 [M+H]+. $^1$H-NMR (400 Hz, CDCl$_3$): δ8.25 (s, 1H), 7.33 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 55

Synthesis of Compound 55

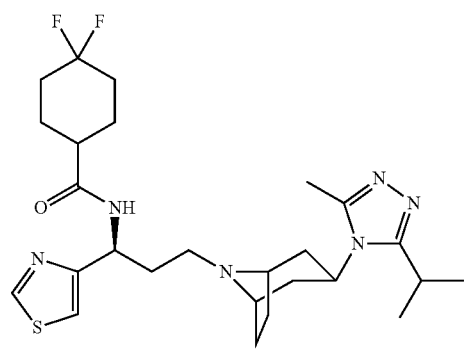

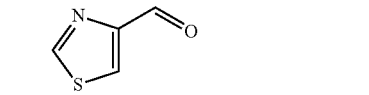

4,4-difluoro-N-[(1S)-3-[exo-3-(3-isopropyl-5-methyl-4H-1,2,4-triazol-4-yl)-8-azabicyclo[3.2.1]octane-8-yl]-1-(thiazol-4-yl)propyl]cyclohexane-1-carboxamide According to the synthesis method of Example 5, Compound 10-1 was used to replace compound 2-1 in Example 5, and compound 2f was used to replace compound 1f in Example 5 to obtain compound 55, MS: 520.91 [M+H]+. $^1$H-NMR (400 Hz, CDCl$_3$): δ8.20 (s, 1H), 7.19 (s, 1H), 5.14 (m, 1H), 3.91 (m, 1H), 3.03 (m, 1H), 2.52 (s, 3H), 2.40 (m,2H), 2.27-1.93 (m,12H), 1.93-1.62 (m, 9H), 1.32 (d, 6H).

EXAMPLE 56

Synthesis of Compound 56

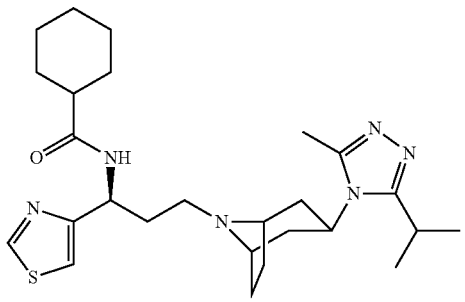 [SMILES: Cc1nnc(C(C)C)n1C1CC2CCC(C1)N2CC[C@H](NC(=O)C1CCCCC1)c1cscn1]

N-[(1S)-3-[exo-3-(3-isopropyl-5-methyl-4H-1,2,4-triazol-4-yl)-8-azabicyclo[3.2.1]octane-8-yl]-1-(thiazol-5-yl)propyl]cyclohexane-1-carboxamide According to the synthesis method of Example 5, Compound 10-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 56, MS: 484.9 [M+H]+. $^1$H-NMR (400 Hz, CDCl$_3$): δ8.18 (s, 1H), 7.23 (s, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 57

Synthesis of Compound 57

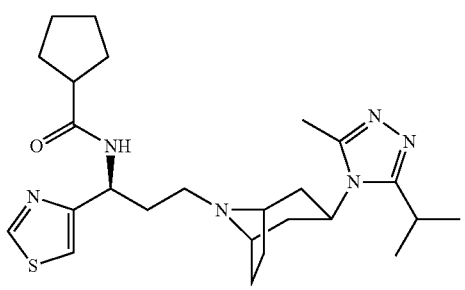 [SMILES: Cc1nnc(C(C)C)n1C1CC2CCC(C1)N2CC[C@H](NC(=O)C1CCCC1)c1cscn1]

N-[(1S)-3-[exo-3-(3-isopropyl-5-methyl-4H-1,2,4-triazol-4-yl)-8-azabicyclo[3.2.1]octane-8-yl]-1-(thiazol-5-yl)propyl]cyclopentane-1-carboxamide According to the synthesis method of Example 5, Compound 10-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 57, MS: 470.9 [M+H]+. $^1$H-NMR (400 Hz, CDCl$_3$): δ8.20 (s, 1H), 7.33 (s, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 58

Synthesis of Compound 58

N-{(1S)-1-(thiazol-5-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide

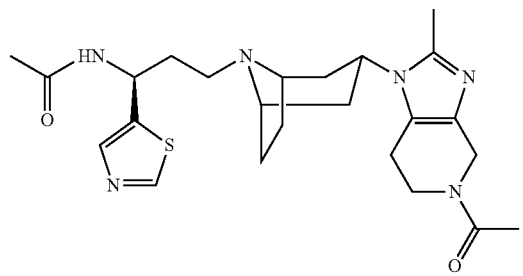 [SMILES: CC(=O)N[C@@H](CCN1C2CCC1CC(n1c(C)nc3c1CCN(C(C)=O)C3)C2)c1cncs1]

According to the synthesis method of compound 40, Compound 8-1 was used to replace compound 3-1 in Example 40 to obtain compound 58, MS: 471.3 [M+H]+. $^1$H-NMR (400 Hz, CDCl$_3$): δ8.10 (s, 1H), 7.17 (s, 1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,6H), 1.59-1.30 (m, 4H).

EXAMPLE 59

Synthesis of Compound 59

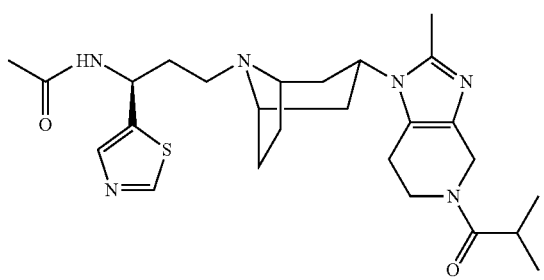 [SMILES: CC(=O)N[C@@H](CCN1C2CCC1CC(n1c(C)nc3c1CCN(C(=O)C(C)C)C3)C2)c1cncs1]

N-{(1S)-1-(thiazol-5-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 8-1 was used to replace compound 3-1 in Example 40 and isobutyryl chloride was used to replace acetyl chloride in Example 40 to obtain compound 59, MS: 499.31 [M+H]+. ¹H-NMR (400 Hz, CDCl₃): δ7.87 (s, 1H), 7.07 (s,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,6H), 1.69-1.53 (m, 4H), 1.13-1.06 (m,6H).

EXAMPLE 60

Synthesis of Compound 60

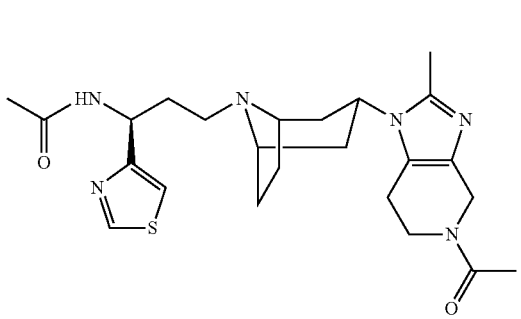 [SMILES: CC(=O)N[C@@H](CCN1C2CCC1CC(n1c(C)nc3c1CCN(C(C)=O)C3)C2)c1cscn1]

N-{(1S)-1-(thiazol-4-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 10-1 was used to replace compound 3-1 in Example 40 to obtain compound 60, MS: 471.3 [M+H]+. ¹H-NMR (400 Hz, CDCl₃): δ8.13 (s,1H), 7.13 (s,1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,6H), 1.59-1.30 (m, 4H).

EXAMPLE 61

Synthesis of Compound 61

N-{(1S)-1-(thiazol-4-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide

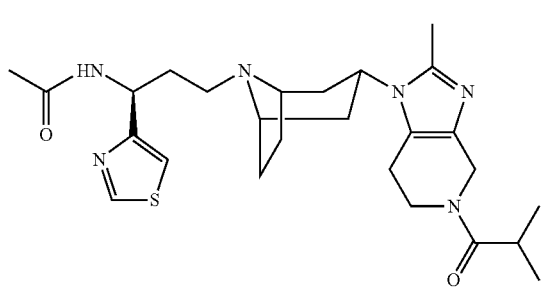 [SMILES: CC(=O)N[C@@H](CCN1C2CCC1CC(n1c(C)nc3c1CCN(C(=O)C(C)C)C3)C2)c1cscn1]

According to the synthesis method of compound 40, Compound 10-1 was used to replace compound 3-1 in Example 40 and isobutyryl chloride was used to replace acetyl chloride in Example 40 to obtain compound 61, MS: 499.3 [M+H]+. ¹H-NMR (400 Hz, CDCl₃): δ8.07 (s, 1H), 7.37 (s,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,6H), 1.69-1.53 (m,4H), 1.13-1.06 (m,6H).

EXAMPLE 62

Synthesis of Compound 62

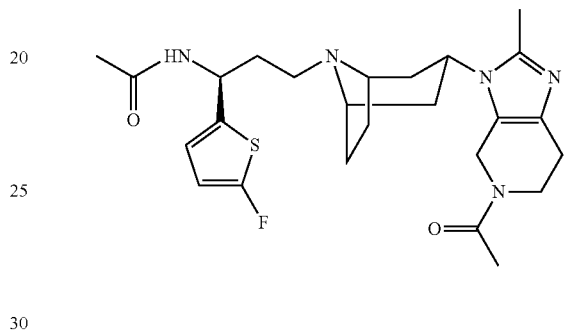

N-{(1S)-1-(5-fluorothiophen-2-yl)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 7-1 was used to replace compound 3-1 in Example 40, compound 4h was used to replace compound 3h in Example 40 and isobutyryl chloride was used to replace acetyl chloride in Example 40 to obtain compound 62, MS: 488.3 [M+H]+. ¹H-NMR (400 Hz, CDCl₃): δ7.13 (d,1H), 7.03 (d,1H), 5.17 (m, 1H), 4.65 (m,1H), 4.43 (m,2H), 4.09 (m,2H), 3.43 (m,2H), 3.07 (m,1H), 2.83-2.69 (m,5H), 2.51-2.39 (m,2H), 2.36-1.84 (m,6H), 1.59-1.30 (m, 4H).

EXAMPLE 63

Synthesis of Compound 63

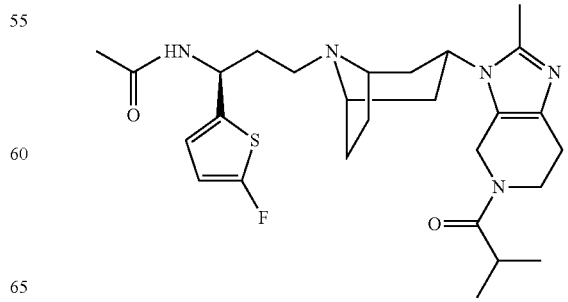

N-{(1S)-1-(5-fluorothiophen-2-yl)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]propyl}acetamide According to the synthesis method of compound 40, Compound 7-1 was used to replace compound 3-1 in Example 40, and compound 4h was used to replace compound 3h in Example 40 to obtain compound 63, MS: 516.3 [M+H]+. ¹H-NMR (400 Hz, CDCl₃): δ7.37 (d, 1H), 7.01 (d,1H), 5.17 (m, 1H), 4.65 (m,1H), 4.43 (m,2H), 4.09 (m,2H), 3.43 (m,2H), 3.07 (m,1H), 2.83-2.69 (m,2H), 2.51-2.39 (m,2H), 2.36-1.84 (m,6H), 1.69-1.53 (m,4H), 1.13-1.06 (m,6H).

EXAMPLE 64

Synthesis of Compound 64

4,4-difluoro-N-[(1S)-3-[exo-3-(3-isopropyl-5-methyl-4H-1,2,4-triazol-4-yl)-8-azabicyclo[3.2.1]octane-8-yl]-1-(5-ethylthiophen-2-yl)propyl]cyclohexane-1-carboxamide

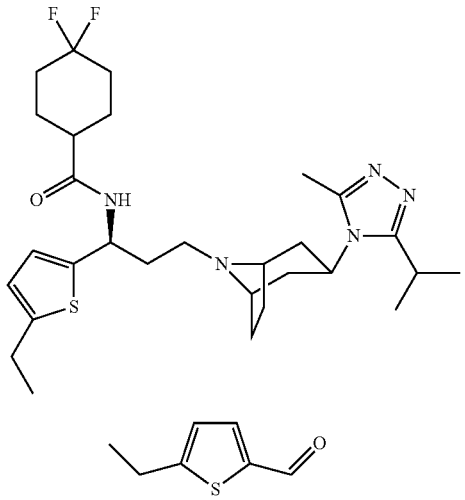

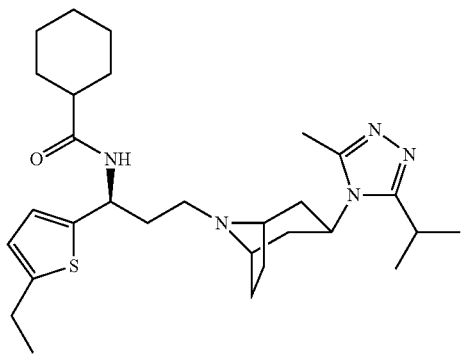 [SMILES: CCc1ccc([C@H](CCN2C3CCC2CC(n2c(C)nnc2C(C)C)C3)NC(=O)C2CCCCC2)s1]

11-1

According to the synthesis method of Example 5, Compound 11-1 was used to replace 2-1 in Example 5 and compound 2f was used to replace if in Example 5 to obtain compound 64, MS: 548.2 [M+H]+δ7.27 (d, 1H), 7.20 (d, 1H), 5.14 (m,1H), 3.91 (m, 1H), 3.03 (m, 1H), 2.52 (q, 2H), 2.40 (m,5H), 2.27-1.93 (m,12H), 1.93-1.62 (m, 9H), 1.32 (m, 9H).

EXAMPLE 65

Synthesis of Compound 65

N-[(1S)-3-[exo-3-(3-isopropyl-5-methyl-4H-1,2,4-triazol-4-yl)-8-azabicyclo[3.2.1]octane-8-yl]-1-(5-ethylthiophen-2-yl)propyl]cyclohexane-1-carboxamide According to the synthesis method of Example 5, Compound 11-1 was used to replace 2-1 in Example 5, compound 2f was used to replace if in Example 5 and cyclohexanecarboxylic acid was used to replace 4,4-difluoro-cyclohexanecarboxylic acid in Example 5 to obtain compound 65, MS: 512.2 [M+H]+. ¹H-NMR (400 Hz, CDCl₃): δ7.28 (d, 1H), 7.21 (d, 1H), 5.19 (m,1H), 3.91 (m, 1H), 3.02 (m, 1H), 2.54 (q, 2H), 2.43 (m,5H), 2.26-1.93 (m,13H), 1.93-1.61 (m, 10H), 1.36 (m, 9H).

EXAMPLE 66

Synthesis of Compound 66

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]cyclopentane-1-carboxamide

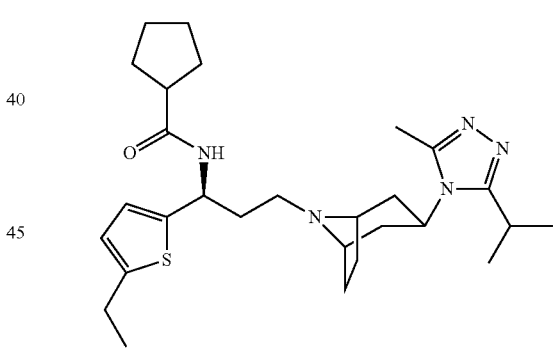

According to the synthesis method of Example 5, Compound 11-1 was used to replace 2-1 in Example 5, compound 2f was used to replace if in Example 5 and cyclopentanecarboxylic acid was used to replace 4,4-difluoro-cyclohexanecarboxylic acid in Example 5 to obtain compound 66, MS: 498.2 [M+H]+. ¹H-NMR (400 Hz, CDCl₃): δ7.25 (d, 1H), 7.17 (d, 1H), 5.19 (m,1H), 3.91 (m, 1H), 3.02 (m, 1H), 2.54 (q, 2H), 2.43 (m,5H), 2.27-1.93 (m,11H), 1.93-1.61 (m, 10H), 1.35 (m, 9H).

EXAMPLE 67

Synthesis of Compound 67

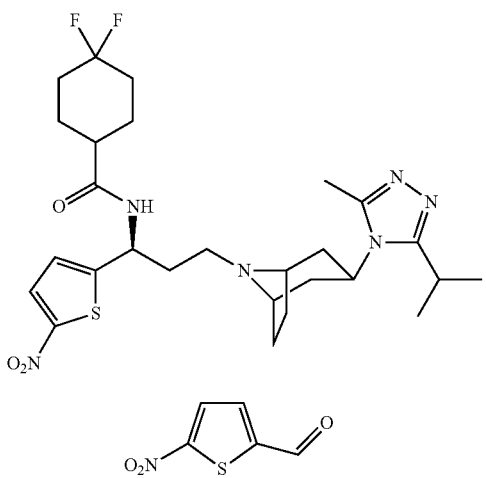

12-1

4,4-difluoro-N-[(1S)-3-[exo-3-(3-isopropyl-5-methyl-4H-1,2,4-triazol-4-yl)-8-azabicyclo[3.2.1]octane-8-yl]-1-(5-nitrothiophen-2-yl)propyl]cyclohexane-1-carboxamide According to the synthesis method of Example 5, Compound 12-1 was used to replace 2-1 in Example 5 and compound 2f was used to replace if in Example 5 to obtain compound 67, MS: 565.2 [M+H]+. $^1$H-NMR (400 Hz, CDCl$_3$): δ7.97 (d, 1H), 7.05 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 68

Synthesis of Compound 68

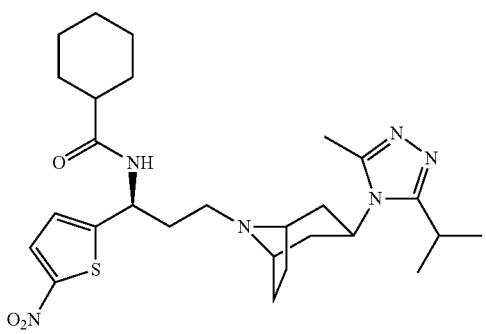 [SMILES: Cc1nnc(C(C)C)n1C1CC2CCC(C1)N2CC[C@H](NC(=O)C1CCCCC1)c1ccc([N+](=O)[O-])s1]

N-[(1S)-3-[exo-3-(3-isopropyl-5-methyl-4H-1,2,4-triazol-4-yl)-8-azabicyclo[3.2.1]octane-8-yl]-1-(5-nitrothiophen-2-yl)propyl]cyclohexane-1-carboxamide According to the synthesis method of Example 5, Compound 12-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 68, MS: 529.2 [M+H]+. $^1$H-NMR (400 Hz, CDCl$_3$): δ7.93 (d, 1H), 6.94 (d,1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 69

Synthesis of Compound 69

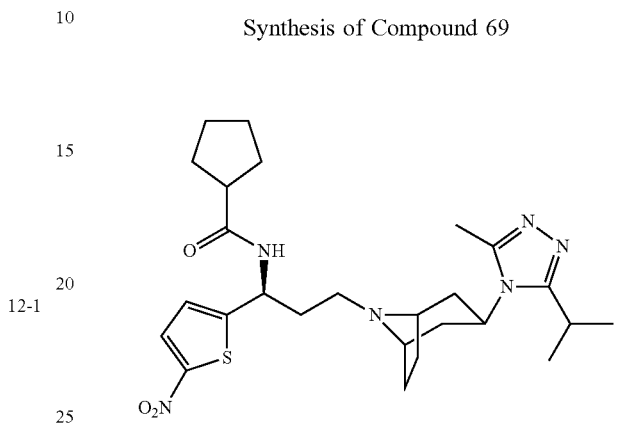

N-[(1S)-3-[exo-3-(3-isopropyl-5-methyl-4H-1,2,4-triazol-4-yl)-8-azabicyclo[3.2.1]octane-8-yl]-1-(5-nitrothiophen-2-yl)propyl]cyclopentane-1-carboxamide According to the synthesis method of Example 5, Compound 12-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 69, MS: 515.2 [M+H]+. $^1$H-NMR (400 Hz, CDCl$_3$): δ7.90 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 70

Synthesis of Compound 70

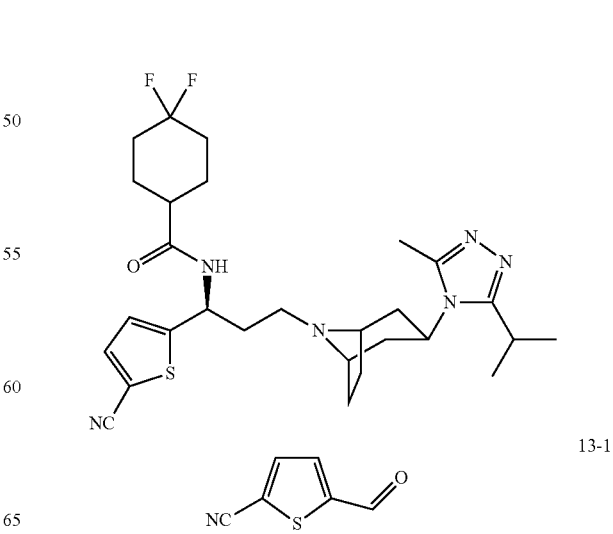

13-1

4,4-difluoro-N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]cyclohexane-1-carboxamide According to the synthesis method of Example 5, Compound 13-1 was used to replace 2-1 in Example 5 and compound 2f was used to replace if in Example 5 to obtain compound 70, MS: 545.2 [M+H]+. ¹H-NMR (400 Hz, CDCl₃): δ7.27 (d, 1H), 6.95 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 71

Synthesis of Compound 71

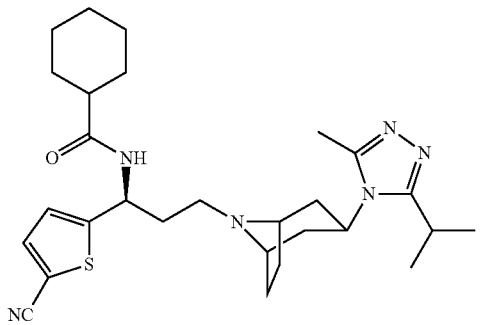 [SMILES: Cc1nnc(C(C)C)n1C1CC2CCC(C1)N2CC[C@H](NC(=O)C1CCCCC1)c1ccc(C#N)s1]

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]cyclohexane-1-carboxamide According to the synthesis method of Example 5, Compound 13-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 71, MS: 509.2 [M+H]+. ¹H-NMR (400 Hz, CDCl₃): δ7.33 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 72

Synthesis of Compound 72

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]cyclopentane-1-carboxamide

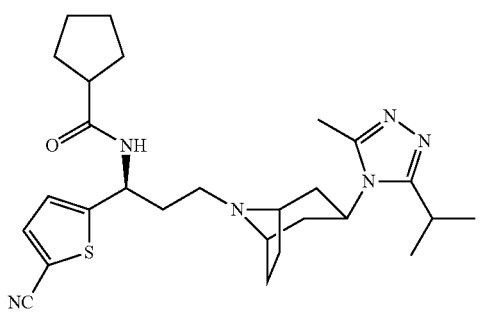 [SMILES: Cc1nnc(C(C)C)n1C1CC2CCC(C1)N2CC[C@H](NC(=O)C1CCCC1)c1ccc(C#N)s1]

According to the synthesis method of Example 5, Compound 13-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 72, MS: 495.2 [M+H]+. ¹H-NMR (400 Hz, CDCl₃): δ7.30 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 73

Synthesis of Compound 73

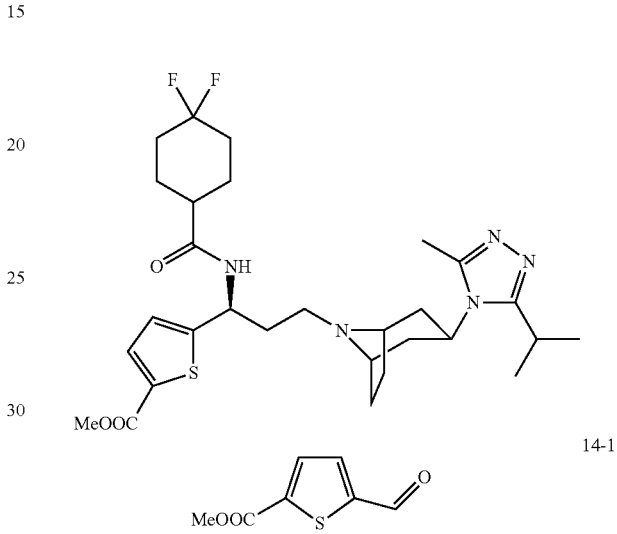

4,4-difluoro-N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclohexane-1-carboxamide According to the synthesis method of Example 5, Compound 14-1 was used to replace 2-1 in Example 5 and compound 2f was used to replace if in Example 5 to obtain compound 73, MS: 578.2 [M+H]+. ¹H-NMR (400 Hz, CDCl₃): δ7.77 (d, 1H), 6.95 (d, 1H), 5.19 (m,1H), 3.91 (m, 4H), 3.02 (m, 1H), 2.54 (s, 3H), 2.43 (m,2H), 2.27-1.95 (m,10H), 1.95-1.61 (m, 9H), 1.34 (d, 6H).

EXAMPLE 74

Synthesis of Compound 74

N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclohexane-1-carboxamide According to the synthesis method of Example 5, Compound 14-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 74.

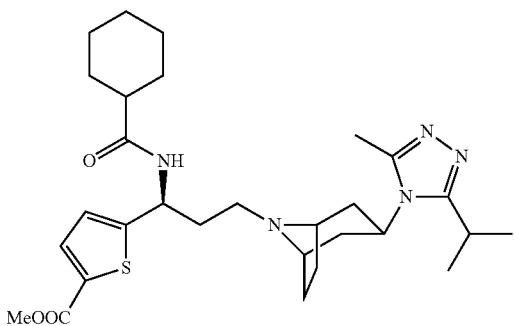 [SMILES: COC(=O)c1ccc([C@H](CCN2C3CCC2CC(n2c(C)nnc2C(C)C)C3)NC(=O)C2CCCCC2)s1]

MS: 542.2 [M+H]+. ¹H-NMR (400 Hz, CDCl₃): δ7.83 (d, 1H), 6.94 (d, 1H), 5.19 (m,1H), 3.91 (m, 4H), 3.02 (m, 1H), 2.54 (s, 3H), 2.43 (m,2H), 2.26-1.93 (m, 13H), 1.93-1.61 (m, 10H), 1.36 (d, 6H).

EXAMPLE 75

Synthesis of Compound 75

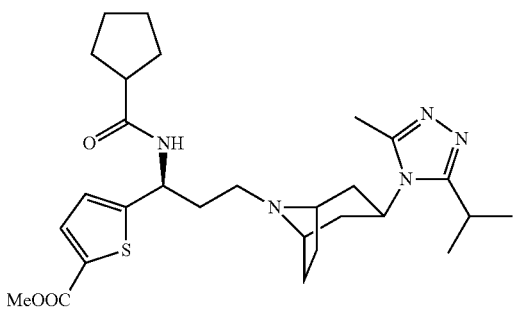 [SMILES: COC(=O)c1ccc([C@H](CCN2C3CCC2CC(n2c(C)nnc2C(C)C)C3)NC(=O)C2CCCC2)s1]

N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclopentane-1-carboxamide According to the synthesis method of Example 5, Compound 14-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 75, MS: 528.2 [M+H]+. ¹H-NMR (400 Hz, CDCl₃): δ7.80 (d, 1H), 6.97 (d, 1H), 5.19 (m,1H), 3.91 (m, 4H), 3.02 (m, 1H), 2.54 (s, 3H), 2.43 (m,2H), 2.27-1.93 (m,11H), 1.93-1.61 (m, 10H), 1.35 (d, 6H).

EXAMPLE 76

Synthesis of Compound 76

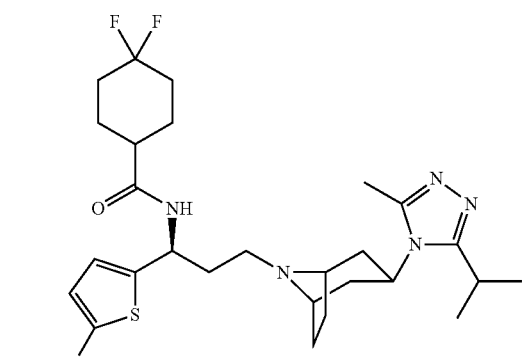

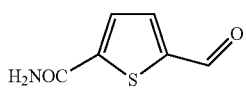

4,4-difluoro-N-[(1S)-3-[exo-3-(3-isopropyl-5-methyl-4H-1,2,4-triazol-4-yl)-8-azabicyclo[3.2.1]octane-8-yl]-1-(5-carbamoylthiophen-2-yl)propyl]cyclohexane-1-carboxamide According to the synthesis method of Example 5, Compound 15-1 was used to replace 2-1 in Example 5 and compound 2f was used to replace if in Example 5 to obtain compound 76, MS: 563.2 [M+H]+. ¹H-NMR (400 Hz, CDCl₃): δ7.87 (d, 2H), 7.57 (d, 1H), 6.95 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 77

Synthesis of Compound 77

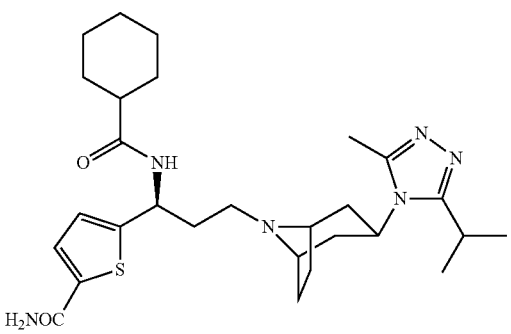 [SMILES: Cc1nnc(C(C)C)n1C1CC2CCC(C1)N2CC[C@H](NC(=O)C1CCCCC1)c1ccc(C(N)=O)s1]

N-[(1S)-3-[exo-3-(3-isopropyl-5-methyl-4H-1,2,4-triazol-4-yl)-8-azabicyclo[3.2.1]octane-8-yl]-1-(5-carbamoylthiophen-2-yl)propyl]cyclohexane-1-carboxamide According to the synthesis method of Example 5, Compound 15-1 was used to replace 2-1 in Example 5, compound 2f was used to replace if in Example 5 and cyclohexanecarboxylic acid was used to replace 4,4-difluoro-cyclohexanecarboxylic acid in Example 5 to obtain compound 77, MS: 528.2 [M+H]+. ¹H-NMR (400 Hz, CDCl₃): δ7.87 (d, 2H), 7.63 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 78

Synthesis of Compound 78

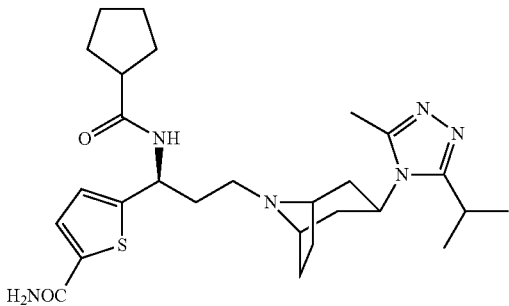 [SMILES: Cc1nnc(C(C)C)n1C1CC2CCC(C1)N2CC[C@H](NC(=O)C1CCCC1)c1ccc(C(N)=O)s1]

N-[(1S)-3-[exo-3-(3-isopropyl-5-methyl-4H-1,2,4-triazol-4-yl)-8-azabicyclo[3.2.1]octane-8-yl]-1-(5-carbamoylthiophen-2-yl)propyl]cyclopentane-1-carboxamide According to the synthesis method of Example 5, Compound 15-1 was used to replace 2-1 in Example 5, compound 2f was used to replace if in Example 5 and cyclopentanecarboxylic acid was used to replace 4,4-difluoro-cyclohexanecarboxylic acid in Example 5 to obtain compound 78, MS: 513.2 [M+H]+. ¹H-NMR (400 Hz, CDCl₃): δ7.87 (d, 2H), 7.60 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 79

Synthesis of Compound 79

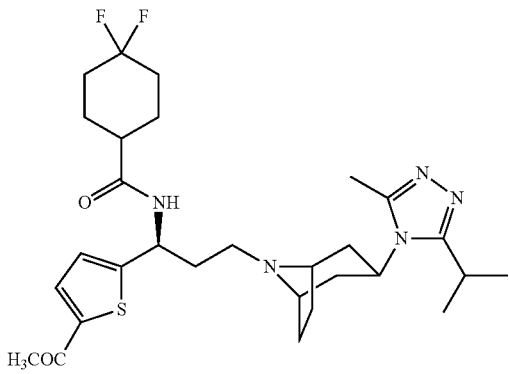

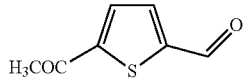

4,4-difluoro-N-[(1S)-3-[exo-3-(3-isopropyl-5-methyl-4H-1,2,4-triazol-4-yl)-8-azabicyclo[3.2.1]octane-8-yl]-1-(5-acetylthiophen-2-yl)propyl]cyclohexane-1-carboxamide According to the synthesis method of Example 5, Compound 16-1 was used to replace 2-1 in Example 5 and compound 2f was used to replace if in Example 5 to obtain compound 79, MS: 562.2 [M+H]+. ¹H-NMR (400 Hz, CDCl₃): δ7.27 (d, 1H), 6.95 (d, 1H), 5.19 (m,1H), 3.91 (m, 1H), 3.02 (m, 1H), 2.54 (s, 3H), 2.43 (m,5H), 2.27-1.95 (m,10H), 1.95-1.61 (m, 9H), 1.34 (d, 6H).

EXAMPLE 80

Synthesis of Compound 80

N-[(1S)-3-[exo-3-(3-isopropyl-5-methyl-4H-1,2,4-triazol-4-yl)-8-azabicyclo[3.2.1]octane-8-yl]-1-(5-acetylthiophen-2-yl)propyl]cyclohexane-1-carboxamide

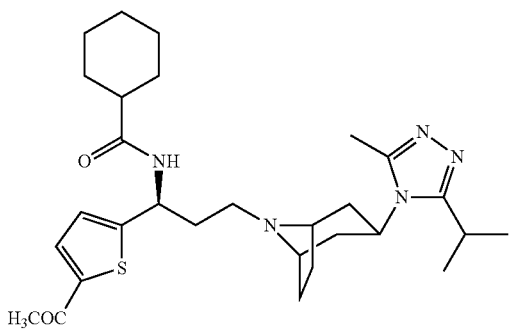

According to the synthesis method of Example 5, Compound 16-1 was used to replace 2-1 in Example 5, compound 2f was used to replace if in Example 5 and cyclohexanecarboxylic acid was used to replace 4,4-difluoro-cyclohexanecarboxylic acid in Example 5 to obtain compound 80, MS: 526.2 [M+H]+. ¹H-NMR (400 Hz, CDCl₃): δ7.23 (d, 1H), 6.94 (d, 1H), 5.19 (m,1H), 3.91 (m, 1H), 3.02 (m, 1H), 2.54 (s, 3H), 2.43 (m,5H), 2.26-1.93 (m,13H), 1.93-1.61 (m, 10H), 1.36 (d, 6H).

EXAMPLE 81

Synthesis of Compound 81

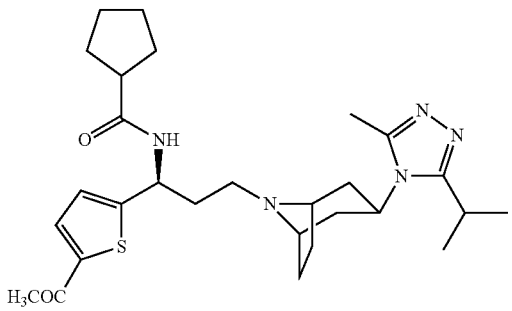

N-[(1S)-3-[exo-3-(3-isopropyl-5-methyl-4H-1,2,4-triazol-4-yl)-8-azabicyclo[3.2.1]octane-8-yl]-1-(5-acetylthiophen-2-yl)propyl]cyclopentane-1-carboxamide According to the synthesis method of Example 5, Compound 16-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 81, MS: 512.2 [M+H]+. $^1$H-NMR (400 Hz, CDCl$_3$): δ7.20 (d, 1H), 6.97 (d, 1H), 5.19 (m,1H), 3.91 (m, 1H), 3.02 (m, 1H), 2.54 (s, 3H), 2.43 (m,5H), 2.27-1.93 (m,11H), 1.93-1.61 (m, 10H), 1.35 (d, 6H).

EXAMPLE 82

Synthesis of Compound 82

4,4-difluoro-N-[(1S)-3-[exo-3-(3-isopropyl-5-methyl-4H-1,2,4-triazol-4-yl)-8-azabicyclo[3.2.1]octane-8-yl]-1-(5-formamidothiophen-2-yl)propyl]cyclohexane-1-carboxamide According to the synthesis method of Example 5, Compound 17-1 was used to replace 2-1 in Example 5 and compound 2f was used to replace if in Example 5 to obtain compound 82.

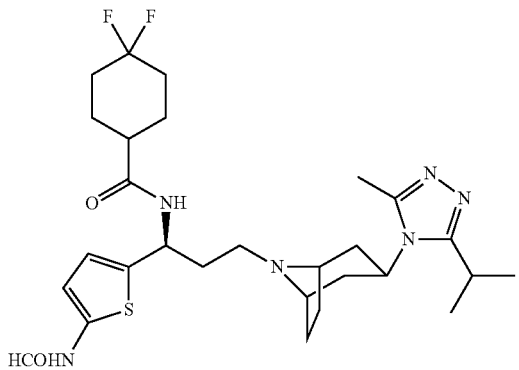

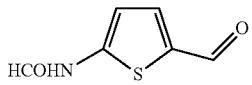

MS: 562.2 [M+H]+. $^1$H-NMR (400 Hz, CDCl$_3$): δ8.10 (s, 1H), 7.07 (d, 1H), 6.95 (d, 1H), 5.19 (m,1H), 3.91 (m, 1H), 3.02 (m, 1H), 2.54 (s, 3H), 2.43 (m,2H), 2.27-1.95 (m,10H), 1.95-1.61 (m, 9H), 1.34 (d, 6H).

EXAMPLE 83

Synthesis of Compound 83

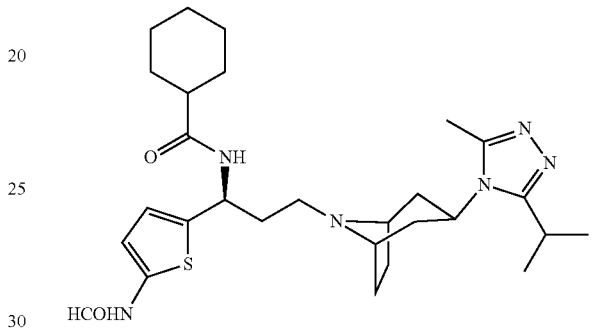

N-[(1S)-3-[exo-3-(3-isopropyl-5-methyl-4H-1,2,4-triazol-4-yl)-8-azabicyclo[3.2.1]octane-8-yl]-1-(5-formamidothiophen-2-yl)propyl]cyclohexane-1-carboxamide According to the synthesis method of Example 5, Compound 17-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 83, MS: 527.2 [M+H]+. $^1$H-NMR (400 Hz, CDCl$_3$): δ8.10 (s, 1H), 7.13 (d, 1H), 6.94 (d, 1H), 5.19 (m,1H), 3.91 (m, 1H), 3.02 (m, 1H), 2.54 (s, 3H), 2.43 (m,2H), 2.26-1.93 (m,13H), 1.93-1.61 (m, 10H), 1.36 (d, 6H).

EXAMPLE 84

Synthesis of Compound 84

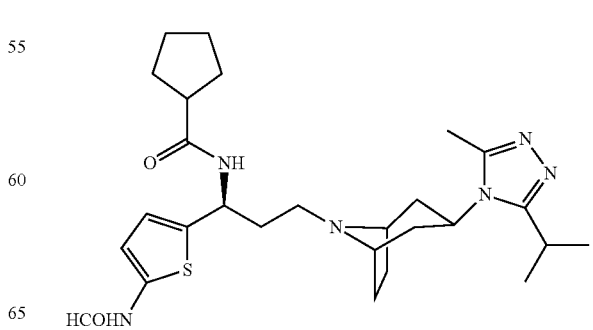

N-[(1S)-3-[exo-3-(3-isopropyl-5-methyl-4H-1,2,4-triazol-4-yl)-8-azabicyclo[3.2.1]octane-8-yl]-1-(5-formamidothiophen-2-yl)propyl]cyclopentane-1-carboxamide According to the synthesis method of Example 5, Compound 17-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 84, MS: 513.2 [M+H]+. $^1$H-NMR (400 Hz, CDCl$_3$): δ8.10 (s, 1H), 7.10 (d, 1H), 6.97 (d, 1H), 5.19 (m,1H), 3.91 (m, 1H), 3.02 (m, 1H), 2.54 (s, 3H), 2.43 (m,2H), 2.27-1.93 (m,11H), 1.93-1.61 (m, 10H), 1.35 (d, 6H).

EXAMPLE 85

Synthesis of Compound 85

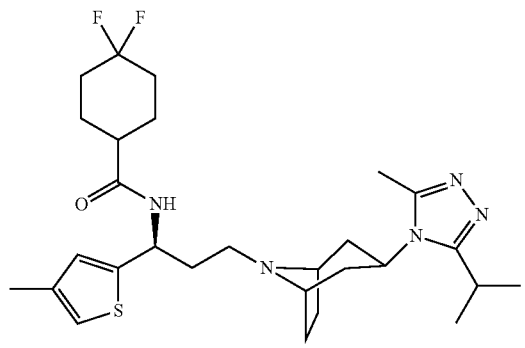

4,4-difluoro-N-[(1S)-3-[exo-3-(3-isopropyl-5-methyl-4H-1,2,4-triazol-4-yl)-8-azabicyclo[3.2.1]octane-8-yl]-1-(4-methylthiophen-2-yl)propyl]cyclohexane-1-carboxamide According to the synthesis method of Example 5, Compound 18-1 was used to replace 2-1 in Example 5 and compound 2f was used to replace if in Example 5 to obtain compound 85, MS: 533.2 [M+H]+. $^1$H-NMR (400 Hz, CDCl$_3$): δ7.07 (s, 1H), 6.95 (s, 1H), 5.19 (m,1H), 3.91 (m, 1H), 3.02 (m, 1H), 2.54 (s, 3H), 2.43 (m,5H), 2.27-1.95 (m,10H), 1.95-1.61 (m, 9H), 1.34 (d, 6H).

EXAMPLE 86

Synthesis of Compound 86

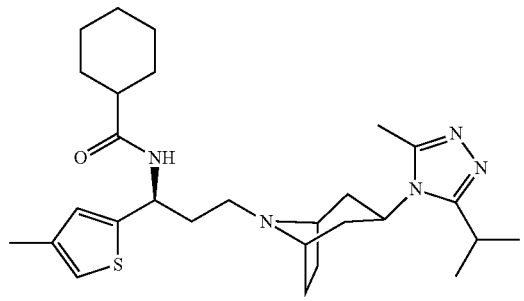 [SMILES: Cc1csc([C@H](CCN2C3CCC2CC(n2c(C)nnc2C(C)C)C3)NC(=O)C2CCCCC2)c1]

N-[(1S)-3-[exo-3-(3-isopropyl-5-methyl-4H-1,2,4-triazol-4-yl)-8-azabicyclo[3.2.1]octane-8-yl]-1-(4-methylthiophen-2-yl)propyl]cyclohexane-1-carboxamide According to the synthesis method of Example 5, Compound 18-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 86, MS: 498.2 [M+H]+. $^1$H-NMR (400 Hz, CDCl$_3$): δ7.13 (s, 1H), 6.94 (s, 1H), 5.19 (m,1H), 3.91 (m, 1H), 3.02 (m, 1H), 2.54 (s, 3H), 2.43 (m,5H), 2.26-1.93 (m,13H), 1.93-1.61 (m, 10H), 1.36 (d, 6H).

EXAMPLE 87

Synthesis of Compound 87

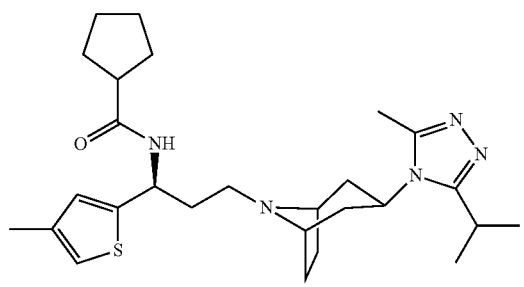 [SMILES: Cc1csc([C@H](CCN2C3CCC2CC(n2c(C)nnc2C(C)C)C3)NC(=O)C2CCCC2)c1]

N-[(1S)-3-[exo-3-(3-isopropyl-5-methyl-4H-1,2,4-triazol-4-yl)-8-azabicyclo[3.2.1]octane-8-yl]-1-(4-methylthiophen-2-yl)propyl]cyclopentane-1-carboxamide According to the synthesis method of Example 5, Compound 18-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 87, MS: 484.2 [M+H]+. $^1$H-NMR (400 Hz, CDCl$_3$): δ7.10 (s, 1H), 6.97 (s, 1H), 5.19 (m,1H), 3.91 (m, 1H), 3.02 (m, 1H), 2.54 (s, 3H), 2.43 (m,5H), 2.27-1.93 (m,11H), 1.93-1.61 (m, 10H), 1.35 (d, 6H).

EXAMPLE 88

Synthesis of Compound 88

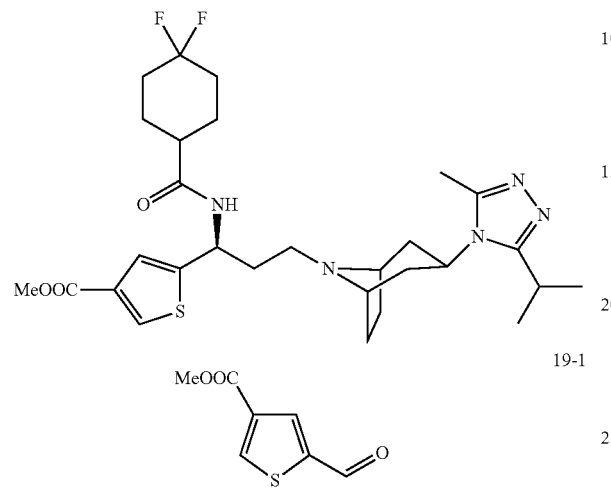

4,4-difluoro-N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclohexane-1-carboxamide According to the synthesis method of Example 5, Compound 19-1 was used to replace 2-1 in Example 5 and compound 2f was used to replace if in Example 5 to obtain compound 88, MS: 578.2 [M+H]+. $^1$H-NMR (400 Hz, CDCl$_3$): δ8.17 (s, 1H), 7.27 (s, 1H), 5.19 (m,1H), 3.91 (m, 4H), 3.02 (m, 1H), 2.54 (s, 3H), 2.43 (m,2H), 2.27-1.95 (m,10H), 1.95-1.61 (m, 9H), 1.34 (d, 6H).

EXAMPLE 89

Synthesis of Compound 89

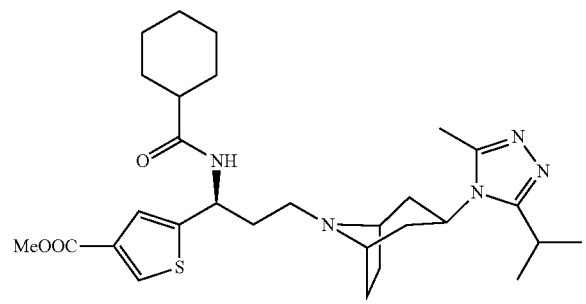 [SMILES: COC(=O)c1csc([C@H](CCN2C3CCC2CC(n2c(C)nnc2C(C)C)C3)NC(=O)C2CCCCC2)c1]

N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclohexane-1-carboxamide According to the synthesis method of Example 5, Compound 19-1 was used to replace 2-1 in Example 5, compound 2f was used to replace if in Example 5 and cyclohexanecarboxylic acid was used to replace 4,4-difluoro-cyclohexanecarboxylic acid in Example 5 to obtain compound 89, MS: 542.2 [M+H]+. $^1$H-NMR (400 Hz, CDCl$_3$): δ8.13 (s, 1H), 7.26 (s, 1H), 5.19 (m,1H), 3.91 (m, 4H), 3.02 (m, 1H), 2.54 (s, 3H), 2.43 (m,2H), 2.26-1.93 (m,13H), 1.93-1.61 (m, 10H), 1.36 (d, 6H).

EXAMPLE 90

Synthesis of Compound 90

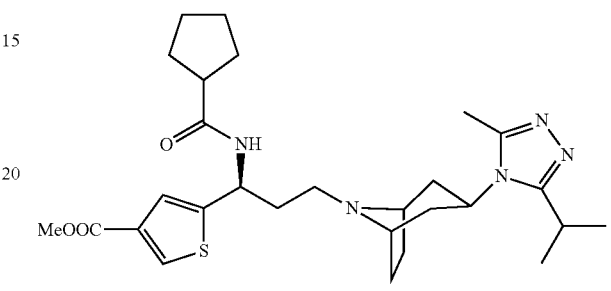

N-[(1S)-3-[exo-3-(3-isopropyl-5-methyl-4H-1,2,4-triazol-4-yl)-8-azabicyclo[3.2.1]octane-8-yl]-1-(5-methoxycarbonylthiophen-2-yl)propyl]cyclopentane-1-carboxamide According to the synthesis method of Example 5, Compound 19-1 was used to replace compound 2-1 in Example 5, compound 2f was used to replace 1f in Example 5 and cyclopentanecarboxylic acid was used to replace 4,4-difluoro-cyclohexanecarboxylic acid in Example 5 to obtain compound 90, MS: 528.2 [M+H]+. $^1$H-NMR (400 Hz, CDCl$_3$): δ8.10 (s, 1H), 7.27 (s, 1H), 5.19 (m,1H), 3.91 (m, 4H), 3.02 (m, 1H), 2.54 (s, 3H), 2.43 (m,2H), 2.27-1.93 (m,11H), 1.93-1.61 (m, 10H), 1.35 (d, 6H).

EXAMPLE 91

Synthesis of Compound 91

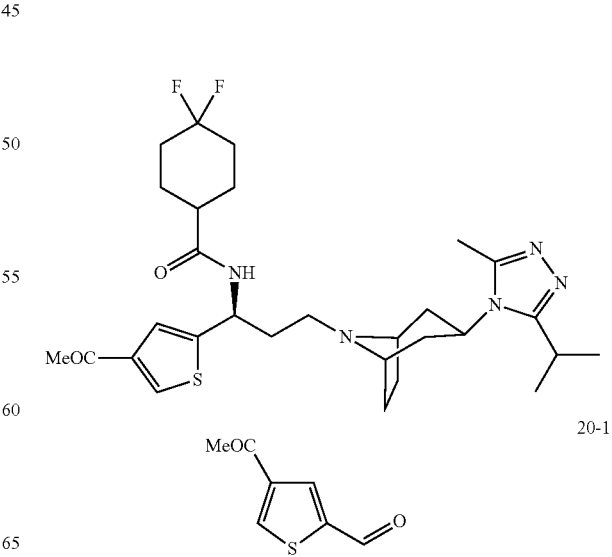

4,4-difluoro-N-[(1S)-3-[exo-3-(3-isopropyl-5-methyl-4H-1,2,4-triazol-4-yl)-8-azabicyclo[3.2.1]octane-8-yl]-1-(4-acetylthiophen-2-yl)propyl]cyclohexane-1-carboxamide According to the synthesis method of Example 5, Compound 20-1 was used to replace 2-1 in Example 5 and compound 2f was used to replace 1f in Example 5 to obtain compound 91, MS: 562.2 [M+H]+. ¹H-NMR (400 Hz, CDCl₃): δ8.07 (s, 1H), 7.15 (s, 1H), 5.19 (m,1H), 3.91 (m, 1H), 3.02 (m, 1H), 2.54 (s, 3H), 2.43 (m,5H), 2.27-1.95 (m,10H), 1.95-1.61 (m, 9H), 1.34 (d, 6H).

EXAMPLE 92

Synthesis of Compound 92

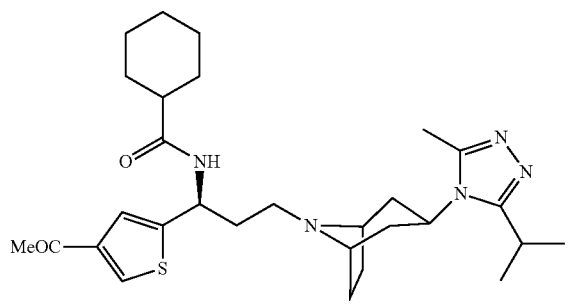

N-[(1S)-3-[exo-3-(3-isopropyl-5-methyl-4H-1,2,4-triazol-4-yl)-8-azabicyclo[3.2.1]octane-8-yl]-1-(4-acetylthiophen-2-yl)propyl]cyclohexane-1-carboxamide According to the synthesis method of Example 5, Compound 20-1 was used to replace 2-1 in Example 5, compound 2f was used to replace 1f in Example 5 and cyclohexanecarboxylic acid was used to replace 4,4-difluorocyclohexanecarboxylic acid in Example 5 to obtain compound 92, MS: 526.2 [M+H]+. ¹H-NMR (400 Hz, CDCl₃): δ8.13 (s, 1H), 7.14 (s, 1H), 5.19 (m,1H), 3.91 (m, 1H), 3.02 (m, 1H), 2.54 (s, 3H), 2.43 (m,5H), 2.26-1.93 (m,13H), 1.93-1.61 (m, 10H), 1.36 (d, 6H).

EXAMPLE 93

Synthesis of Compound 93

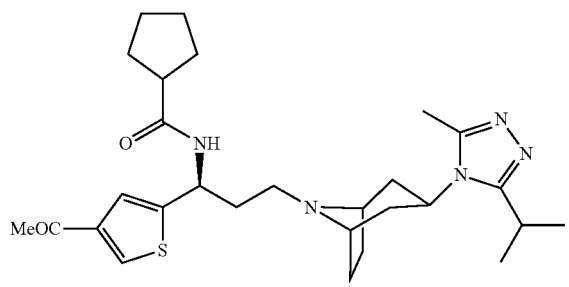

N-[(1S)-3-[exo-3-(3-isopropyl-5-methyl-4H-1,2,4-triazol-4-yl)-8-azabicyclo[3.2.1]octane-8-yl]-1-(4-acetylthiophen-2-yl)propyl]cyclopentane-1-carboxamide According to the synthesis method of Example 5, Compound 20-1 was used to replace 2-1 in Example 5, compound 2f was used to replace 1f in Example 5 and cyclopentanecarboxylic acid was used to replace 4,4-difluorocyclohexanecarboxylic acid in Example 5 to obtain compound 93, MS: 512.2 [M+H]+. ¹H-NMR (400 Hz, CDCl₃): δ8.10 (s, 1H), 6.97 (s, 1H), 5.19 (m,1H), 3.91 (m, 1H), 3.02 (m, 1H), 2.54 (s, 3H), 2.43 (m,5H), 2.27-1.93 (m,11H), 1.93-1.61 (m, 10H), 1.35 (d, 6H).

EXAMPLE 94

Synthesis of Compound 94

4,4-difluoro-N-[(1S)-3-[exo-3-(3-isopropyl-5-methyl-4H-1,2,4-triazol-4-yl)-8-azabicyclo[3.2.1]octane-8-yl]-1-(4,5-dimethylthiophen-2-yl)propyl]cyclohexane-1-carboxamide

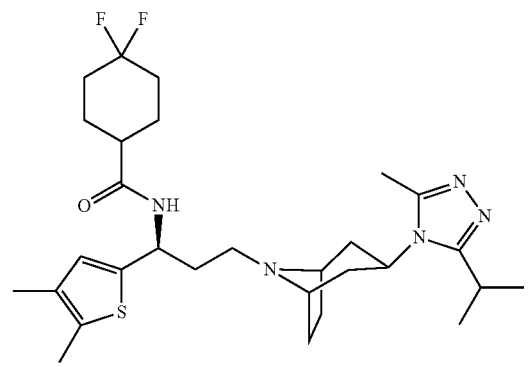

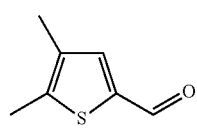

21-1

According to the synthesis method of Example 5, Compound 21-1 was used to replace 2-1 in Example 5 and compound 2f was used to replace 1f in Example 5 to obtain compound 94, MS: 548.2 [M+H]+. ¹H-NMR (400 Hz, CDCl₃): δ6.05 (s, 1H), 5.19 (m,1H), 3.91 (m, 1H), 3.02 (m, 1H), 2.54 (s, 3H), 2.43 (m,2H), 2.25 (s,6H), 2.17-1.95 (m,10H), 1.95-1.61 (m, 9H), 1.34 (d, 6H).

EXAMPLE 95

Synthesis of Compound 95

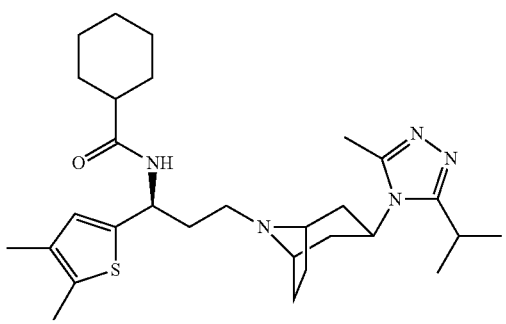 [SMILES: Cc1cc([C@H](CCN2C3CCC2CC(n2c(C)nnc2C(C)C)C3)NC(=O)C2CCCCC2)sc1C]

N-[(1S)-3-[exo-3-(3-isopropyl-5-methyl-4H-1,2,4-triazol-4-yl)-8-azabicyclo[3.2.1]octane-8-yl]-1-(4,5-dimethylthiophen-2-yl)propyl]cyclohexane-1-carboxamide According to the synthesis method of Example 5, Compound 21-1 was used to replace 2-1 in Example 5, compound 2f was used to replace if in Example 5 and cyclohexanecarboxylic acid was used to replace 4,4-difluorocyclohexanecarboxylic acid in Example 5 to obtain compound 95, MS: 512.2 [M+H]+. $^1$H-NMR (400 Hz, CDCl$_3$): δ6.04 (s, 1H), 5.19 (m,1H), 3.91 (m, 1H), 3.02 (m, 1H), 2.54 (s, 3H), 2.43 (m,2H), 2.25 (s,6H), 2.16-1.93 (m,13H), 1.93-1.61 (m, 10H), 1.36 (d, 6H).

EXAMPLE 96

Synthesis of Compound 96

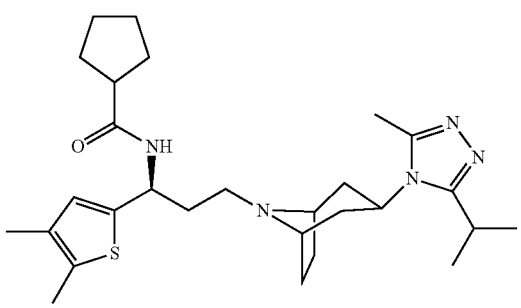 [SMILES: Cc1cc([C@H](CCN2C3CCC2CC(n2c(C)nnc2C(C)C)C3)NC(=O)C2CCCC2)sc1C]

N-[(1S)-3-[exo-3-(3-isopropyl-5-methyl-4H-1,2,4-triazol-4-yl)-8-azabicyclo[3.2.1]octane-8-yl]-1-(4,5-dimethylthiophen-2-yl)propyl]cyclopentane-1-carboxamide According to the synthesis method of Example 5, Compound 21-1 was used to replace 2-1 in Example 5, compound 2f was used to replace if in Example 5 and cyclopentanecarboxylic acid was used to replace 4,4-difluorocyclohexanecarboxylic acid in Example 5 to obtain compound 96, MS: 498.2 [M+H]+. $^1$H-NMR (400 Hz, CDCl$_3$): δ6.07 (s, 1H), 5.19 (m,1H), 3.91 (m, 1H), 3.02 (m, 1H), 2.54 (s, 3H), 2.43 (m,2H), 2.25 (s,6H), 2.17-1.93 (m,11H), 1.93-1.61 (m, 10H), 1.35 (d, 6H).

EXAMPLE 97

Synthesis of Compound 97

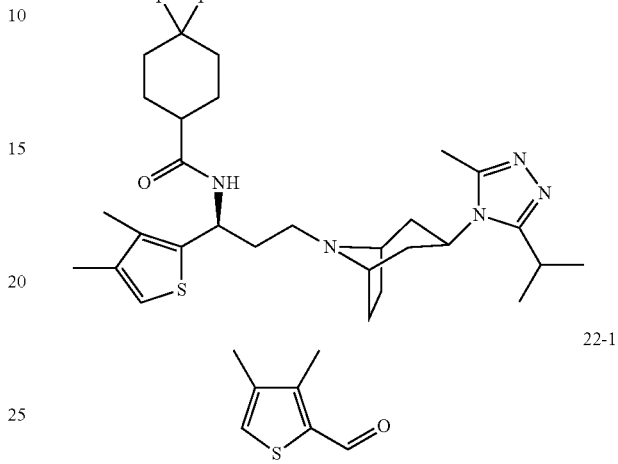

4,4-difluoro-N-[(1S)-3-[exo-3-(3-isopropyl-5-methyl-4H-1,2,4-triazol-4-yl)-8-azabicyclo[3.2.1]octane-8-yl]-1-(3,4-dimethylthiophen-2-yl)propyl]cyclohexane-1-carboxamide According to the synthesis method of Example 5, Compound 22-1 was used to replace 2-1 in Example 5 and compound 2f was used to replace if in Example 5 to obtain compound 97, MS: 548.2 [M+H]+. $^1$H-NMR (400 Hz, CDCl$_3$): δ6.05 (d, 1H), 5.19 (m,1H), 3.91 (m, 1H), 3.02 (m, 1H), 2.54 (s, 3H), 2.43 (m,2H), 2.25 (s,6H), 2.17-1.95 (m,10H), 1.95-1.61 (m, 9H), 1.34 (d, 6H).

EXAMPLE 98

Synthesis of Compound 98

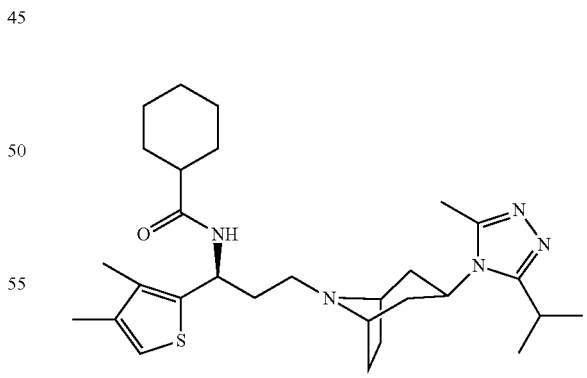

N-[(1S)-3-[exo-3-(3-isopropyl-5-methyl-4H-1,2,4-triazol-4-yl)-8-azabicyclo[3.2.1]octane-8-yl]-1-(3,4-dimethylthiophen-2-yl)propyl]cyclohexane-1-carboxamide According to the synthesis method of Example 5, Compound 22-1 was used to replace 2-1 in Example 5, compound 2f was used to replace if in Example 5 and cyclohexanecarboxylic acid was used to replace 4,4-difluoro-cyclohexanecarboxylic acid in Example 5 to obtain compound 98, MS: 512.2 [M+H]+. $^1$H-NMR (400 Hz, CDCl$_3$): δ6.04 (s, 1H), 5.19 (m,1H), 3.91 (m, 1H), 3.02 (m, 1H), 2.54 (s, 3H), 2.43 (m,2H), 2.25 (s,6H), 2.16-1.93 (m,13H), 1.93-1.61 (m, 10H), 1.36 (d, 6H).

EXAMPLE 99

Synthesis of Compound 99

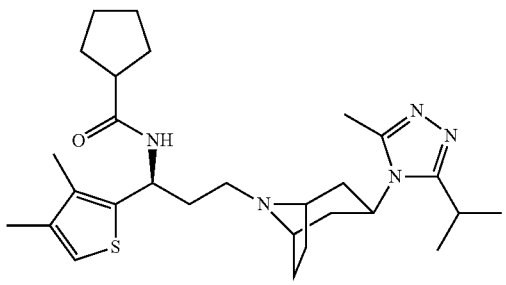 [SMILES: Cc1csc([C@H](CCN2C3CCC2CC(n2c(C)nnc2C(C)C)C3)NC(=O)C2CCCC2)c1C]

N-[(1S)-3-[exo-3-(3-isopropyl-5-methyl-4H-1,2,4-triazol-4-yl)-8-azabicyclo[3.2.1]octane-8-yl]-1-(3,4-dimethylthiophen-2-yl)propyl]cyclopentane-1-carboxamide According to the synthesis method of Example 5, Compound 22-1 was used to replace 2-1 in Example 5, compound 2f was used to replace if in Example 5 and cyclopentanecarboxylic acid was used to replace 4,4-difluoro-cyclohexanecarboxylic acid in Example 5 to obtain compound 99, MS: 498.2 [M+H]+. $^1$H-NMR (400 Hz, CDCl$_3$): δ6.07 (s, 1H), 5.19 (m,1H), 3.91 (m, 1H), 3.02 (m, 1H), 2.54 (s, 3H), 2.43 (m,2H), 2.25 (s,6H), 2.17-1.93 (m,11H), 1.93-1.61 (m, 10H), 1.35 (d, 6H).

EXAMPLE 100

Synthesis of Compound 100

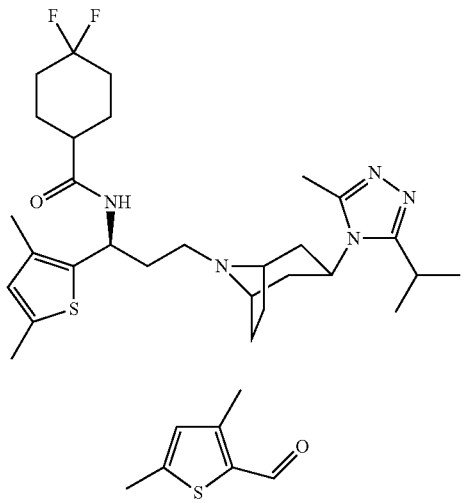

23-1

4,4-difluoro-N-[(1S)-3-[exo-3-(3-isopropyl-5-methyl-4H-1,2,4-triazol-4-yl)-8-azabicyclo[3.2.1]octane-8-yl]-1-(3,5-dimethylthiophen-2-yl)propyl]cyclohexane-1-carboxamide According to the synthesis method of Example 5, Compound 23-1 was used to replace 2-1 in Example 5 and compound 2f was used to replace if in Example 5 to obtain compound 100, MS: 548.2 [M+H]+. $^1$H-NMR (400 Hz, CDCl$_3$): δ6.15 (s, 1H), 5.19 (m,1H), 3.91 (m, 1H), 3.02 (m, 1H), 2.54 (s, 3H), 2.43 (m,2H), 2.29 (s,6H), 2.17-1.95 (m,10H), 1.95-1.61 (m, 9H), 1.34 (d, 6H).

EXAMPLE 101

Synthesis of Compound 101

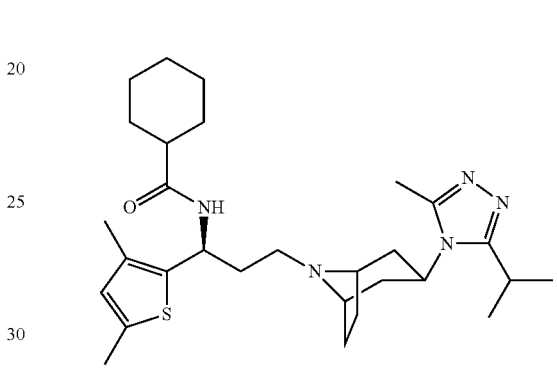

N-[(1S)-3-[exo-3-(3-isopropyl-5-methyl-4H-1,2,4-triazol-4-yl)-8-azabicyclo[3.2.1]octane-8-yl]-1-(3,5-dimethylthiophen-2-yl)propyl]cyclohexane-1-carboxamide According to the synthesis method of Example 5, Compound 23-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 101, MS: 512.2 [M+H]+. $^1$H-NMR (400 Hz, CDCl$_3$): δ6.14 (s, 1H), 5.19 (m,1H), 3.91 (m, 1H), 3.02 (m, 1H), 2.54 (s, 3H), 2.43 (m,2H), 2.29 (s,6H), 2.16-1.93 (m,13H), 1.93-1.61 (m, 10H), 1.36 (d, 6H).

EXAMPLE 102

Synthesis of Compound 102

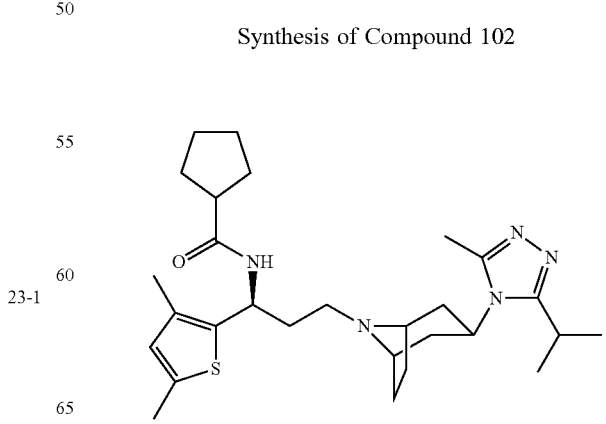

N-[(1S)-3-[exo-3-(3-isopropyl-5-methyl-4H-1,2,4-triazol-4-yl)-8-azabicyclo[3.2.1]octane-8-yl]-1-(3,5-dimethylthiophen-2-yl)propyl]cyclohexane-1-carboxamide According to the synthesis method of Example 5, Compound 23-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 102, MS: 498.21 [M+H]+. ¹H-NMR (400 Hz, CDCl₃): δ6.17 (s, 1H), 5.19 (m,1H), 3.91 (m, 1H), 3.02 (m, 1H), 2.54 (s, 3H), 2.43 (m,2H), 2.29 (s,6H), 2.17-1.93 (m,11H), 1.93-1.61 (m, 10H), 1.35 (d, 6H).

EXAMPLE 103

Synthesis of Compound 103

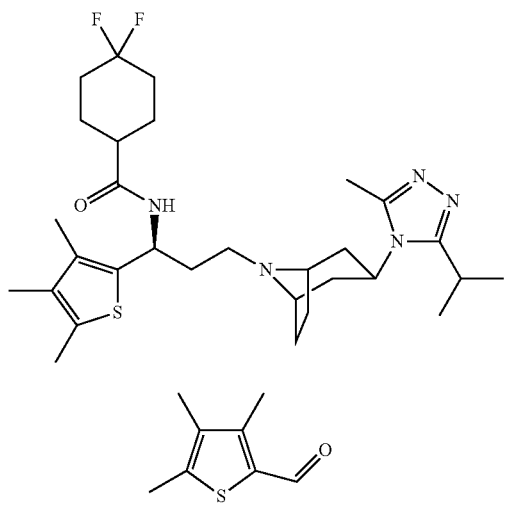

4,4-difluoro-N-[(1S)-3-[exo-3-(3-isopropyl-5-methyl-4H-1,2,4-triazol-4-yl)-8-azabicyclo[3.2.1]octane-8-yl]-1-(3,4,5-trimethylthiophen-2-yl)propyl]cyclohexane-1-carboxamide According to the synthesis method of Example 5, Compound 24-1 was used to replace compound 2-1 in Example 5 and compound 2f was used to replace compound 1f in Example 5 to obtain compound 103, MS: 562.2 [M+H]+. ¹H-NMR (400 Hz, CDCl₃): δ5.19 (m, 1H), 3.91 (m, 1H), 3.02 (m, 1H), 2.54 (s, 3H), 2.43 (m,2H), 2.26 (s,9H), 2.17-1.95 (m,10H), 1.95-1.61 (m, 9H), 1.34 (d, 6H).

EXAMPLE 104

Synthesis of Compound 104

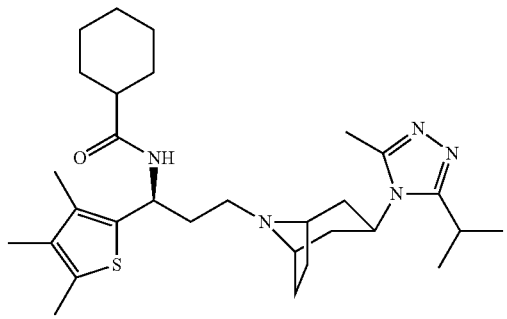 [SMILES: Cc1sc([C@H](CCN2C3CCC2CC(n2c(C)nnc2C(C)C)C3)NC(=O)C2CCCCC2)c(C)c1C]

N-[(1S)-3-[exo-3-(3-isopropyl-5-methyl-4H-1,2,4-triazol-4-yl)-8-azabicyclo[3.2.1]octane-8-yl]-1-(3,4,5-trimethylthiophen-2-yl)propyl]cyclohexane-1-carboxamide According to the synthesis method of Example 5, Compound 24-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 104, MS: 526.2 [M+H]+. ¹H-NMR (400 Hz, CDCl₃): δ5.19 (m,1H), 3.91 (m, 1H), 3.02 (m, 1H), 2.54 (s, 3H), 2.43 (m,2H), 2.27 (s,9H), 2.16-1.93 (m,13H), 1.93-1.61 (m, 10H), 1.36 (d, 6H).

EXAMPLE 105

Synthesis of Compound 105

N-[(1S)-3-[exo-3-(3-isopropyl-5-methyl-4H-1,2,4-triazol-4-yl)-8-azabicyclo[3.2.1]octane-8-yl]-1-(3,4,5-trimethylthiophen-2-yl)propyl]cyclopentane-1-carboxamide

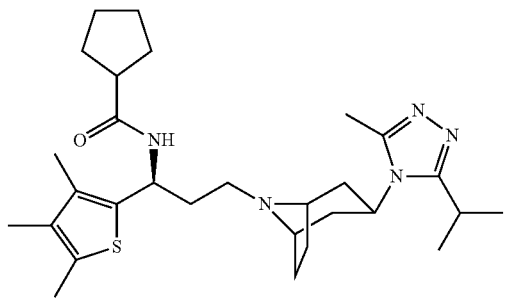 [SMILES: Cc1sc([C@H](CCN2C3CCC2CC(n2c(C)nnc2C(C)C)C3)NC(=O)C2CCCC2)c(C)c1C]

According to the synthesis method of Example 5, Compound 24-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 105, MS: 512.21 [M+H]+. ¹H-NMR (400 Hz, CDCl₃): δ5.19 (m,1H), 3.91 (m, 1H), 3.02 (m, 1H), 2.54 (s, 3H), 2.43 (m,2H), 2.29 (s,9H), 2.17-1.93 (m,11H), 1.93-1.61 (m, 10H), 1.35 (d, 6H).

EXAMPLE 106

Synthesis of Compound 106

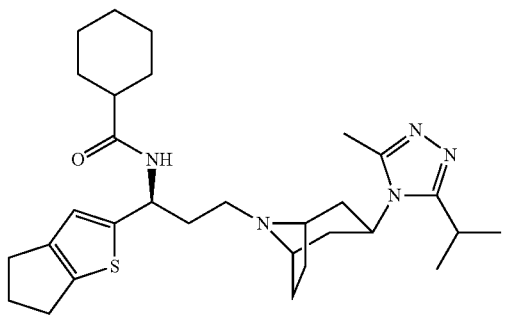

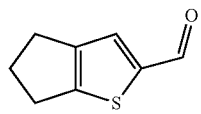

N-[(1S)-3-[exo-3-(3-isopropyl-5-methyl-4H-1,2,4-triazol-4-yl)-8-azabicyclo[3.2.1]octane-8-yl]-1-(5,6-dihydro-cyclopentathiophen-2-yl)propyl]cyclohexane-1-carboxamide According to the synthesis method of Example 5, Compound 25-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 106, MS: 524.2 [M+H]+. $^1$H-NMR (400 Hz, CDCl$_3$): δ6.83 (s, 1H), 5.19 (m,1H), 3.91 (m, 1H), 3.02 (m, 5H), 2.54 (s, 3H), 2.43 (m,4H), 2.16-1.93 (m,13H), 1.93-1.61 (m, 10H), 1.36 (d, 6H).

EXAMPLE 107

Synthesis of Compound 107

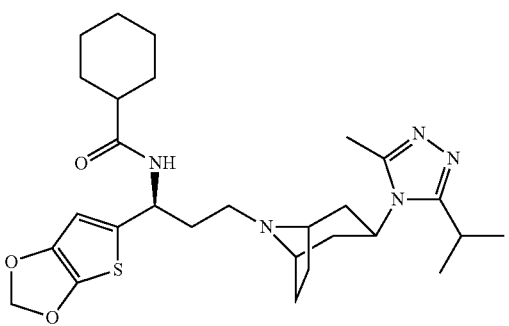

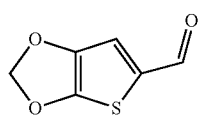

N-[(1S)-3-[exo-3-(3-isopropyl-5-methyl-4H-1,2,4-triazol-4-yl)-8-azabicyclo[3.2.1]octane-8-yl]-1-(thieno[2,3-d][1,3]dioxol-2-yl)propyl]cyclohexane-1-carboxamide According to the synthesis method of Example 5, Compound 26-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 107, MS: 528.21 [M+H]+. $^1$H-NMR (400 Hz, CDCl$_3$): δ6.03 (s,2H), 5.79 (m,1H), 3.91 (m, 1H), 3.02 (m, 1H), 2.54 (s, 3H), 2.43 (m,2H), 2.16-1.93 (m,13H), 1.93-1.61 (m, 10H), 1.36 (d, 6H).

EXAMPLE 108

Synthesis of Compound 108

N-[(1S)-3-[exo-3-(3-isopropyl-5-methyl-4H-1,2,4-triazol-4-yl)-8-azabicyclo[3.2.1]octane-8-yl]-1-(5-methoxythiophen-2-yl)propyl]cyclopentane-1-carboxamide

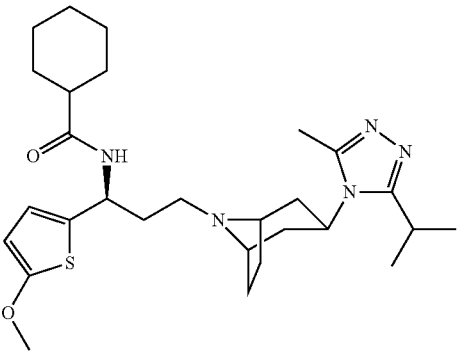

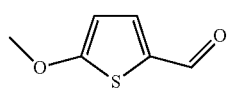

According to the synthesis method of Example 5, Compound 27-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 108, MS: 514.2 [M+H]+. $^1$H-NMR (400 Hz, CDCl$_3$): δ6.43 (m,2H), 5.79 (m,1H), 3.91 (m, 1H), 3.02 (m, 1H), 2.54 (s, 3H), 2.43 (m,5H), 2.16-1.93 (m,13H), 1.93-1.61 (m, 10H), 1.36 (d, 6H).

EXAMPLE 109

Synthesis of Compound 109

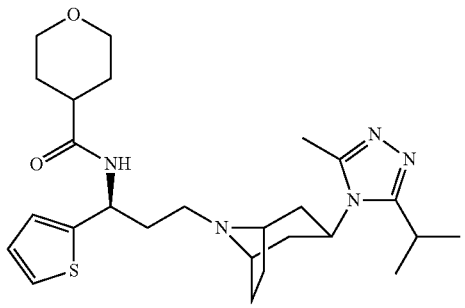 [SMILES: Cc1nnc(C(C)C)n1C1CC2CCC(C1)N2CC[C@H](NC(=O)C1CCOCC1)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]tetrahydropyran-4-carboxamide According to the synthesis method of Example 5, Compound 1-1 was used to replace compound 2-1 in Example 5, compound 2f was used to replace compound 1f in Example 5 and tetrahydropyran-4-carboxylic acid was used to replace 4,4-difluoro-cyclohexanecarboxylic acid in Example 5 to obtain compound 109, MS: 485.9 [M+H]+. $^1$H-NMR (400 Hz, CDCl$_3$): δ7.28 (t, 1H), 7.13 (d, 1H), 6.94 (d, 1H), 5.19 (m,1H), 3.91 (m, 1H), 3.61 (m, 4H), 3.02 (m, 1H), 2.54 (s, 3H), 2.43 (m,2H), 2.26-1.93 (m,13H), 1.93-1.61 (m, 6H), 1.36 (d, 6H).

EXAMPLE 110

Synthesis of Compound 110

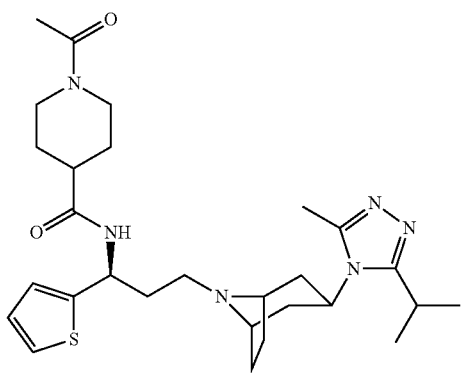 [SMILES: CC(=O)N1CCC(C(=O)N[C@@H](CCN2C3CCC2CC(n2c(C)nnc2C(C)C)C3)c2cccs2)CC1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-1-acetylpiperidine-4-carboxamide According to the synthesis method of Example 5, Compound 1-1 was used to replace compound 2-1 in Example 5, compound 2f was used to replace compound 1f in Example 5 and 1-acetyl-4-piperidinecarboxylic acid was used to replace 4,4-difluoro-cyclohexanecarboxylic acid in Example 5 to obtain compound 110, MS: 527.3 [M+H]+. $^1$H-NMR (400 Hz, CDCl$_3$): δ7.28 (t, 1H), 7.13 (d, 1H), 6.94 (d, 1H), 5.19 (m,1H), 3.91 (m, 1H), 3.31 (m, 4H), 3.02 (m, 1H), 2.54 (s, 3H), 2.43 (m,5H), 2.26-1.93 (m,13H), 1.93-1.61 (m, 6H), 1.36 (d, 6H).

EXAMPLE 111

Synthesis of Compound 111

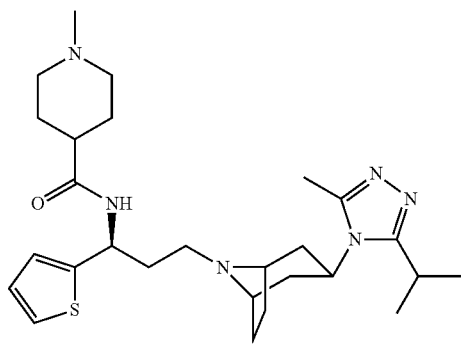 [SMILES: Cc1nnc(C(C)C)n1C1CC2CCC(C1)N2CC[C@H](NC(=O)C1CCN(C)CC1)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-1-methylpiperidine-4-carboxamide According to the synthesis method of Example 5, Compound 1-1 was used to replace compound 2-1 in Example 5, compound 2f was used to replace compound 1f in Example 5 and 1-methylpiperidine-4-carboxylic acid was used to replace 4,4-difluoro-cyclohexanecarboxylic acid in Example 5 to obtain compound 111, MS: 499.3 [M+H]+. $^1$H-NMR (400 Hz, CDCl$_3$): δ7.28 (t, 1H), 7.13 (d, 1H), 6.94 (d, 1H), 5.19 (m,1H), 3.91 (m, 1H), 3.02 (m, 1H), 2.51 (m, 7H), 2.43 (m,5H), 2.26-1.93 (m,13H), 1.93-1.61 (m, 6H), 1.36 (d, 6H).

EXAMPLE 112

Synthesis of Compound 112

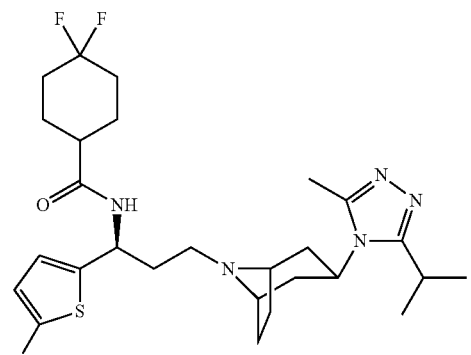

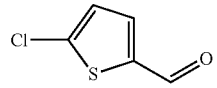

28-1

4,4-difluoro-N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]cyclohexane-1-carboxamide According to the synthesis method of Example 5, Compound 28-1 was used to replace compound 2-1 in Example 5 and compound 2f was used to replace compound 1f in Example 5 to obtain compound 112, MS: 554.25 [M+H]+. $^1$H-NMR (400 Hz, CDCl$_3$): δ6.67 (m, 2H), 4.78 (m,1H), 3.70 (m, 1H), 3.18 (m, 1H), 2.38-2.43 (m, 3H), 2.36 (s,3H), 1.40-1.82 (m,20H), 1.26 (d, 6H).

EXAMPLE 113

Synthesis of Compound 113

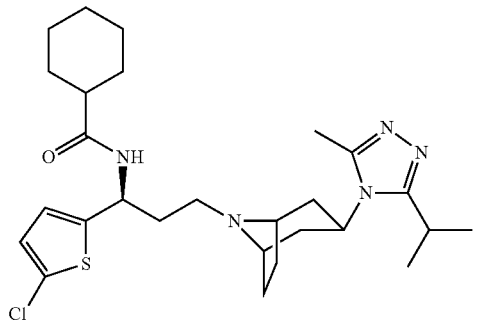 [SMILES: Cc1nnc(C(C)C)n1C1CC2CCC(C1)N2CC[C@H](NC(=O)C1CCCCC1)c1ccc(Cl)s1]

N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]cyclohexane-1-carboxamide According to the synthesis method of Example 5, Compound 28-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 113, MS: 518.26 [M+H]+. $^1$H-NMR (400 Hz, CDCl$_3$): δ6.65-6.80 (m, 2H), 4.78 (m,1H), 3.72 (m, 1H), 3.20 (m, 1H), 2.31-2.45 (m, 3H), 2.33 (s,3H), 1.44-1.82 (m,22H), 1.36 (d, 6H).

EXAMPLE 114

Synthesis of Compound 114

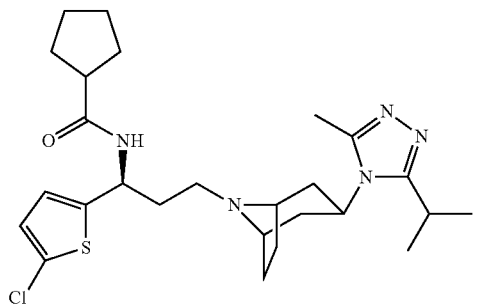 [SMILES: Cc1nnc(C(C)C)n1C1CC2CCC(C1)N2CC[C@H](NC(=O)C1CCCC1)c1ccc(Cl)s1]

N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]cyclopentane-1-carboxamide According to the synthesis method of Example 5, Compound 28-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 114, MS: 504.25 [M+H]+. $^1$H-NMR (400 Hz, CDCl$_3$): δ6.65-6.80 (m, 2H), 4.78 (m,1H), 3.72 (m, 1H), 3.20 (m, 1H), 2.31-2.45 (m, 3H), 2.33 (s,3H), 1.44-1.82 (m,20H), 1.36 (d, 6H).

EXAMPLE 115

Synthesis of Compound 115

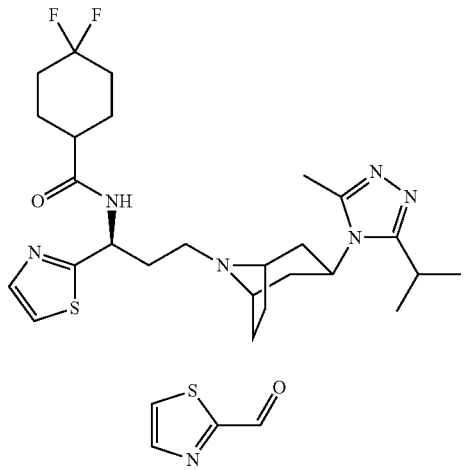

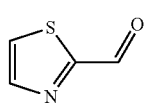

29-1

4,4-difluoro-N-[(1S)-3-[exo-3-(3-isopropyl-5-methyl-4H-1,2,4-triazol-4-yl)-8-azabicyclo[3.2.1]octane-8-yl]-1-(thiazol-2-yl)propyl]cyclohexane-1-carboxamide According to the synthesis method of Example 5, Compound 29-1 was used to replace compound 2-1 in Example 5 and compound 2f was used to replace compound 1f in Example 5 to obtain compound 115, MS: 521.28 [M+H]+. $^1$H-NMR (400 Hz, CDCl$_3$): δ7.67 (d, 1H), 7.20 (d, 1H), 4.78 (m,1H), 3.72 (m, 1H), 3.20 (m, 1H), 2.31-2.45 (m, 3H), 2.36 (s,3H), 1.44-1.82 (m,20H), 1.36 (d, 6H).

EXAMPLE 116

Synthesis of Compound 116

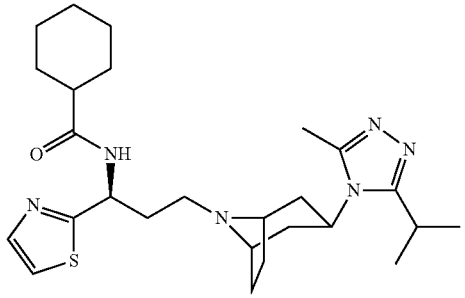 [SMILES: Cc1nnc(C(C)C)n1C1CC2CCC(C1)N2CC[C@H](NC(=O)C1CCCCC1)c1nccs1]

N-[(1S)-3-[exo-3-(3-isopropyl-5-methyl-4H-1,2,4-triazol-4-yl)-8-azabicyclo[3.2.1]octane-8-yl]-1-(thiazol-2-yl)propyl]cyclohexane-1-carboxamide According to the synthesis method of Example 5, Compound 29-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 116, MS: 485.30 [M+H]+. $^1$H-NMR (400 Hz, CDCl$_3$): δ7.65 (d, 1H), 7.23 (d, 1H), 4.74 (m,1H), 3.71 (m, 1H), 3.21 (m, 1H), 2.31-2.45 (m, 3H), 2.33 (s,3H), 1.34-1.83 (m,22H), 1.26 (d, 6H).

EXAMPLE 117

Synthesis of Compound 117

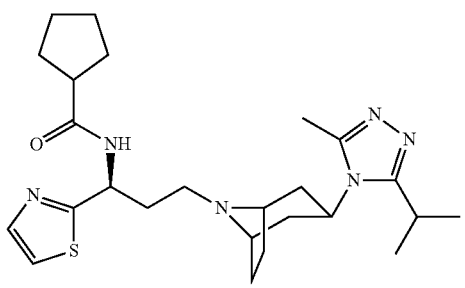 [SMILES: Cc1nnc(C(C)C)n1C1CC2CCC(C1)N2CC[C@H](NC(=O)C1CCCC1)c1nccs1]

N-[(1S)-3-[exo-3-(3-isopropyl-5-methyl-4H-1,2,4-triazol-4-yl)-8-azabicyclo[3.2.1]octane-8-yl]-1-(thiazol-2-yl)propyl]cyclopentane-1-carboxamide According to the synthesis method of Example 5, Compound 29-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 117, MS: 471.28 [M+H]+. $^1$H-NMR (400 Hz, CDCl$_3$): δ7.62 (d, 1H), 7.22 (d, 1H), 4.73 (m,1H), 3.74 (m, 1H), 3.22 (m, 1H), 2.31-2.45 (m, 3H), 2.33 (s,3H), 1.44-1.82 (m,20H), 1.33 (d, 6H).

EXAMPLE 118

Synthesis of Compound 118

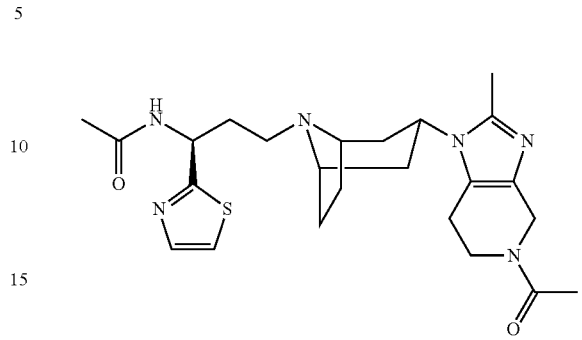

N-{(1S)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]-1-(thiazol-2-yl)-propyl}acetamide According to the synthesis method of compound 40, Compound 29-1 was used to replace compound 3-1 in Example 40 to obtain compound 118, MS: 471.25 [M+H]+. $^1$H-NMR (400 Hz, CDCl$_3$): δ7.65 (d, 1H), 7.26 (d, 1H), 4.78 (t,1H), 4.38 (m,2H), 3.86 (m,2H), 3.74 (m, 1H), 2.66 (m, 2H), 2.53 (s, 3H), 2.43 (m, 2H), 2.32 (s, 3H), 1.44-2.12 (m, 15H).

EXAMPLE 119

Synthesis of Compound 119

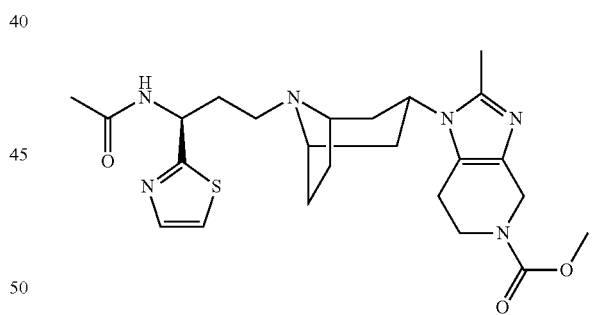

Methyl 1-{(endo)-8-[(S)-3-acetamido-3-(thiazol-2-yl)-propyl]-8-azabicyclo[3.2.1]octan-3-yl}-2-methyl-1,4,6,7-tetrahydro-5H-imidazo[4,5-c]pyridine-5-carboxylate According to the synthesis method of compound 40, Compound 29-1 was used to replace compound 3-1 in Example 40 and methyl chloroformate was used to replace acetyl chloride in Example 40 to obtain compound 119, MS: 487.24 [M+H]+. $^1$H-NMR (400 Hz, CDCl$_3$): δ7.65 (d, 1H), 7.26 (d, 1H), 4.78 (t,1H), 4.18 (m,2H), 3.76 (s, 3H), 3.65-3.733 (m, 3H), 2.66 (m, 2H), 2.43 (m, 2H), 2.32 (s, 3H), 1.44-2.12 (m, 15H).

EXAMPLE 120

Synthesis of Compound 120

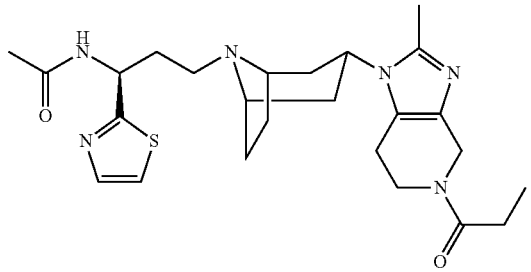 [SMILES: CCC(=O)N1CCc2c(nc(C)n2C2CC3CCC(C2)N3CC[C@H](NC(C)=O)c2nccs2)C1]

N-{(1S)-3-[(3-endo)-3-(5-propionyl-2-methyl-4,5,6,
7-tetrahydro-1H-imidazo[4,5-c]pyridin-1-yl)-8-
azabicyclo[3.2.1]octane-8-yl]-1-(thiazol-2-yl)-
propyl}acetamide According to the synthesis method of compound 40, Compound 29-1 was used to replace compound 3-1 in Example 40 and propionyl chloride was used to replace acetyl chloride in Example 40 to obtain compound 120, MS: 485.26 [M+H]+. $^1$H-NMR (400 Hz, CDCl$_3$): δ7.65 (d, 1H), 7.26 (d, 1H), 4.78 (t,1H), 4.38 (m, 2H), 3.86 (m, 2H), 3.74 (m, 1H), 2.66 (m, 2H), 2.53 (s, 3H), 2.43 (m, 2H), 2.27 (q, 2H), 1.44-2.12 (m, 15H), 1.21 (t, 3H).

EXAMPLE 121

Synthesis of Compound 121

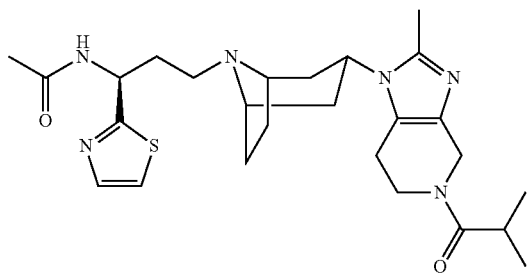 [SMILES: CC(=O)N[C@@H](CCN1C2CCC1CC(n1c(C)nc3c1CCN(C(=O)C(C)C)C3)C2)c1nccs1]

N-{(1S)-3-[(3-endo)-3-(5-isobutyryl-2-methyl-4,5,6,
7-tetrahydro-1H-imidazo[4,5-c]pyridin-1-yl)-8-
azabicyclo[3.2.1]octane-8-yl]-1-(thiazol-2-yl)-
propyl}acetamide According to the synthesis method of compound 40, Compound 29-1 was used to replace compound 3-1 in Example 40 and isobutyryl chloride was used to replace acetyl chloride in Example 40 to obtain compound 121, MS: 499.28 [M+H]+. $^1$H-NMR (400 Hz, CDCl$_3$): δ7.65 (d, 1H), 7.26 (d, 1H), 4.78 (t,1H), 4.38 (m, 2H), 3.86 (m, 2H), 3.74 (m, 1H), 2.66-2.69 (m, 3H), 2.53 (s, 3H), 2.43 (m, 2H), 1.44-2.12 (m, 15H), 1.10 (d, 6H).

EXAMPLE 122

Synthesis of Compound 122

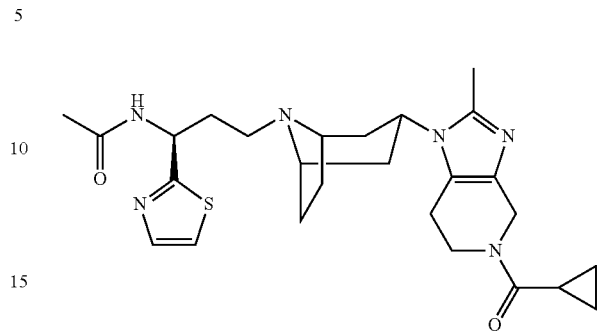

N-{(1S)-3-[(3-endo)-3-(5-cyclopropionyl-2-methyl-
4,5,6,7-tetrahydro-1H-imidazo[4,5-c]pyridin-1-yl)-8-
azabicyclo[3.2.1]octane-8-yl]-1-(thiazol-2-yl)-
propyl}acetamide According to the synthesis method of compound 40, Compound 29-1 was used to replace compound 3-1 in Example 40 and cyclopropionyl chloride was used to replace acetyl chloride in Example 40 to obtain compound 122, MS: 497.26 [M+H]+. $^1$H-NMR (400 Hz, CDCl$_3$): δ7.65 (d, 1H), 7.26 (d, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 1.44-2.12 (m, 16H), 0.53-0.78 (m, 4H).

EXAMPLE 123

Synthesis of Compound 123

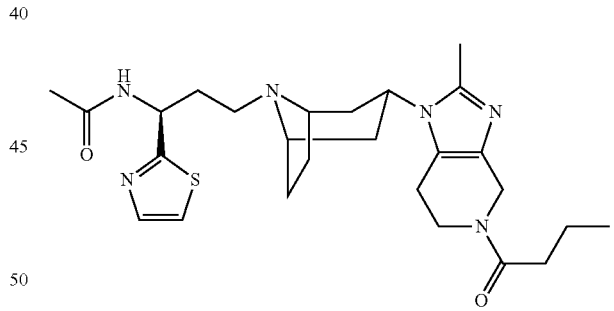

N-{(1S)-3-[(3-endo)-3-(5-n-butyryl-2-methyl-4,5,6,
7-tetrahydro-1H-imidazo[4,5-c]pyridin-1-yl)-8-
azabicyclo[3.2.1]octane-8-yl]-1-(thiazol-2-yl)-
propyl}acetamide According to the synthesis method of compound 40, Compound 29-1 was used to replace compound 3-1 in Example 40 and n-butyryl chloride was used to replace acetyl chloride in Example 40 to obtain compound 123, MS: 499.28 [M+H]+. $^1$H-NMR (400 Hz, CDCl$_3$): δ7.65 (d, 1H), 7.26 (d, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 2.34 (m, 2H), 1.44-2.12 (m, 17H), 0.96 (t, 3H).

EXAMPLE 124

Synthesis of Compound 124

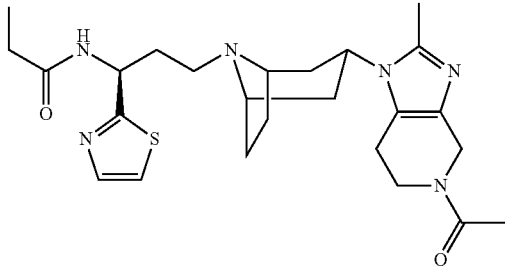 [SMILES: CCC(=O)N[C@@H](CCN1C2CCC1CC(n1c(C)nc3c1CCN(C(C)=O)C3)C2)c1nccs1]

N-{(1S)-3-[(3-endo)-3-(5-acetyl-2-methyl-4,5,6,7-tetrahydro-1H-imidazo[4,5-c]pyridin-1-yl)-8-azabi-cyclo[3.2.1]octane-8-yl]-1-(thiazol-2-yl)-propyl}propanamide According to the synthesis method of compound 40, Compound 29-1 was used to replace compound 3-1 in Example 40, propionic acid was used to replace acetic acid in Example 40 and n-butyryl chloride was used to replace acetyl chloride in Example 40 to obtain compound 124, MS: 485.26 [M+H]+. $^1$H-NMR (400 Hz, CDCl$_3$): δ7.65 (d, 1H), 7.26 (d, 1H), 4.78 (t,1H), 4.38 (m,2H), 3.86 (m,2H), 3.74 (m, 1H), 2.66 (m, 2H), 2.53 (s, 3H), 2.43 (m, 2H), 2.32 (s, 3H), 2.23 (q, 2H), 1.44-1.96 (m, 12H), 1.11 (t, 3H).

EXAMPLE 125

Synthesis of Compound 125

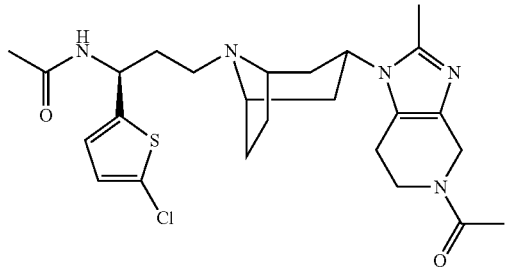 [SMILES: CC(=O)N[C@@H](CCN1C2CCC1CC(n1c(C)nc3c1CCN(C(C)=O)C3)C2)c1ccc(Cl)s1]

N-{(1S)-3-[(3-endo)-3-(5-acetyl-2-methyl-4,5,6,7-tetrahydro-1H-imidazo[4,5-c]pyridin-1-yl)-8-azabi-cyclo[3.2.1]octane-8-yl]-1-(5-chlorothiophen-2-yl)-propyl}acetamide According to the synthesis method of compound 40, Compound 28-1 was used to replace compound 3-1 in Example 40 to obtain compound 125, MS: 504.21 [M+H]+. $^1$H-NMR (400 Hz, CDCl$_3$): δ6.65 (d, 1H), 6.26 (d, 1H), 4.78 (t,1H), 4.38 (m,2H), 3.86 (m,2H), 3.74 (m, 1H), 2.66 (m, 2H), 2.53 (s, 3H), 2.43 (m, 2H), 2.32 (s, 3H), 1.44-2.12 (m, 15H).

EXAMPLE 126

Synthesis of Compound 126

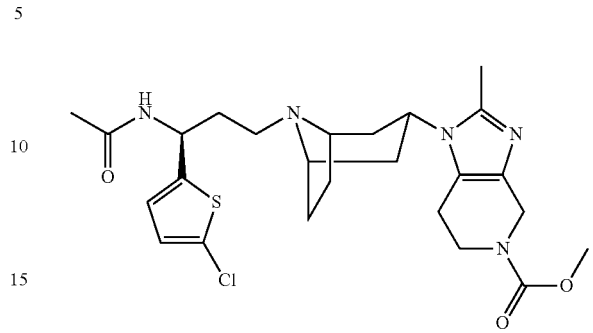

Methyl 1-{(endo)-8-[(S)-3-acetamido-3-(5-chlorothiophen-2-yl)-propyl]-8-azabicyclo[3.2.1]octan-3-yl}-2-methyl-1,4,6,7-tetrahydro-5H-imidazo[4,5-c]pyridine-5-carboxylate According to the synthesis method of compound 40, Compound 28-1 was used to replace compound 3-1 in Example 40 and methyl chloroformate was used to replace acetyl chloride in Example 40 to obtain compound 126, MS: 520.21 [M+H]+. $^1$H-NMR (400 Hz, CDCl$_3$): δ6.45 (d, 1H), 6.16 (d, 1H), 4.78 (t,1H), 4.18 (m,2H), 3.76 (s, 3H), 3.65-3.733 (m, 3H), 2.66 (m, 2H), 2.43 (m, 2H), 2.32 (s, 3H), 1.44-2.12 (m, 15H).

EXAMPLE 127

Synthesis of Compound 127

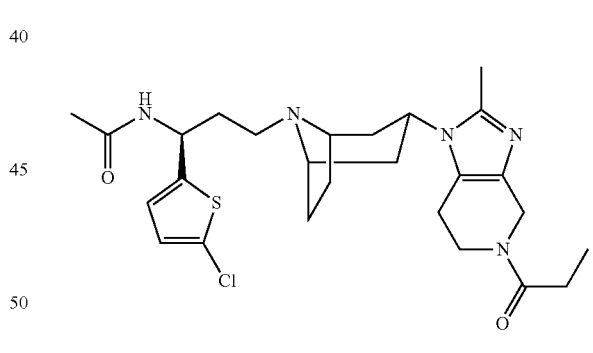

N-{(1S)-3-[(3-endo)-3-(5-propionyl-2-methyl-4,5,6,7-tetrahydro-1H-imidazo[4,5-c]pyridin-1-yl)-8-azabicyclo[3.2.1]octane-8-yl]-1-(5-chlorothiophen-2-yl)-propyl}acetamide According to the synthesis method of compound 40, Compound 28-1 was used to replace compound 3-1 in Example 40 and propionyl chloride was used to replace acetyl chloride in Example 40 to obtain compound 127, MS: 518.23 [M+H]+. $^1$H-NMR (400 Hz, CDCl$_3$): δ6.45 (d, 1H), 6.16 (d, 1H), 4.78 (t,1H), 4.38 (m,2H), 3.86 (m,2H), 3.74 (m, 1H), 2.66 (m, 2H), 2.53 (s, 3H), 2.43 (m, 2H), 2.27 (q, 2H), 1.44-2.12 (m, 15H), 1.21 (t, 3H).

EXAMPLE 128

Synthesis of Compound 128

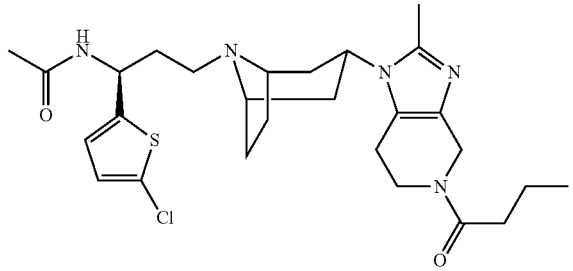 [SMILES: CCCC(=O)N1CCc2c(nc(C)n2C2CC3CCC(C2)N3CC[C@H](NC(C)=O)c2ccc(Cl)s2)C1]

N-{(1S)-3-[(3-endo)-3-(5-n-butyryl-2-methyl-4,5,6,7-tetrahydro-1H-imidazo[4,5-c]pyridin-1-yl)-8-azabicyclo[3.2.1]octane-8-yl]-1-(5-chlorothiophen-2-yl)-propyl}acetamide According to the synthesis method of compound 40, Compound 28-1 was used to replace compound 3-1 in Example 40 and n-butyryl chloride was used to replace acetyl chloride in Example 40 to obtain compound 128, MS: 532.24 [M+H]+. $^1$H-NMR (400 Hz, CDCl$_3$): δ6.48 (d, 1H), 6.12 (d, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 2.34 (m, 2H), 1.44-2.12 (m, 17H), 0.96 (t, 3H).

EXAMPLE 129

Synthesis of Compound 129

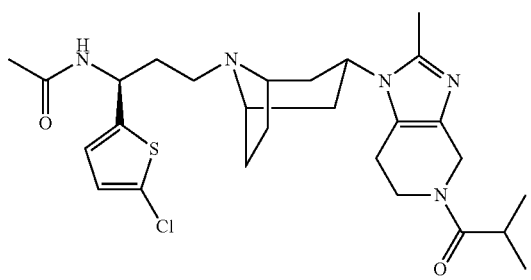 [SMILES: CC(=O)N[C@@H](CCN1C2CCC1CC(n1c(C)nc3c1CCN(C(=O)C(C)C)C3)C2)c1ccc(Cl)s1]

N-{(1S)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]-1-(5-chlorothiophen-2-yl)-propyl}acetamide According to the synthesis method of compound 40, Compound 28-1 was used to replace compound 3-1 in Example 40 and isobutyryl chloride was used to replace acetyl chloride in Example 40 to obtain compound 129, MS: 532.24 [M+H]+. $^1$H-NMR (400 Hz, CDCl$_3$): δ6.48 (d, 1H), 6.12 (d, 1H), 4.78 (t,1H), 4.38 (m,2H), 3.86 (m,2H), 3.74 (m, 1H), 2.66-2.69 (m, 3H), 2.53 (s, 3H), 2.43 (m, 2H), 1.44-2.12 (m, 15H), 1.10 (d, 6H).

EXAMPLE 130

Synthesis of Compound 130

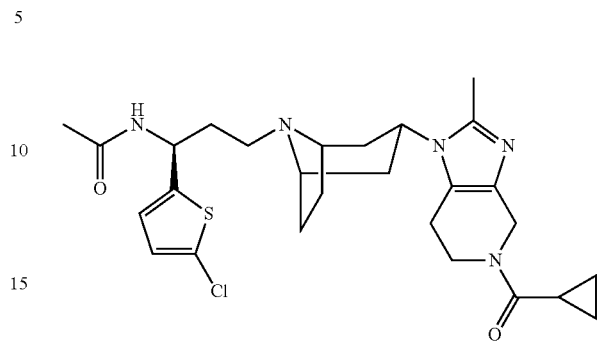

N-{(1S)-3-[(3-endo)-3-(5-cyclopropionyl-2-methyl-4,5,6,7-tetrahydro-1H-imidazo[4,5-c]pyridin-1-yl)-8-azabicyclo[3.2.1]octane-8-yl]-1-(5-chlorothiophen-2-yl)-propyl}acetamide According to the synthesis method of compound 40, Compound 28-1 was used to replace compound 3-1 in Example 40 and cyclopropionyl chloride was used to replace acetyl chloride in Example 40 to obtain compound 130, MS: 530.23 [M+H]+. $^1$H-NMR (400 Hz, CDCl$_3$): δ6.78 (d, 1H), 6.22 (d, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 1.44-2.12 (m, 16H), 0.53-0.78 (m, 4H).

EXAMPLE 131

Synthesis of Compound 131

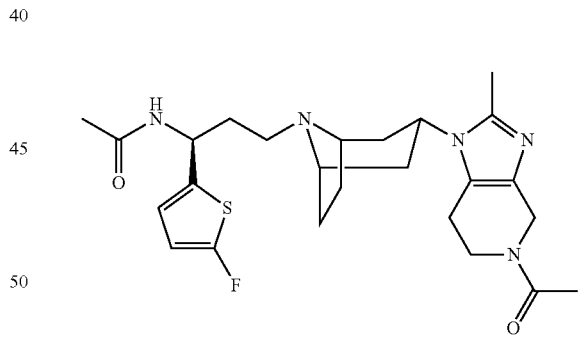

N-{(1S)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]-1-(5-fluorothiophen-2-yl)-propyl}acetamide According to the synthesis method of compound 40, Compound 7-1 was used to replace compound 3-1 in Example 40 to obtain compound 131, MS: 488.24 [M+H]+. $^1$H-NMR (400 Hz, CDCl$_3$): δ6.46 (m, 1H), 6.27 (m, 1H), 4.78 (t,1H), 4.38 (m,2H), 3.86 (m,2H), 3.74 (m, 1H), 2.66 (m, 2H), 2.53 (s, 3H), 2.43 (m, 2H), 2.32 (s, 3H), 1.44-2.12 (m, 15H).

EXAMPLE 132

Synthesis of Compound 132

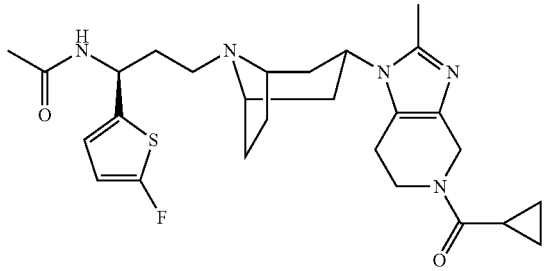 [SMILES: CC(=O)N[C@@H](CCN1C2CCC1CC(n1c(C)nc3c1CCN(C(=O)C1CC1)C3)C2)c1ccc(F)s1]

N-{(1S)-3-[(3-endo)-3-(5-cyclopropionyl-2-methyl-4,5,6,7-tetrahydro-1H-imidazo[4,5-c]pyridin-1-yl)-8-azabicyclo[3.2.1]octane-8-yl]-1-(5-fluorothiophen-2-yl)-propyl}acetamide According to the synthesis method of compound 40, Compound 7-1 was used to replace compound 3-1 in Example 40 and cyclopropionyl chloride was used to replace acetyl chloride in Example 40 to obtain compound 132, MS: 514.26 [M+H]+. $^1$H-NMR (400 Hz, CDCl$_3$): δ6.36 (m, 1H), 6.15 (m, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 1.44-2.12 (m, 16H), 0.53-0.78 (m, 4H).

EXAMPLE 133

Synthesis of Compound 133

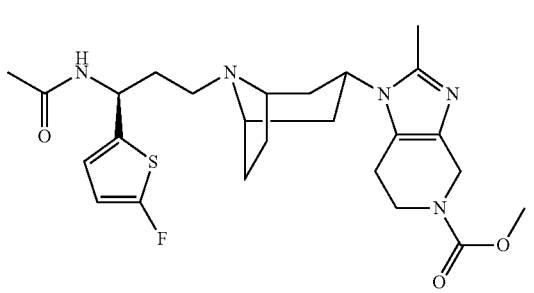

Methyl 1-{(endo)-8-[(S)-3-acetamido-3-(5-fluorothiophen-2-yl)-propyl]-8-azabicyclo[3.2.1]octan-3-yl}-2-methyl-1,4,6,7-tetrahydro-5H-imidazo[4,5-c]pyridine-5-carboxylate According to the synthesis method of compound 40, Compound 7-1 was used to replace compound 3-1 in Example 40 and methyl chloroformate was used to replace acetyl chloride in Example 40 to obtain compound 133, MS: 504.24 [M+H]+. $^1$H-NMR (400 Hz, CDCl$_3$): δ6.47 (m, 1H), 6.25 (m, 1H), 4.78 (t,1H), 4.18 (m,2H), 3.76 (s, 3H), 3.65-3.733 (m, 3H), 2.66 (m, 2H), 2.43 (m, 2H), 2.32 (s, 3H), 1.44-2.12 (m, 15H).

EXAMPLE 134

Synthesis of Compound 134

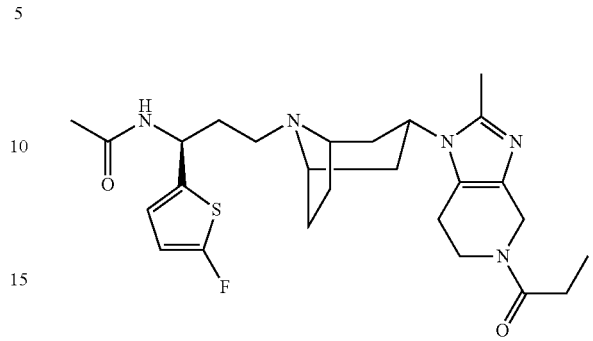

N-{(1S)-3-[(3-endo)-3-(5-propionyl-2-methyl-4,5,6,7-tetrahydro-1H-imidazo[4,5-c]pyridin-1-yl)-8-azabicyclo[3.2.1]octane-8-yl]-1-(5-fluorothiophen-2-yl)-propyl}acetamide According to the synthesis method of compound 40, Compound 7-1 was used to replace compound 3-1 in Example 40 and propionyl chloride was used to replace acetyl chloride in Example 40 to obtain compound 134, MS: 502.26 [M+H]+. $^1$H-NMR (400 Hz, CDCl$_3$): δ6.48 (m, 1H), 6.23 (m, 1H), 4.78 (t,1H), 4.38 (m,2H), 3.86 (m,2H), 3.74 (m, 1H), 2.66 (m, 2H), 2.53 (s, 3H), 2.43 (m, 2H), 2.27 (q, 2H), 1.44-2.12 (m, 15H), 1.21 (t, 3H).

EXAMPLE 135

Synthesis of Compound 135

N-{(1S)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]-1-(5-fluorothiophen-2-yl)-propyl}acetamide

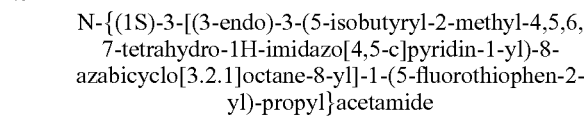
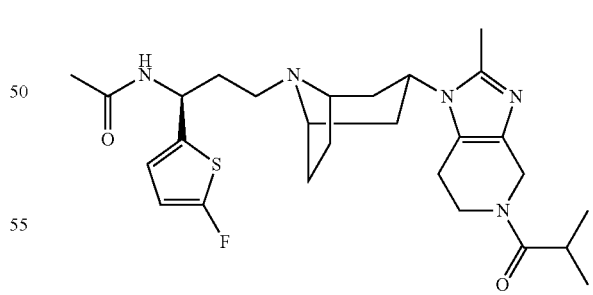

According to the synthesis method of compound 40, Compound 7-1 was used to replace compound 3-1 in Example 40 and isobutyryl chloride was used to replace acetyl chloride in Example 40 to obtain compound 135, MS: 516.27 [M+H]+. $^1$H-NMR (400 Hz, CDCl$_3$): δ6.42 (m, 1H), 6.13 (m, 1H), 4.78 (t,1H), 4.38 (m,2H), 3.86 (m,2H), 3.74 (m, 1H), 2.66-2.69 (m, 3H), 2.53 (s, 3H), 2.43 (m, 2H), 1.44-2.12 (m, 15H), 1.10 (d, 6H).

EXAMPLE 136

Synthesis of Compound 136

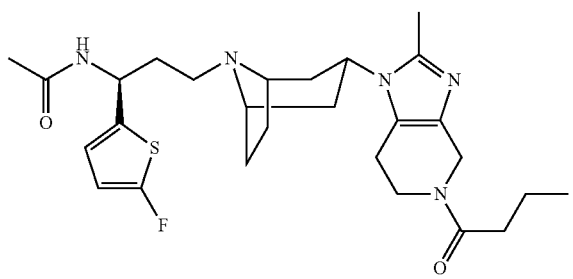 [SMILES: CCCC(=O)N1CCc2c(nc(C)n2C2CC3CCC(C2)N3CC[C@H](NC(C)=O)c2ccc(F)s2)C1]

N-{(1S)-3-[(3-endo)-3-(5-n-butyryl-2-methyl-4,5,6,7-tetrahydro-1H-imidazo[4,5-c]pyridin-1-yl)-8-azabicyclo[3.2.1]octane-8-yl]-1-(5-fluorothiophen-2-yl)-propyl}acetamide According to the synthesis method of compound 40, Compound 7-1 was used to replace compound 3-1 in Example 40 and n-butyryl chloride was used to replace acetyl chloride in Example 40 to obtain compound 136, MS: 516.27 [M+H]+. $^1$H-NMR (400 Hz, CDCl$_3$): δ6.41 (m, 1H), 6.12 (m, 1H), 4.78 (t,1H), 4.38 (m,2H), 3.86 (m,2H), 3.74 (m, 1H), 2.66-2.69 (m, 2H), 2.53 (s, 3H), 2.43 (m, 2H), 2.34 (m, 2H), 1.44-2.12 (m, 17H), 0.96 (t, 3H).

EXAMPLE 137

Synthesis of Compound 137

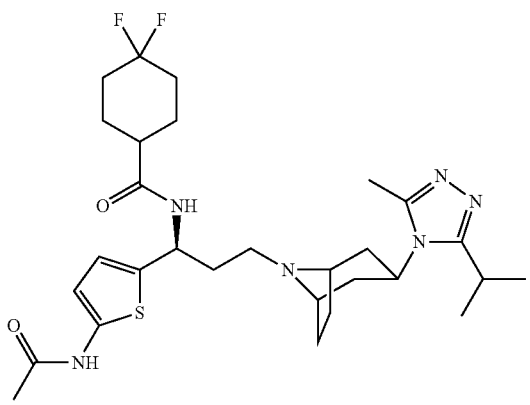

4,4-difluoro-N-[(1S)-3-[exo-3-(3-isopropyl-5-methyl-4H-1,2,4-triazol-4-yl)-8-azabicyclo[3.2.1]octane-8-yl]-1-(acetamidothiophen-2-yl)propyl]cyclohexane-1-carboxamide According to the synthesis method of Example 5, Compound 30-1 was used to replace compound 2-1 in Example 5 and compound 2f was used to replace compound 1f in Example 5 to obtain compound 137, MS: 577.31 [M+H]+. $^1$H-NMR (400 Hz, CDCl$_3$): δ7.32 (d, 1H), 7.07 (d, 1H), 4.74 (m,1H), 3.71 (m, 1H), 3.21 (m, 1H), 2.31-2.45 (m, 6H), 2.33 (s,3H), 1.34-1.83 (m,20H), 1.26 (d, 6H).

EXAMPLE 138

Synthesis of Compound 138

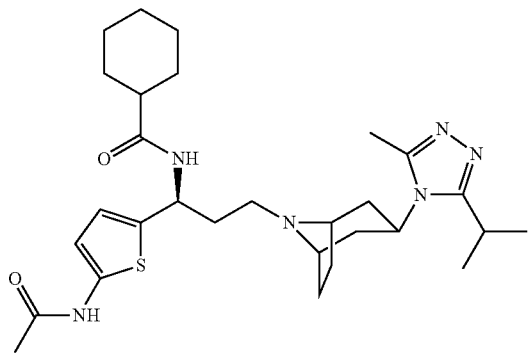 [SMILES: CC(=O)Nc1ccc([C@H](CCN2C3CCC2CC(n2c(C)nnc2C(C)C)C3)NC(=O)C2CCCCC2)s1]

N-[(1S)-3-[exo-3-(3-isopropyl-5-methyl-4H-1,2,4-triazol-4-yl)-8-azabicyclo[3.2.1]octane-8-yl]-1-(5-acetamidothiophen-2-yl)propyl]cyclohexane-1-carboxamide According to the synthesis method of Example 5, Compound 30-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 138, MS: 541.32 [M+H]+. $^1$H-NMR (400 Hz, CDCl$_3$): δ7.31 (d, 1H), 7.03 (d, 1H), 4.74 (m,1H), 3.71 (m, 1H), 3.21 (m, 1H), 2.36-2.43 (m, 6H), 2.30 (s,3H), 1.34-1.83 (m,22H), 1.26 (d, 6H).

EXAMPLE 139

Synthesis of Compound 139

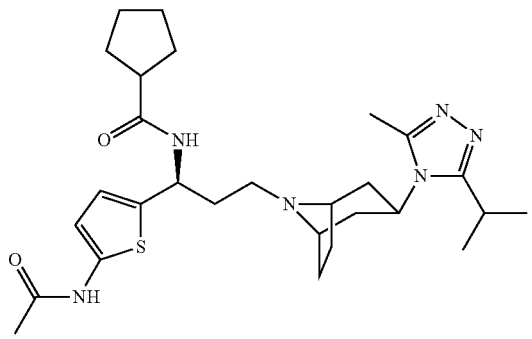 [SMILES: CC(=O)Nc1ccc([C@H](CCN2C3CCC2CC(n2c(C)nnc2C(C)C)C3)NC(=O)C2CCCC2)s1]

N-[(1S)-3-[exo-3-(3-isopropyl-5-methyl-4H-1,2,4-triazol-4-yl)-8-azabicyclo[3.2.1]octane-8-yl]-1-(5-acetamidothiophen-2-yl)propyl]cyclopentane-1-carboxamide According to the synthesis method of Example 5, Compound 30-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 139, MS: 527.31 [M+H]+. $^1$H-NMR (400 Hz, CDCl$_3$): δ7.31 (d, 1H), 7.03 (d, 1H), 4.74 (m,1H), 3.71 (m, 1H), 3.21 (m, 1H), 2.36-2.43 (m, 6H), 2.26 (s,3H), 1.34-1.83 (m,20H), 1.26 (d, 6H).

EXAMPLE 140

Synthesis of Compound 140

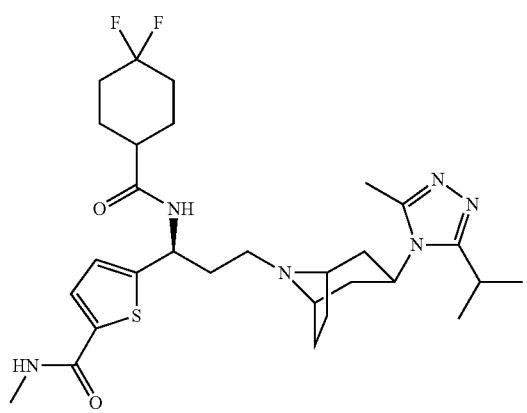

5-[(1S)-1-(4,4-difluorocyclohexyl-1-formamido)-3-[exo-3-(3-isopropyl-5-methyl-4H-1,2,4-triazol-4-yl)-8-azabicyclo[3.2.1]octane-8-yl]-propyl]-N-methylthiophene-2carboxamide According to the synthesis method of Example 5, Compound 31-1 was used to replace compound 2-1 in Example 5 and compound 2f was used to replace compound 1f in Example 5 to obtain compound 140, MS: 577.31 [M+H]+. $^1$H-NMR (400 Hz, CDCl$_3$): δ8.26 (d, 1H), 7.07 (d, 1H), 4.74 (m,1H), 3.71 (m, 1H), 3.21 (m, 1H), 2.86 (s,3H), 2.39-2.45 (m, 3H), 2.33 (s,3H), 1.34-1.83 (m,20H), 1.26 (d, 6H).

EXAMPLE 141

Synthesis of Compound 141

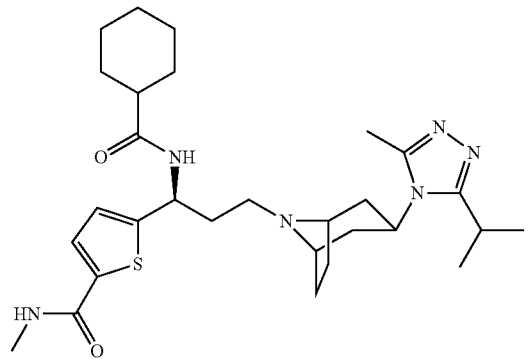 [SMILES: CNC(=O)c1ccc([C@H](CCN2C3CCC2CC(n2c(C)nnc2C(C)C)C3)NC(=O)C2CCCCC2)s1]

5-[(1S)-1-(cyclohexaneformamido)-3-[exo-3-(3-isopropyl-5-methyl-4H-1,2,4-triazol-4-yl)-8-azabicyclo[3.2.1]octane-8-yl]-propyl]-N-methylthiophene-2carboxamide According to the synthesis method of Example 5, Compound 31-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 141, MS: 541.32 [M+H]+. $^1$H-NMR (400 Hz, CDCl$_3$): δ8.14 (d, 1H), 7.13 (d, 1H), 4.74 (m,1H), 3.71 (m, 1H), 3.21 (m, 1H), 2.86 (s,3H), 2.39-2.45 (m, 3H), 2.33 (s,3H), 1.34-1.83 (m,22H), 1.26 (d, 6H).

EXAMPLE 142

Synthesis of Compound 142

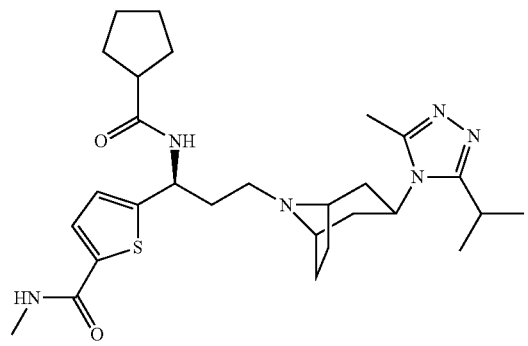 [SMILES: CNC(=O)c1ccc([C@H](CCN2C3CCC2CC(n2c(C)nnc2C(C)C)C3)NC(=O)C2CCCC2)s1]

5-[(1S)-1-(cyclopentaneformamido)-3-[exo-3-(3-isopropyl-5-methyl-4H-1,2,4-triazol-4-yl)-8-azabicyclo[3.2.1]octane-8-yl]-propyl]-N-methylthiophene-2carboxamide According to the synthesis method of Example 5, Compound 31-1 was used to replace compound 2-1 in Example 5, compound 2f was used to replace compound 1f in Example 5 and cyclopentanecarboxylic acid was used to replace 4,4-difluoro-cyclohexanecarboxylic acid in Example 5 to obtain compound 142, MS: 527.31 [M+H]+. ¹H-NMR (400 Hz, CDCl₃): δ8.36 (d, 1H), 7.13 (d, 1H), 4.74 (m,1H), 3.71 (m, 1H), 3.21 (m, 1H), 2.86 (s,3H), 2.39-2.45 (m, 3H), 2.33 (s,3H), 1.34-1.83 (m,20H), 1.26 (d, 6H).

EXAMPLE 143

Synthesis of Compound 143

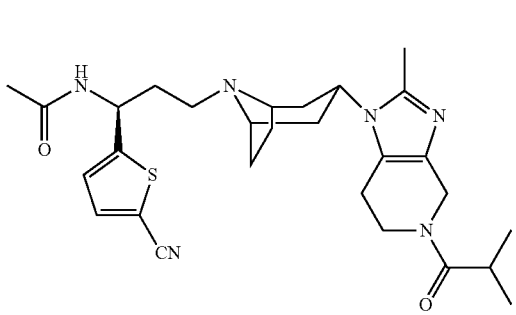 [SMILES: CC(=O)N[C@@H](CCN1C2CCC1CC(n1c(C)nc3c1CCN(C(=O)C(C)C)C3)C2)c1ccc(C#N)s1]

N-{(1S)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]-1-(5-cyanothiophen-2-yl)-propyl}acetamide According to the synthesis method of compound 40, Compound 13-1 was used to replace compound 3-1 in Example 40 and isopropionyl chloride was used to replace acetyl chloride in Example 40 to obtain compound 143, MS: 523.28 [M+H]+. ¹H-NMR (400 Hz, CDCl₃): δ7.44 (m, 1H), 6.87 (m, 1H), 4.78 (t,1H), 4.38 (m,2H), 3.86 (m,2H), 3.74 (m, 1H), 2.66-2.69 (m, 3H), 2.53 (s, 3H), 2.43 (m, 2H), 1.44-2.12 (m, 15H), 1.10 (d, 6H).

EXAMPLE 144

Synthesis of Compound 144

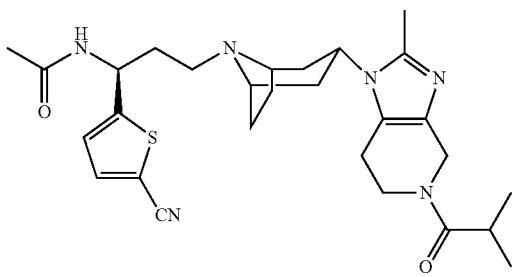 [SMILES: CC(=O)N[C@@H](CCN1C2CCC1CC(n1c(C)nc3c1CCN(C(=O)C(C)C)C3)C2)c1ccc(C#N)s1]

N-{(1S)-3-[(3-endo)-3-(5-acetyl-2-methyl-4,5,6,7-tetrahydro-1H-imidazo[4,5-c]pyridin-1-yl)-8-azabicyclo[3.2.1]octane-8-yl]-1-(5-cyanothiophen-2-yl)-propyl}acetamide According to the synthesis method of compound 40, Compound 13-1 was used to replace compound 3-1 in Example 40 to obtain compound 144, MS: 495.25 [M+H]+. ¹H-NMR (400 Hz, CDCl₃): δ7.56 (m, 1H), 6.93 (m, 1H), 4.78 (t,1H), 4.38 (m,2H), 3.86 (m,2H), 3.74 (m, 1H), 2.66 (m, 2H), 2.53 (s, 3H), 2.43 (m, 2H), 2.32 (s, 3H), 1.44-2.12 (m, 15H).

EXAMPLE 145

Synthesis of Compound 145

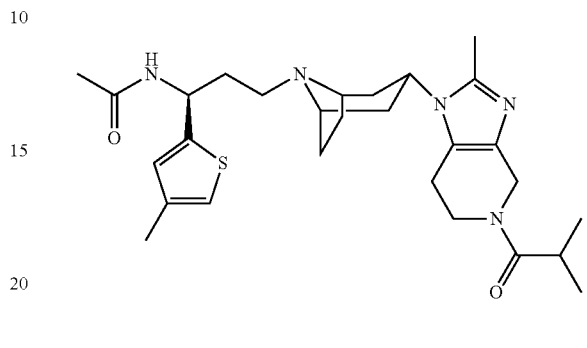

N-{(1S)-3-[(3-endo)-3-(5-isobutyryl-2-methyl-4,5,6,7-tetrahydro-1H-imidazo[4,5-c]pyridin-1-yl)-8-azabicyclo[3.2.1]octane-8-yl]-1-(4-methylthiophen-2-yl)-propyl}acetamide According to the synthesis method of compound 40, Compound 18-1 was used to replace compound 3-1 in Example 40 and isopropionyl chloride was used to replace acetyl chloride in Example 40 to obtain compound 145, MS: 512.30 [M+H]+. ¹H-NMR (400 Hz, CDCl₃): δ7.59 (m, 1H), 6.91 (m, 1H), 4.78 (t,1H), 4.38 (m,2H), 3.86 (m,2H), 3.74 (m, 1H), 2.66-2.69 (m, 3H), 2.53 (s, 3H), 2.43 (m, 2H), 1.44-2.12 (m, 15H), 1.10 (d, 6H).

EXAMPLE 146

Synthesis of Compound 146

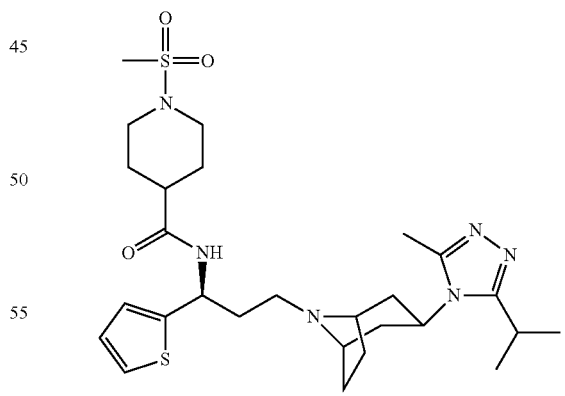

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-1-methylsulfonylpiperidine-4-carboxamide According to the synthesis method of Example 5, Compound 1-1 was used to replace compound 2-1 in example 5, compound 2f was used to replace compound 1f in example 5 and 1-methylsulfonyl-4-piperidine carboxylic acid was used to replace 4,4-difluoro-cyclohexanecarboxylic acid in Example 5 to obtain compound 146, MS: 563.3 [M+H]+. ¹H-NMR (400 Hz, CDCl₃): δ7.28 (t, 1H), 7.13 (d, 1H), 6.94 (d, 1H), 5.19 (m,1H), 3.91 (m, 1H), 3.31 (m, 4H), 3.02 (m, 1H), 2.54 (s, 3H), 2.43 (m,5H), 2.26-1.93 (m,13H), 1.93-1.61 (m, 6H), 1.36 (d, 6H).

EXAMPLE 147

Synthesis of Compound 147

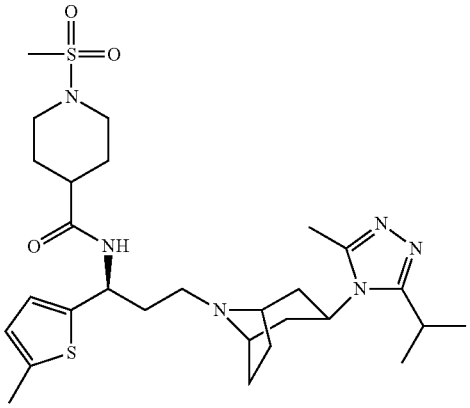 [SMILES: Cc1ccc([C@H](CCN2C3CCC2CC(n2c(C)nnc2C(C)C)C3)NC(=O)C2CCN(S(C)(=O)=O)CC2)s1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-1-methylsulfonylpiperidine-4-carboxamide According to the synthesis method of Example 5, Compound 5-1 was used to replace compound 2-1 in Example 5, compound 2f was used to replace compound 1f in Example 5 and 1-methylsulfonyl-4-piperidine carboxylic acid was used to replace 4,4-difluoro-cyclohexanecarboxylic acid in Example 5 to obtain compound 147, MS: 577.3 [M+H]+. ¹H-NMR (400 Hz, CDCl₃): δ7.28 (t, 1H), 7.13 (d, 1H), 5.19 (m,1H), 3.91 (m, 1H), 3.31 (m, 4H), 3.02 (m, 1H), 2.54 (s, 3H), 2.43 (m,5H), 2.36 (s,3H), 2.26-1.93 (m,13H), 1.93-1.61 (m, 6H), 1.36 (d, 6H).

EXAMPLE 148

Synthesis of Compound 148

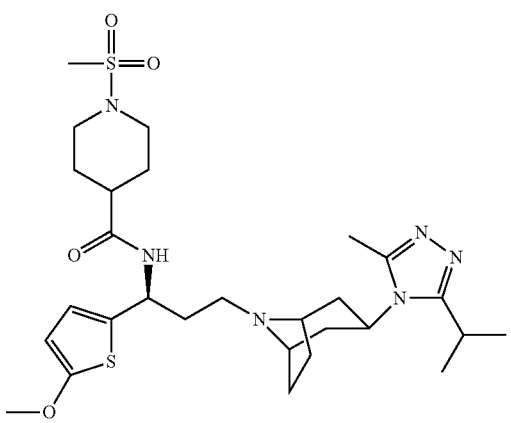 [SMILES: COc1ccc([C@H](CCN2C3CCC2CC(n2c(C)nnc2C(C)C)C3)NC(=O)C2CCN(S(C)(=O)=O)CC2)s1]

N-[(1S)-3-[exo-3-(3-isopropyl-5-methyl-4H-1,2,4-triazol-4-yl)-8-azabicyclo[3.2.1]octane-8-yl]-1-(5-methoxythiophen-2-yl)propyl]-1-methylsulfonylpiperidine-4-carboxamide According to the synthesis method of Example 5, Compound 27-1 was used to replace compound 2-1 in Example 5, compound 2f was used to replace compound 1f in Example 5 and 1-methylsulfonyl-4-piperidine carboxylic acid was used to replace 4,4-difluoro-cyclohexanecarboxylic acid in Example 5 to obtain compound 148, MS: 593.3 [M+H]+. ¹H-NMR (400 Hz, CDCl₃): δ7.28 (t, 1H), 7.13 (d, 1H) 5.19 (m,1H), 3.91 (m, 4H), 3.31 (m, 4H), 3.02 (m, 1H), 2.54 (s, 3H),2.43 (m, 5H), 2.36 (s,3H), 2.26-1.93 (m,13H), 1.93-1.61 (m, 6H), 1.36 (d, 6H).

EXAMPLE 149

Synthesis of Compound 149

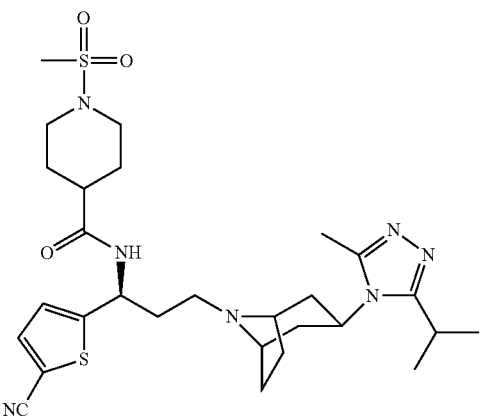 [SMILES: Cc1nnc(C(C)C)n1C1CC2CCC(C1)N2CC[C@H](NC(=O)C1CCN(S(C)(=O)=O)CC1)c1ccc(C#N)s1]

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]-1-methylsulfonylpiperidine-4-carboxamide According to the synthesis method of Example 5, Compound 13-1 was used to replace compound 2-1 in Example 5, compound 2f was used to replace compound 1f in Example 5 and 1-methylsulfonyl-4-piperidine carboxylic acid was used to replace 4,4-difluoro-cyclohexanecarboxylic acid in Example 5 to obtain compound 149, MS: 588.3 [M+H]+. ¹H-NMR (400 Hz, CDCl₃): δ7.38 (t, 1H), 7.24 (d, 1H), 5.19 (m,1H), 3.91 (m, 4H), 3.31 (m, 4H), 3.02 (m, 1H), 2.54 (s, 3H), 2.43 (m,5H), 2.36 (s,3H), 2.26-1.93 (m,13H), 1.93-1.61 (m, 6H), 1.36 (d, 6H).

EXAMPLE 150

Synthesis of Compound 150

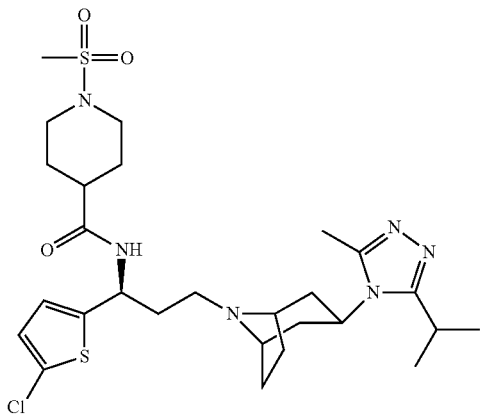 [SMILES: Cc1nnc(C(C)C)n1C1CC2CCC(C1)N2CC[C@H](NC(=O)C1CCN(S(C)(=O)=O)CC1)c1ccc(Cl)s1]

N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]-1-methylsulfonylpiperidine-4-carboxamide According to the synthesis method of Example 5, Compound 28-1 was used to replace compound 2-1 in Example 5, compound 2f was used to replace compound 1f in Example 5 and 1-methylsulfonyl-4-piperidine carboxylic acid was used to replace 4,4-difluoro-cyclohexanecarboxylic acid in Example 5 to obtain compound 150, MS: 597.3 [M+H]+. $^1$H-NMR (400 Hz, CDCl$_3$): δ7.38 (t, 1H), 7.23 (d, 1H), 5.19 (m, 1H), 3.91 (m, 4H), 3.31 (m, 4H), 3.02 (m, 1H), 2.54 (s, 3H), 2.43 (m,5H), 2.36 (s,3H), 2.26-1.93 (m,13H), 1.93-1.61 (m, 6H), 1.36 (d, 6H).

EXAMPLE 151

Synthesis of Compound 151

N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]-1-methylsulfonylpiperidine-4-carboxamide

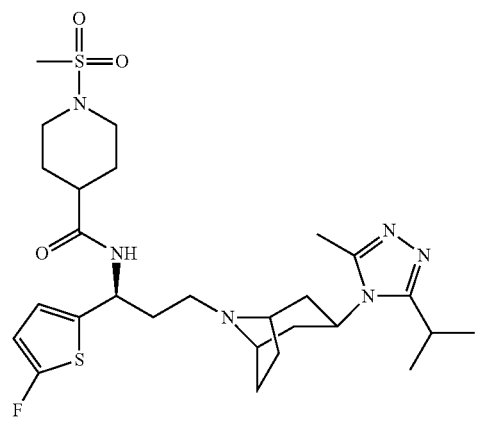 [SMILES: Cc1nnc(C(C)C)n1C1CC2CCC(C1)N2CC[C@H](NC(=O)C1CCN(S(C)(=O)=O)CC1)c1ccc(F)s1]

According to the synthesis method of Example 5, Compound 7-1 was used to replace compound 2-1 in Example 5, compound 2f was used to replace compound 1f in Example 5 and 1-methylsulfonyl-4-piperidine carboxylic acid was used to replace 4,4-difluoro-cyclohexanecarboxylic acid in Example 5 to obtain compound 151, MS: 581.3 [M+H]+. $^1$H-NMR (400 Hz, CDCl$_3$): δ7.48 (t, 1H), 7.24 (d, 1H), 5.19 (m,1H), 3.91 (m, 4H), 3.31 (m, 4H), 3.02 (m, 1H), 2.54 (s, 3H), 2.43 (m,5H), 2.37 (s,3H), 2.26-1.93 (m,13H), 1.93-1.61 (m, 6H), 1.36 (d, 6H).

EXAMPLE 152

Synthesis of Compound 152

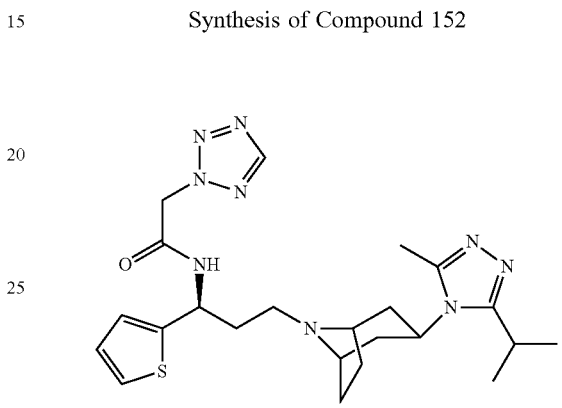

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-(2H-tetrazol-2-yl)acetamide According to the synthesis method of Example 5, Compound 1-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 152, MS: 484.31 [M+H]+. $^1$H-NMR (400 Hz, CDCl$_3$): δ8.53 (s, 1H), 7.23 (t, 1H), 7.15 (d, 1H), 6.99 (d, 1H), 5.21 (m,1H), 4.62 (s, 2H), 3.95 (m, 1H), 3.03 (m, 1H), 2.40 (m,2H), 2.25-1.67 (m,14H), 1.32 (d, 6H).

EXAMPLE 153

Synthesis of Compound 153

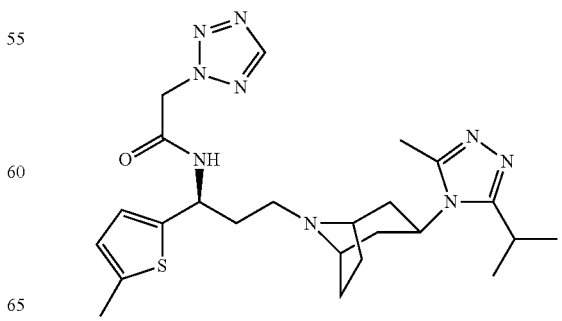

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]-2-(2H-tetrazol-2-yl)acetamide According to the synthesis method of Example 5, Compound 5-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 153, MS: 498.3 [M+H]+. $^1$H-NMR (400 Hz, CDCl$_3$): δ8.53 (s, 1H), 7.23 (t, 1H), 7.15 (d, 1H), 6.99 (d, 1H), 5.21 (m,1H), 4.62 (s, 2H), 3.95 (m, 1H), 3.03 (m, 1H), 2.36 (s, 3H), 2.40 (m,2H), 2.25-1.67 (m,14H), 1.32 (d, 6H).

EXAMPLE 154

Synthesis of Compound 154

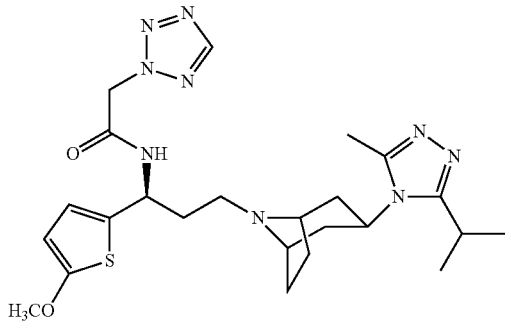 [SMILES: COc1ccc([C@H](CCN2C3CCC2CC(n2c(C)nnc2C(C)C)C3)NC(=O)Cn2ncnn2)s1]

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]-2-(2H-tetrazol-2-yl)acetamide According to the synthesis method of Example 5, Compound 27-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 154, MS: 514.3 [M+H]+. $^1$H-NMR (400 Hz, CDCl$_3$): δ7.53 (s, 1H), 7.23 (t, 1H), 5.21 (m,1H), 4.62 (s, 2H), 3.95 (m, 1H), 3.85 (s, 3H), 3.03 (m, 1H), 2.36 (s, 3H), 2.40 (m,2H), 2.25-1.67 (m,14H), 1.32 (d, 6H).

EXAMPLE 155

Synthesis of Compound 155

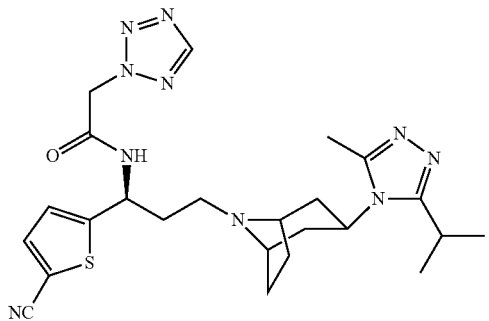 [SMILES: Cc1nnc(C(C)C)n1C1CC2CCC(C1)N2CC[C@H](NC(=O)Cn1ncnn1)c1ccc(C#N)s1]

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]-2-(2H-tetrazol-2-yl)acetamide According to the synthesis method of Example 5, Compound 13-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 155, MS: 509.3 [M+H]+. $^1$H-NMR (400 Hz, CDCl$_3$): δ8.53 (s, 1H), 7.23 (t, 1H), 5.21 (m,1H), 4.62 (s, 2H), 3.95 (m, 1H), 3.03 (m, 1H), 2.36 (s, 3H), 2.40 (m,2H), 2.25-1.67 (m,14H), 1.32 (d, 6H).

EXAMPLE 156

Synthesis of Compound 156

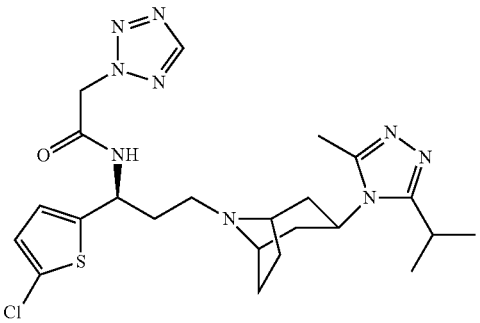 [SMILES: Cc1nnc(C(C)C)n1C1CC2CCC(C1)N2CC[C@H](NC(=O)Cn1ncnn1)c1ccc(Cl)s1]

N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]-2-(2H-tetrazol-2-yl)acetamide According to the synthesis method of Example 5, Compound 28-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 156, MS: 518.3 [M+H]+. $^1$H-NMR (400 Hz, CDCl$_3$): δ8.03 (s, 1H), 7.53 (t, 1H), 5.21 (m,1H), 4.62 (s, 2H), 3.95 (m, 1H), 3.03 (m, 1H), 2.36 (s, 3H), 2.40 (m,2H), 2.25-1.67 (m,14H), 1.32 (d, 6H).

EXAMPLE 157

Synthesis of Compound 157

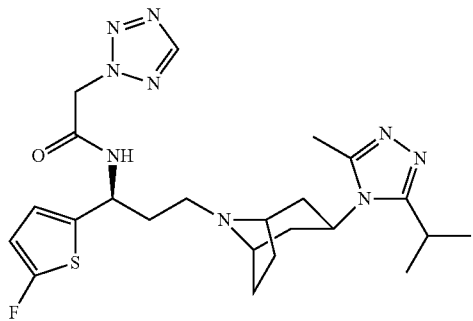 [SMILES: Cc1nnc(C(C)C)n1C1CC2CCC(C1)N2CC[C@H](NC(=O)Cn1ncnn1)c1ccc(F)s1]

111

N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]-2-(2H-tetrazol-2-yl)acetamide According to the synthesis method of Example 5, Compound 7-1 was used to replace compound 2-1 in Example 5, compound 2f was used to replace compound 1f in Example 5 and 2-(2H-tetrazol-2-yl)acetic acid was used to replace 4,4-difluoro-cyclohexanecarboxylic acid in Example 5 to obtain compound 157, MS: 502.3 [M+H]+. ¹H-NMR (400 Hz, CDCl₃): δ8.13 (s, 1H), 7.23 (t, 1H), 5.21 (m,1H), 4.62 (s, 2H), 3.95 (m, 1H), 3.03 (m, 1H), 2.36 (s, 3H), 2.40 (m,2H), 2.25-1.67 (m,14H), 1.32 (d, 6H).

EXAMPLE 158

Synthesis of Compound 158

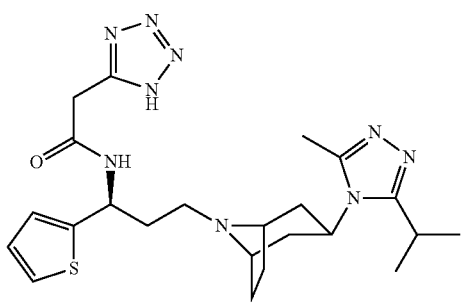 [SMILES: Cc1nnc(C(C)C)n1C1CC2CCC(C1)N2CC[C@H](NC(=O)Cc1nnn[nH]1)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-(1H-tetrazol-5-yl)acetamide According to the synthesis method of Example 5, Compound 1-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 158, MS: 484.3 [M+H]+. ¹H-NMR (400 Hz, CDCl₃): δ7.23 (t, 1H), 7.15 (d, 1H), 6.99 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXAMPLE 159

Synthesis of Compound 159

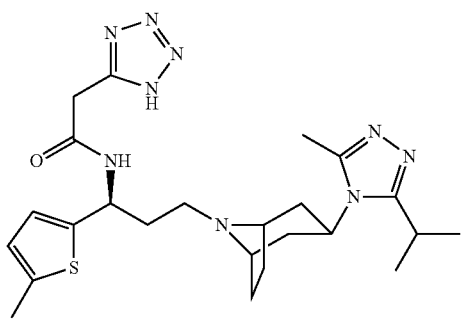 [SMILES: Cc1ccc([C@H](CCN2C3CCC2CC(n2c(C)nnc2C(C)C)C3)NC(=O)Cc2nnn[nH]2)s1]

112

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]-2-(1H-tetrazol-5-yl)acetamide According to the synthesis method of Example 5, Compound 5-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 159, MS: 498.3 [M+H]+. ¹H-NMR (400 Hz, CDCl₃): δ7.23 (t, 1H), 7.15 (d, 1H), 5.21 (m,1H), 3.95 (m, 1H), 3.42 (s, 2H), 3.03 (m, 1H), 2.40 (m,2H), 2.36 (s,3H), 2.25-1.67 (m,14H), 1.32 (d, 6H).

EXAMPLE 160

Synthesis of Compound 160

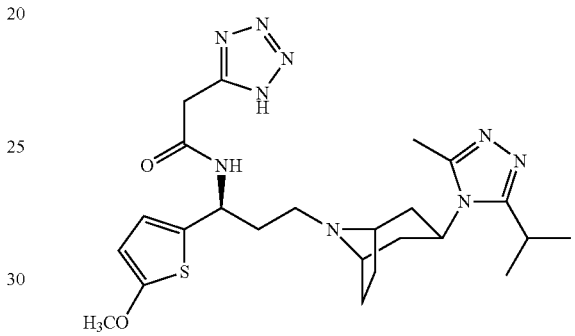

N-[(1S)-3-[exo-3-(3-isopropyl-5-methyl-4H-1,2,4-triazol-4-yl)-8-azabicyclo[3.2.1]octane-8-yl]-1-(5-methoxythiophen-2-yl)propyl]-2-(1H-tetrazol-5-yl)acetamide According to the synthesis method of Example 5, Compound 27-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 160, MS: 514.3 [M+H]+. ¹H-NMR (400 Hz, CDCl₃): δ7.23 (t, 1H), 7.15 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXAMPLE 161

Synthesis of Compound 161

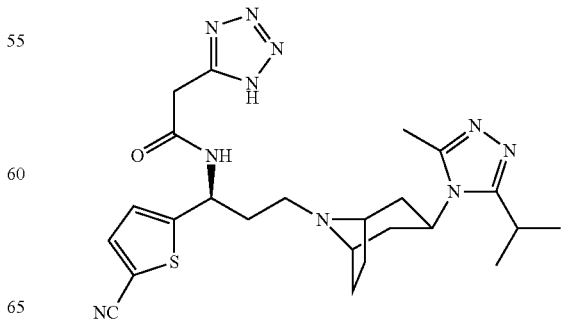

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]-2-(1H-tetrazol-5-yl)acetamide According to the synthesis method of Example 5, Compound 13-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 161, MS: 509.3 [M+H]+. $^1$H-NMR (400 Hz, CDCl$_3$): δ7.43 (t, 1H), 7.35 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXAMPLE 162

Synthesis of Compound 162

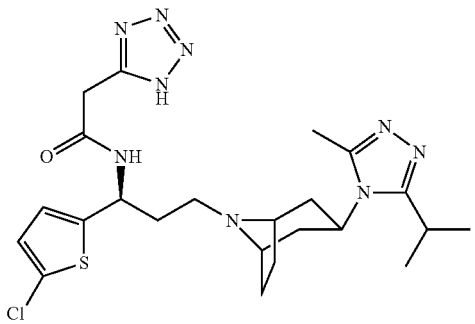 [SMILES: Cc1nnc(C(C)C)n1C1CC2CCC(C1)N2CC[C@H](NC(=O)Cc1nnn[nH]1)c1ccc(Cl)s1]

N-[(1S)-3-[exo-3-(3-isopropyl-5-methyl-4H-1,2,4-triazol-4-yl)-8-azabicyclo[3.2.1]octane-8-yl]-1-(5-chlorothiophen-2-yl)propyl]-2-(1H-tetrazol-5-yl)acetamide According to the synthesis method of Example 5, Compound 28-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 162, MS: 518.3 [M+H]+. $^1$H-NMR (400 Hz, CDCl$_3$): δ7.53 (t, 1H), 7.45 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXAMPLE 163

Synthesis of Compound 163

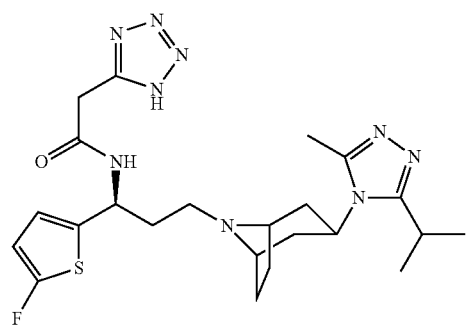 [SMILES: Cc1nnc(C(C)C)n1C1CC2CCC(C1)N2CC[C@H](NC(=O)Cc1nnn[nH]1)c1ccc(F)s1]

N-[(1S)-3-[exo-3-(3-isopropyl-5-methyl-4H-1,2,4-triazol-4-yl)-8-azabicyclo[3.2.1]octane-8-yl]-1-(5-fluorothiophen-2-yl)propyl]-2-(1H-tetrazol-5-yl)acetamide According to the synthesis method of Example 5, Compound 7-1 was used to replace compound 2-1 in Example 5, compound 2f was used to replace compound 1f in Example 5 and 2-(1H-tetrazol-5-yl)acetic acid was used to replace 4,4-difluoro-cyclohexanecarboxylic acid in Example 5 to obtain compound 163, MS: 502.3 [M+H]+. $^1$H-NMR (400 Hz, CDCl$_3$): δ7.63 (t, 1H), 7.55 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXAMPLE 164

Synthesis of Compound 164

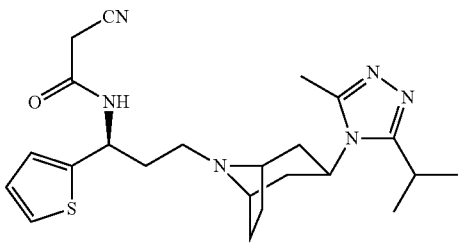 [SMILES: Cc1nnc(C(C)C)n1C1CC2CCC(C1)N2CC[C@H](NC(=O)CC#N)c1cccs1]

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-cyanoacetamide According to the synthesis method of Example 5, Compound 1-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 164, MS: 441.3 [M+H]+. $^1$H-NMR (400 Hz, CDCl$_3$): δ7.23 (t, 1H), 7.15 (d, 1H), 6.99 (d, 1H), 5.21 (m,1H), 3.95 (m, 1H), 3.32 (s, 2H), 3.03 (m, 1H), 2.40 (m,2H), 2.25-1.67 (m,14H), 1.32 (d, 6H).

EXAMPLE 165

Synthesis of Compound 165

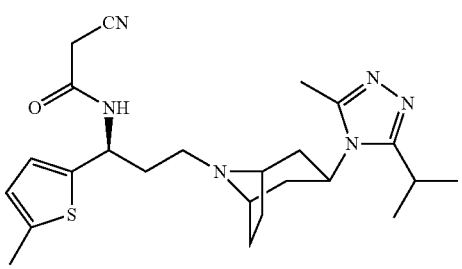 [SMILES: Cc1ccc([C@H](CCN2C3CCC2CC(n2c(C)nnc2C(C)C)C3)NC(=O)CC#N)s1]

115

N-[(1S)-3-[exo-3-(3-isopropyl-5-methyl-4H-1,2,4-triazol-4-yl)-8-azabicyclo[3.2.1]octane-8-yl]-1-(5-methylthiophen-2-yl)propyl]-2-cyanoacetamide According to the synthesis method of Example 5, Compound 5-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 165, MS: 454.3 [M+H]+. $^1$H-NMR (400 Hz, CDCl$_3$): δ7.23 (t, 1H), 7.15 (d, 1H), 5.21 (m,1H), 3.95 (m, 1H), 3.32 (s, 2H), 3.03 (m, 1H), 2.37 (s, 3H), 2.40 (m,2H), 2.25-1.67 (m,14H), 1.32 (d, 6H).

EXAMPLE 166

Synthesis of Compound 166

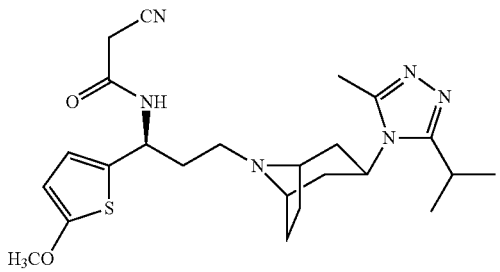 [SMILES: COc1ccc([C@H](CCN2C3CCC2CC(n2c(C)nnc2C(C)C)C3)NC(=O)CC#N)s1]

N-[(1S)-3-[exo-3-(3-isopropyl-5-methyl-4H-1,2,4-triazol-4-yl)-8-azabicyclo[3.2.1]octane-8-yl]-1-(5-methoxythiophen-2-yl)propyl]-2-cyanoacetamide According to the synthesis method of Example 5, Compound 27-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 166, MS: 471.3 [M+H]+. $^1$H-NMR (400 Hz, CDCl$_3$): δ7.23 (t, 1H), 7.15 (d, 1H), 5.21 (m,1H), 3.95 (m, 1H), 3.87 (s, 3H), 3.32 (s, 2H), 3.03 (m, 1H), 2.40 (m,2H), 2.25-1.67 (m,14H), 1.32 (d, 6H).

EXAMPLE 167

Synthesis of Compound 167

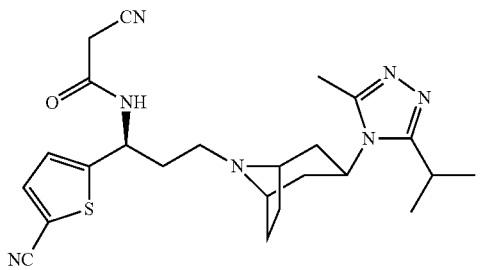 [SMILES: Cc1nnc(C(C)C)n1C1CC2CCC(C1)N2CC[C@H](NC(=O)CC#N)c1ccc(C#N)s1]

116

N-[(1S)-3-[exo-3-(3-isopropyl-5-methyl-4H-1,2,4-triazol-4-yl)-8-azabicyclo[3.2.1]octane-8-yl]-1-(5-cyanothiophen-2-yl)propyl]-2-cyanoacetamide According to the synthesis method of Example 5, Compound 13-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 167, MS: 465.3 [M+H]+. $^1$H-NMR (400 Hz, CDCl$_3$): δ7.23 (t, 1H), 7.15 (d, 1H), 5.21 (m,1H), 3.95 (m, 1H), 3.32 (s, 2H), 3.03 (m, 1H), 2.40 (m,2H), 2.25-1.67 (m,14H), 1.32 (d, 6H).

EXAMPLE 168

Synthesis of Compound 168

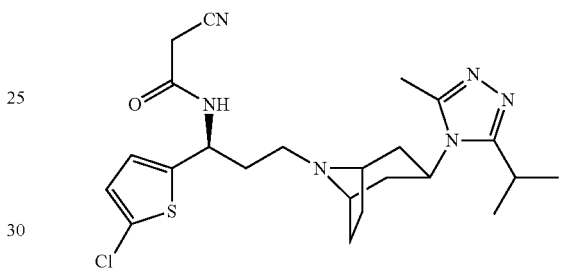

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-cyanoacetamide According to the synthesis method of Example 5, Compound 28-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 167, MS: 465.3 [M+H]+. $^1$H-NMR (400 Hz, CDCl$_3$): δ7.43 (t, 1H), 7.35 (d, 1H), 5.21 (m,1H), 3.95 (m, 1H), 3.32 (s, 2H), 3.03 (m, 1H), 2.40 (m,2H), 2.25-1.67 (m,14H), 1.32 (d, 6H).

EXAMPLE 169

Synthesis of Compound 169

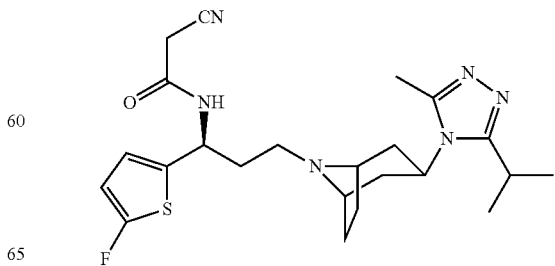

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-cyanoacetamide According to the synthesis method of Example 5, Compound 7-1 was used to replace compound 2-1 in Example 5, compound 2f was used to replace compound 1f in Example 5 and 2-cyanoacetic acid was used to replace 4,4-difluoro-cyclohexanecarboxylic acid in Example 5 to obtain compound 169, MS: 458.3 [M+H]+. $^1$H-NMR (400 Hz, CDCl$_3$): δ7.48 (t, 1H), 7.37 (d, 1H), 5.21 (m,1H), 3.95 (m, 1H), 3.32 (s, 2H), 3.03 (m, 1H), 2.40 (m,2H), 2.25-1.67 (m,14H), 1.32 (d, 6H).

EXAMPLE 170

Synthesis of Compound 170

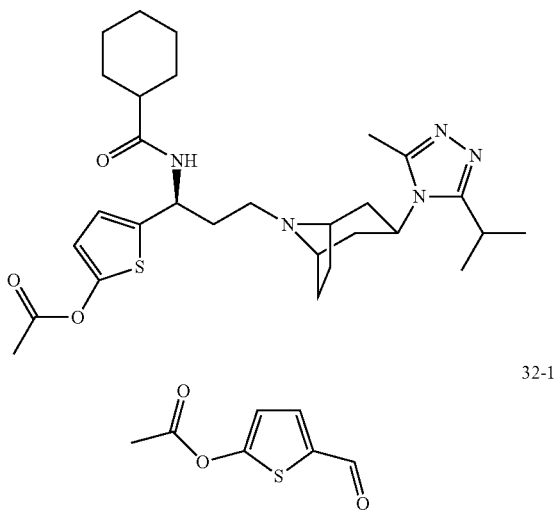

N-[(1S)-3-[exo-3-(3-isopropyl-5-methyl-4H-1,2,4-triazol-4-yl)-8-azabicyclo[3.2.1]octane-8-yl]-1-(5-acetoxythiophen-2-yl)propyl]cyclohexane-1-carboxamide According to the synthesis method of Example 5, Compound 32-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 170, MS: 542.2 [M+H]+. $^1$H-NMR (400 Hz, CDCl$_3$): δ6.43 (m,2H), 5.79 (m,1H), 3.91 (m, 1H), 3.02 (m, 1H), 2.43 (m,5H), 2.28 (s, 3H), 2.16-1.93 (m,13H), 1.93-1.61 (m, 10H), 1.36 (d, 6H).

EXAMPLE 171

Synthesis of Compound 171

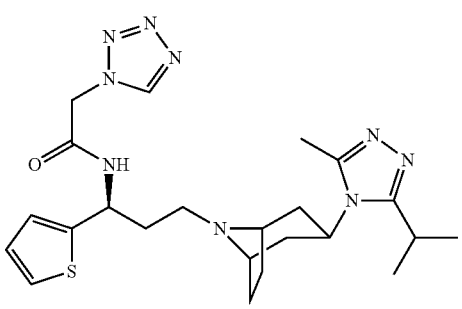 [SMILES: Cc1nnc(C(C)C)n1C1CC2CCC(C1)N2CC[C@H](NC(=O)Cn1cnnn1)c1cccs1]

5-[(1S)-1-(cyclohexaneformamido)-3-[exo-3-(3-isopropyl-5-methyl-4H-1,2,4-triazol-4-yl)-8-azabicyclo[3.2.1]octane-8-yl]-propyl]-N,N-dimethylthiophene-2carboxamide According to the synthesis method of Example 5, Compound 33-1 was used to replace compound 2-1 in Example 5, compound 2f was used to replace compound 1f in Example 5 and cyclohexanecarboxylic acid was used to replace 4,4-difluoro-cyclohexanecarboxylic acid in Example 5 to obtain compound 171, MS: 555.2 [M+H]+. $^1$H-NMR (400 Hz, CDCl$_3$): δ6.43 (m,2H), 5.79 (m,1H), 3.91 (m, 1H), 3.02 (m, 1H), 2.93 (s, 6H), 2.85 (s, 6H), 2.43 (m,5H), 2.16-1.93 (m,13H), 1.93-1.61 (m, 10H), 1.36 (d, 6H).

EXAMPLE 172

Synthesis of Compound 172

N-[(1S)-3-[exo-3-(3-isopropyl-5-methyl-4H-1,2,4-triazol-4-yl)-8-azabicyclo[3.2.1]octane-8-yl]-1-(thiophen-2-yl)propyl]-2-(1H-tetrazol-1-yl)acetamide According to the synthesis method of Example 5, Compound 1-1 was used to replace compound 2-1 in Example 5, compound 2f was used to replace compound 1f in Example 5 and 2-(1H-tetrazol-1-yl)acetic acid was used to replace 4,4-difluoro-cyclohexanecarboxylic acid in Example 5 to obtain compound 172, MS: 484.3 [M+H]+. $^1$H-NMR (400 Hz, CDCl$_3$): δ8.73 (s, 1H), 7.23 (t, 1H), 7.15 (d, 1H), 6.99 (d, 1H), 5.21 (m,1H), 3.95 (m, 1H), 3.42 (s, 2H), 3.03 (m, 1H), 2.40 (m,2H), 2.25-1.67 (m,14H), 1.32 (d, 6H).

EXPERIMENT EXAMPLE

Example 1

Calcium Flux Inhibition Experiment

Experiment apparatus: FlexStation II

Experiment materials: HEK293/CCR5-Gα16 cell line, Fluo-4calcium dye (fluorescent-4 calcium ion dye) and FlexStation instrument.

Experiment theory: Activation of the receptor can cause the activation of Gα16 protein, thereby activating phospholipase C (PLC) to generate IP3 and DAG by establishing CCR5 and Ga16 co-transfected cell line. IP3 can bind to IP3 receptors on the endoplasmic reticulum and mitochondria in a cell, which can cause the release of intracellular calcium. Thus, determination of changes in intracellular calcium can be used as a method to detect CCR5 activation state. Fluo-4/AM is a fluorescent probe indicator for calcium used to measure calcium ion. As a non-polar lipid-soluble compound, after it enters into cells, AM group is dissociated to release Fluo-4 under the effect of cell lipolysis enzyme. Fluo-4 is a polar molecule and not easy to go through the lipid bilayer membrane, therefore it can stay within the cells for a long time. Ultimately, the level of activated Ga protein can be reflected by measuring the excited fluorescence intensity. If the screened compound can activate CCR5, it can greatly increase the calcium flux reaction; on the contrary, if the screened compound can antagonize CCR5, it can greatly reduce calcium flux reaction.

Experiment steps

1. HEK293 cells which can stably express CCR5 were inoculated in a 96-well plate and incubated overnight.
2. The medium in each well into which cells were innoculated was removed and 40 μl/well of freshly prepared dye was added. The plate was placed in a 37° C. incubator and incubated for 40 minutes at constant temperature.
3. The medicament to be determined was diluted with calcium buffer to eight concentration gradients, which is $1\times10^{-4}$ M, $1\times10^{-5}$ M, $1\times10^{-6}$ M, $1\times10^{-7}$ M, $1\times10^{-8}$ M, $1\times10^{-9}$ M, $1\times10^{-10}$ M, and $1\times10^{-11}$ M, respectively, and homogeneously mixed.
4. The dye was removed. Freshly prepared calcium buffer was used to wash for one time, 50 μl of calcium buffer was added.
5. FlexStation II was used for detection. 25 μl of calcium buffer containing the medicament to be determined was added automatically from the 15$^{th}$ second. The fluorescence value at 525 nm was read ultimately.

Experiment Results

TABLE 1

The results from Calcium flux inhibition experiment of compounds

| compound | CCR5 IC$_{50}$ (nM) |
|---|---|
| 1 | 36.56 |
| 2 | 32.57 |
| 3 | 1.953 |

TABLE 1-continued

The results from Calcium flux inhibition experiment of compounds

| compound | CCR5 IC$_{50}$ (nM) |
|---|---|
| 4 | 15.04 |
| 5 | 29.68 |
| 6 | 6.904 |
| 7 | 35.23 |
| 8 | 21.92 |
| 9 | 79.34 |
| 10 | 36.56 |
| 13 | 3.397 |
| 14 | 2.334 |
| 15 | 9.222 |
| 16 | 2.234 |
| 17 | 2.547 |
| 18 | 3.733 |
| 19 | 21.52 |
| 20 | 5.145 |
| 21 | 11.89 |
| 22 | 1.051 |
| 23 | 27.26 |
| 24 | 44.61 |
| 25 | 37.85 |
| 26 | 5.063 |
| 27 | 11.42 |
| 28 | 68.02 |
| 29 | 7.282 |
| 30 | 24.04 |
| 31 | 9.763 |
| 32 | 8.354 |
| 33 | 25.01 |
| 34 | 143.4 |
| 35 | 270.4 |
| 36 | 31.78 |
| 37 | 9.334 |
| 38 | 9.331 |
| 39 | 1.412 |
| 42 | 15.90 |
| 43 | 8.340 |
| 64 | 4.628 |
| 65 | 1.625 |
| 66 | 2.015 |
| 70 | 9.45 |
| 73 | 8.23 |
| 88 | 9.26 |
| 112 | 10.37 |
| 113 | 8.14 |
| 114 | 9.27 |
| 115 | 10.32 |
| 116 | 15.57 |
| 117 | 16.13 |
| 118 | 16.87 |
| 119 | 4.77 |
| 120 | 27.72 |
| 121 | 32.32 |
| 122 | 24.52 |
| 123 | 12.13 |
| 124 | 11.25 |
| 125 | 12.19 |
| 126 | 21.97 |
| 127 | 22.94 |
| 128 | 17.52 |
| 129 | 14.2 |
| 130 | 18.51 |
| 131 | 6.57 |
| 132 | 22.2 |
| 133 | 1.785 |
| 134 | 22.13 |
| 135 | 8.279 |
| 136 | 22.13 |
| 137 | 8.23 |
| 138 | 9.75 |
| 139 | 12.32 |
| 140 | 13.73 |
| 141 | 8.36 |
| 142 | 9.55 |

TABLE 1-continued

The results from Calcium flux inhibition experiment of compounds

| compound | CCR5 IC$_{50}$ (nM) |
|---|---|
| 143 | 13.89 |
| 144 | 8.53 |
| 145 | 13.32 |
| 146 | 1.75 |
| 147 | 2.48 |
| 148 | 3.42 |
| 149 | 7.89 |
| 150 | 2.22 |
| 151 | 3.45 |
| 152 | 7.98 |
| 153 | 13.45 |
| 154 | 23.14 |
| 155 | 8.23 |
| 156 | 9.85 |
| 157 | 1.23 |
| 158 | 14.86 |
| 159 | 8.76 |
| 160 | 1.34 |
| 161 | 8.36 |
| 162 | 1.85 |
| 163 | 13.32 |
| 164 | 7.38 |
| 165 | 8.29 |
| 166 | 6.54 |
| 167 | 7.98 |
| 168 | 1.54 |
| 169 | 6.32 |
| 170 | 1.38 |
| 171 | 1.64 |
| 172 | 9.385 |
| Maraviroc | 7.385 |
| PF-232798 | 8.290 |

Note:
The structures of PF-232798 and Maraviroc used as positive control compounds (similarly hereinafter are as follows:

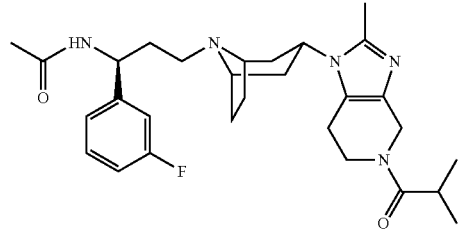

PF-232798

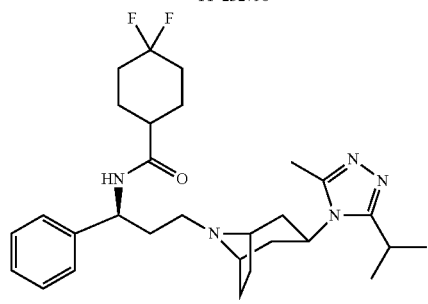

Maraviroc

Experiment conclusion: It can be seen from the data in table 1 that all of the compounds have good calcium influx inhibition effects, wherein, compound 3, 6, 13, 14, 16, 17, 18, 20, 22, 26, 29, 39, 64, 65, 66, 119, 123, 124, 131, 133, 146, 147, 148, 150, 151, 157, 160, 162, 164, 166, 168, 169, 170, 171 and 172 are better than the positive control compounds, and compound 15, 21, 27, 31, 32, 37, 38, 135, 137, 138, 141, 142, 149, 152, 155, 156, 159, 161, 165 and 167 are comparable to the positive control compounds.

Example 2

Thermal Stability of Protein Test (CPM-Assay)

Experimental theory: many cysteines are present in CCR5 protein sequence. Cysteines located in loop region form disulfide bonds to stabilize the tertiary structure of the protein. Some free cysteines in reduced state are located in the transmembrane region. Under excitation by incident light of 387 nm, the combination of free sulfhydryl and fluorescent dye CPM can emit excitation light of 436 nm. If the temperature is gradually increased artificially, the tertiary structure of the membrane protein gradually become loose as the temperature rises. The free sulfhydryls originally located in the transmembrane region expose and combine with the fluorescent dye. And then the detector will detect changes in signal enhancement. Therefore, the thermal stability of membrane proteins can be determined according to the temperature (Tm) at the midpoint of changes in signal intensity.

Experimental steps: Upon preliminary purification, the obtained protein solution was transferred into a small concentration tube (100 kd, 500 ul) for concentration (1000 rcf, 12 min, 4° C.). After centrifugation, the concentration tube was taken out and flicked to prevent protein coagulation due to high local concentration. The final concentrated volume was about 50 μl. 117 μl of purified solution (volume is suitable to make the total volume up to 120 μl), 1 μl fluorescent dye cpm (in-house prepared) and 2 μl of concentrated protein solution (the amount of added protein is 3-5 μg according to the calculated concentration of the protein solution and the concentrated volume) were added to 2 ml Ependorf tube and incubated at room temperature for 20 min. And then the mixture was added to the cuvette (Qwan) and put in the testing equipment Cary, wherein the surface of the frosted glass faced out. The temperature was set in the range of 4-90° C. with 1° C. increase per minute and the program was run. Tm value can be obtained by processing the data and graph with a mapping software and can be used to compare the difference of protein thermal stability under different conditions.

TABLE 2

The results of effects of compounds on thermal stability of protein

| compound | Tm (° C.) |
|---|---|
| 1 | 60.59 |
| 2 | 65.23 |
| 3 | 67.71 |
| 4 | 65.64 |
| 5 | 57.31 |
| 6 | 58.56 |
| 7 | 57.21 |
| 8 | 60.61 |
| 9 | 61.32 |
| 10 | 63.21 |
| 13 | 65.32 |
| 14 | 68.10 |
| 15 | 64.30 |
| 16 | 71.32 |
| 17 | 66.97 |
| 18 | 71.73 |
| 19 | 69.20 |
| 20 | 70.27 |
| 21 | 64.68 |
| 22 | 68.21 |
| 23 | 63.90 |
| 24 | 62.31 |
| 25 | 62.31 |

TABLE 2-continued

The results of effects of compounds on thermal stability of protein

| compound | Tm (° C.) |
|---|---|
| 26 | 71.02 |
| Maraviroc | 72.17 |

It can be seen from table 2 that all compounds have good protein stability effect, wherein compound 16, 18, 20 and 26 are comparable with the positive control compound.

Example 3

Preliminary Screening Test of Anti-HIV-1 Activity In Vitro

1. Experiment Materials

Phosphate buffered saline (PBS), Streptomycin sulfate, HEPES (N-2 (2-Hydroxyothyl) piperazine-N'-(2-ethanesufonic acid), MTT (3,(4,5-Dimethylthiazol-2-yl)-2,5-diphenyl tetrazolium bromide), Penicillin, Glutamine, 2-Mercaptoethanol, RPMI-1640, RPMI-1640 complete medium and fetal bovine serum (FBS).

2. HIV-1 Infectivity Titration

The virus was titrated according to the modified method of Johnson & Byington. Briefly, the HIV-1 stock solution was subject to four-fold dilution in a 96-well plate (ten gradients) sextuplicate for each gradient, while setting six control-wells. Into each well was added 100 μl ($5 \times 10^6$/ml) PHA-stimulated PBMC cells and final volume per well was 200 μl. The cells were cultured at 37° C. with 5% $CO_2$. On the third day, 100 μl of fresh RPMI-1640 complete medium was supplemented. On the seventh day, the infected supernatant was collected and lysed with 0.5% Triton X100. The p24 antigen was detected by ELISA and $TCID_{50}$ of virus was calculated according to Reed & Muench method (50% Tissue culture infection dose).

3. Toxicity Test of Compounds on HOS-CD4-CCR5, PM1 and PBMC Cells

The compound to be tested was subject to 5-fold dilution in a 96-well microtiter plate with RPMI-1640 or DMEM complete medium (containing 10% FBS) (Six dilution) triplicate for each dilution and 100 μl for each well. While wells not containing drugs were set as control. Into each well was added 100 μl of $4 \times 10^5$/ml PM1, HOS-CD4-CCR5 cells or 100 μl of $5 \times 10^6$/ml PHA stimulated PBMC. The cells were cultured at 37° C. with 5% $CO_2$ for three days (PBMC cells were cultured for seven days and 100 μl of fresh RPMI-1640 complete medium was supplemented on the third day). Cytotoxicity was tested with MTT assay. OD values were measured by ELx800 microplate reader. The detection wavelength was 570 nm, and the reference wavelength was 630 nm. $CC_{50}$ values were calculated (50% Cytotoxic concentration).

4. Inhibition Assay of Compounds on Viral Replication in HOS-CD4-CCR5 Cells Infected with HIV-1$_{SF162}$ or HIV-1$_{Ba-L}$ On the day before the test, $1 \times 10^5$/ml of HOS-CD4-CCR5 cells were inoculated in 96-well plates with 100 μl for each well. The compound to be tested was subject to 5-fold dilution in 96-well microtiter plate with DMEM complete medium (containing 10% FBS). The starting concentration was 1 μM and six dilutions were obtained. Triplicate wells were set for each dilution and each well contained 100 μl mixture. While wells not containing drugs were set as control. The supernatant was removed and 100 μl of drug was added and incubated for 2 h. Then 100 μl of HIV-1$_{SF162}$ and HIV-1$_{Ba-L}$ were added to dilute supernatant. The cells were infected for 1 h, free virus was washed out and drug with the same final concentration was added. MVC was used as positive control. The cells were cultured at 37° C. with 5% $CO_2$ for three days. The supernatant was collected, lysed and inactivated with 0.5% Triton X-100. The inhibition effect of drug on HIV-1 replication was detected using p24 antigen capture ELISA method.

5. Inhibition Assay of Compounds on Viral Replication in PBMC Infected with HIV-1$_{SF162}$, HIV-1$_{Ba-L}$ or HIV-1$_{11018}$ The compound to be tested was subject to 5-fold dilution in 48-well plate with RPMI-1640 complete medium (containing 10% FBS). The starting concentration was 1 μM, six dilutions were obtained, and each well contained 200 μl mixture. While wells not containing drugs were set as control. Virus (MOI=0.01) was added to $5 \times 10^6$/ml of PBMC cells which have been stimulated by PHA for 72 h. After homogeneously mixed, the mixture was immediately added to 48-well plate containing diluted drug and each well was added with 200 μl of mixture. MVC was used as positive control. The cells were cultured at 37° C. with 5% $CO_2$ for seven days (drug with the same concentration was added on the third day). The supernatant was collected, lysed and inactivated with 0.5% Triton X-100. The inhibition effect of drug on HIV-1 replication was detected using p24 antigen capture ELISA method.

6. Experiment Results

TABLE 3

Inhibition activities of compounds on TZM-bl cells infected with HIV-1$_{SF162}$ virus strain

| compound | $CC_{50}$(μg/mL) | $EC_{50}$(μg/mL) | therapeutic index (TI) |
|---|---|---|---|
| 1 | >100 | 0.29 | >340.14 |
| 2 | >100 | 0.326 | >306.75 |
| 3 | >100 | 0.0024 | >41666.67 |
| 4 | 42.761 | 1.46 | 29.29 |
| 6 | >100 | 1.51 | 66.23 |
| 7 | >100 | 2.34 | 50.31 |
| 8 | >100 | 2.69 | >37.17 |
| 9 | >100 | 1.81 | 55.42 |
| 10 | >100 | 1.42 | >70.42 |
| 13 | >100 | 0.18296 | >1093.14 |
| 14 | >200 | 0.00359 | >55710.31 |
| 15 | >200 | 0.31602 | >632.87 |
| 16 | >200 | 0.01179 | >16963.53 |
| 17 | >200 | 0.01295 | >15444.02 |
| 18 | >200 | 0.00123 | >162601.63 |
| 19 | 85.74 | 0.00959 | 8940.56 |
| 20 | 69.68 | 0.00487 | 14308.01 |
| 21 | >200 | 0.14993 | >1333.96 |
| 22 | >200 | 0.00153 | >130718.95 |
| 23 | >200 | 0.06001 | >3332.78 |
| 25 | >200 | 0.16801 | >1190.41 |
| 26 | >200 | 0.00558 | >35842.29 |
| 27 | 96.141 | 0.511 | 188.14 |
| 28 | >200 | >40 | — |
| 29 | >200 | 0.012 | >16666.67 |
| 30 | >200 | 0.060 | >2150.54 |
| 31 | >200 | 0.033 | >5714.29 |
| 32 | >200 | >40 | — |
| 33 | >200 | 0.147 | >328.95 |
| 34 | >200 | >40 | — |
| 35 | >200 | >40 | — |
| 36 | >200 | >40 | — |
| 37 | >200 | 0.647 | >309.12 |
| 38 | >200 | 2.610 | >73.64 |
| 39 | >200 | 1.020 | >196.08 |
| 118 | >200 | 0.669 | >168.03 |
| 119 | >200 | 0.738 | >270.84 |
| 120 | >200 | 0.831 | >240.76 |
| 121 | >200 | 0.328 | >386.37 |

TABLE 3-continued

Inhibition activities of compounds on TZM-bl cells infected with HIV-1$_{SF162}$ virus strain

| compound | $CC_{50}$(μg/mL) | $EC_{50}$(μg/mL) | therapeutic index (TI) |
|---|---|---|---|
| 122 | >200 | 0.690 | >290.06 |
| 125 | >200 | 0.286 | >699.27 |
| 126 | >200 | 0.091 | >2207.68 |
| 127 | >200 | 0.145 | >1379.94 |
| 128 | >200 | 0.174 | >1150.82 |
| 129 | >200 | 0.072 | >1526.72 |
| 130 | >200 | 0.053 | >2562.98 |
| 131 | >200 | 0.098 | >1302.27 |
| 132 | >200 | 0.097 | >2063.25 |
| 133 | >200 | 0.152 | >1313.56 |
| 134 | >200 | 0.113 | >1772.41 |
| 135 | >200 | 0.155 | >1222.11 |
| 136 | >200 | 0.011 | >4834.51 |
| Maraviroc | >200 | 0.00814 | 24570 |

Experimental conclusion: It can be seen from the data shown in the above table that for TZM-bl cells infected with HIV-1$_{SF162}$ virus strain, compounds of the present invention exhibit lower cytotoxicity in vitro and higher therapeutic index, wherein compounds 3, 14, 18, 22 and 26 are better than positive control compound, and compounds 16, 17, 20 and 29 are comparable with the positive control compound.

TABLE 4

Inhibition activities of compounds on PBMC cells infected with HIV-1$_{SF162}$ virus strain

| compound | $EC_{50}$ (ng/mL) | $CC_{50}$(μg/mL) | therapeutic index (TI) |
|---|---|---|---|
| 3 | 145.81 | 273.30 | 1874 |
| 14 | 1.58 | 267.79 | 169487 |
| 16 | 455.15 | 266.85 | 586.3 |
| 17 | 41.29 | 438.58 | 10621 |
| 18 | 92.74 | 345.12 | 3721 |
| 22 | 2.65 | 634.56 | 239456 |
| 29 | 5.05 | >200 | >39604 |

Experimental conclusion: It can be seen from the data shown in the above table that for PBMC cells infected with HIV-1$_{SF162}$ virus strain, compounds of the present invention exhibit lower cytotoxicity in vitro and higher therapeutic index, wherein compounds 14, 22 and 29 have relatively higher therapeutic index, and the therapeutic index of compound 22 even reaches 239456.

TABLE 5

Inhibition activities of compounds on PBMC cells infected with HIV-1$_{KM018}$ virus strain

| compound | $EC_{50}$ (ng/mL) | $CC_{50}$(μg/mL) | therapeutic index (TI) |
|---|---|---|---|
| 3 | 15.66 | 273.30 | 17452.1 |
| 14 | 3.77 | 267.79 | 71031.8 |
| 16 | 554.66 | 266.85 | 481.1 |
| 17 | >1000 | 438.58 | <438.6 |
| 18 | 69.93 | 345.12 | 4935.2 |
| 22 | 5.33 | 634.56 | 119054.4 |
| 29 | 103.24 | >200 | 1937.2 |

Experimental conclusion: It can be seen from the date shown in the above table that for PBMC cells infected with HIV-1$_{KM018}$ virus strain, compounds of the present invention have lower cytotoxicity in vitro and higher therapeutic index, wherein compounds 3, 14 and 22 have relatively higher therapeutic index, and the therapeutic index of compound 22 even reaches 119054.4.

TABLE 6

Inhibition activities of compounds on PBMC cells infected with HIV-1$_{Ba-L}$ virus strain

| compound | $EC_{50}$ (ng/mL) | $CC_{50}$(μg/mL) | therapeutic index (TI) |
|---|---|---|---|
| 3 | 91.25 | 273.30 | 3328.9 |
| 14 | 19.72 | 267.79 | 13579.6 |
| 16 | 364.55 | 266.85 | 1301.1 |
| 17 | 847.67 | 438.58 | 438.6 |
| 18 | 289.12 | 345.12 | 2266.5 |
| 22 | 5.13 | 634.56 | 123695.9 |
| 29 | 235.84 | >200 | 818.3 |

Experimental conclusion: It can be seen from the date shown in the above table that for PBMC cells infected with HIV-1$_{Ba-L}$ virus strain, compounds of the present invention have lower cytotoxicity in vitro and higher therapeutic index, wherein compounds 14 and 22 have relatively higher therapeutic index, and the therapeutic index of compound 22 even reach 123695.9.

TABLE 7

Inhibition activities of compounds on HOS-CD4$^+$-CCR5 cells infected with HIV-1$_{Ba-L}$ virus strain

| compound | $EC_{50}$ (ng/mL) | $CC_{50}$(μg/mL) | therapeutic index (TI) |
|---|---|---|---|
| 3 | 17.15 | 334.35 | 19495 |
| 14 | 0.74 | 369.63 | 499500 |
| 16 | 10.46 | 343.09 | 32800 |
| 17 | 15.52 | 439.04 | 28288 |
| 18 | 3.40 | 506.78 | 149052 |
| 22 | 4.83 | >800 | >165631 |
| 29 | 21.87 | >200 | >9144 |

Experimental conclusion: It can be seen from the data shown in the above table that for HOS-CD4$^+$-CCR5 cells infected with HIV-1$_{Ba-L}$ virus Strain, compounds of the present invention have lower cytotoxicity in vitro and higher therapeutic index, wherein compounds 14, 16, 17, 18 and 22 have relatively higher therapeutic index, and the therapeutic index of compound 14 even reach 499500.

TABLE 8

Inhibition activities of compounds on HOS-CD4$^+$-CCR5 cells infected with HIV-1$_{SF162}$ virus strain

| compound | $EC_{50}$ (ng/mL) | $CC_{50}$(μg/mL) | therapeutic index (TI) |
|---|---|---|---|
| 3 | 24.45 | 334.35 | 13674 |
| 14 | 13.06 | 369.63 | 28302 |
| 16 | 42.66 | 343.09 | 8042 |
| 17 | 50.86 | 439.04 | 8632 |
| 18 | 20.31 | 506.78 | 24952 |
| 22 | 9.15 | >800 | >87431 |
| 29 | 18.59 | >200 | >10758 |

Experimental conclusion: It can be seen from the data shown in the above table that for PBMC cells infected with HIV-1$_{Ba-L}$ Virus strain, compounds of the present invention have lower cytotoxicity in vitro and higher therapeutic index, wherein compounds 3, 14, 18, 22 and 29 have relatively higher therapeutic index, and the therapeutic index of compound 14 even reach 28302.

Example 4 hERG Inhibition Activity Assay

1. Experiment Materials

Fetal calf serum (Gibco, Cat#10099), hygromycin B (Invitrogen, Cat#B13871010), FluxOR™ assay kit (Invitrogen, Cat#F0017), 96-well plate (Corning, Cat#3894), positive control Dofetilide, Cisapride and Maraviroc.

2. Experiment Steps

1. CHO-hERG cells which have been incubated overnight were added with sample buffer and incubated for 90 minutes at room temperature in darkness.

2. The sample buffer was removed and assay buffer was added.

3. The compound is added to the cell plate and incubated for 20 minutes in darkness.

4. Cell plate was placed into FDSS. The fluorescence signal was recorded every second for 10 seconds. Exciting buffer was added to the cells at the $10^{th}$ second and the fluorescence signal was recorded every second for 180 seconds 5. Data were processed.

3. Experiment Results

TABLE 9

Results of hERG inhibition activity assay for compounds

| compound | $IC_{50}$ (μM) |
| --- | --- |
| 8 | >40 |
| 12 | 9.45 |
| 14 | 3.1 |
| 16 | 3.02 |
| 18 | 1.89 |
| 20 | 14.42 |
| 22 | 10.58 |
| 26 | 3.51 |
| 29 | 8.44 |
| 43 | 1.36 |
| 65 | 0.84 |
| 101 | 0.81 |
| 103 | 3.47 |
| 107 | >40 |
| Dofetilide | 0.09 |

TABLE 9-continued

Results of hERG inhibition activity assay for compounds

| compound | $IC_{50}$ (μM) |
| --- | --- |
| Cisapride | 0.19 |
| Maraviroc | 7.75 |

Experiment conclusion: It can be seen from the data shown in the above table that compounds of the present invention have weaker hERG inhibition activity, wherein hERG inhibition activities of compounds 8, 12, 20, 22, 29 and 107 are better that those of positive control compounds.

Example 5

Pharmacokinetic Experiment of Rats

1. Experiment steps:

Six healthy male rats with weight of 150-200 g were randomly divided into 2 groups with 3 rats for each group. The rats in each group were administrated by gavage or intravenous injection with compounds 14, 16, 17, 18, 22 and 29, respectively. The administration volume was 10 mL/kg and drug was formulated with DMSO/Tween 80/physiological saline (5:5:90, v/v/v). The rats were fasted for 12 h and can drink water ad libitum before test. 2 h after dosing, the rats ate together.

2. The time point for collecting blood samples and the sample processing:

Intragastric administration: 0.25, 0.5, 1.0, 2.0, 4.0, 6.0, 8.0 and 24 h after administration.

Intravenous administration: 5 min, 0.25, 0.5, 1.0, 2.0, 4.0, 6.0, 8.0 and 24 h after administration.

At above time points, 0.3 ml of venous blood was taken from retrobulbar venous plexus of the rat and loaded into EDTA-2K anticoagulative tube. After centrifuged at 11000 rpm for 5 mm, the plasma was separated and frozen at −20° C. in a refrigerator.

3. The sample test and data analysis

The concentration of each compound in rat plasma was determined by LC/MS/MS.

The pharmacokinetic parameters after administration were calculated by using non-compartment model of Win-Nonlin 5.3 software (Pharsight Corporation, USA).

4. Experiment results:

TABLE 10

Pharmacokinetic experiment results of rats in vivo

| compound | Route | Dose mg/kg | $T_{max}$ h | $C_{max}$ ng/mL | $AUC_{0-t}$ ng/mL * h | $AUC_{0-\infty}$ ng/mL * h | MRT h | $t_{1/2}$ h | CLz L/h/kg | F % |
| --- | --- | --- | --- | --- | --- | --- | --- | --- | --- | --- |
| 14 | gavage | 20 | 4 | 266.2 | 1108 | 1190 | 3.33 | 2.12 | / | 7.85% |
|  | vein | 10 | 0.25 | 6841 | 7053 | 7055 | 0.71 | 0.77 | 1.42 | / |
| 16 | gavage | 20 | 0.25 | 631.3 | 1512.3 | 1512.3 | 2.11 | 1.16 | / | 14.8% |
|  | vein | 10 | 0.25 | 4316.7 | 5114.9 | 5114.9 | 0.79 | 0.31 | 1.96 | / |
| 17 | gavage | 20 | 0.5 | 121.8 | 347.9 | 364.5 | 2.31 | 1.78 | / | 46.6% |
|  | vein | 10 | 0.25 | 245.9 | 373.5 | 394.5 | 1.42 | 2.22 | 25.4 | / |
| 18 | gavage | 20 | 2 | 690.4 | 2801.1 | 3067.8 | 2.94 | 2.05 | / | 90.5% |
|  | vein | 10 | 0.25 | 771.1 | 1547.0 | 1602.5 | 1.98 | 1.81 | 6.24 | / |
| 22 | gavage | 20 | 2 | 306.4 | 1206 | 1259 | 2.55 | 1.55 | / | 14.5% |
|  | vein | 10 | 0.25 | 3778 | 4154 | 4162 | 0.84 | 1.00 | 2.40 | / |
| 29 | gavage | 20 | 2 | 580.2 | 1870.7 | 2790.3 | 4.79 | 32.84 | / | 40.1% |
|  | vein | 10 | 0.25 | 1692.5 | 2330.2 | 2330.2 | 2.29 | 1.60 | 4.29 | / | compound 14: After 20 mg/kg of compound 14 was administered to rats through gavage, Tmax (time for the plasma concentration reaching the peak concentration) is 4 h, the peak concentration Cmax is 266.2 ng/ml, the area below the curve of drug vs time AUC0-t is 1108 ng·h/ml, and the terminal elimination half-life t½ is 2.12 h. After 10 mg/kg of compound 14 was administered to rats through vein, AUC0-t is 7053 ng·h/ml. After dose-normalized, absolute bioavailability of 20 mg/kg of compound 14 administrated to rats through gavage is 7.85%.

compound 16: After 20 mg/kg of compound 16 was administered to rats through gavage, Tmax (time for the plasma concentration reaching the peak concentration) is 0.25 h, the peak concentration Cmax is 631.3 ng/ml, the area below the curve of drug vs time AUC0-t is 1512.3 ng·h/ml, and the terminal elimination half-life t½ is 1.16 h. After 10 mg/kg of compound 16 was administered to rats through vein, AUC0-t is 5114.9 ng·h/ml. After dose-normalized, absolute bioavailability of 20 mg/kg of compound 16 administrated to rats through gavage is 14.8%.

compound 17: After 20 mg/kg of compound 17 was administered to rats through gavage, Tmax (time for the plasma concentration reaching the peak concentration) is 0.5 h, the peak concentration Cmax is 121.8 ng/ml, the area below the curve of drug vs time AUC0-t is 347.9 ng·h/ml, and the terminal elimination half-life t½ is 1.78 h. After 10 mg/kg of compound 17 was administered to rats through vein, AUC0-t is 373.5 ng·h/ml. After dose-normalized, absolute bioavailability of 20 mg/kg of compound 17 administrated to rats through gavage is 46.6%.

compound 18: After 20 mg/kg of compound 18 was administered to rats through gavage, Tmax (time for the plasma concentration reaching the peak concentration) is 2 h, the peak concentration Cmax is 690.4 ng/ml, the area below the curve of drug vs time AUC0-t is 2801.1 ng·h/ml, and the terminal elimination half-life t½ is 2.05 h. After 10 mg/kg of compound 18 was administered to rats through vein, AUC0-t is 1547.0 ng·h/ml. After dose-normalized, absolute bioavailability of 20 mg/kg of compound 18 administrated to rats through gavage is 90.5%.

compound 22: After 20 mg/kg of compound 22 was administered to rats through gavage, Tmax (time for the plasma concentration reaching the peak concentration) is 2 h, the peak concentration Cmax is 306.4 ng/ml, the area below the curve of drug vs time AUC0-t is 1206 ng·h/ml, and the terminal elimination half-life t½ is 1.55 h. After 10 mg/kg of compound 22 was administered to rats through vein, AUC0-t is 4154 ng·h/ml. After dose-normalized, absolute bioavailability of 20 mg/kg of compound 22 administrated to rats through gavage to the rat is 14.5%.

compound 29: After 20 mg/kg of compound 29 was administered to rats through gavage, Tmax (time for the plasma concentration reaching the peak concentration) is 2 h, the peak concentration Cmax is 580.2 ng/ml, the area below the curve of drug vs time AUC0-t is 1870.7 ng·h/ml, and the terminal elimination half-life t½ is 32.84 h. After 10 mg/kg of compound 29 was administered to rats through vein, AUC0-t is 2330.2 ng·h/ml. After dose-normalized, absolute bioavailability of 20 mg/kg of compound 29 administrated to rats through gavage to the rat is 40.1%.

Experimental conclusion: It can be seem from the above test results that in the pharmacokinetic experiment of rats, compound 18 exhibits excellent absolute bioavailability which reach 90.5%; and compounds 17 and 29 exhibit good absolute bioavailability which reach 46.6% and 40.1%, respectively and is much higher than that of Mara Calvino MVC which has been marketed (only 5% bioavailability as reported).

Example 6

Pharmacokinetic Experiment on Beagles

1. Experimental steps:

Six healthy male Beagles with the weight of 9-11 kg were randomly divided into 2 groups with 3 in each group. The Beagles in each group were administrated by gavage or intravenous injection with compound 22 of the present invention. The administration volume was 2 mL/kg and 1 mL/kg, respectively. The compound was suspended in 20% PEG400 (4:96) for gavage and formulated in DMSO/Tween 80/physiological saline (5:1:94, v/v/v) for intravenous injection. The Beagles were fasted for 12 h and can drink water ad libitum before test. 2 h after dosing, all of Beagles ate together.

2. The time point for collecting blood samples and the sample processing:

Intragastric administration: 0.25, 0.5, 1.0, 2.0, 4.0, 6.0, 8.0 and 24 h after administration.

Intravenous administration: 5 min, 0.25, 0.5, 1.0, 2.0, 4.0, 6.0, 8.0 and 24 h after administration.

At above time points, 0.6 ml venous blood was taken from limb venous and loaded into EDTA-2K anticoagulative tube. After centrifuged at 11000 rpm for 5 mm, the plasma was separated and frozen at −20° C. in a refrigerator.

3. The sample test and data analysis

The concentration of compound 22 in plasma of Beagles was determined by LC/MS/MS.

The pharmacokinetic parameters after administration were calculated by using non-compartment model of WinNonlin 5.3 software (Pharsight Corporation, USA).

4. Experiment results:

TABLE 11

Pharmacokinetic experiment results of compound in Beagles

| compound | Route | Dose mg/kg | $T_{max}$ h | $C_{max}$ ng/mL | $AUC_{0-t}$ ng/mL * h | $AUC_{0-\infty}$ ng/mL * h | MRT h | $t_{1/2}$ h | CLz L/h/kg | F % |
|---|---|---|---|---|---|---|---|---|---|---|
| 22 | gavage | 15 | 0.833 | 4613 | 5426 | 5520 | 2.11 | 3.89 | / | 9.98% |
|  | vein | 3 | / | / | 10877 | 10889 | 1.65 | 1.73 | 0.278 | / | compound 22: After 15 mg/kg of compound 22 was administered to Beagles through gavage, $T_{max}$ (time for the plasma concentration in Beagles reaching the peak concentration) is 0.8333 h, the peak concentration $C_{max}$ is 4613 ng/ml, the area below the curve of drug vs time $AUC_{0-t}$ is 5426 ng·h/ml, and the terminal elimination half-life t½ is 3.89 h. After 3 mg/kg of compound 22 was administered to Beagles through vein, $AUC_{0-t}$ is 10877 ng·h/ml. After dose-normalized, absolute bioavailability of 15 mg/kg of compound 22 administrated through gavage to rats is 9.98%.

Experimental conclusion: It can be seem from the above test results that in the pharmacokinetic experiment of Beagles, compound 22 exhibits good absolute bioavailability.

Example 7

Bacterial Reverse Mutation Assay

1. Experiment Design

The mutagenic effects of compounds 18 and 22 of the present invention on *Salmonella typhimurium* strains TA98 and TA100 in non-metabolic activation (-S9) condition were determined. Two strains, TA98 and TA100 were chosen in bacterial reverse mutation assay for compounds 18 and 22. 9 doses containing 1, 3, 10, 30, 100, 300, 1000, 3000 and 5000 pig/dish, negative and positive controls were set in experiments. 3 dishes were used for each dose. The experiment was carried out under -S9 condition.

2. Experiment Results

Compounds 18 and 22 at each dose did not increase the number of reverent colonies of TA98 and TA100 and no significant bacteria toxicity was observed at each dose. It can be concluded that compounds 18 and 22 have no mutagenic effect on *Salmonella typhimurium* strains TA98 and TA100.

TABLE 12

The number of revertant colonies of *Salmonella typhimurium* TA98 and TA100 under compounds 18 and 22 (-$S_9$)

| Group and dose | number of revertant colonies (Mean ± SD) | | | |
|---|---|---|---|---|
| | TA98 | | TA100 | |
| (μg/dish) | 18 | 22 | 18 | 22 |
| Negative control | 24 ± 2.5 | 24 ± 2.5 | 105 ± 5.5 | 105 ± 5.5 |
| 1 | 24 ± 5.0 | 23 ± 3.2 | 116 ± 9.0 | 107 ± 16.7 |
| 3 | 23 ± 2.6 | 24 ± 3.6 | 96 ± 10.0 | 109 ± 9.3 |
| 10 | 20 ± 2.3 | 23 ± 2.6 | 95 ± 13.1 | 112 ± 10.7 |
| 30 | 19 ± 1.5 | 21 ± 5.2 | 100 ± 8.3 | 90 ± 11.0 |
| 100 | 15 ± 4.6 | 23 ± 6.7 | 88 ± 0.6 | 97 ± 4.6 |
| 300 | 20 ± 4.2 | 23 ± 6.5 | 91 ± 18.2 | 102 ± 2.9 |
| 1000 | 18 ± 1.5 | 19 ± 6.4 | 106 ± 17.6 | 90 ± 6.5 |
| 3000 | 21 ± 1.5 | 22 ± 5.0 | 108 ± 6.9 | 86 ± 13.1 |
| 5000 | 20 ± 4.9 | 25 ± 7.2 | 95 ± 7.2 | 109 ± 17.5 |
| Positive control* | 999 ± 145.2 | 999 ± 145.2 | 1231 ± 146.1 | 1231 ± 146.1 |

*TA98: 2-Nitrofluorene (20 μg/dish); TA100: Methyl methanesulfonate (1300 μg/dish)

Experimental conclusion: It can be seen from the above test results that compounds 18 and 22 have no mutagenic effect on *Salmonella typhimurium* strains TA98 and TA100 under the present experiment conditions.

Example 8

Inhibition Activity Assay of Different CYP450 Enzyme Subfamilies

1. Experiment Materials

VividR CYP450 Screening Kits, and Envision 2101 multifunction microplate reader, etc.

2. Experiment Theory

VividR CYP450 Screening Kits can be used to evaluate the effects on CYP450 subtypes (CYP1A2, CYP2D6, CYP2C9, CYP2C19, CYP3A4-T and CYP3A4-M) and the substrate VividR in the kit can be metabolizd to a product which can emit strong fluorescence in an aqueous solution by specific CYP450 enzymes.

3. Experiment Steps

1. The compounds to be tested and positive compound were added to corresponding wells and DMSO was added to control wells.

2. CYP450 enzyme was added to the compounds to be tested, positive compound and DMSO control wells. The enzyme dilution was used to replace enzyme and added to DMSO wells as test background. The mixture was vibrated and mixed for 1 minute, and then incubated at room temperature for 20 minutes.

3. NADP$^+$ regeneration system and the substrate were added to initiate the reaction and incubated at room temperature for 60 minutes.

4. Envision 2101 multifunction microplate reader was used to record the fluorescence signal under the conditions of 480 nm excitation and 530 nm emission.

4. Experiment Results

TABLE 13

Inhibition activity effects of compounds on CYP450 enzyme of different subfamilies

| | CYP450 subtype (μM) | | | | | |
|---|---|---|---|---|---|---|
| compound | 1A2 | 2C9 | 2C19 | 2D6 | 3A4-M | 3A4-T |
| 16 | >25 | >25 | >25 | 15.1 | 12.3 | 21.7 |
| 17 | >25 | >25 | >25 | >25 | >25 | >25 |
| 18 | >25 | >25 | >25 | 16.8 | >25 | >25 |
| 22 | >25 | >25 | >25 | >25 | >25 | >25 |
| 29 | >25 | >25 | >25 | >25 | 10.9 | 23.4 |
| Maraviroc | >25 | 14.4 | >25 | >25 | 3.1 | 14.9 |

$IC_{50} < 1$ μM: high inhition;
$1$ μM $< IC_{50} < 10$ μM: medium inhition;
$IC_{50} > 10$ μM: low inhibition Experimental conclusion: IC50 values of inhibition activities of compounds 16, 17, 18, 22 and 29 on six subtypes of CYP450 are greater than 10 μM. The inhibition activities of compounds are quite weak and better than that of Maraviroc.

Example 9

Four Days Subacute Toxicity Test of Rats

1. Experiment Purpose

After compounds 18 and 22 of the present invention were administered to SD rats through gavage for 4 consecutive days, the toxic reaction was preliminarily assessed to confirm the possible target organ of toxic reaction.

2. Experiment Design

Four dose groups containing 100 and 1000 mg/kg of compound 18, 100 and 1000 mg/kg of compound 22 were set. One vehicle control group was set. Each group contained four rats including two male rats and two female rats. During the experiment stage, the animals were daily clinically observed. The body weight was regularly measured. On the 5$^{th}$ day, all animals were subject to pathological examination and gross anatomy.

3. Experiment Results

Compared with the animals in vehicle control group, the weight gain of some male and female animals in compound 18 (100 and 1000 mg/kg) and compound 22 (100 and 1000 mg/kg) dose group increased slowly or exhibited negative growth. Clinical observations, clinical pathology detection (hematology and serum biochemistry) and macroscopic morphological observation showed no significant drug-related changes.

Experiment conclusion: In summary, under the conditions of this experiment, No Observed Adverse Effect Level (NOAEL) is 1000 mg/kg for SD rats which have been administrated with compound 18 through gavage for 4 days, and NOAEL is 1000 mg/kg for SD rats which have been administrated with compound 22 through gavage for 4 days. Thus, the compounds have good safety.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A compound of formula I, a pharmaceutically acceptable salt, enantiomer, diastereoisomer, racemate or mixture thereof,

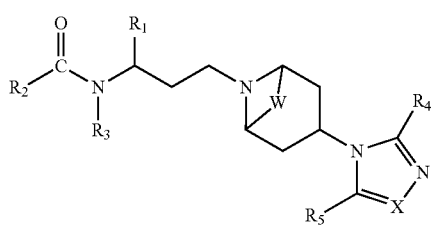

(I)

wherein,
W is absent or —CH$_2$CH$_2$—;
X is N or CR$_6$;

R$_1$ is selected from a 5 to 7-membered heteroaryl unsubstituted or substituted with 1-3 substituents, wherein said heteroaryl contains 1 to 3 heteroatoms selected from oxygen, sulfur or nitrogen and each of said substituents is independently selected from a halogen, a C1-C4 straight or branched alkyl, a C1-C4 straight or branched haloalkyl, a C1-C4 straight or branched alkyloxy, a C1-C4 straight or branched chain haloalkoxy, —NR$_{10}$R$_{11}$, —C(═O)R$_{12}$, a C1-C4 straight or branched alkanoyloxy, a cyano, a nitro and a hydroxy, or two adjacent R$_1$ substituents with the atoms to which each is attached are combined to form a fused 5-7 membered ring;

each of R$_{10}$ and R$_{11}$ is independently selected from a group consisting of H, a C1-C4 straight or branched alkyl and —C(═O)R$_{13}$;

R$_{12}$ is selected from a group consisting of a C1-C4 straight or branched alkyl, a C1-C4 straight or branched alkyloxy, a hydroxyl, an amino (NH$_2$) and a C1-C4 straight or branched alkylamino;

R$_{13}$ is selected from a group consisting of H and a C1-C4 straight or branched alkyl;

R$_2$ is selected from the following groups unsubstituted or substituted with 1-3 substituents: a C1-C6 straight or branched alkyl, a C3-C7 cycloalkyl, a 4 to 7-membered heterocyclic group, a C6-C12 aryl or a 5-7 membered heteroaryl; wherein, said substituent is selected from a group consisting of a halogen, a hydroxy, a C1-C4 straight or branched alkyl, a C1-C4 straight or branched haloalkyl, a C1-C4 straight or branched alkyloxy, a C1-C4 straight or branched alkyl carbonyl, a C1-C4 straight or branched haloalkoxy, a C1-C4 straight or branched alkylsulfonyl group, a C1-C4 straight or branched alkylsulfonylcarbamoyl, a tetrazolyl, a cyano, a nitro, an amino, a carboxy, a phenyl, a halophenyl, a phenoxy, and a halophenoxy;

each of R$_3$, R$_4$ and R$_5$ is independently selected from a group consisting of H, a C1-C6 straight or branched alkyl and a C3-C7 cycloalkyl;

R$_6$ is selected from a group consisting of H and a C1-C6 straight or branched alkyl; alternatively, R$_5$ and R$_6$ may bind together with

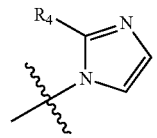

to form

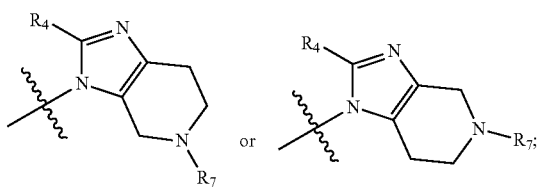

R$_7$ is selected from a group consisting of H, C(═O)R$_8$, C(═O)OR$_8$, C(═O)NR$_8$R$_9$, SO$_2$R$_8$ and the following groups substituted by 1-3 substituents a C1-C6 straight or branched alkyl, a C3-C7 cycloalkyl, a 4 to 7-membered heterocyclic group, a benzyl, a C6-C12 aryl and a 5-7 membered heteroaryl; wherein said substituent is selected from a halogen, a hydroxy, a C1-C4 straight or branched alkyloxy, a C1-C4 straight or branched alkyl, a C1-C4 straight or branched haloalkyl, a C1-C4 straight or branched haloalkoxy, a cyano, a nitro, an amino and a carboxyl;

each of $R_8$ and $R_9$ is independently selected from a group consisting of a hydrogen and the following groups unsubstituted or substituted with 1-3 substituents: a C1-C6 straight or branched alkyl, a C3-C7 cycloalkyl, a 4-7 membered heterocyclic group, a benzyl, a C6-C12 aryl and a 5-7 membered heteroaryl; wherein said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, a nitro, an amino, and a carboxyl.

2. The compound according to claim 1, a pharmaceutically acceptable salt, enantiomer, diastereoisomer, racemate or mixture thereof, wherein, $R_1$ is selected from the following groups unsubstituted or substituted with 1-3 substituents:

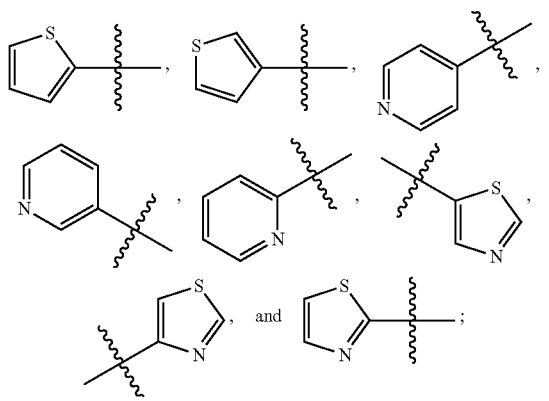

said substituent is defined as claim 1;

each of $R_{10}$ and $R_{11}$ is independently selected from a group consisting of H, a C1-C2 alkyl and —C(=O)$R_{13}$;

$R_{12}$ is selected from a group consisting of a C1-C2 alkyl, a C1-C2 alkoxy, a hydroxy, an amino ($NH_2$) and a C1-C2 alkylamino;

$R_{13}$ is selected from a group consisting of H and a C1-C2 straight or branched alkyl;

$R_2$ is selected from the following groups unsubstituted or substituted with 1-3 substituents: a C1-C4 straight or branched alkyl, a C3-C7 cycloalkyl, a 4-7 membered heterocyclic group and a phenyl, wherein, said substituent is selected from a group consisting of a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, a cyano, a nitro, an amino, a carboxyl, a phenyl, a halophenyl, a phenoxy and a halophenoxy;

each of $R_3$, $R_4$ and R5 is independently selected from a group consisting of H, a C1-C4 straight or branched alkyl and a C3-C7 cycloalkyl;

$R_6$ is selected from a group consisting of H and a C1-C4 straight or branched alkyl, or $R_5$ and $R_6$ can bind together with

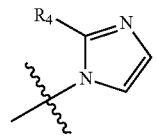

to form

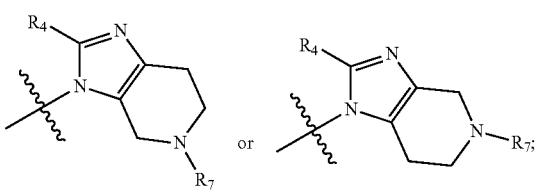

$R_7$ is selected from a group consisting of H, C(=O)$R_8$, C(=O)O$R_8$, C(=O)N$R_8R_9$, $SO_2R_8$ and the following groups substituted with 1-3 substituents: a C1-C4 straight or branched alkyl, a C3-C7 cycloalkyl, a 4-7 membered heterocyclic group, a benzyl and a phenyl, wherein, said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, an nitro, an amino and a carboxyl; each of $R_8$ and $R_9$ is independently selected from a group consisting of H and the following groups unsubstituted or substituted with 1-3 substituents: a C1-C4 straight or branched alkyl, a C1-C4 straight or branched haloalkyl, a C3-C7 cycloalkyl, a 4-7 membered heterocyclic group, a benzyl, a phenyl and a 5-7 membered heteroaryl, wherein, said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy, a cyano, a nitro, an amino and a carboxyl.

3. The compound according to claim 2, a pharmaceutically acceptable salt, enantiomer, diastereoisomer, racemate or mixture thereof, wherein said substituent on $R_1$ is selected from a group consisting of a halogen, a C1-C2 alkyl, a C1-C2 haloalkyl, a C1-C2 alkoxy, $NR_{10}R_{11}$, —C(=O)$R_{12}$, a C1-C2 alkylcarbonyloxy, a C1-C2 haloalkoxy, a cyano, a nitro and a hydroxyl, or two adjacent $R_1$ substituents with the atoms to which each is attached are combined to form a fused 5-7 membered carbocycle, 5-7 membered heteroaryl ring or 5-7 membered heterocycle.

4. The compound according to claim 3, a pharmaceutically acceptable salt, enantiomer, diastereoisomer, racemate or mixture thereof, wherein said substituent on $R_1$ is selected from a group consisting of a halogen, a methyl, a methoxy, an ethyl, an amino, a hydroxy, a formamido, an acetamido, a carbamoyl, N-methylcarbamoyl, N,N-dimethylcarbamoyl, a formyloxy, an acetoxy, a methoxycarbonyl, a trifluoromethyl, a cyano, a nitro, an acetyl and a trifluoromethoxy, or two adjacent $R_1$ substituents together with the atoms to which each is attached form a benzene ring, a cyclopentene ring or dioxole ring.

5. The compound according to claim 4, a pharmaceutically acceptable salt, enantiomer, diastereoisomer, racemate or mixture thereof, wherein $R_2$ is selected from a C1-C4 straight or branched alkyl, a cyclopropyl, a cyclobutyl, a cyclopentyl, a cyclohexyl, a tetrahydropyran-4-yl, a 1-methylpiperidin-4-yl, 1-acetylpiperidin-4-yl, 1-methylsulfonylpiperidin-4-yl,

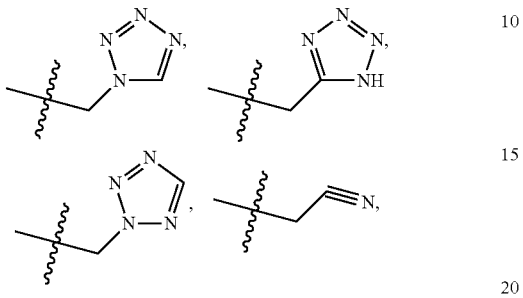

4-fluorobenzyl, a phenyl, a difluorocyclohexyl, an ethylcyclohexyl and a phenoxymethyl.

6. The compound according to claim 4, a pharmaceutically acceptable salt, enantiomer, diastereoisomer, racemate or mixture thereof, wherein $R_6$ is selected from a group consisting of H, a methyl and an ethyl.

7. The compound according to claim 4, a pharmaceutically acceptable salt, enantiomer, diastereoisomer, racemate or mixture thereof, wherein $R_7$ is selected from a group consisting of H, C(=O)$R_8$ and SO$_2$$R_8$.

8. The compound according to claim 4, a pharmaceutically acceptable salt, enantiomer, diastereoisomer, racemate or mixture thereof, wherein said substituent on each of $R_8$ and $R_9$ is selected from a group consisting of halogen, a hydroxy, a methoxy, an ethoxy, a methyl, an ethyl, a trifluoromethyl, a trifluoromethoxy, a cyano, a nitro, an amino and a carboxyl.

9. The compound according to claim 7, a pharmaceutically acceptable salt, enantiomer, diastereoisomer, racemate or mixture thereof, wherein each of $R_3$, $R_4$ and $R_5$ is independently selected from a group consisting of H, a methyl, an ethyl, an n-propyl, an isopropyl, an n-butyl, a sec-butyl, a tertiary butyl, a cyclopropyl, a cyclobutyl, a cyclopentyl and a cyclohexyl.

10. The compound according to claim 9, a pharmaceutically acceptable salt, enantiomer, diastereoisomer, racemate or mixture thereof, wherein each of $R_3$, $R_4$ and $R_5$ is independently selected from a group consisting of H, a methyl, an ethyl, an n-propyl, an isopropyl, an n-butyl, a sec-butyl, a tertiary butyl and a cyclopropyl.

11. The compound according to claim 4, a pharmaceutically acceptable salt, enantiomer, diastereoisomer, racemate or mixture thereof, wherein each of $R_8$ and $R_9$ is independently selected from a group consisting of H, a C1-C4 straight or branched alkyl, a C1-C4 straight or branched haloalkyl, a C3-C7 cycloalkyl, a benzyl and a phenyl.

12. The compound according to claim 11, a pharmaceutically acceptable salt, enantiomer, diastereoisomer, racemate or mixture thereof, wherein each of $R_8$ and $R_9$ is independently selected from a group consisting of a methyl, an ethyl, an n-propyl, a cyclopropyl, an isopropyl, an n-butyl, a sec-butyl and a tert-butyl.

13. The compound according to claim 1, a pharmaceutically acceptable salt, enantiomer, diastereoisotner, racemate or mixture thereof, wherein, the compound of formula (I) is selected from the following compounds:

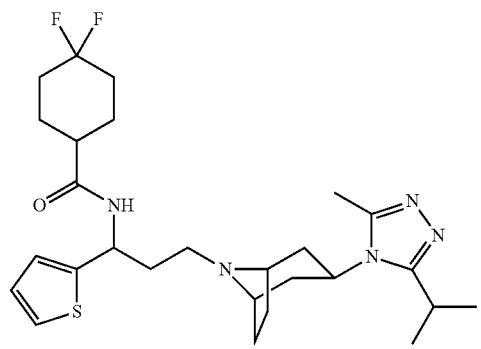

3

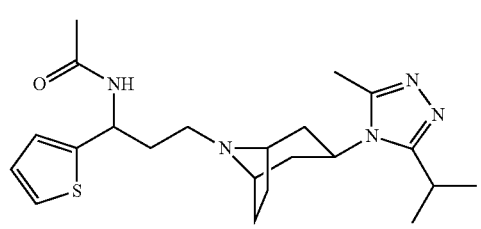

4

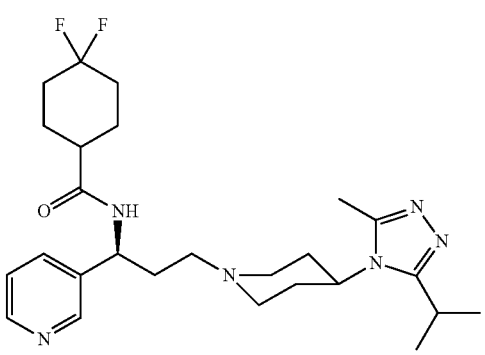

5

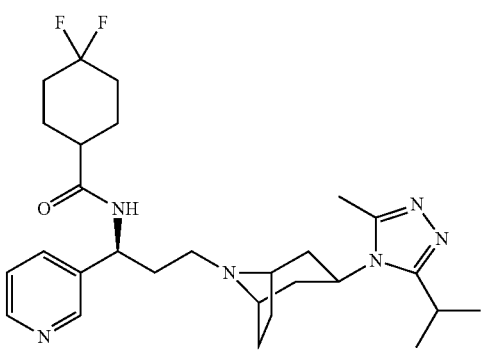

6

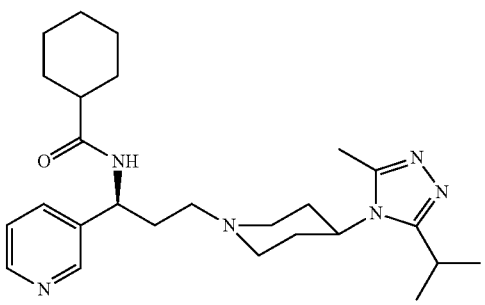

7

-continued
8
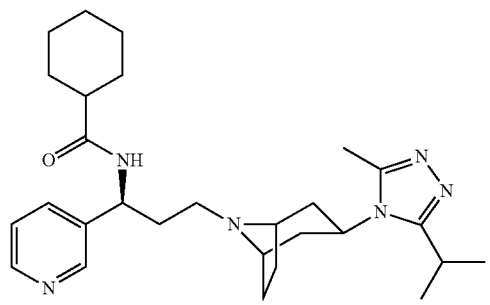
9
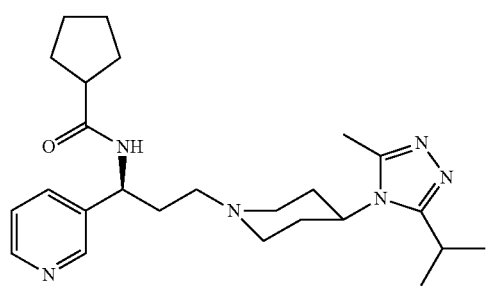
10
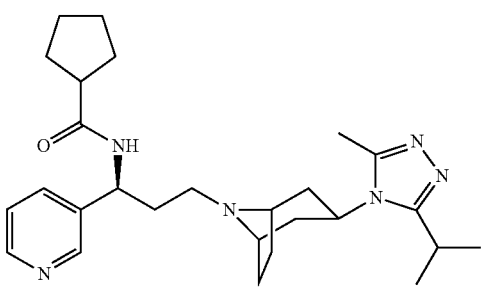
11
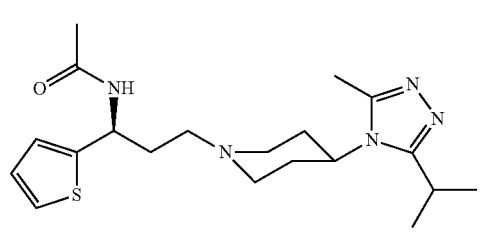
12
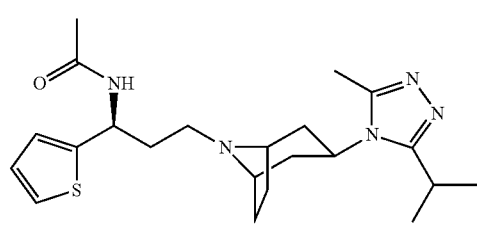
-continued
13
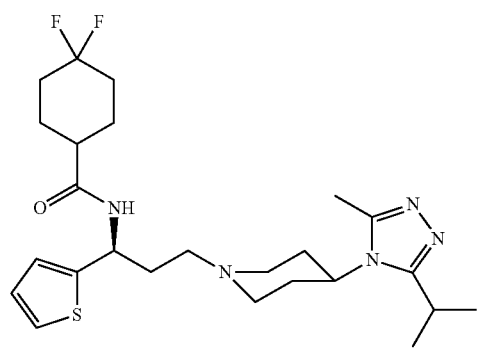
14
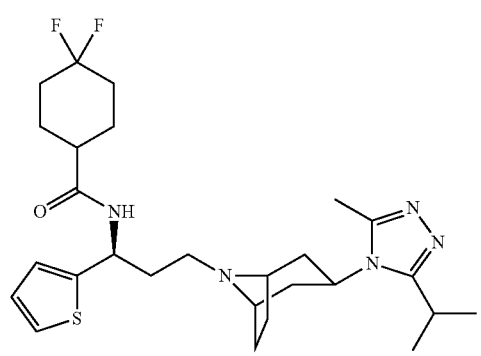
15
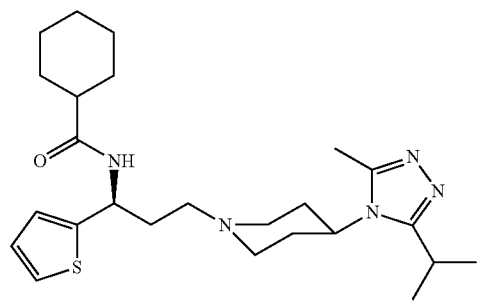
16
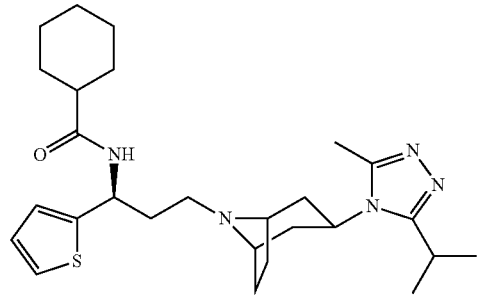
17
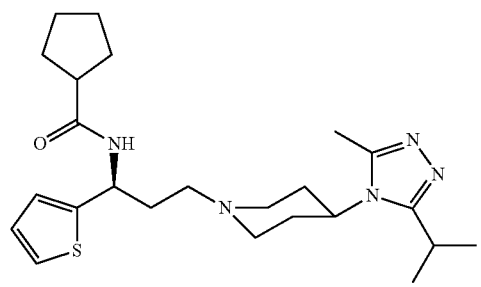

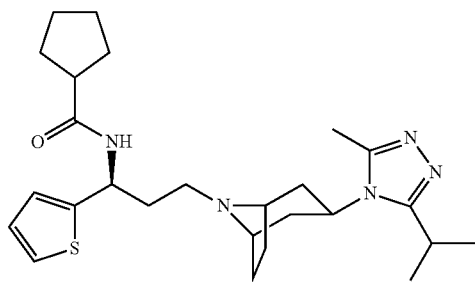
18
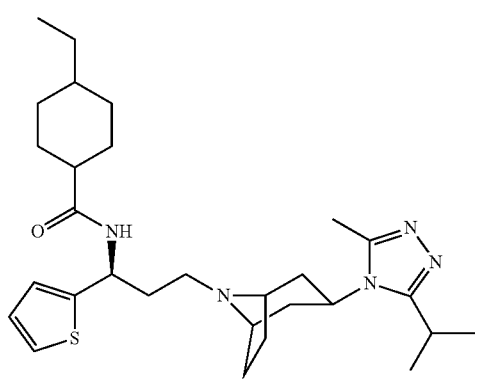
19
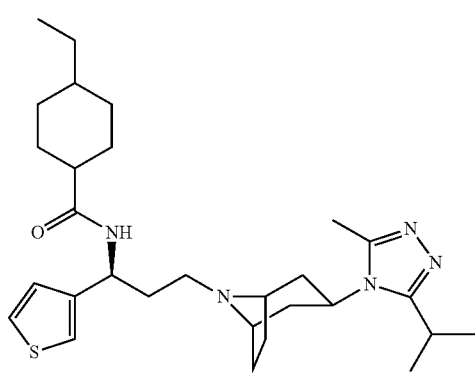
20
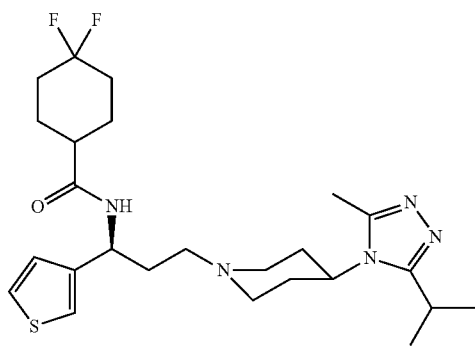
21
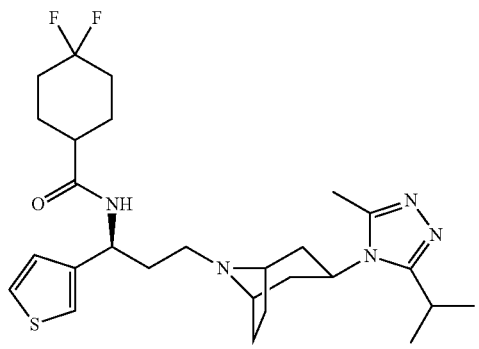
22
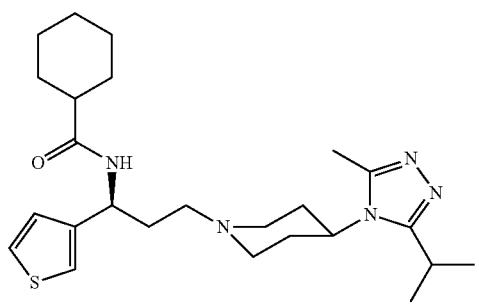
23
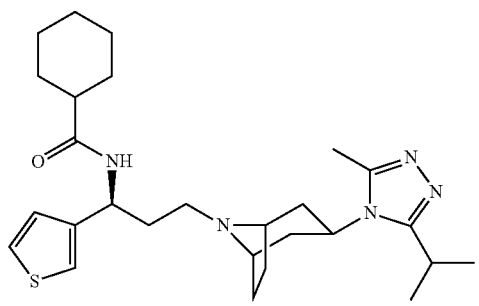
24
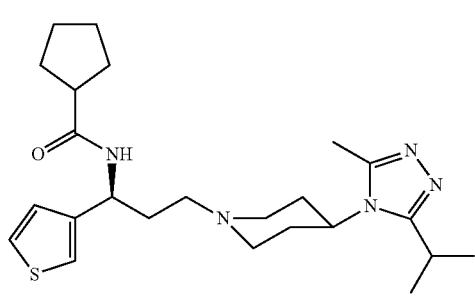
25
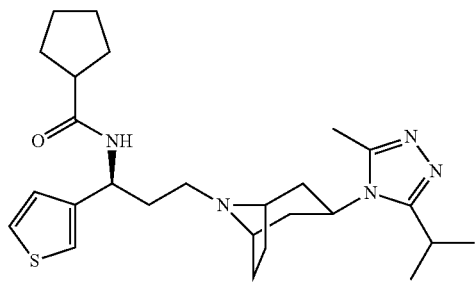
26

27
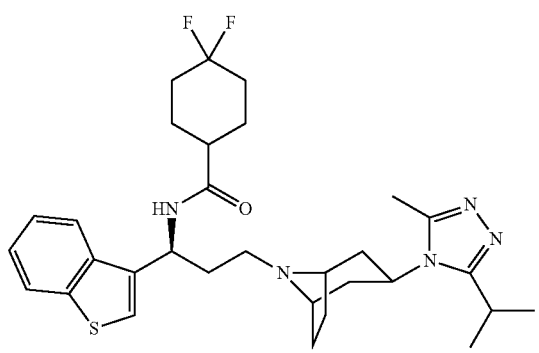
28
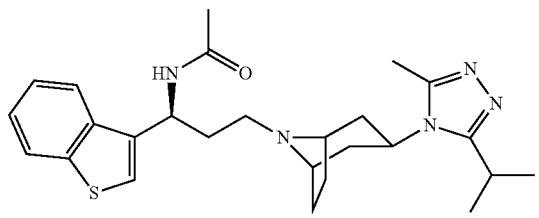
29
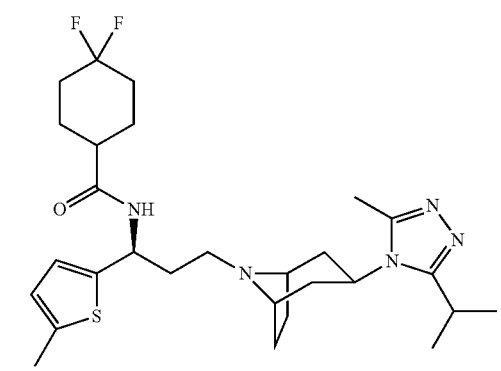
30
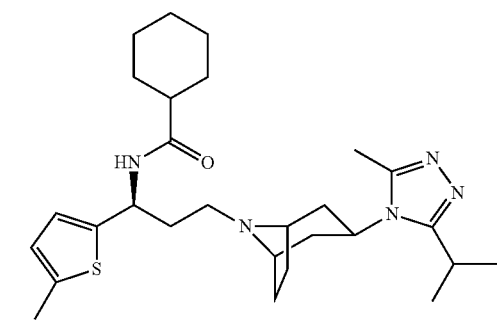
31
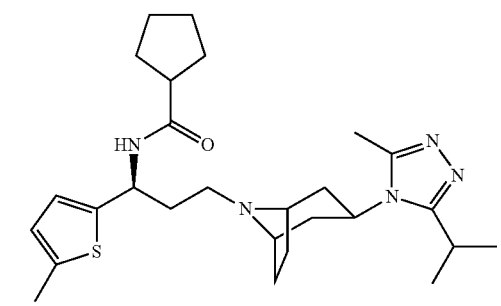
32
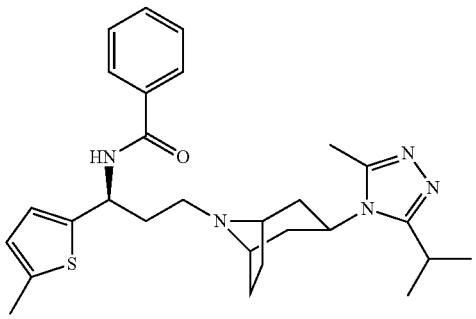
33
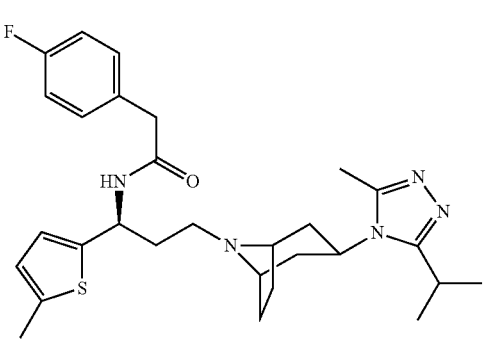
34
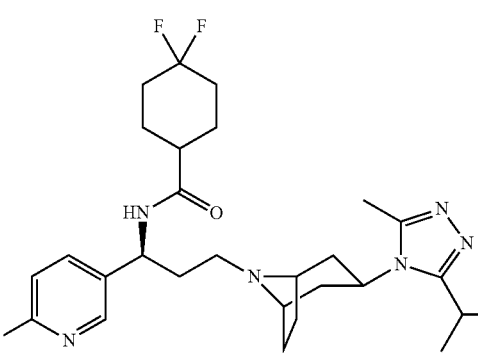
35
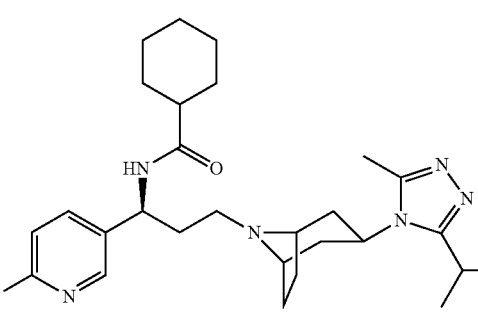
36
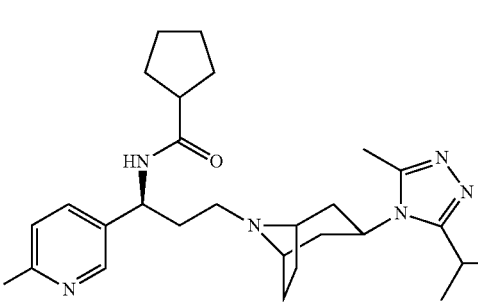

37
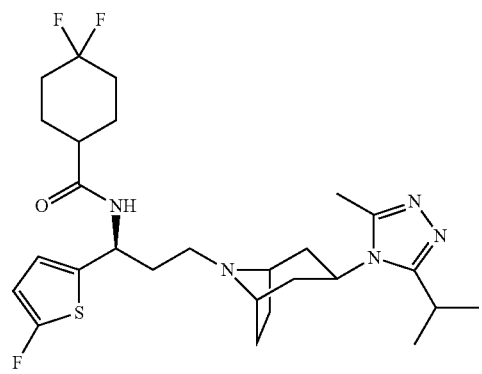
38
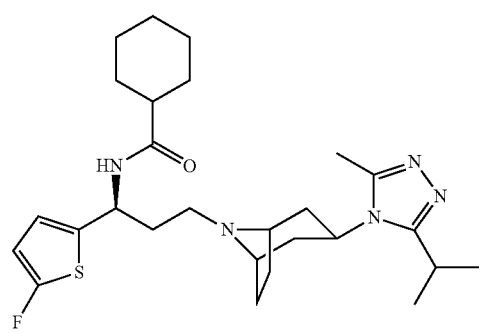
39
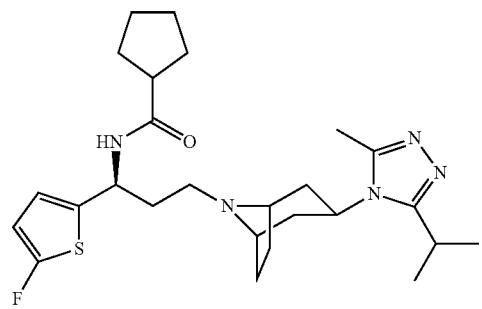
40
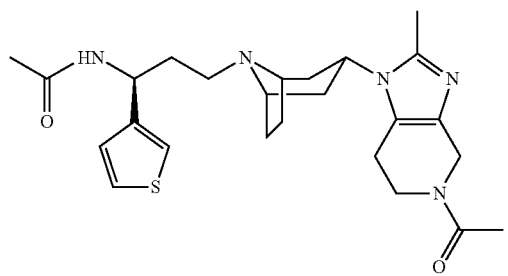
41
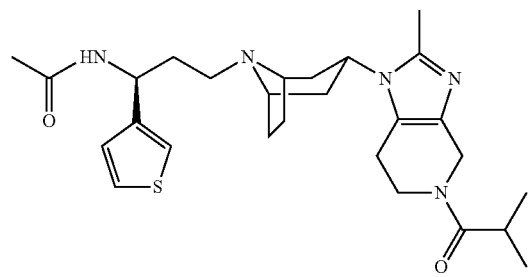
42
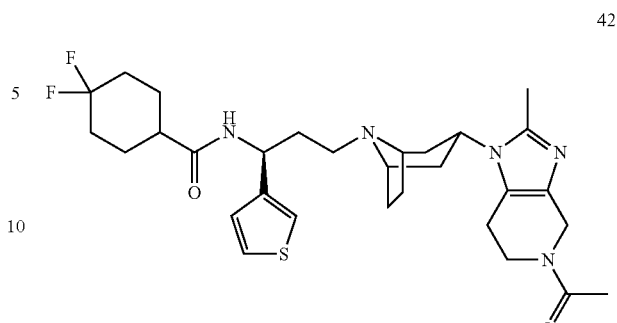
43
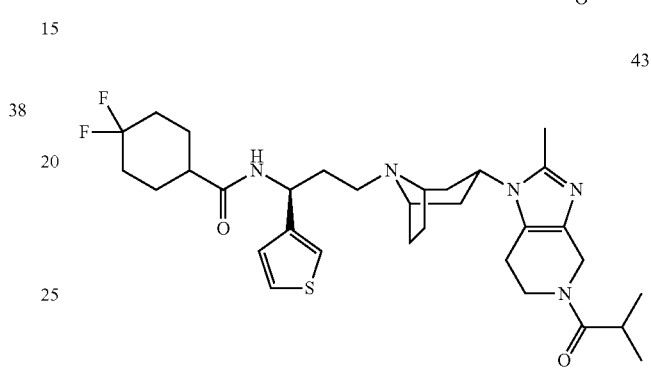
44
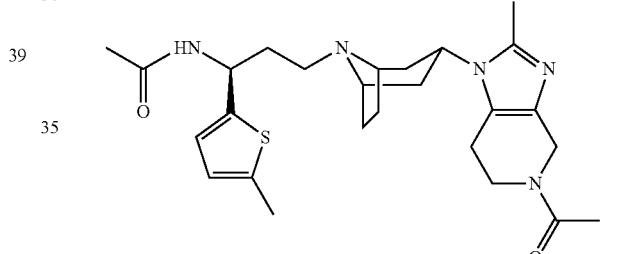
45
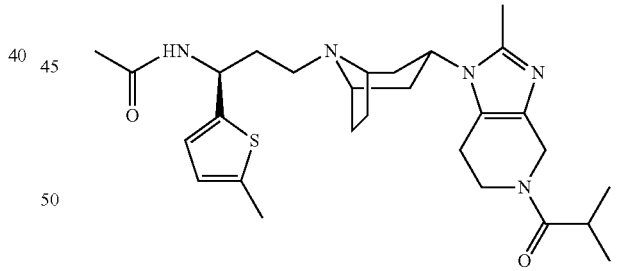
46
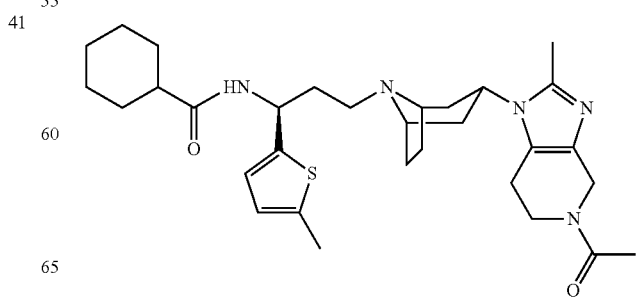

47
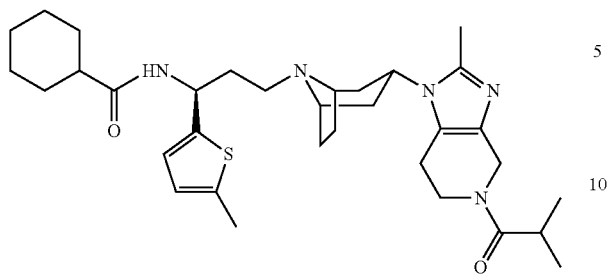
48
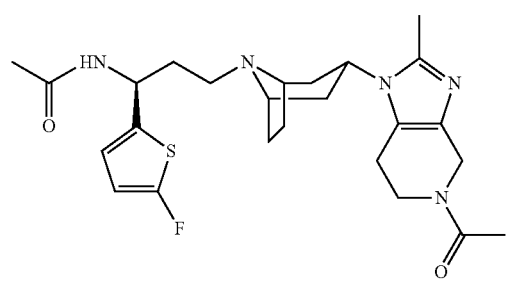
49
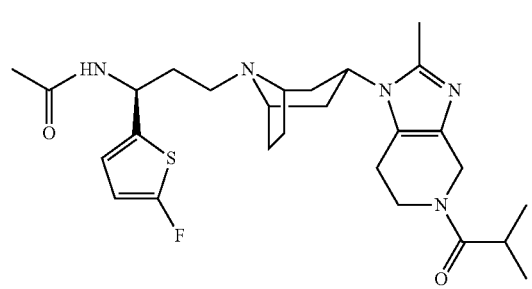
50
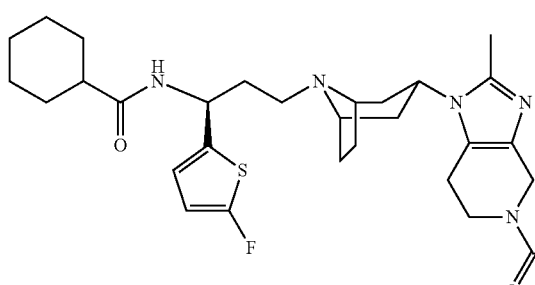
51
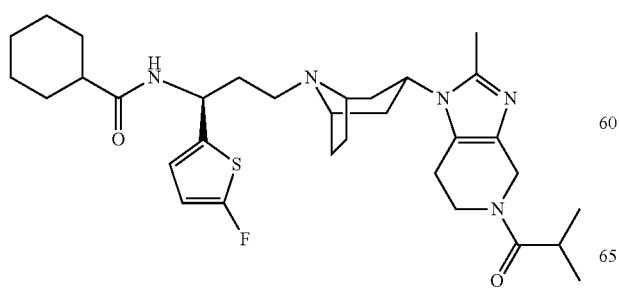
52
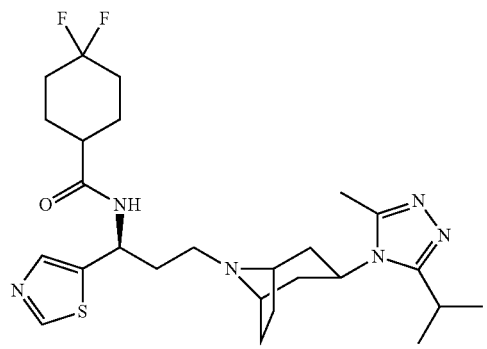
53
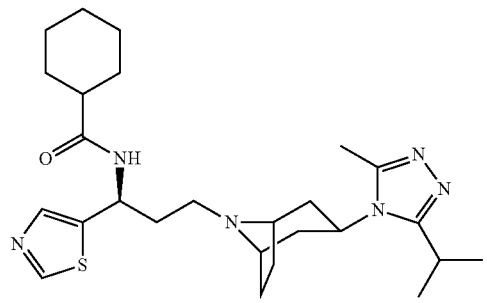
54
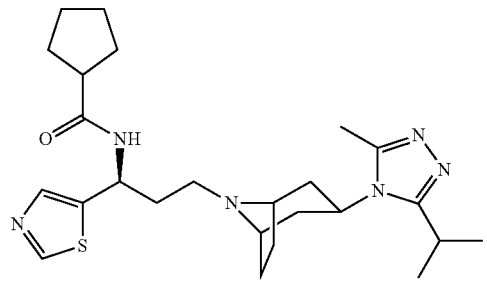
55
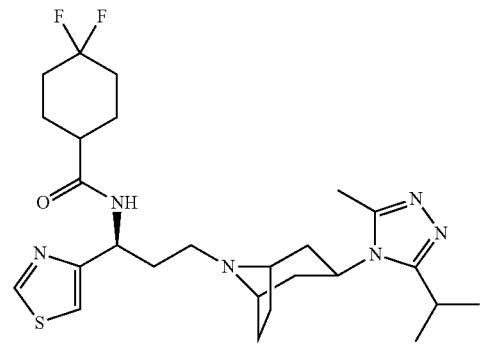
56
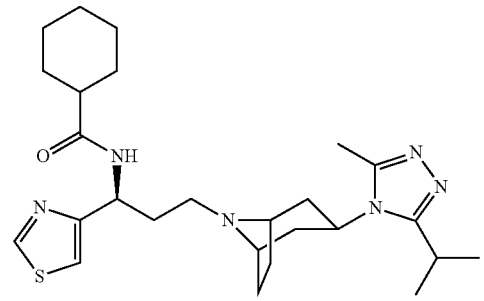

57
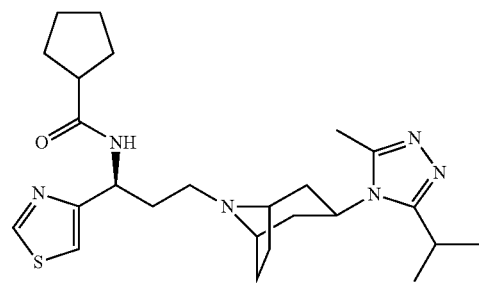
58
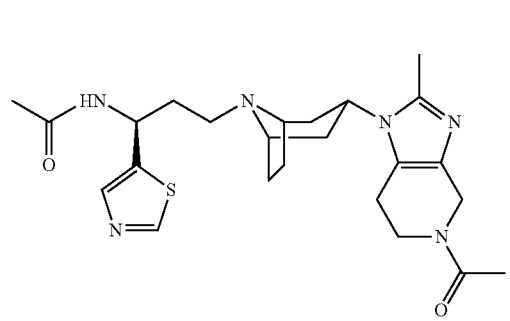
59
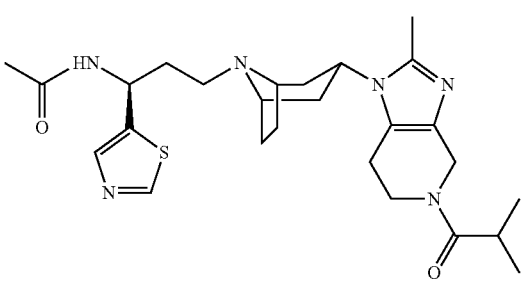
60
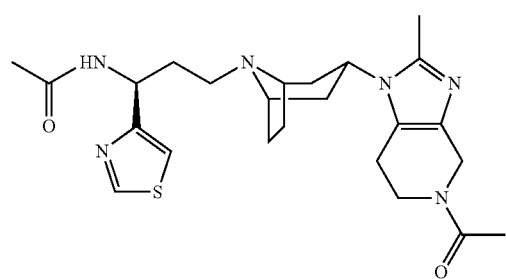
61
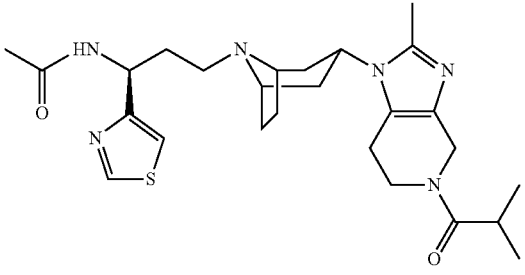
62
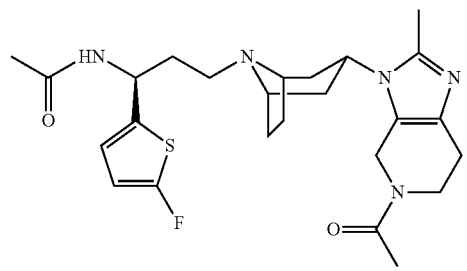
63
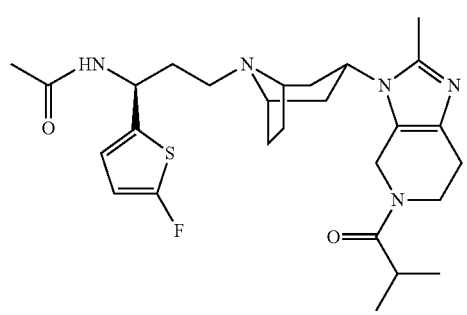
64
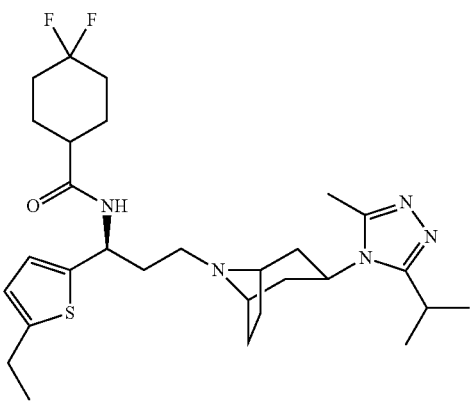
65
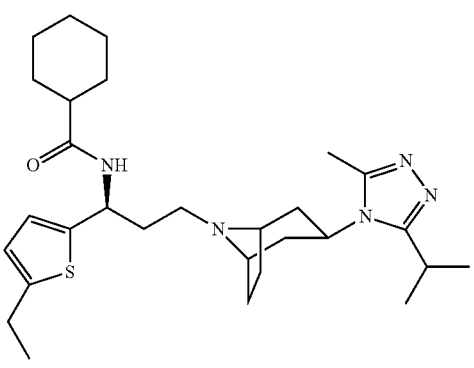

-continued
66
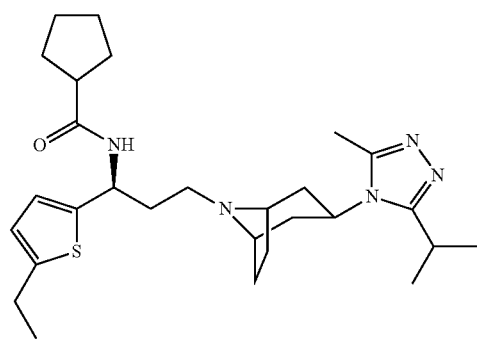
67
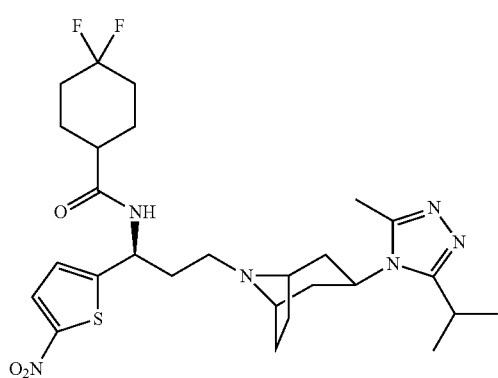
68
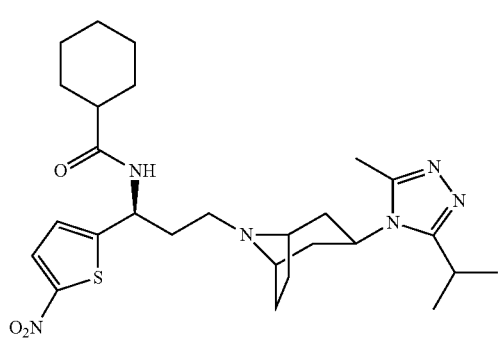
69
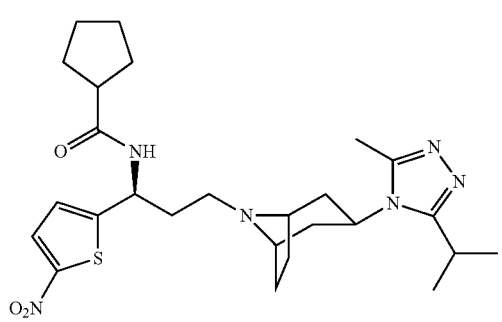
-continued
70
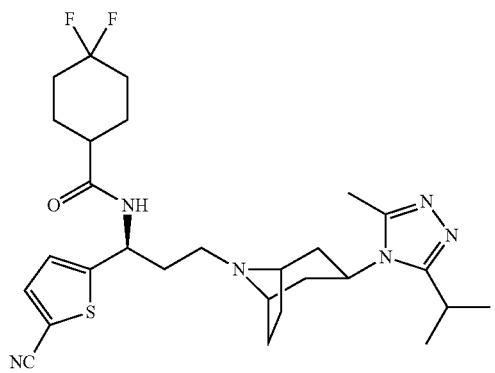
71
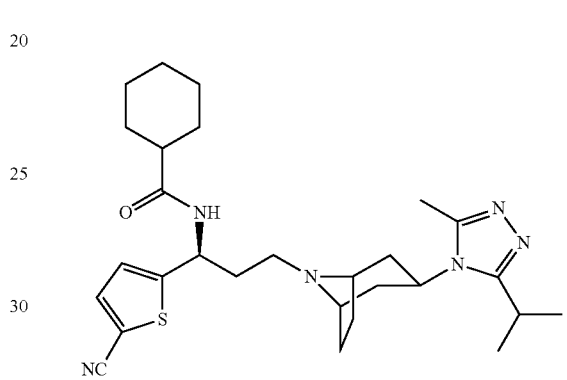
72
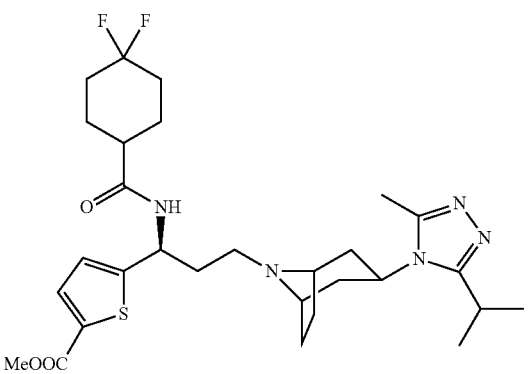
73
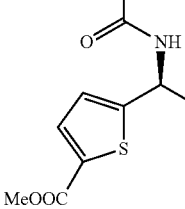

74
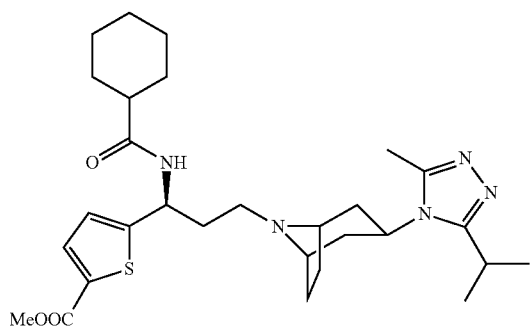
78
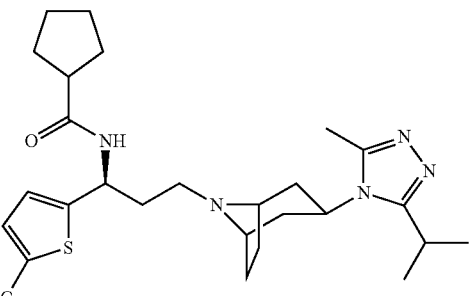
75
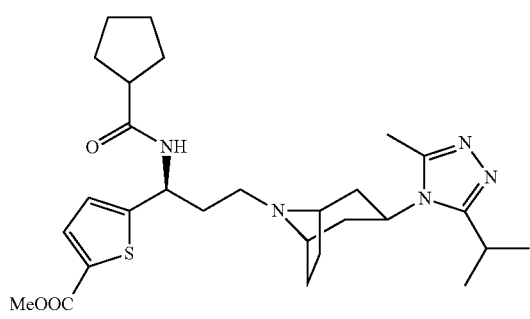
79
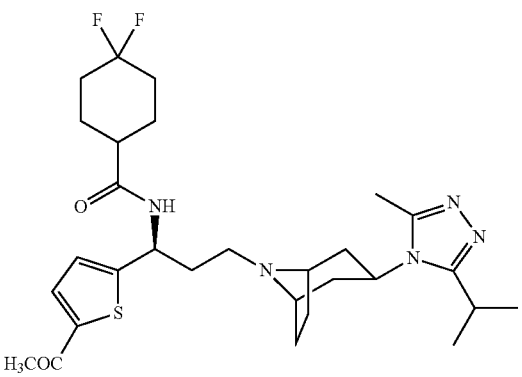
76
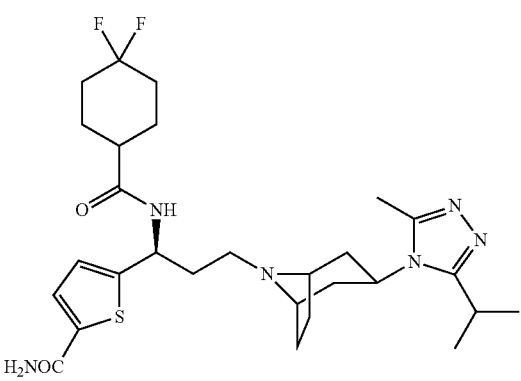
80
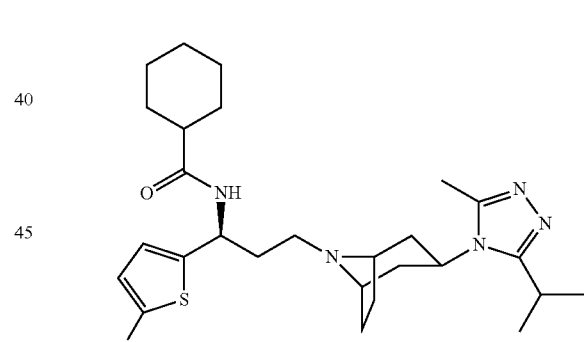
77
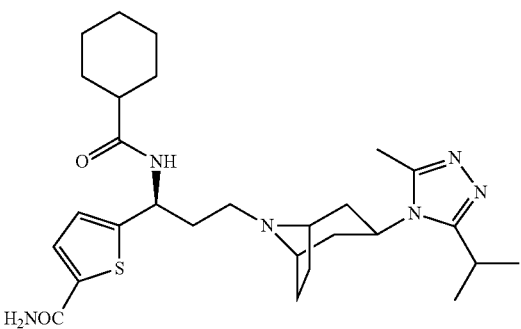
81
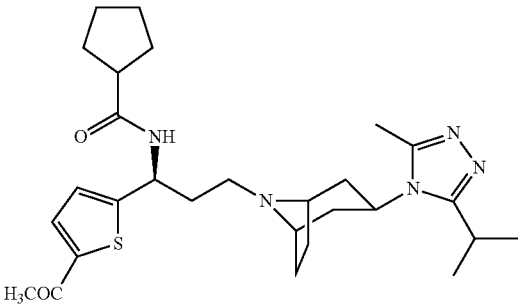

82
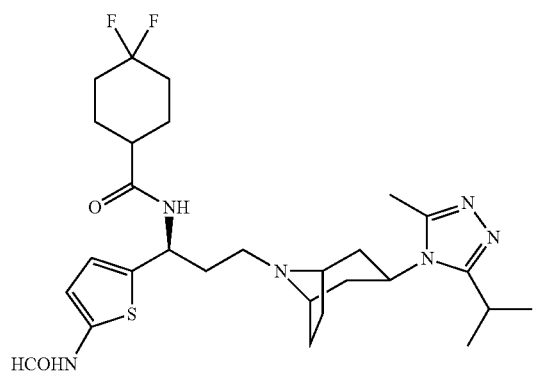
83
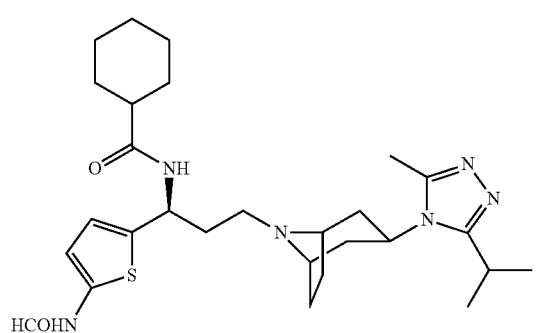
84
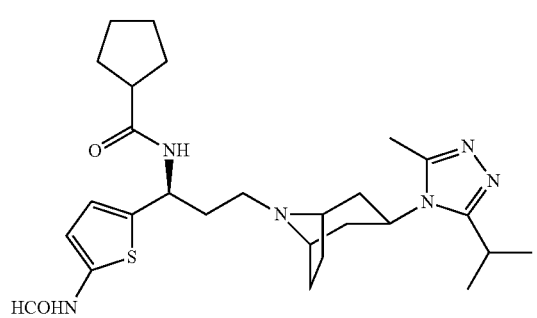
85
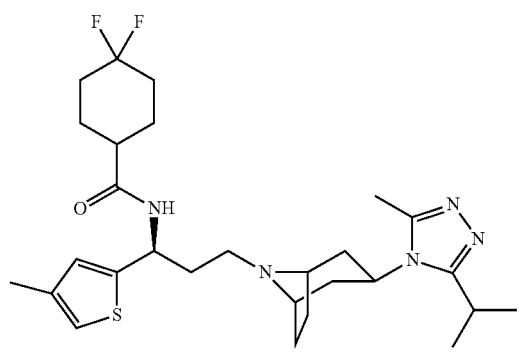
86
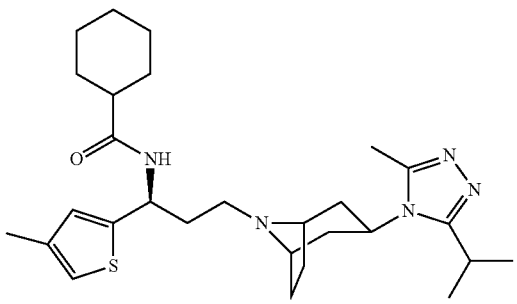
87
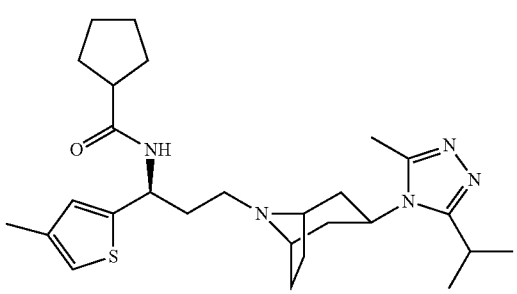
88
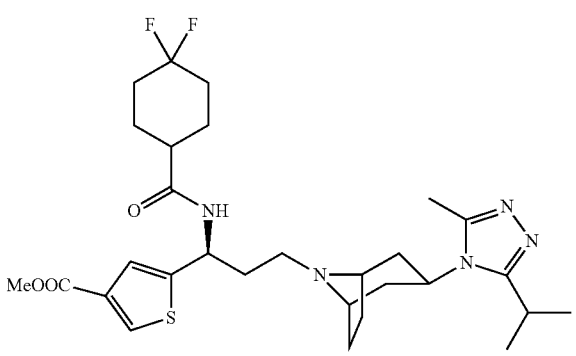
89
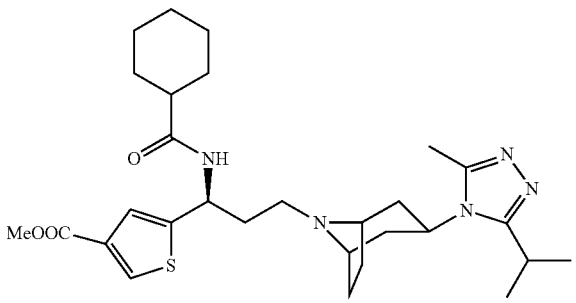
90
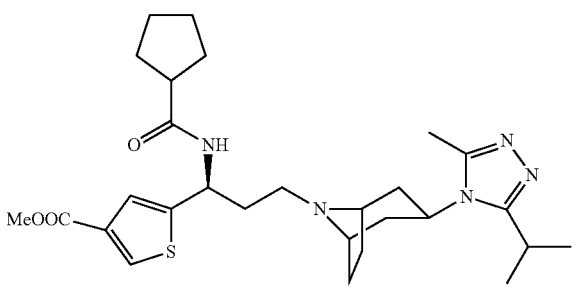

157
-continued
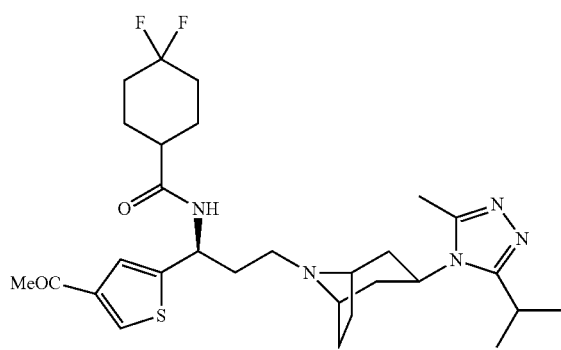
91
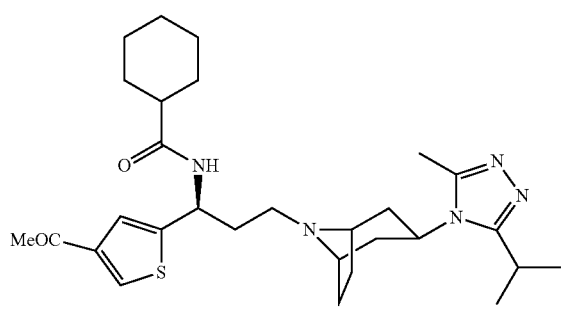
92
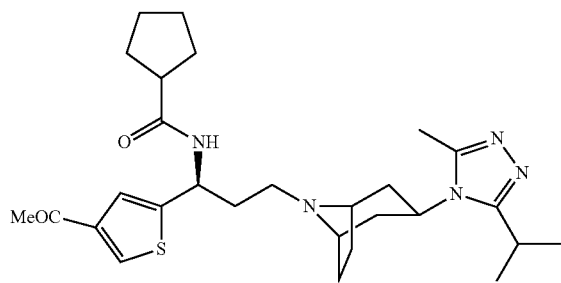
93
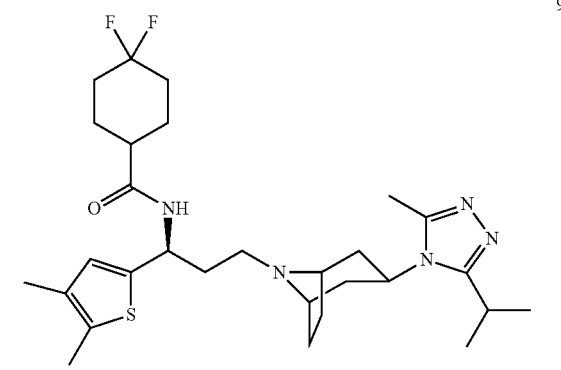
94
158
-continued
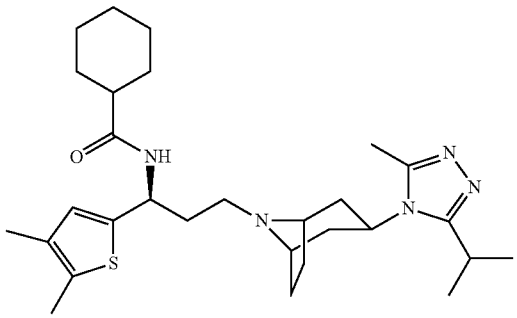
95
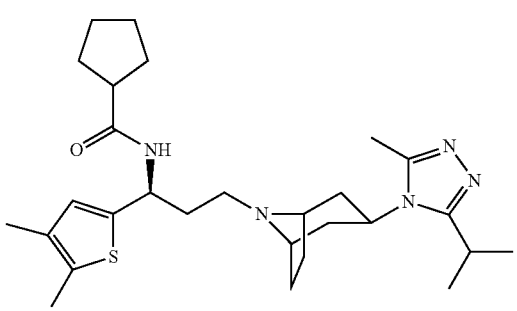
96
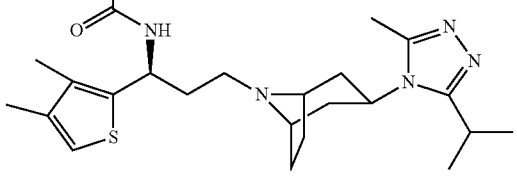
97
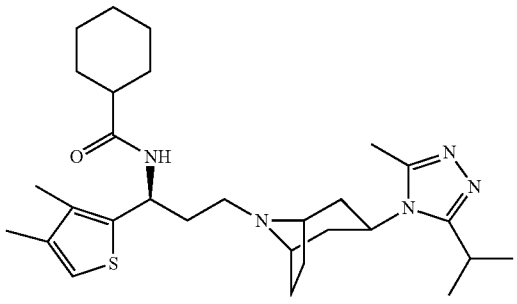
98
99

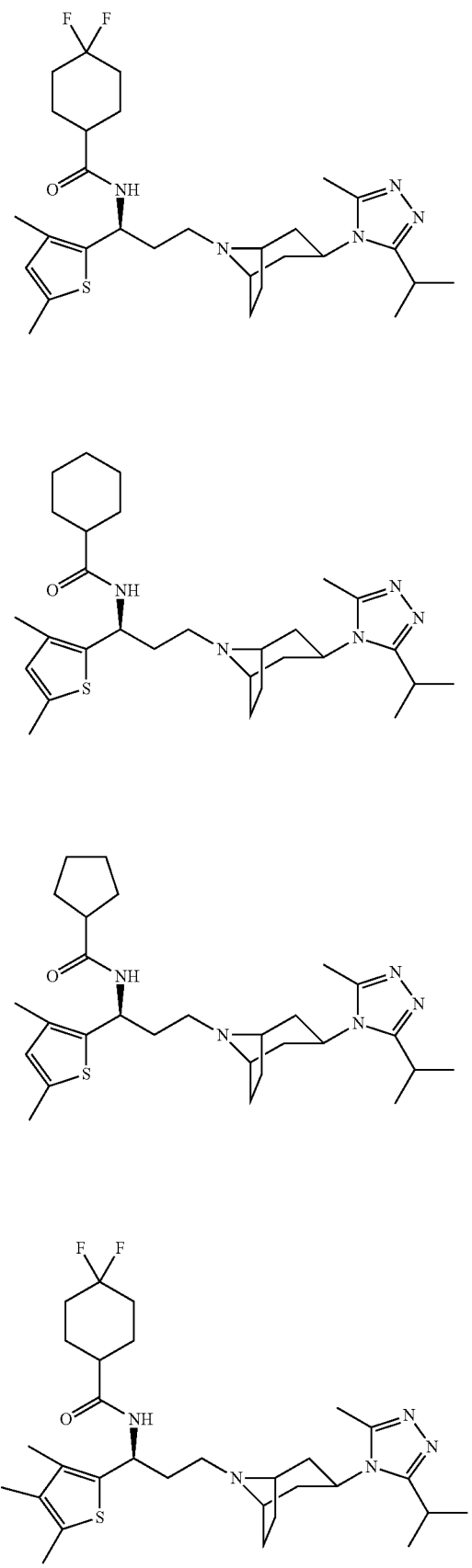

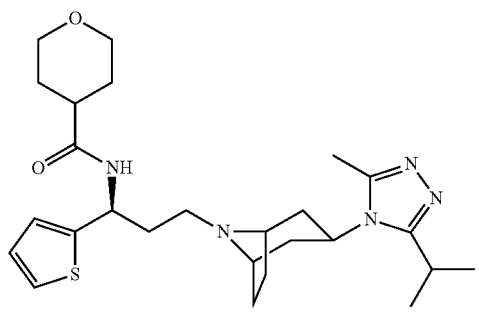
109
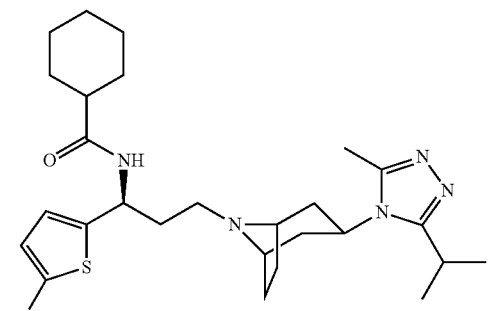
113
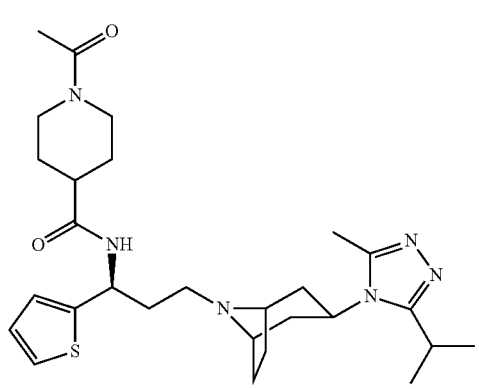
110
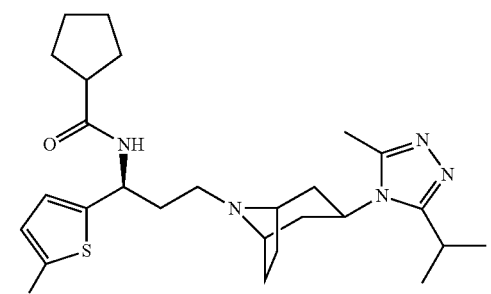
114
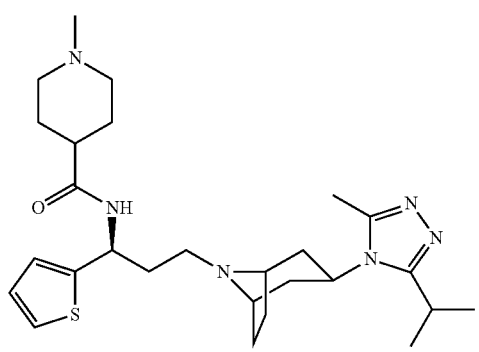
111
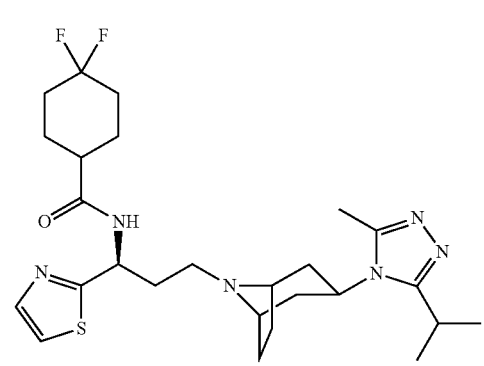
115
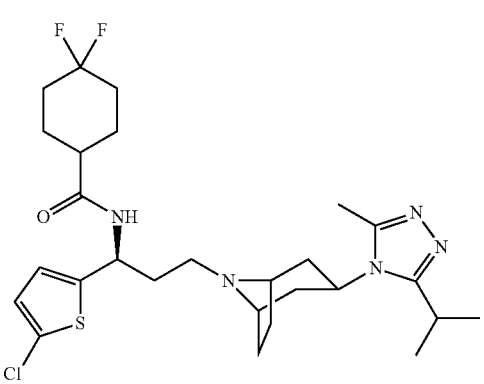
112
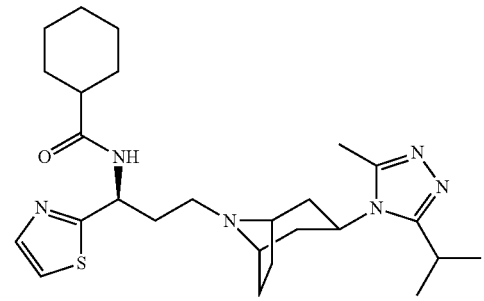
116
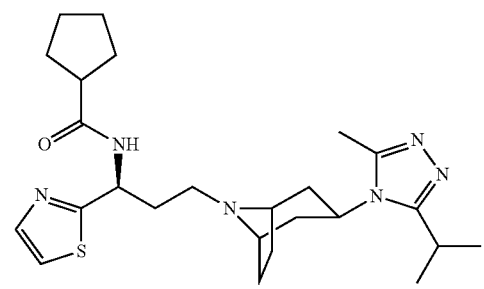
117

118 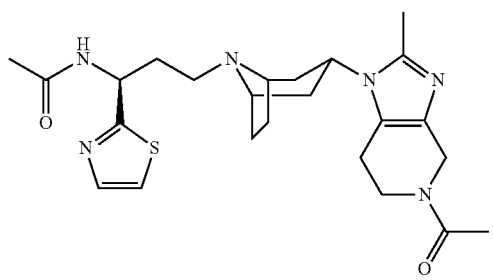
119 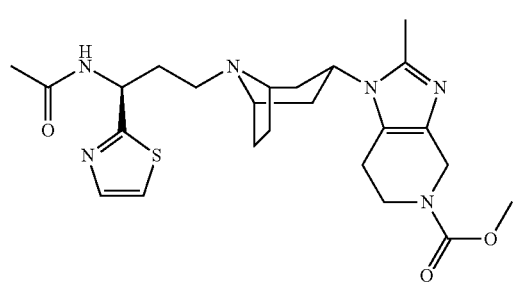
120 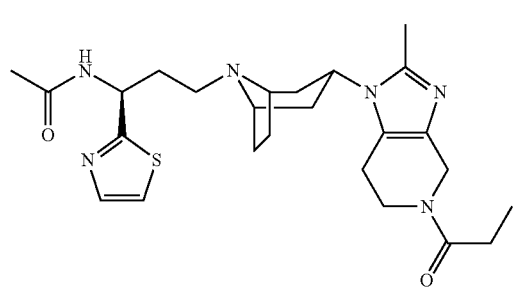
121 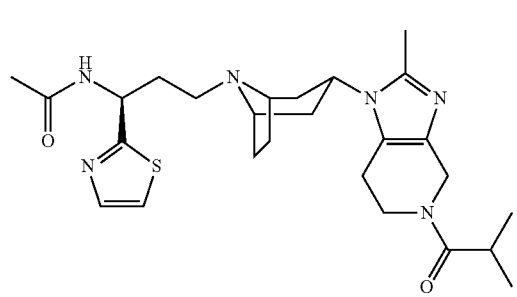
122 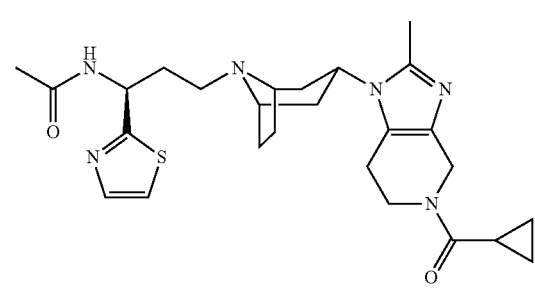
123 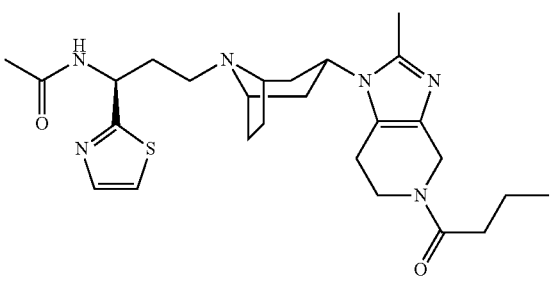
124 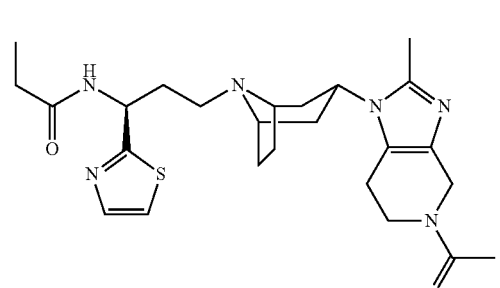
125 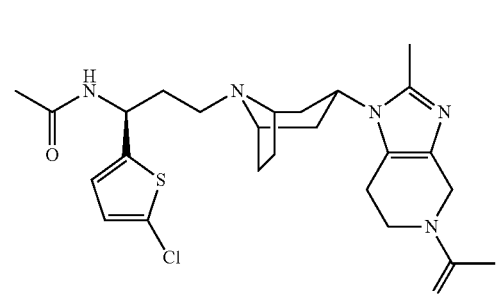
126 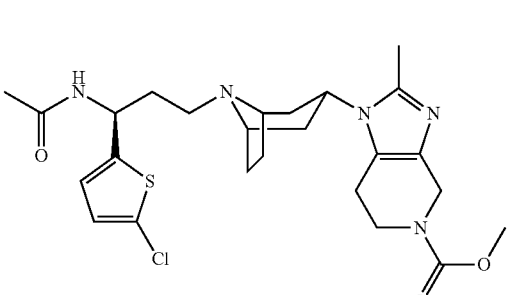
127 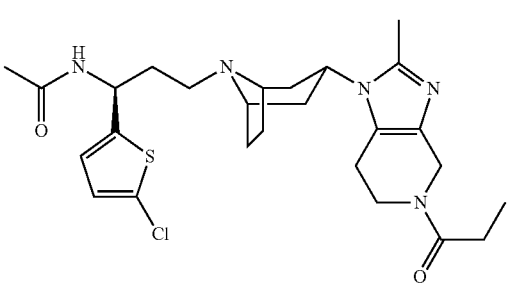

128 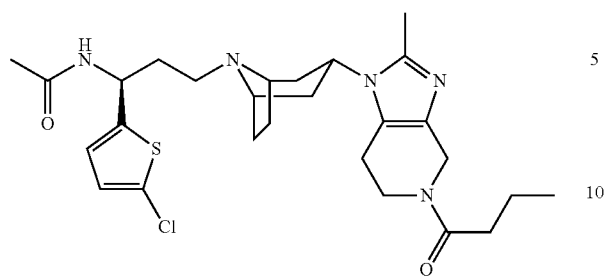
129 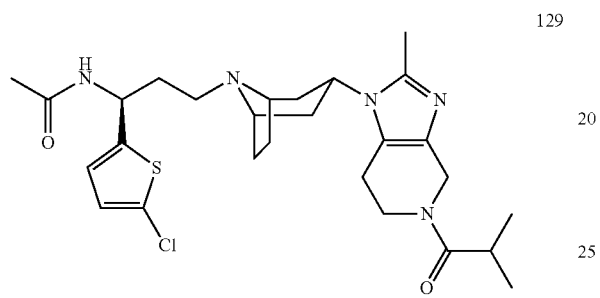
130 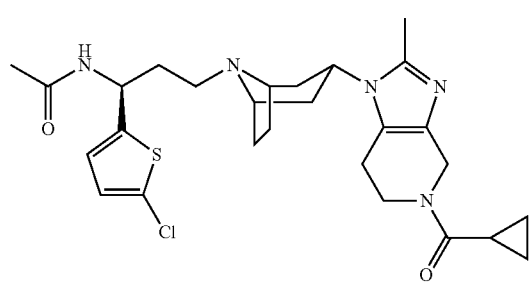
131 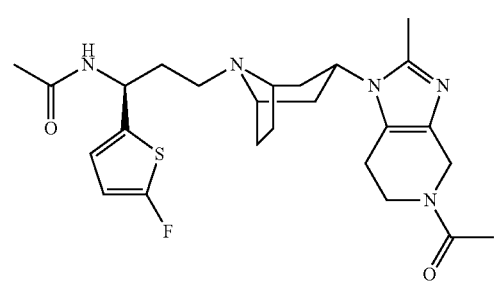
132 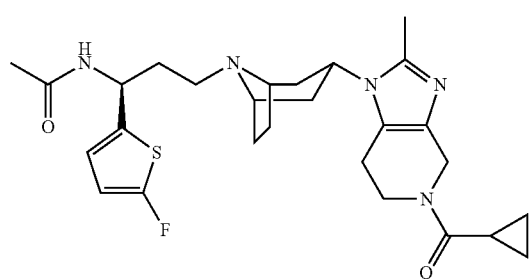
133 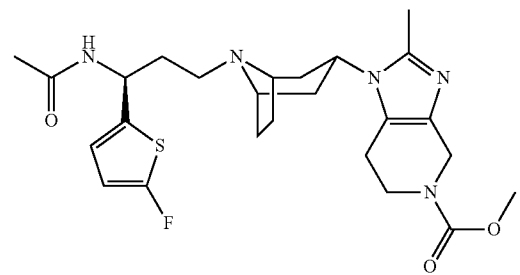
134 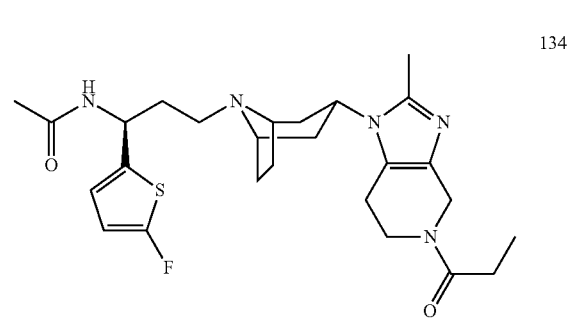
135 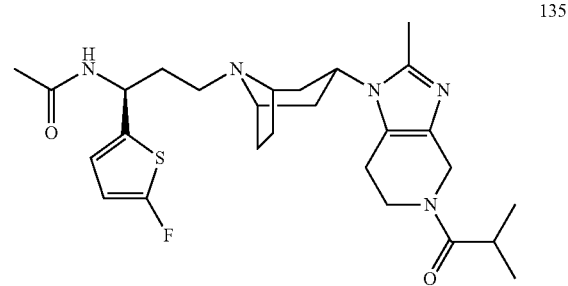
136 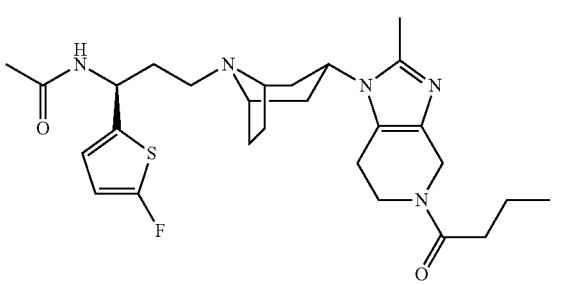
137 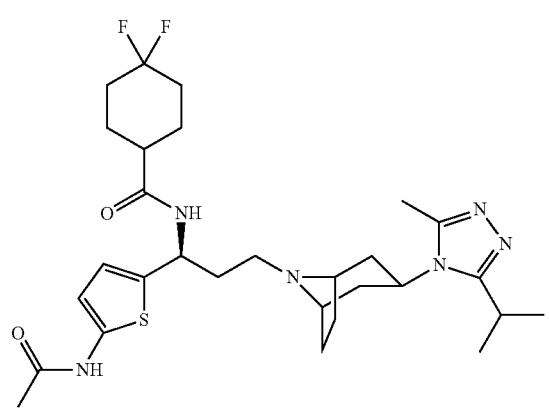

138
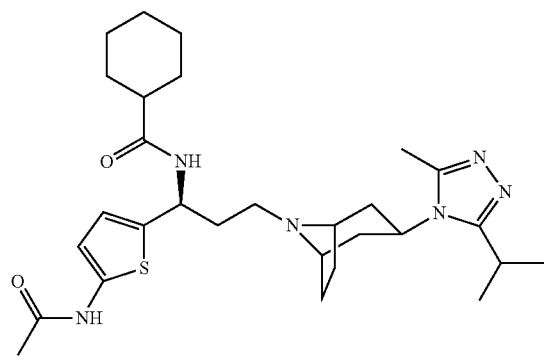
139
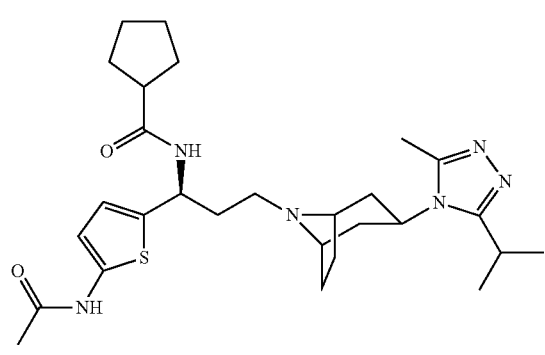
140
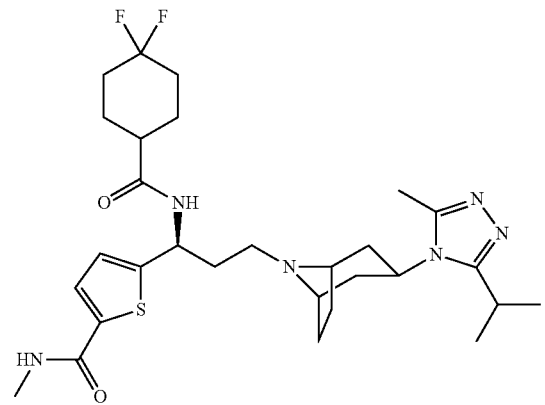
141
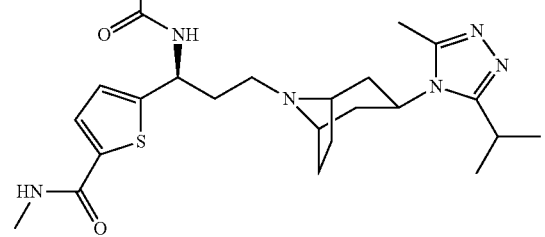
142
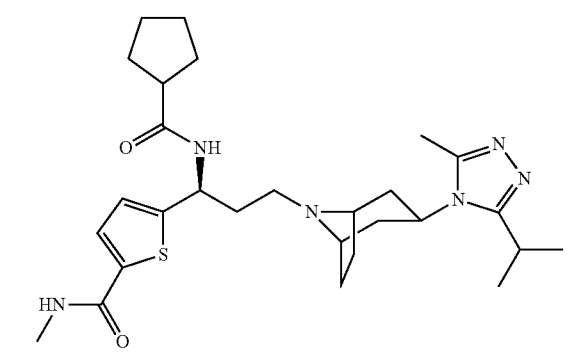
143
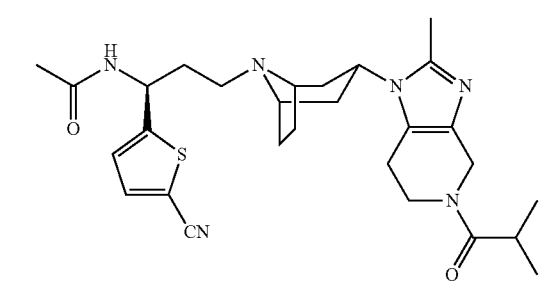
144
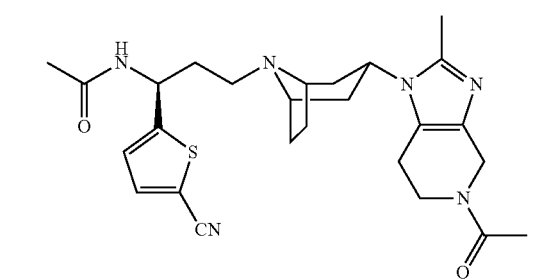
145
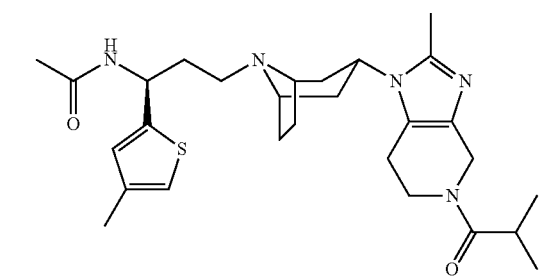
146
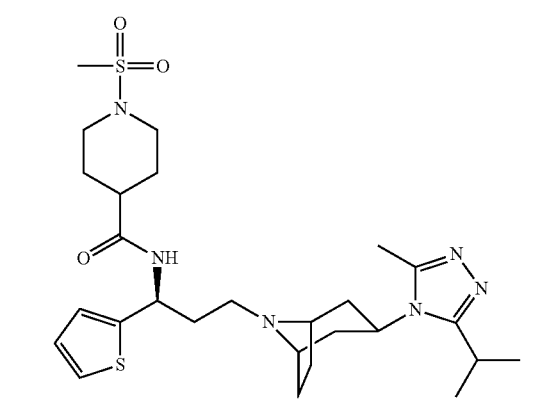

169
-continued
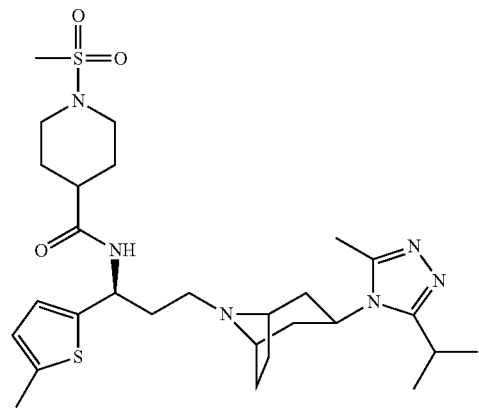
147
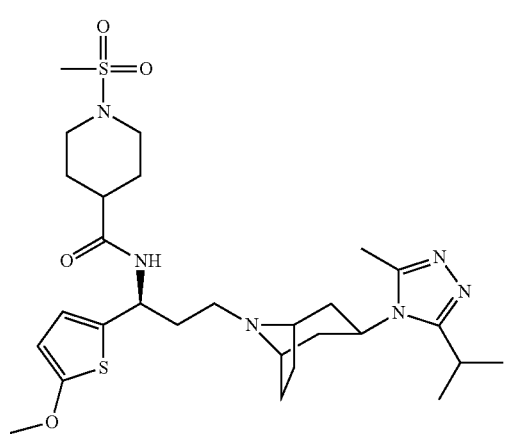
148
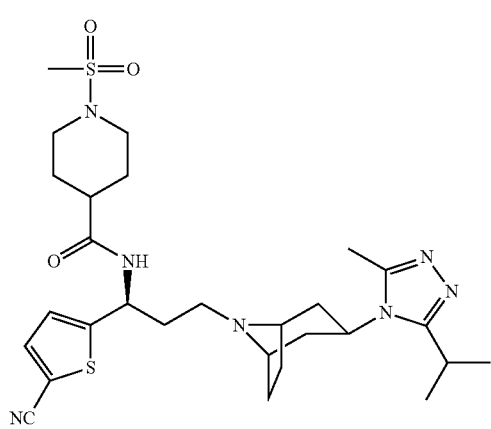
149
170
-continued
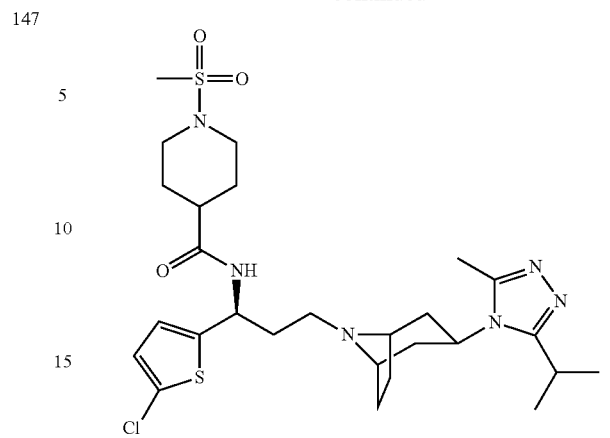
150
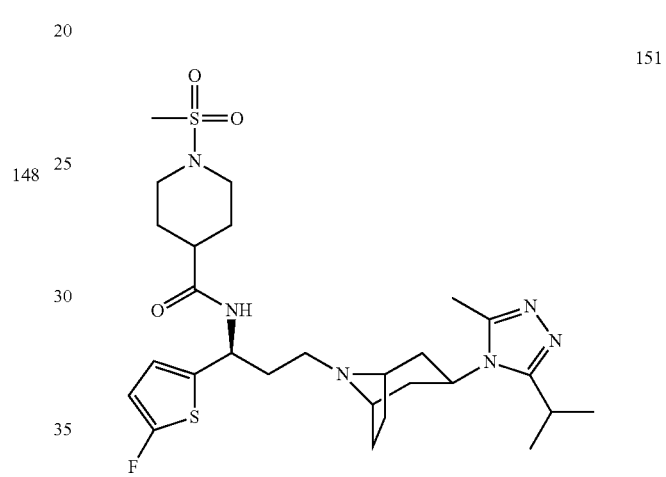
151
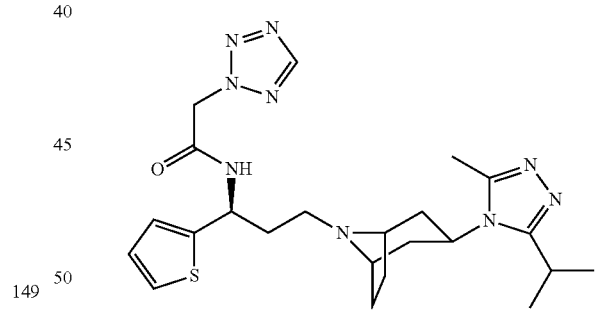
152
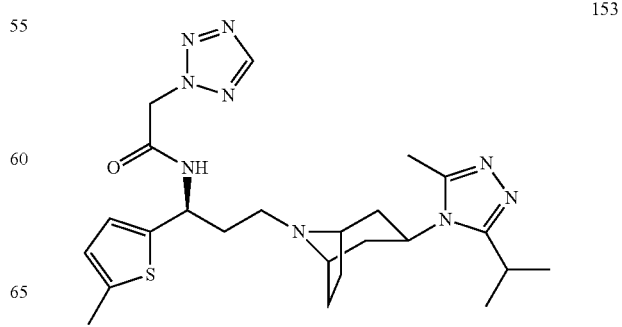
153

154
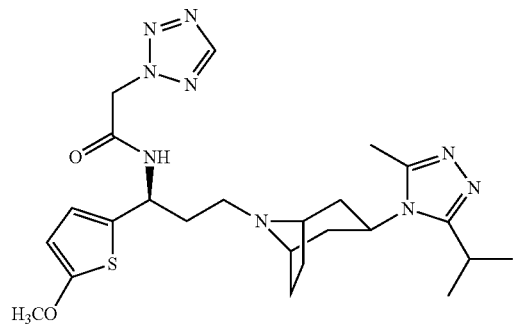
155
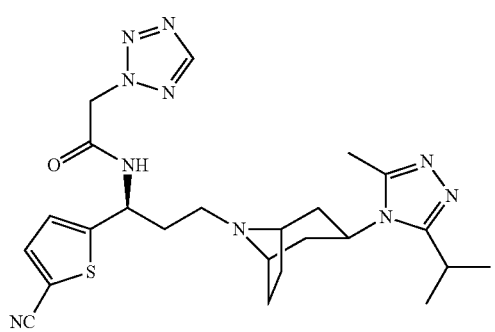
156
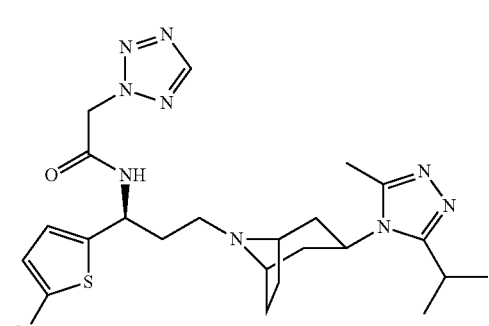
157
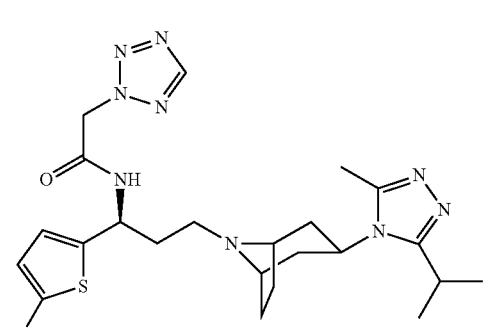
158
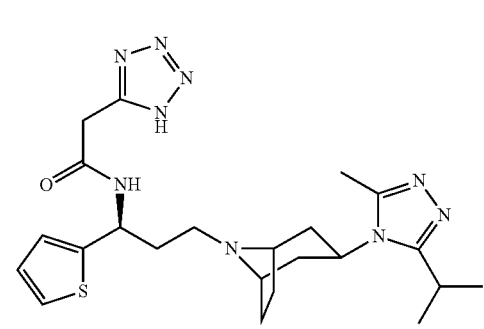
159
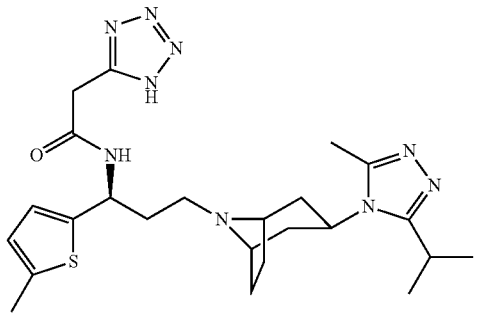
160
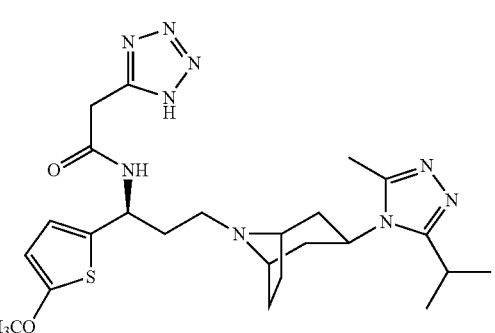
161
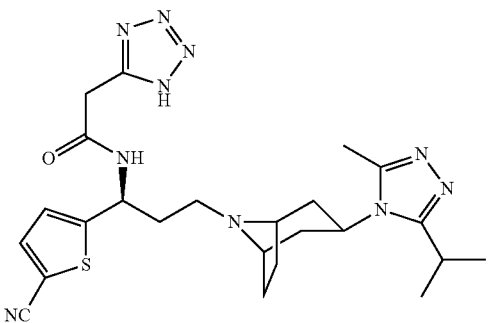
162
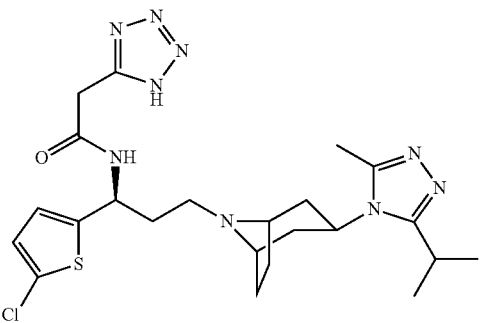
163
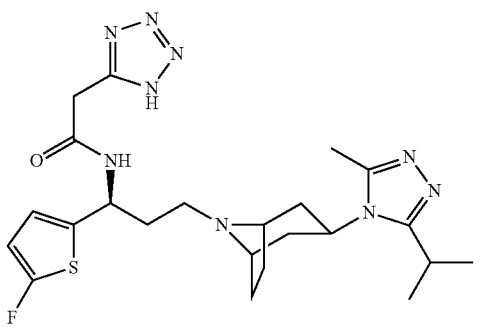

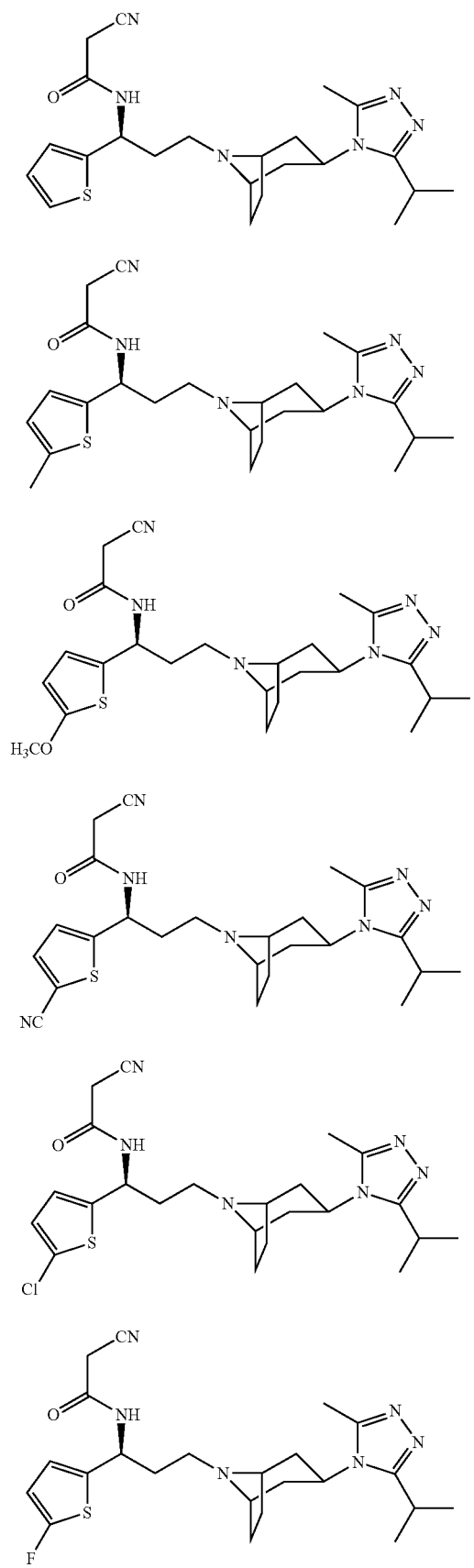
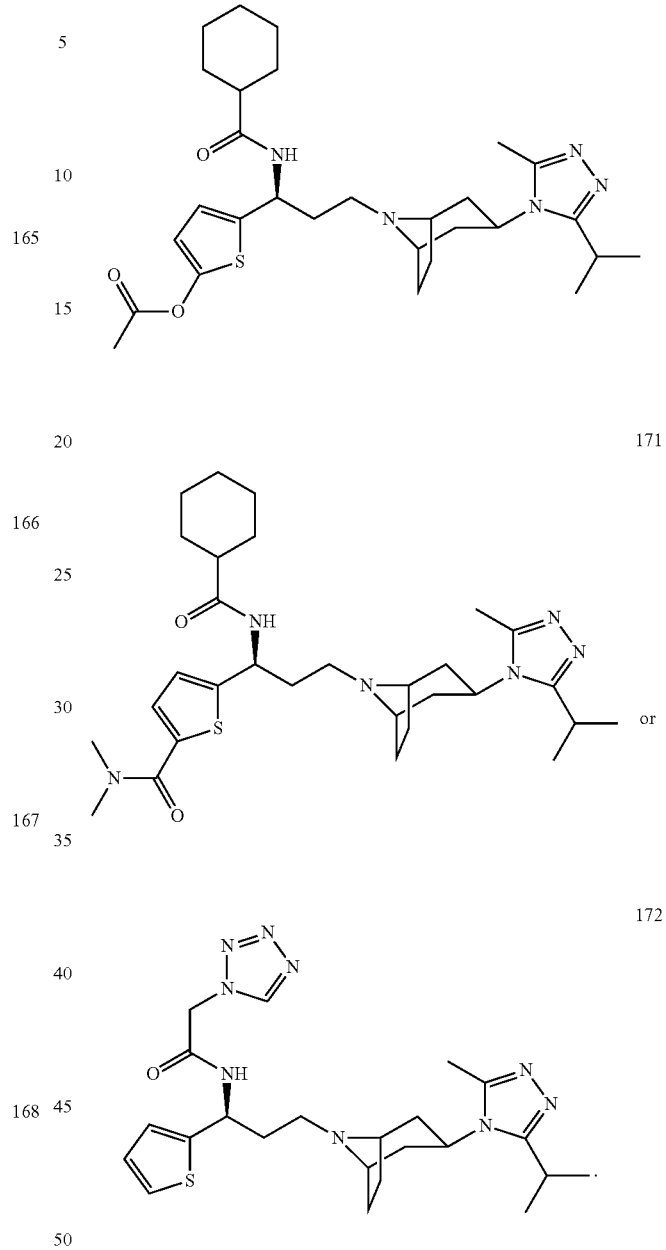
14. The compound according to claim 1, a pharmaceutically acceptable salt, enantiomer, diastereoisotner, racemate or mixture thereof, wherein, the compound of formula I is selected from the following compounds:

-continued

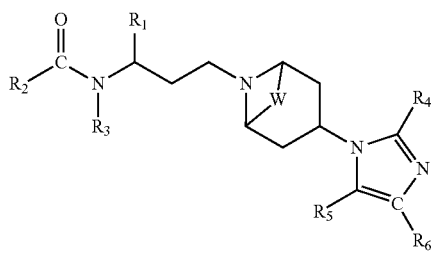

III wherein, the definitions of $R_1$, $R_2$, $R_3$, $R_4$, $R_5$, $R_6$ and W are described as those in claim 1.

15. The compound according to claim 3, a pharmaceutically acceptable salt, enantiomer, diastereoisomer, racemate or mixture thereof, wherein, in formula (II), $R_1$ is selected from the following groups unsubstituted or substituted with 1-3 substituents:

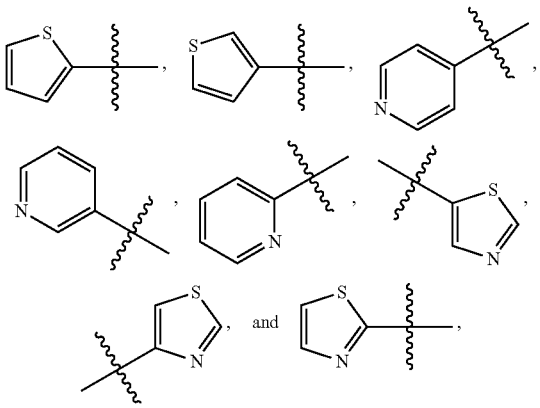

said substituent is defined as claim 1;

each of $R_{10}$ and $R_{11}$ is independently selected from a group consisting of H, a C1-C4 straight or branched alkyl and —C(=O)$R_{13}$;

$R_{12}$ is selected from a group consisting of a C1-C4 straight or branched alkyl, a C1-C4 straight or branched alkoxy, a hydroxy, an amino (NH$_2$) and a C1-C4 straight or branched alkylamino;

$R_{13}$ is selected from a group consisting of H and a C1-C4 straight or branched alkyl;

$R_2$ is selected from the following groups unsubstituted or substituted with 1-3 substituents: a phenyl, a C1-C4 straight or branched alkyl, a C3-C7 cycloalkyl, a tetrahydropyran-4-yl, 1-methylpiperidin-4-yl, 1-acetylpiperidin-4-yl, 1-methylsulfonylpiperidin-4-yl,

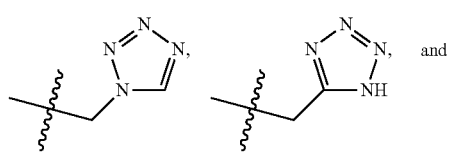

-continued

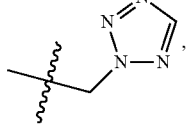

wherein said substituent is selected from a group consisting of a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, an amino, a phenyl, a halophenyl, a phenoxy and a halophenoxy;

each of $R_3$, $R_4$ and $R_5$ is independently selected from a group consisting of H and a C1-C4 straight or branched alkyl;

in formula (III), $R_1$ is selected from the following groups unsubstituted or substituted with 1-3 substituents:

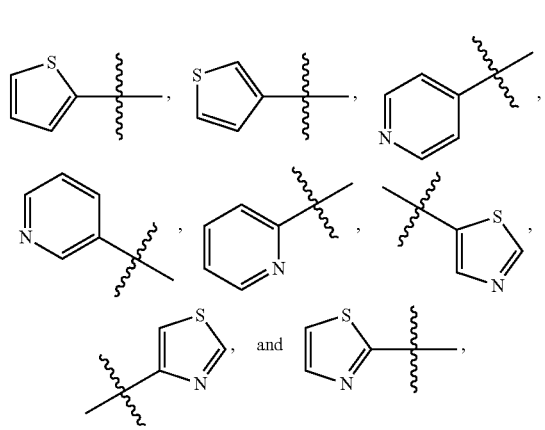

said substituent is defined as claim 1;

each of $R_{10}$ and $R_{11}$ is independently selected from a group consisting of H, a C1-C4 straight or branched alkyl and —C(=O)$R_{13}$;

$R_{12}$ is selected from a group consisting of a C1-C4 straight or branched alkyl, a C1-C4 straight or branched alkoxy, a hydroxy, an amino (NH$_2$) and a C1-C4 straight or branched alkylamino;

$R_{13}$ is selected from a group consisting of H and a C1-C4 straight or branched alkyl;

$R_2$ is selected from the following groups unsubstituted or substituted with 1-3 substituents: a C1-C4 straight or branched alkyl, a C3-C7 cycloalkyl, a tetrahydropyran-4-yl, 1-methylpiperidin-4-yl, 1-acetylpiperidin-4-yl, 1-methylsulfonylpiperidin-4-yl,

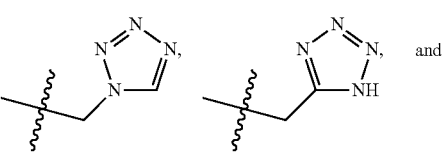

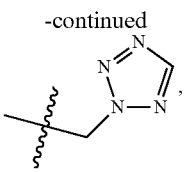

wherein said substituent is selected from a halogen, a hydroxy, a C1-C4 straight or branched alkyl, a C1-C4 straight or branched haloalkyl, a C1-C4 straight or branched alkoxy, a C1-C4 straight or branched alkylcarbonyl, a C1-C4 straight or branched haloalkoxy, a C1-C4 straight or branched alkylsulfonyl, a C1-C4 straight or branched alkylsulfonylcarbamoyl, a tetrazolyl, a cyano and an amino;

each of $R_3$ and $R_4$ is independently selected from a group consisting of H and a C1-C4 straight or branched alkyl;

$R_5$ and $R_6$ can bind together with

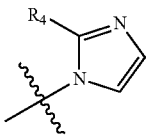

to form

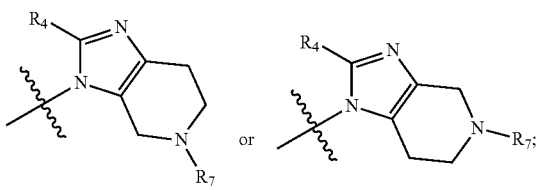

$R_7$ is selected from a group consisting of H, C(=O)$R_8$, C(=O)O$R_8$, C(=O)N$R_8R_9$ and SO$_2R_8$;

each of $R_8$ and $R_9$ is independently selected from a group consisting of H and the following groups unsubstituted or substituted with 1-3 substituents: a C1-C4 straight or branched alkyl, a C1-C4 straight or branched haloalkyl, a C3-C7 cycloalkyl and a benzyl, wherein, said substituent is selected from a group consisting of a halogen, a hydroxy, a C1-C4 straight or branched alkoxy, a C1-C4 straight or branched alkyl, a C1-C4 straight or branched haloalkyl, a C1-C4 straight or branched haloalkoxy and an amino.

16. The compound according to claim 4, a pharmaceutically acceptable salt, enantiomer, diastereoisomer, racemate or mixture thereof, wherein, in formula (II), said substituent on $R_1$ is selected from a group consisting of a halogen, a C1-C2 alkyl, a C1-C2 haloalkyl, a C1-C2 alkylcarbonyloxy, a C1-C2 alkoxy, a C1-C2 haloalkoxy, N$R_{10}$, —C(=O)$R_{12}$, a cyano, a nitro and a hydroxyl, or two adjacent $R_1$ substituents with the atoms to which each is attached are combined to form a fused 5-7 membered carbocycle, a 5-7 membered heteroaryl ring or a 5-7 membered heterocycle.

17. The compound according to claim 16, a pharmaceutically acceptable salt, enantiomer, diastereoisomer, racemate or mixture thereof, wherein said substituent on $R_1$ is selected from a group consisting of a halogen, a methyl, a trifluoromethyl, a trifluoromethoxy, a methoxy, an ethyl, an amino, a cyano, a nitro, an acetyl, a formamido, an acetamido, a carbamoyl, N-methylcarbamoyl, N,N-dimethylcarbamoyl, an acetoxy, a formyloxy and a methoxycarbonyl, or two adjacent $R_1$ substituents together with the atoms to which each is attached form a benzene ring, a cyclopentane ring or dioxole ring.

18. The compound according to claim 4, a pharmaceutically acceptable salt, enantiomer, diastereoisomer, racemate or mixture thereof, wherein, in formula (II), each of $R_{10}$ and $R_{11}$ is independently selected from a group consisting of a C1-C2 alkyl and —C(=O)$R_{13}$.

19. The compound according to claim 4, a pharmaceutically acceptable salt, enantiomer, diastereoisomer, racemate or mixture thereof, wherein, in formula (II), $R_{12}$ is selected from a group consisting of a C1-C2 alkyl, a C1-C2 alkoxy, a hydroxy, an amino (NH$_2$) and a C1-C2 alkylamino.

20. The compound according to claim 4, a pharmaceutically acceptable salt, enantiomer, diastereoisomer, racemate or mixture thereof, wherein, in formula (II), $R_{13}$ is selected from a group consisting of H and a C1-C2 straight or branched alkyl.

21. The compound according to claim 4, a pharmaceutically acceptable salt, enantiomer, diastereoisomer, racemate or mixture thereof, wherein, in formula (II), $R_2$ is selected from a group consisting of a methyl, an ethyl, a cyclopropyl, a cyclobutyl, a cyclopentyl, a cyclohexyl, a tetrahydropyran-4-yl, 1-methylpiperidin-4-yl, 1-acetylpiperidin-4-yl, 1-methylsulfonylpiperidin-4-yl,

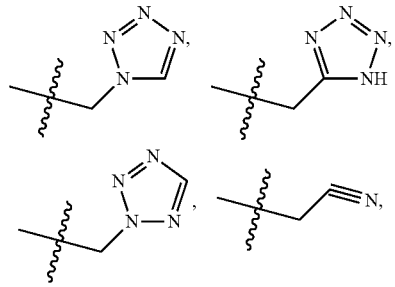

a phenyl, 4-fluorobenzyl, an ethylcyclohexyl and a difluorocyclohexyl.

22. The compound according to claim 15, a pharmaceutically acceptable salt, enantiomer, diastereoisomer, racemate or mixture thereof, wherein, in formula (11), each of $R_3$, $R_4$ and $R_5$ is independently selected from a group consisting of H and a methyl, an ethyl, an n-propyl, an isopropyl, an n-butyl, a sec-butyl and a tert-butyl.

23. The compound according to claim 22, a pharmaceutically acceptable salt, enantiomer, diastereoisomer, racemate or mixture thereof, wherein each of $R_3$, $R_4$ and $R_5$ is independently selected from a group consisting of H, a methyl, an ethyl, an n-propyl and an isopropyl.

24. The compound according to claim 4, a pharmaceutically acceptable salt, enantiomer, diastereoisotner, racemate or mixture thereof; wherein, in formula (III),
said substituent on $R_1$ is selected from a group consisting of a halogen, a C1-C2 alkyl, a C1-C2 haloalkyl, a C1-C2 alkoxy, a C1-C2 alkylcarbonyloxy, a C1-C2 haloalkoxy, $NR_{10}R_{11}$, —C(=O)$R_{12}$, a cyano, a nitro and a hydroxyl, or two adjacent $R_1$ substituents with the atoms to which each is attached are combined to form a fused 5-7 membered carbocycle, 5-7 membered heteroaryl ring or 5-7 membered heterocycle.

25. The compound according to claim 24, a pharmaceutically acceptable salt, enantiomer, diastereoisomer, racemate or mixture thereof, wherein said substituent on $R_1$ is selected from a group consisting of a halogen, a methyl, a trifluoromethyl, a trifluoromethoxy, a methoxy, an ethyl, an amino, a cyano, a nitro, an acetyl, a forrnamido, an acetamido, a carbamoyl, N-methylcarbamoyl, N,N-dimethylcarbamoyl, a formyloxy, an acetoxy and a methoxycarbonyl, or two adjacent $R_1$ substituents together with the atoms to which each is attached form a benzene ring, a cyclopentene ring or dioxole ring.

26. The compound according to claim 15, a pharmaceutically acceptable salt, enantiomer, diastereoisomer, racemate or mixture thereof, wherein, in formula (III),
each of $R_{10}$ and $R_{11}$ is independently selected from a group consisting of H, a C1-C2 alkyl and —C(=O)$R_{13}$.

27. The compound according to claim 15, a pharmaceutically acceptable salt, enantiomer, diastereoisomer, racemate or mixture thereof, wherein, in formula (III),
$R_{12}$ is selected from a group consisting of a C1-C2 alkyl, a C1-C2 alkoxy, a hydroxy, an amino ($NH_2$) and a C1-C2 alkylamino.

28. The compound according to claim 15, a pharmaceutically acceptable salt, enantiomer, diastereoisomer, racemate or mixture thereof, wherein, in formula (III),
$R_{13}$ is selected from a group consisting of H and a C1-C2 straight or branched alkyl.

29. The compound according to claim 15, a pharmaceutically acceptable salt, enantiomer, diastereoisomer, racemate or mixture thereof, wherein, in formula (III),
$R_2$ is selected from a group consisting of a methyl, an ethyl, a cyclopropyl, a cyclobutyl, a cyclopentyl, a cyclohexyl, a tetrahydropyran-4-yl, 1-methylpiperidin-4-yl, 1-acetylpiperidin-4-yl, 1-methylsulfonylpiperidin-4-yl,

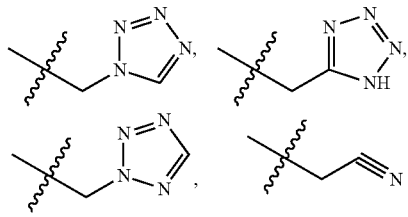

and a difluorocyclohexyl.

30. The compound according to claim 15, a pharmaceutically acceptable salt, enantiomer, diastereoisomer, racemate or mixture thereof, wherein, in formula (III),
each of $R_3$ and $R_4$ is independently selected from a group consisting of H and a methyl, an ethyl, an n-propyl, an isopropyl, an n-butyl, a sec-butyl and a tert-butyl.

31. The compound according to claim 30, a pharmaceutically acceptable salt, enantiomer, diastereoisomer, racemate or mixture thereof, wherein each of $R_3$ and $R_4$ is independently selected from a group consisting of H, a methyl and an ethyl.

32. The compound according to claim 15, a pharmaceutically acceptable salt, enantiomer, diastereoisomer, racemate or mixture thereof, wherein, in formula (III),
$R_7$ is selected from a group consisting of H, C(=O)$R_8$ and $SO_2R_8$.

33. The compound according to claim 15, a pharmaceutically acceptable salt, enantiomer, diastereoisomer, racemate or mixture thereof, wherein, in formula (III),
said substituent on each of Rs and Ry is selected from a group consisting of a halogen, a hydroxy, a methoxy, an ethoxy, a methyl, an ethyl, a trilluoromethyl, a trifluoromethoxy and an amino.

34. The compound according to claim 15, a pharmaceutically acceptable salt, enantiomer, diastereoisomer, racemate or mixture thereof, wherein, in formula
each of $R_8$ and $R_9$ is independently selected from a group consisting of H, a C1-C4 straight or branched alkyl, a C1-C4 straight or branched haloalkyl and a C3-C7 cycloalkyl.

35. The compound according to claim 33, a pharmaceutically acceptable salt, enantiomer, diastereoisomer, racemate or mixture thereof, wherein each of $R_8$ and $R_9$ is independently selected from a group consisting of a methyl, an ethyl, an n-propyl, a cyclopropyl, an isopropyl, an n-butyl, a sec-butyl and a tert-butyl.

36. The compound according to claim 15, a pharmaceutically acceptable salt, enantiomer, diastereoisomer, racemate or mixture thereof, wherein each of $R_3$, $R_4$ and $R_5$ is independently selected from a group consisting of H and a methyl, an ethyl, an n-propyl, an isopropyl, an n-butyl, a sec-butyl and a tert-butyl.

37. The compound according to claim 15, a pharmaceutically acceptable salt, enantiomer, diastereoisomer, racemate or mixture thereof, wherein each of $R_8$ and $R_9$ is independently selected from a group consisting of a halogen, a hydroxy, a methoxy, an ethoxy, a methyl, an ethyl, a trifluoromethyl, a trifluoromethoxy and an amino.

38. A pharmaceutical composition comprising one of the compounds according to claim 1, a pharmaceutically acceptable salt, enantiomer, diastereoisomer, racemate or mixture thereof; and optionally a pharmaceutically acceptable carrier.

39. A method for treating HIV infection comprising administering to a subject in need thereof, a compound according to claim 1, a pharmaceutically acceptable salt, enantiomer, diastereoisomer, racemate or mixture thereof.

40. A method for preparing a medicament for treating a CCR5-mediated disease comprising combining a compound according to claim 1, a pharmaceutically acceptable salt, enantiomer, diastereoisomer, racemate or mixture thereof with a pharmaceutically acceptable carrier.

41. A method for preparing a compound of formula I, wherein, the method includes the following steps:

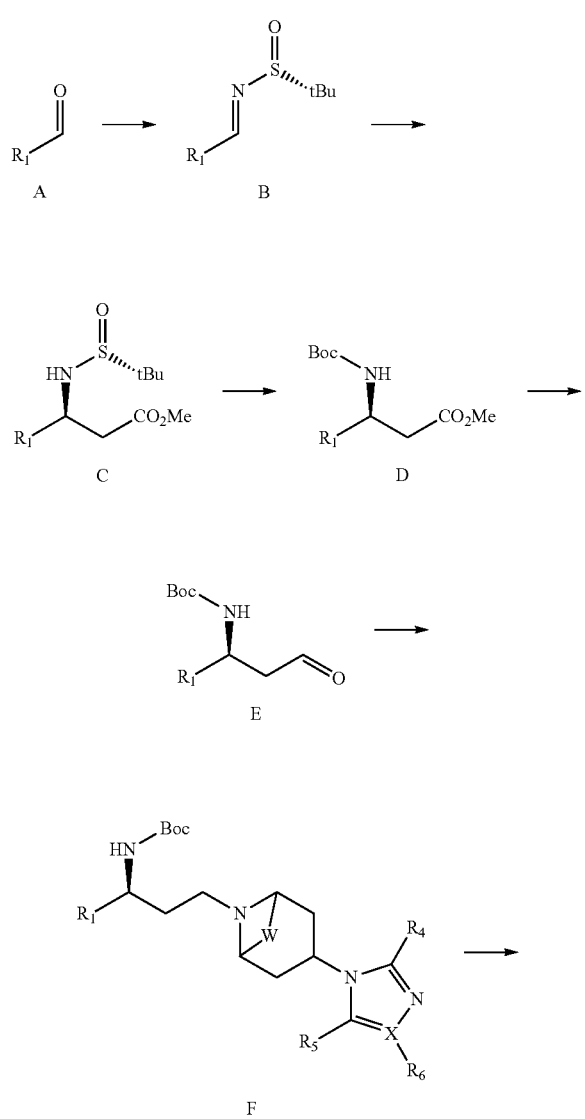

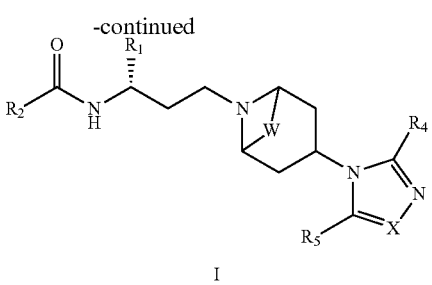

1) Sulfinylimine Compound B is obtained from Compound A through imidization;
2) Compound C is Obtained from Sulfinylimine compound B through Mannich reaction;
3) Compound D is obtained from Compound C through removal of sulfinyl and t-butyloxycarbonyl (BOC) protection;
4) Compound E is obtained from Compound D through ester reduction and oxidation;
5) Compound F is obtained from Compound E and

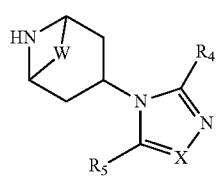

through reductive amination reaction;
6) Compound F is subjected to deprotection and condensation reaction with

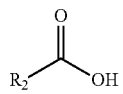

to give compound I,
in each formula, $R_1$, $R_2$, $R_4$, $R_5$, $R_6$, X and W are defined as those in claim 1.

* * * * *